United States Patent
Ghosh et al.

(10) Patent No.: US 12,421,223 B2
(45) Date of Patent: Sep. 23, 2025

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Shomir Ghosh, Brookline, MA (US); Jason Katz, Newton, MA (US); William Roush, Boston, MA (US); Hans Martin Seidel, Concord, MA (US); Dong-Ming Shen, Edison, NJ (US); Shankar Venkatraman, Lansdale, PA (US)

(73) Assignee: Novartis AG, Basel (CH)

( * ) Notice: Subject to any disclaimer, the term of this patent is extended or adjusted under 35 U.S.C. 154(b) by 1089 days.

(21) Appl. No.: 17/292,891

(22) PCT Filed: Nov. 11, 2019

(86) PCT No.: PCT/US2019/060772
§ 371 (c)(1),
(2) Date: May 11, 2021

(87) PCT Pub. No.: WO2020/102098
PCT Pub. Date: May 22, 2020

(65) Prior Publication Data
US 2023/0025630 A1 Jan. 26, 2023

Related U.S. Application Data

(60) Provisional application No. 62/760,195, filed on Nov. 13, 2018, provisional application No. 62/760,244, (Continued)

(51) Int. Cl.
*C07D 417/06* (2006.01)
*A61P 35/00* (2006.01)
(Continued)

(52) U.S. Cl.
CPC ............ *C07D 417/06* (2013.01); *A61P 35/00* (2018.01); *C07D 401/06* (2013.01); *C07D 417/12* (2013.01); *C07D 417/14* (2013.01)

(58) Field of Classification Search
CPC .. C07D 417/06; C07D 401/06; C07D 417/12; C07D 417/14; A61P 35/00
See application file for complete search history.

(56) References Cited

U.S. PATENT DOCUMENTS

2020/0216389 A1    7/2020   Miller et al.

FOREIGN PATENT DOCUMENTS

EP   0552553 A1   7/1993
EP   2927214 A1   10/2015
(Continued)

OTHER PUBLICATIONS

Goldstein et al., Journal of Medicinal Chemistry, 2006, vol. 49, No. 5 (Year: 2006).*
(Continued)

*Primary Examiner* — Clinton A Brooks
*Assistant Examiner* — Izabela Schmidt
(74) *Attorney, Agent, or Firm* — Timothy P. O'Dea

(57) ABSTRACT

In one aspect, compounds of Formula AA, or a pharmaceutically acceptable salt thereof, are featured: or a pharmaceutically acceptable salt thereof, wherein the variables shown in Formula A can be as defined anywhere herein.

Formula AA

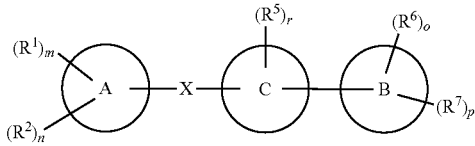

1 Claim, 5 Drawing Sheets

Related U.S. Application Data filed on Nov. 13, 2018, provisional application No. 62/760,248, filed on Nov. 13, 2018.

(51) Int. Cl.
  *C07D 401/06* (2006.01)
  *C07D 417/12* (2006.01)
  *C07D 417/14* (2006.01)

(56) References Cited

FOREIGN PATENT DOCUMENTS

| | | | | |
|---|---|---|---|---|
| WO | WO-9957101 A1 | * | 11/1999 | ............... A61P 1/02 |
| WO | 2005/009973 A1 | | 2/2005 | |
| WO | 2008/114023 A2 | | 9/2008 | |
| WO | WO-2016131098 A1 | * | 8/2016 | ............. A61K 31/18 |
| WO | WO-2017074832 A1 | * | 5/2017 | ......... A61K 31/4427 |
| WO | WO-2017129897 A1 | * | 8/2017 | ............. A61K 31/18 |
| WO | 2017184746 A1 | | 10/2017 | |
| WO | WO-2017184604 A1 | * | 10/2017 | ............... A61P 1/00 |
| WO | WO-2017184623 A1 | * | 10/2017 | ............... A61P 1/00 |
| WO | 2017/218617 A1 | | 12/2017 | |
| WO | 2018136890 A1 | | 7/2018 | |
| WO | 2018225018 A1 | | 12/2018 | |
| WO | 2019023147 A1 | | 1/2019 | |
| WO | 2020018975 A1 | | 1/2020 | |
| WO | 2020035466 A1 | | 2/2020 | |
| WO | 2020053282 A1 | | 3/2020 | |
| WO | 2020150674 A1 | | 7/2020 | |
| WO | 2020254697 A1 | | 12/2020 | |

OTHER PUBLICATIONS

Chang et al., J. Chem. Inf. Model. 2013, 53, 1775-1786 (Year: 2013).*

Patent Pack—WO 2017/074832A1—Substance Table (Year: 2017).*

Saxena, et al., Estimation of Antitumor Activity of Sulphonimidamide Analogs of Oncolytic Sulphonylureas, Oxidation Communications, 26(1), 9-13, 2003.

Scozzafava, et al., Arylsulfonyl-N,N-diethyl-dithiocarbamates: A Novel Class of Antitumor Agents, Bioorganic & Medicinal Chemistry Letters, 10, 1887-1891, 2000.

Supuran, et al., Carbonic anhydrase inhibitors—Part 94. 1,3,4-Thiadiazole-2-sulfonamide derivatives as antitumor agents?, Eur. J. Med. Chem., 35, 867-874, 2000.

Toth, et al., Synthesis and Resolution of Sulfonimidamide Analogs of Sulfonylureas, Journal of Organic Chemistry, 58(12), 3469-3472, 1993.

Kim et al., "An Effective Antiviral Approach Targeting Hepatitis B Virus with NJK14047, a Novel and Selective Biphenyl Amide p38 Mitogen-Activated Protein Kinase Inhibitor," Antimicrobial Agents and Chemotherapy. 61(8):e00214-17 (10 pages) (2017).

International Search Report and Written Opinion for PCT/US2019/060772, mailed Feb. 11, 2020 (14 pages).

Izzo, et al., Exploration of Novel Chemical Space: Synthesis and in vitro Evaluation of N-Functionalized Tertiary Sulfonimidamides, Chemistry—A European Journal, 2018, 9295-9304, 24.

Toth, et al., Sulfonimidamide Analogs of Oncolytic Sulfonylureas, Journal of Medicinal Chemistry, 1997, 1018-1025, 40.

Nandi, et al., Direct Synthesis of N-Acyl Sulfonimidamides and N-Sulfonimidoyl Amidines from Sulfonimidoyl Azides, Adv. Synth. Catal., May 15, 2018, 2465-2469, 360.

Wakchaure, et al., Synthesis of Vinyl- and Aryl-Acyl Sulfonimidamides Through Pd-Catalyzed Carbonylation Using Mo(CO)6 as ex situ CO Source, European Journal of Organic Chemistry, 2015, 213-219.

\* cited by examiner

FIGURE. 5

COMPOUNDS AND COMPOSITIONS FOR TREATING CONDITIONS ASSOCIATED WITH NLRP ACTIVITY

TECHNICAL FIELD

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) contributes to the pathology and/or symptoms and/or progression of the condition, disease or disorder in a subject (e.g., a human). This disclosure also features compositions as well as other methods of using and making the same. The present disclosure also relates to, in part, methods and compositions for treating anti-TNFα resistance in a subject with an NLRP3 antagonist. The present disclosure also relates, in part, to methods, combinations and compositions for treating TFNα related diseases and anti-TNFα resistance in a subject that include administration of an NLRP3 antagonist, an NLRP3 antagonist and an anti-TNFα agent, or a composition encompassing an NLRP3 antagonist and an anti-TNFα agent.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

NLRP3 can form a complex and has been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP3.

Several patients having inflammatory or autoimmune diseases are treated with anti-TNFα agents. A subpopulation of such patients develop resistance to treatment with the anti-TNFα agents. It is desirable to develop methods for reducing a patient's resistance to anti-TNFα agents. In light of the this, it would also be desirable to provide alternative therapies for treating inflammatory or autoimmune diseases (for example NLRP3 inflammasome inhibitors) to avoid or minimise the use of anti-TNFα agents.

Intestinal bowel disease (IBD), encompassing Ulcerative Colitis (UC) and Crohn's disease (CD), are chronic diseases characterized by barrier dysfunction and uncontrolled inflammation and mucosal immune reactions in the gut. A number of inflammatory pathways have been implicated in the progression of IBD, and anti-inflammatory therapy such as tumor necrosis factor-alpha (TNF-α) blockade has shown efficacy in the clinic (Rutgeerts P et al *N Engl J Med* 2005; 353:2462-76). Anti-TNFα therapies, however, do not show complete efficacy, however, other cytokines such as IL-1β, IL-6, IL-12, IL-18, IL-21, and IL-23 have been shown to drive inflammatory disease pathology in IBD (Neurath M F *Nat Rev Immunol* 2014; 14; 329-42). IL-1β and IL-18 are produced by the NLRP3 inflammasome in response to pathogenic danger signals, and have been shown to play a role in IBD. Anti-IL-1β therapy is efficacious in patients with IBD driven by genetic mutations in CARD8 or IL-1 OR (Mao L et al *J Clin Invest* 2018; 238:1793-1806, Shouval D S et al *Gastroenterology* 2016; 151:1100-1104), IL-18 genetic polymorphisms have been linked to UC (Kanai T et al, *Curr Drug Targets* 2013; 14:1392-9), and NLRP3 inflammasome inhibitors have been shown to be efficacious in murine models of IBD (Perera A P et al *Sci Rep* 2018; 8:8618). Resident gut immune cells isolated from the lamina propria of IBD patients can produce IL-1β, either spontaneously or when stimulated by LPS, and this IL-1β production can be blocked by the ex vivo addition of a NLRP3 antagonist. Based on strong clinical and preclinical evidence showing that inflammasome-driven IL-1β and IL-18 play a role in IBD pathology, it is clear that NLRP3 inflammasome inhibitors could be an efficacious treatment option for UC, Crohn's disease, or subsets of IBD patients. These subsets of patients could be defined by their peripheral or gut levels of inflammasome related cytokines including IL-1β, IL-6, and IL-18, by genetic factors that pre-dispose IBD patients to having NLRP3 inflammasome activation such as mutations in genes including ATG16L1, CARD8, IL-10R, or PTPN2 (Saitoh T et al, *Nature* 2008; 456; 264, Spalinger M R, *Cell Rep* 2018; 22:1835), or by other clinical rationale such as non-response to TNF therapy.

Though anti-TNF therapy is an effective treatment option for Crohn's disease, 40% of patients fail to respond. One-third of non-responsive CD patients fail to respond to anti-TNF therapy at the onset of treatment, while another third lose response to treatment over time (secondary non-response). Secondary non-response can be due to the generation of anti-drug antibodies, or a change in the immune compartment that desensitizes the patient to anti-TNF (Ben-Horin S et al, *Autoimmun Rev* 2014; 13; 24-30, Steenholdt C et al *Gut* 2014; 63; 919-27).

Anti-TNF reduces inflammation in IBD by causing pathogenic T cell apoptosis in the intestine, therefore eliminating the T cell mediated inflammatory response (Van den Brande et al *Gut* 2007:56:509-17). There is increased NLRP3 expression and increased production of IL-1β in the gut of TNF-non-responsive CD patients (Leal R F et al Gut 2015; 64:233-42) compared to TNF-responsive patients, suggesting NLRP3 inflammasome pathway activation. Furthermore, there is increased expression of TNF-receptor 2 (TNF-R2), which allows for TNF-mediated proliferation of T cells (Schmitt H et al *Gut* 2018; 0:1-15). IL-1β signaling in the gut promotes T cell differentiation toward Th1/17 cells which can escape anti-TNF-α mediated apoptosis. It is therefore likely that NLRP3 inflammasome activation can cause non-responsiveness in CD patients to anti-TNF-α therapy by sensitizing pathogenic T cells in the gut to anti-TNF-α mediated apoptosis. Experimental data from immune cells isolated from the gut of TNF-resistant Crohn's patients show that these cells spontaneously release IL-1β, which can be inhibited by the addition of an NLRP3 antagonist. NLRP3 inflammasome antagonists—in part by blocking IL-1β secretion—would be expected to inhibit the mechanism leading to anti-TNF non-responsiveness, re-sensitizing the patient to anti-TNF therapy. In IBD patients who are naive to anti-TNF therapy, treatment with an NLRP3 antagonist would be expected to prevent primary- and secondary-non responsiveness by blocking the mechanism leading to non-response.

NLRP3 antagonists that are efficacious locally in the gut can be efficacious drugs to treat IBD; in particular in the treatment of TNF-resistant CD alone or in combination with anti-TNF therapy. Systemic inhibition of both IL-1β and TNF-α has been shown to increase the risk of opportunistic infections (Genovese M C et al, Arthritis Rheum 2004; 50:1412), therefore, only blocking the NLRP3 inflammasome at the site of inflammation would reduce the infection risk inherent in neutralizing both IL-1β and TNF-α. NLRP3 antagonists that are potent in NLRP3-inflammasome driven cytokine secretion assays in cells, but have low permeability in vitro in a permeability assay such as an MDCK assay, have poor systemic bioavailability in a rat or mouse pharmacokinetic experiment, but high levels of compound in the colon and/or small intestine could be a useful therapeutic option for gut restricted purposes.

In light of the above, the present invention also provides alternative therapies for the treatment of inflammatory or autoimmune diseases, including IBD, that solves the above problems associated with anti-TNFα agents.

SUMMARY

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling).

In some embodiments, provided herein is a compound of Formula AA

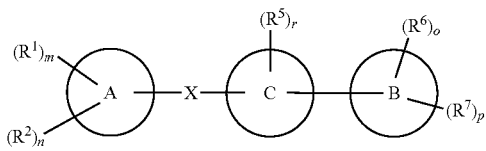

Formula AA or a pharmaceutically acceptable salt thereof, wherein the variables in Formula AA can be as defined anywhere herein.

The present invention is also relates to the Applicant's discovery that inhibition of NLRP3 inflammasomes can increase a subject's sensitivity to an anti-TNFα agent or can overcome resistance to an anti-TNFα agent in a subject, or indeed provide an alternative therapy to anti-TNFα agents.

Provided herein are methods of treating a subject that include: (a) identifying a subject having a cell that has an elevated level of NLRP3 inflammasome activity and/or expression as compared to a reference level; and (b) administering to the identified subject a therapeutically effective amount of an compound of Formula I or a pharmaceutically acceptable salt, solvate, or co-crystal thereof.

Provided herein are methods for the treatment of inflammatory or autoimmune disease including IBD, such as UC and CD in a subject in need thereof, comprising administering to said subject a therapeutically effective amount a compound for Formula I or a pharmaceutically acceptable salt, solvate, or co-crystal thereof, wherein the NLRP3 antagonist is a gut-targeted NLRP3 antagonist.

Provided herein are methods of treating a subject in need thereof, that include: (a) identifying a subject having resistance to an anti-TNFα agent; and (b) administering a treatment comprising a therapeutically effective amount of a compound for Formula I, or a pharmaceutically acceptable salt, solvate, or co-crystal thereof to the identified subject.

Provided herein are methods of treating a subject in need thereof, that include: administering a treatment comprising a therapeutically effective amount of a compound for Formula I or a pharmaceutically acceptable salt, solvate, or co-crystal thereof to a subject identified as having resistance to an anti-TNFα agent.

Provided herein are methods of selecting a treatment for a subject in need thereof, that include: (a) identifying a subject having resistance to an anti-TNFα agent; and (b) selecting for the identified subject a treatment comprising a therapeutically effective amount of a compound for Formula I or a pharmaceutically acceptable salt, solvate, or co-crystal thereof.

Provided herein are methods of selecting a treatment for a subject in need thereof, that include selecting a treatment comprising a therapeutically effective amount of a compound for Formula I or a pharmaceutically acceptable salt, solvate, or co-crystal thereof for a subject identified as having resistance to an anti-TNFα agent.

In some embodiments of any of the methods described herein, the treatment further includes a therapeutically effective amount of an anti-TNFα agent, in addition to the NLRP3 antagonist.

This disclosure also features compositions as well as other methods of using and making the same.

An "antagonist" of NLRP3 includes compounds that inhibit the ability of NLRP3 to induce the production of IL-1β and/or IL-18 by directly binding to NLRP3, or by inactivating, destabilizing, altering distribution, of NLRP3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3, as well as in vivo methods.

In a further aspect, methods of treatment of a disease in which NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP3, or a pharmaceutically acceptable salt and/or hydrate and/or cocrystal thereof;) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington; The Science and Practice of Pharmacy,* 21*st ed.*; Lippincott Williams & Wilkins: Philadelphia, PA, 2005; *Handbook of Pharmaceutical Excipients, 6th ed.*; Rowe et al, Eds.; The Pharmaceutical Press and the American Pharmaceutical Association: 2009; *Handbook of Pharmaceutical Additives,* 3*rd ed.*; Ash and Ash Eds.; Gower Publishing Company: 2007; *Pharmaceutical Preformulation and Formulation,* 2*nd ed.*; Gibson Ed.; CRC Press LLC: Boca Raton, FL, 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, A-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat", "treating", and "treatment", in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

As used herein, the term "prevent", "preventing" or "prevention" in connection to a disease or disorder refers to the prophylactic treatment of a subject who is at risk of developing a condition (e.g., specific disease or disorder or clinical symptom thereof) resulting in a decrease in the probability that the subject will develop the condition.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclic rings include five-membered, six-membered, and seven-membered heterocyclic rings.

The term "cycloalkyl" as used herein includes an non-aromatic cyclic, bicylic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an nonaromatic 5-8 membered monocyclic, 8-12 membered bicyclic, or 11-14 membered tricyclic ring, fused, or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons. Examples include phenyl and naphthyl.

The term "arylene" is intended to mean a aromatic ring diradical containing 6 to 10 ring carbons. Examples include phenyl and naphthyl.

The term "heteroaryl" is intended to mean an aromatic ring system radical containing 5 to 14 aromatic ring atoms that may be a single ring, two fused rings or three fused rings wherein at least one aromatic ring atom is a heteroatom selected from, but not limited to, the group consisting of O, S and N. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "heteroarylene" is intended to mean a aromatic ring system diradical containing 5 to 14 aromatic ring atoms that may be a single ring, two fused rings or three fused rings wherein at least one aromatic ring atom is a heteroatom selected from, but not limited to, the group consisting of O, S and N. Examples include furanylene, thienylene, pyrrolylene, imidazolylene, oxazolylene, thiazolylene, isoxazolylene, pyrazolylene, isothiazolylene, oxadiazolylene, triazolylene, thiadiazolylene, pyridinylene, pyrazinylene, pyrimidinylene, pyridazinylene, triazinylene and the like. Examples also include carbazolylene, quinolizinylene, quinolinylene, isoquinolinylene, cinnolinylene, phthalazinylene, quinazolinylene, quinoxalinylene, triazinylene, indolylene, isoindolylene, indazolylene, indolizinylene, purinylene, naphthyridinylene, pteridinylene, carbazolylene, acridinylene. phenazinylene, phenothiazinylene, phenoxazinylene, benzoxazolylene, benzothiazolylene, 1H-benzimidazolylene, imidazopyridinylene, benzothienylene, benzofuranylene, isobenzofuranylene and the like.

The term "hydroxy" refers to an OH group.

The term "amino" refers to an $NH_2$ group.

The term "oxo" refers to O. By way of example, substitution of a $CH_2$ a group with oxo gives a C=O group.

As used herein, the terms "the ring A" or "A" are used interchangeably to denote

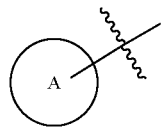

in formula AA, wherein the bond that is shown as being broken by the wavy line / connects A to the X moiety of Formula AA.

As used herein, the terms "the ring B" or "B" are used interchangeably to denote

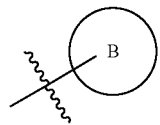

in formula AA wherein the bond that is shown as being broken by the wavy line / connects B to the ring C of Formula AA.

As used herein, the terms "the ring C" or "C" are used interchangeably to denote

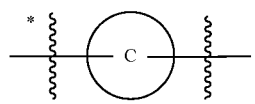

in formula AA wherein the bond that (i) is shown as being broken by the wavy line / and (ii) is spatially closest to the asterisk connects C to the X group of Formula AA; and the bond that (i) is shown as being broken by the wavy line / and (ii) is spatially furthest from the asterisk connects C to the ring B of Formula AA.

As used herein, the term "the optionally substituted ring A" is used to denote

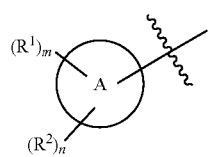

in formula AA, wherein the bond that is shown as being broken by the wavy line / connects A to the X moiety Formula AA.

As used herein, the term "the substituted ring B" is used to denote

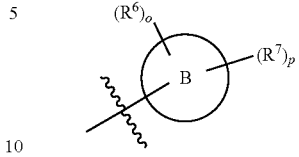

in formula AA, wherein the bond that is shown as being broken by the wavy line / connects B to the ring C of Formula AA.

As used herein, the terms "the optionally substituted ring C" is used to denote

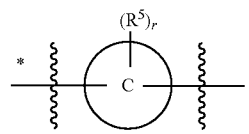

in formula AA wherein the bond that (i) is shown as being broken by the wavy line / and (ii) is spatially closest to the asterisk connects C to the X group of Formula AA; and the bond that (i) is shown as being broken by the wavy line / and (ii) is spatially furthest from the asterisk connects C to the B group of Formula AA.

As used herein, the recitation "$S(O_2)$", alone or as part of a larger recitation, refers to the group

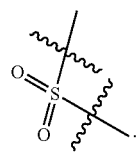 [SMILES: *S(*)(=O)=O]

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The scope of the compounds disclosed herein includes tautomeric form of the compounds. Thus, by way of example, a compound that is represented as containing the moiety

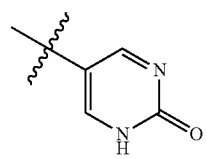 [SMILES: *c1cnc(=O)[nH]c1]

is also intended to include the tautomeric form containing the moiety

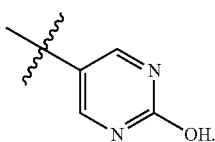 [SMILES: *c1cnc(O)nc1]

Non-limiting exemplified compounds of the formulae described herein may include one or more stereogenic atoms (e.g., carbon or sulfur). This disclosure provides examples of stereoisomer mixtures (e.g., racemic mixture of enantiomers; mixture of diastereomers). This disclosure may also describe and exemplify methods for separating individual components of said stereoisomer mixtures (e.g., resolving the enantiomers of a racemic mixture). In cases of compounds containing a stereogenic atom sulfur, resolved enantiomers are graphically depicted using one of the two following formats: formulas A/B (hashed and solid wedge three-dimensional representation); and formula C ("flat structures with *-labelled stereogenic atom (e.g., carbon or sulfur)).

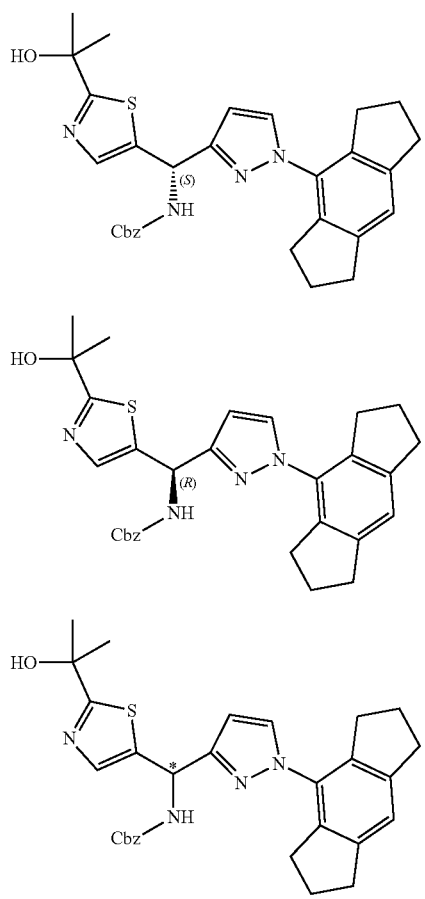

Formula A

Formula B

Formula C

In reaction schemes showing resolution of a racemic mixture, Formulas A/B and C are intended only to convey that the constituent enantiomers were resolved in enantiopure pure form (about 98% ee or greater). The schemes that show resolution products using the formula A/B format are not intended to disclose or imply any correlation between absolute configuration and order of elution. Some of the compounds shown in the tables below are graphically represented using the formula A/B format.

For clarity, the present invention shall not encompass the following compound:

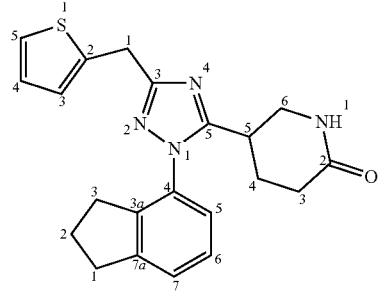 [SMILES: O=C1CCC(c2nc(Cc3cccs3)nn2-c2cccc3c2CCC3)CN1]

or 5-(1-(2,3-dihydro-1H-inden-4-yl)-3-(thiophen-2-ylmethyl)-1H-1,2,4-triazol-5-yl)piperidin-2-one, which is hence disclaimed throughout the invention.

DESCRIPTION OF THE DRAWINGS

FIG. 5: Layout of the microplate to measure the THP-1 activity of the tested compounds.

DETAILED DESCRIPTION

Figure 1:
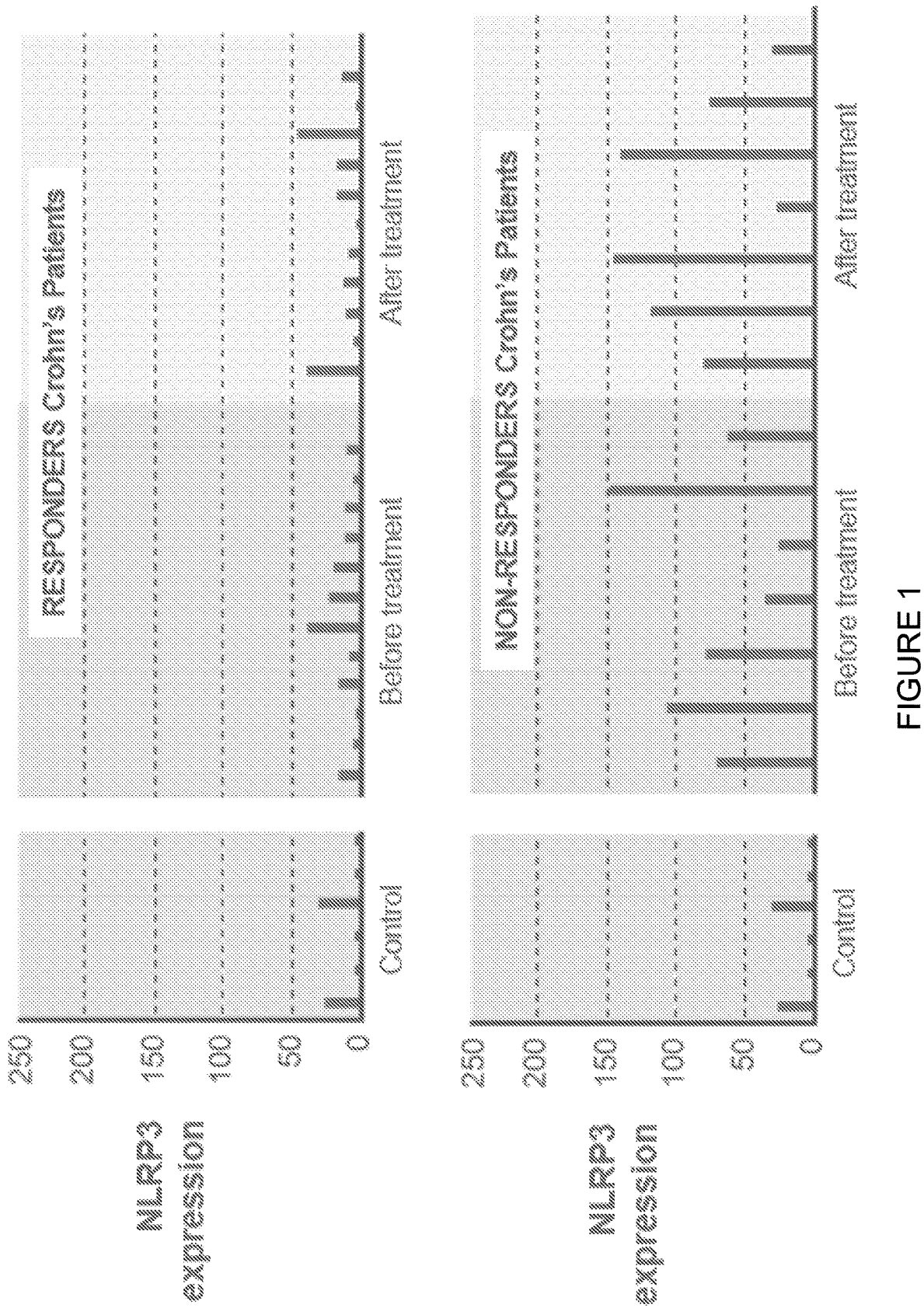
FIG. 1: Expression levels of RNA encoding NLRP3 in Crohn's Disease patients who are responsive and non-responsive to infliximab.

In embodiment one, disclosed herein is a compound of Formula AA

Formula AA

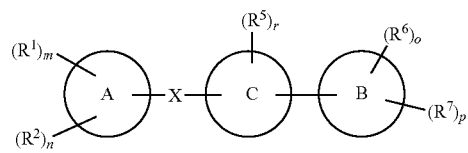

wherein
m=0, 1, or 2;
n=0, 1, or 2;
o=1 or 2;
p=0, 1, 2, or 3;
r=0, 1, 2, or 3;
wherein
A is a 5- to 10-membered monocyclic or bicyclic heteroaryl or a $C_6$-$C_{10}$ monocyclic or bicyclic aryl;
X is selected from the group consisting of —C(O)—, —S(O)$_q$—, —O—, —NR$^{14}$—, —S(O)(NH)—, —S(O)(NR$^{14}$), CHCH$_2$NHCOC$_1$-C$_6$ aryl, and CR$^3$NHR$^4$;

C is a 5- to 10-membered monocyclic or bicyclic heteroarylene or a $C_6$-$C_{10}$ monocyclic or bicyclic arylene;

B is a 5-10 membered monocyclic or bicyclic heteroaryl, or a $C_6$-$C_{10}$ monocyclic or bicyclic aryl;

wherein at least one $R^6$ is ortho to the bond connecting the B ring to the ring C of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

each occurrence of $R^5$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, $OC_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^5$ $C_3$-$C_7$ cycloalkyl or of the $R^5$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

q is 0, 1, or 2;

$R^3$ is selected from H and $C_1$-$C_6$ alkyl;

$R^4$ is selected from H and $COOC_1$-$C_6$ alkyl optionally substituted with one or more $C_6$-$C_{10}$ aryl;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to -seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$;

R$^{10}$ is C$_1$-C$_6$ alkyl;

each of R$^8$ and R$^9$ at each occurrence is independently selected from hydrogen, C$_1$-C$_6$ alkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or R$^8$ and R$^9$ taken together with the nitrogen they are attached to form a 3- to 7-membered ring optionally containing one or more heteroatoms in addition to the nitrogen they are attached to;

R$^{13}$ is C$_1$-C$_6$ alkyl, C$_6$-C$_{10}$ aryl, or 5- to 10-membered heteroaryl;

each of R$^{11}$ and R$^{12}$ at each occurrence is independently selected from hydrogen and C$_1$-C$_6$ alkyl;

wherein the C$_1$-C$_2$ alkylene group is optionally substituted by oxo; and

R$^{14}$ is hydrogen, C$_1$-C$_6$ alkyl, 5- to 10-membered monocyclic or bicyclic heteroaryl or C$_6$-C$_{10}$ monocyclic or bicyclic aryl, wherein each C$_1$-C$_6$ alkyl, aryl or heteroaryl is optionally independently substituted with 1 or 2 R$^6$;

with the proviso that a compound of Formula AA is not 5-(1-(2,3-dihydro-1H-inden-4-yl)-3-(thiophen-2-ylmethyl)-1H-1,2,4-triazol-5-yl)piperidin-2-one;

or a pharmaceutically acceptable salt thereof.

In another embodiment the compound of Formula AA is

Formula AA

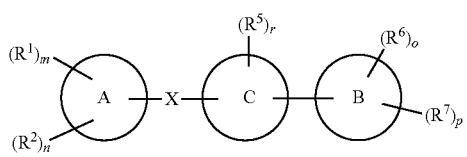

wherein
m=0, 1, or 2;
n=0, 1, or 2;
o=1 or 2;
p=0, 1, 2, or 3;
r=0, 1, 2, or 3;
wherein A is a 5- to 6-membered monocyclic heteroaryl optionally substituted with 1 or 2 R$^1$ and optionally substituted with 1 or 2 R$^2$;
X is selected from the group consisting of —C(O)—, —S(O)$_q$—, —O—, —NR$^{14}$—, —S(O)(NH)—, —S(O)(NR$^{14}$), CHCH$_2$NHCOC$_1$-C$_6$ aryl, and CR$^3$NHR$^4$;

ring C is a 5- to 6-membered monocyclic heteroarylene; wherein ring B is

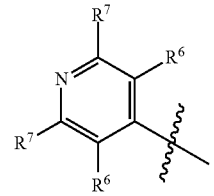

substituted with 1 or 2 R$^6$ and substituted with 1 or 2 R$^7$; or wherein B is phenyl substituted with 1 or 2 R$^6$ and optionally substituted with 1, 2, or 3 R$^7$, with the proviso that the substitution on a ring B contains at least one annulated cyclopentane ring;
wherein
at least one R$^6$ is ortho to the bond connecting the B ring to the C ring of Formula AA;
and wherein the remaining variables are as defined in embodiment 1, with the proviso that a compound of Formula AA is not 5-(1-(2,3-dihydro-1H-inden-4-yl)-3-(thiophen-2-ylmethyl)-1H-1,2,4-triazol-5-yl)piperidin-2-one;
or a pharmaceutically acceptable salt thereof.

In some embodiments the variables shown in any of the formulae herein are as follows:

The Variables m and n
In some embodiments m=0, 1, or 2. In some embodiments m=0 or 1. In some embodiments m=1 or 2. In some embodiments m=0 or 2. In some embodiments m=0. In some embodiments m=1. In some embodiments m=2. In some embodiments n=0, 1, or 2. In some embodiments n=0 or 1. In some embodiments n=1 or 2. In some embodiments n=0 or 2. In some embodiments n=0. In some embodiments n=1. In some embodiments n=2. In some embodiments, m=0 and n=0. In some embodiments, m=1 and n=0. In some embodiments, m=1 and n=1.

The Variable r
In some embodiments r=0, 1, 2, or 3. In some embodiments r=0, 1, or 2. In some embodiments r=0, 1, or 3. In some embodiments r=0, 2, or 3. In some embodiments r=1, 2, or 3. In some embodiments r=0 or 1. In some embodiments r=0 or 2. In some embodiments r=0 or 3. In some embodiments r=1 or 2. In some embodiments r=1 or 3. In some embodiments r=2 or 3. In some embodiments r=0. In some embodiments r=1. In some embodiments r=2. In some embodiments r=3.

The Ring A and Substitutions on the Ring A
In some embodiments, A is a 5- to 10-membered (e.g., 5- to 6-membered) monocyclic or bicyclic heteroaryl or a C$_6$-C$_{10}$ (e.g., C$_6$) monocyclic or bicyclic aryl, such as phenyl.

In some embodiments, A is a 5- to 10-membered (e.g., 5- to 6-membered) monocyclic or bicyclic heteroaryl. In some embodiments, A is a 5- to 6-membered monocyclic heteroaryl optionally substituted with 1 or 2 R$^1$ and optionally substituted with 1 or 2 R$^2$. In some embodiments, A is a 5-membered heteroaryl containing a sulfur and optionally one or more nitrogens. In some embodiments, A is a C$_6$-C$_{10}$ monocyclic or bicyclic aryl. In some embodiments, A is phenyl optionally substituted with 1 or 2 R$^1$ and optionally substituted with 1 or 2 R$^2$. In some embodiments, A is naphthyl optionally substituted with 1 or 2 R$^1$ and optionally substituted with 1 or 2 R$^2$. In some embodiments, A is furanyl optionally substituted with 1 or 2 R¹ and optionally substituted with 1 R². In some embodiments, A is furanyl optionally substituted with 1 R¹ and optionally substituted with 1 or 2 R². In some embodiments, A is thiophenyl optionally substituted with 1 or 2 R¹ and optionally substituted with 1 or 2 R². In some embodiments, A is oxazolyl optionally substituted with 1 or 2 R¹ and optionally substituted with 1 or 2 R². In some embodiments, A is thiazolyl optionally substituted with 1 or 2 R¹ and optionally substituted with 1 or 2 R². In some embodiments, A is oxazolyl optionally substituted with 2 R¹ or optionally substituted with 2 R². In some embodiments, A is thiazolyl optionally substituted with 2 R¹ or optionally substituted with 2 R². In some embodiments, A is pyrazolyl optionally substituted with 1 or 2 R¹ and optionally substituted with 1 or 2 R². In some embodiments, A is pyrazolyl optionally substituted with 1 R¹ and optionally substituted with 1 or 2 R². In some embodiments, A is pyrazolyl optionally substituted with 1 or 2 R¹ and optionally substituted with 1 R². In some embodiments, A is pyridyl optionally substituted with 1 or 2 R¹ and optionally substituted with 1 or 2 R². In some embodiments, A is indazolyl optionally substituted with 1 or 2 R¹ and optionally substituted with 1 or 2 R². In some embodiments, A is phenyl substituted with 1 R¹ and optionally substituted with 1 R². In some embodiments, A is naphthyl substituted with 1 R¹ and optionally substituted with 1 R². In some embodiments, A is furanyl substituted with 1 R¹ and optionally substituted with 1 R². In some embodiments, A is thiophenyl substituted with 1 R¹ and optionally substituted with 1 R². In some embodiments, A is oxazolyl substituted with 1 R¹ and optionally substituted with 1 R². In some embodiments, A is thiazolyl substituted with 1 R¹ and optionally substituted with 1 R². In some embodiments, A is pyrazolyl substituted with 1 R¹ and optionally substituted with 1 R². In some embodiments, A is pyridyl substituted with 1 R¹ and optionally substituted with 1 R². In some embodiments, A is indazolyl optionally substituted with 1 R¹ and optionally substituted with 1 R². In some embodiments, A is phenyl substituted with 1 R¹ and substituted with 1 R². In some embodiments, A is furanyl substituted with 1 R¹ and substituted with 1 R². In some embodiments, A is thiophenyl substituted with 1 R¹ and substituted with 1 R². In some embodiments, A is oxazolyl substituted with 1 R¹ and substituted with 1 R². In some embodiments, A is thiazolyl substituted with 1 R¹ and substituted with 1 R². In some embodiments, A is pyrazolyl substituted with 1 R¹ and substituted with 1 R². In some embodiments, A is pyridyl substituted with 1 R¹ and substituted with 1 R². In some embodiments, A is phenyl, m is 0 or 1, and n is 0, 1, or 2. In some embodiments, A is furanyl, m is 0 or 1, and n is 0, 1, or 2. In some embodiments, A is thiophenyl, m is 0 or 1, and n is 0, 1, or 2. In some embodiments, A is oxazolyl, m is 0 or 1, and n is 0, 1, or 2. In some embodiments, A is thiazolyl, m is 0 or 1, and n is 0, 1, or 2. In some embodiments, A is pyrazolyl, m is 0 or 1, and n is 0, 1, or 2. In some embodiments, A is pyridyl, m is 0 or 1, and n is 0, 1, or 2. In some embodiments, A is indazolyl, m is 0 or 1, and n is 0, 1, or 2. In some embodiments, A is phenyl, m is 0, and n is 0 or 1. In some embodiments, A is furanyl, m is 0, and n is 0 or 1. In some embodiments, A is thiophenyl, m is 0, and n is 0 or 1. In some embodiments, A is oxazolyl, m is 0, and n is 0 or 1. In some embodiments, A is thiazolyl, m is 0, and n is 0 or 1. In some embodiments, A is pyrazolyl, m is 0, and n is 0 or 1. In some embodiments, A is pyridyl, m is 0, and n is 0 or 1. In some embodiments, A is one of the rings disclosed hereinbelow optionally substituted as disclosed hereinbelow, wherein in each case the bond that is shown as being broken by the wavy line / connects A to the X moiety of Formula AA. In some embodiments, the optionally substituted ring A

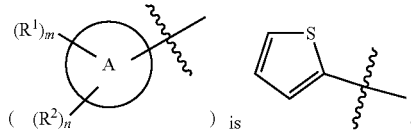

is

In some embodiments, the optionally substituted ring A is

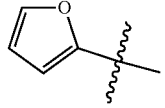

In some embodiments, the optionally substituted ring A is

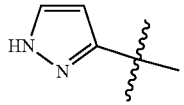

In some embodiments, the optionally substituted ring A is

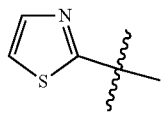

In some embodiments, the optionally substituted ring A is

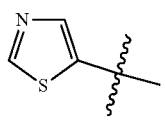

In some embodiments, the optionally substituted ring A is

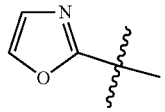

In some embodiments, the optionally substituted ring A is

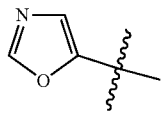

In some embodiments, the optionally substituted ring A is

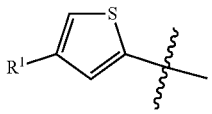

In some embodiments, the optionally substituted ring A is

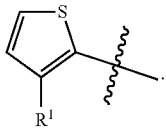

In some embodiments, the optionally substituted ring A is

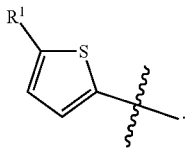

In some embodiments, the optionally substituted ring A is

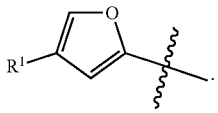

In some embodiments, the optionally substituted ring A is

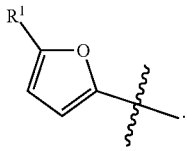

In some embodiments, the optionally substituted ring A is

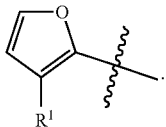

In some embodiments, the optionally substituted ring A is

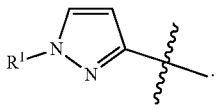

In some embodiments, the optionally substituted ring A is

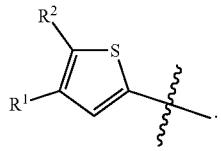

In some embodiments, the optionally substituted ring A is

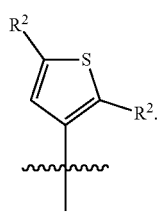

In some embodiments, the optionally substituted ring A is

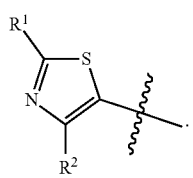

In some embodiments, the optionally substituted ring A is

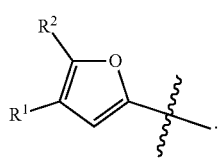

In some embodiments, the optionally substituted ring A is

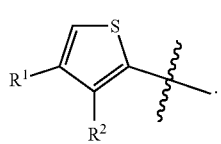

In some embodiments, the optionally substituted ring A is

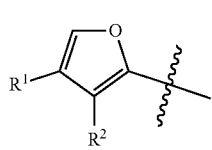

In some embodiments, the optionally substituted ring A is

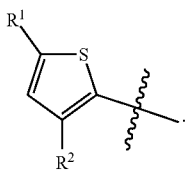

In some embodiments, the optionally substituted ring A is

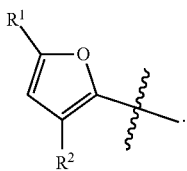

In some embodiments, the optionally substituted ring A is

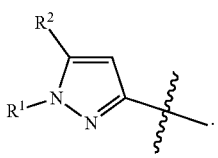

In some embodiments, the optionally substituted ring A is

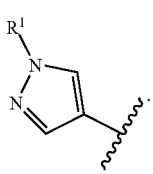

In some embodiments, the optionally substituted ring A is

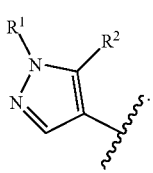

In some embodiments, the optionally substituted ring A is

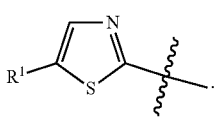

In some embodiments, the optionally substituted ring A is

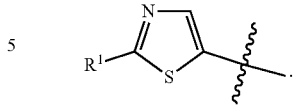

In some embodiments, the optionally substituted ring A is

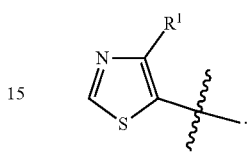

In some embodiments, the optionally substituted ring A is

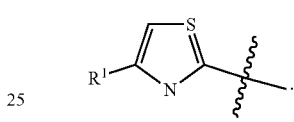

In some embodiments, the optionally substituted ring A is

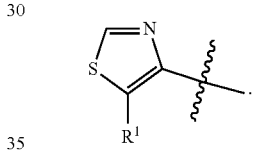

In some embodiments, the optionally substituted ring A is

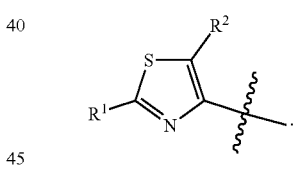

In some embodiments, the optionally substituted ring A is

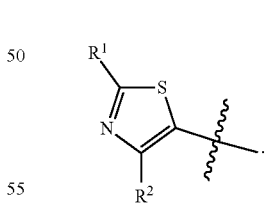

In some embodiments, the optionally substituted ring A is

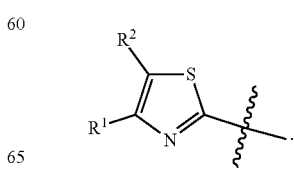

In some embodiments, the optionally substituted ring A is

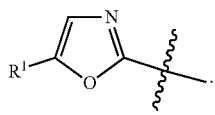

In some embodiments, the optionally substituted ring A is

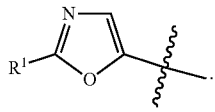

In some embodiments, the optionally substituted ring A is

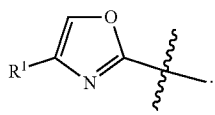

In some embodiments, the optionally substituted ring A is

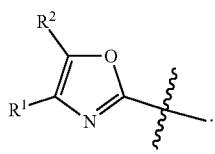

In some embodiments, the optionally substituted ring A is

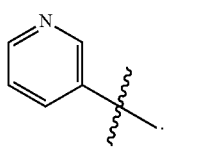 [SMILES: *c1cccnc1]

In some embodiments, the optionally substituted ring A is

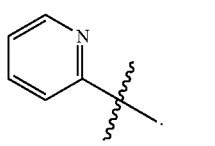

In some embodiments, the optionally substituted ring A is

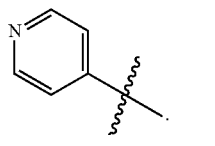 [SMILES: *c1ccncc1]

In some embodiments, the optionally substituted ring A is

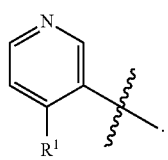

In some embodiments, the optionally substituted ring A is

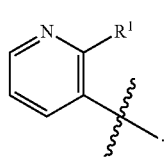

In some embodiments, the optionally substituted ring A is

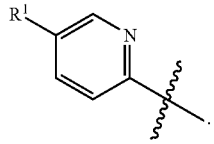

In some embodiments, the optionally substituted ring A is

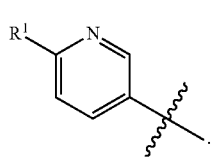

In some embodiments, the optionally substituted ring A is

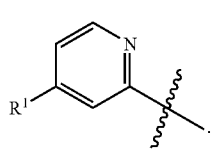

In some embodiments, the optionally substituted ring A is

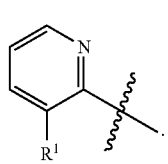

In some embodiments, the optionally substituted ring A is

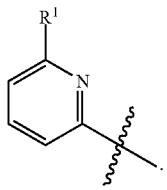

In some embodiments, the optionally substituted ring A is

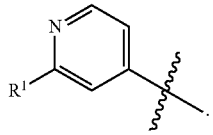

In some embodiments, the optionally substituted ring A is

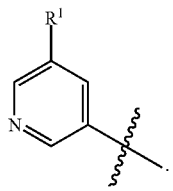

In some embodiments, the optionally substituted ring A is

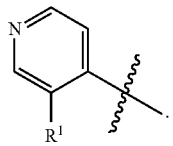

In some embodiments, the optionally substituted ring A is

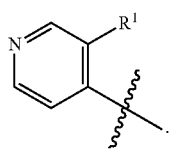

In some embodiments, the optionally substituted ring A is

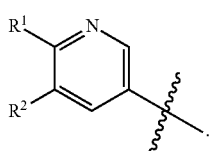

In some embodiments, the optionally substituted ring A is

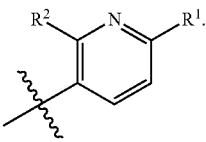

In some embodiments, the optionally substituted ring A is

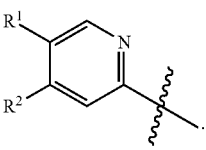

In some embodiments, the optionally substituted ring A is

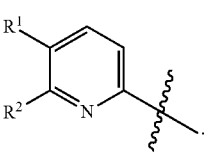

In some embodiments, the optionally substituted ring A is

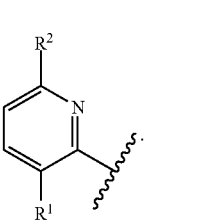

In some embodiments, the optionally substituted ring A is

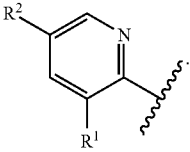

In some embodiments, the optionally substituted ring A is

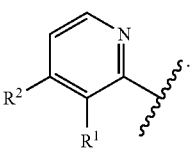

In some embodiments, the optionally substituted ring A is

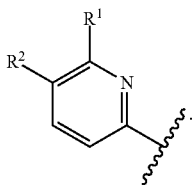

In some embodiments, the optionally substituted ring A is

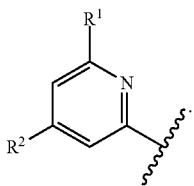

In some embodiments, the optionally substituted ring A is

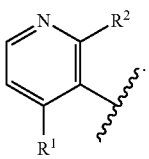

In some embodiments, the optionally substituted ring A is

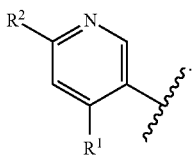

In some embodiments, the optionally substituted ring A is

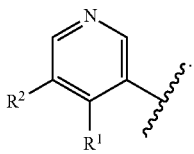

In some embodiments, the optionally substituted ring A is

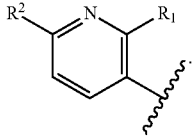

In some embodiments, the optionally substituted ring A is

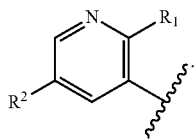

In some embodiments, the optionally substituted ring A is

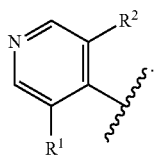

In some embodiments, the optionally substituted ring A is

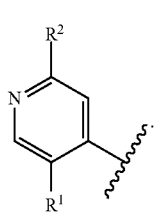

In some embodiments, the optionally substituted ring A is

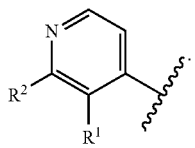

In some embodiments, the optionally substituted ring A is

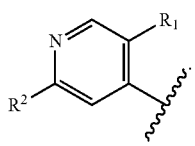

In some embodiments, the optionally substituted ring A is

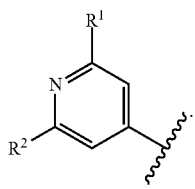

In some embodiments, the optionally substituted ring A is

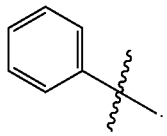

In some embodiments, the optionally substituted ring A is

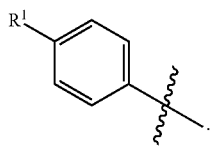

In some embodiments, the optionally substituted ring A is

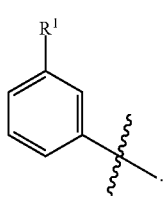

In some embodiments, the optionally substituted ring A is

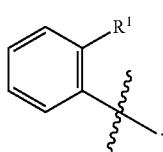

In some embodiments, the optionally substituted ring A is

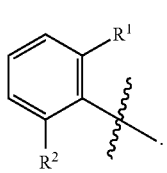

In some embodiments, the optionally substituted ring A is

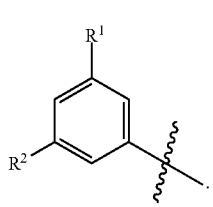

In some embodiments, the optionally substituted ring A is

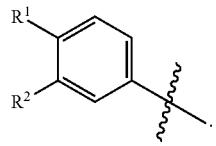

In some embodiments, the optionally substituted ring A is

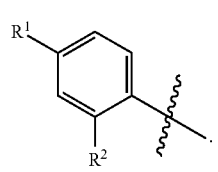

In some embodiments, the optionally substituted ring A is

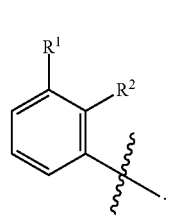

In some embodiments, the optionally substituted ring A is

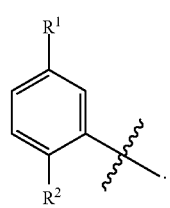

In some embodiments, the optionally substituted ring A is

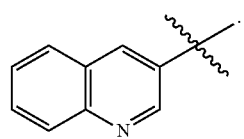 [SMILES: *c1cnc2ccccc2c1]

In some embodiments, the optionally substituted ring A is

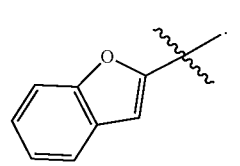 [SMILES: *c1cc2ccccc2o1]

In some embodiments, the optionally substituted ring A is

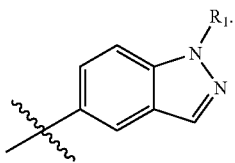

In some embodiments, the optionally substituted ring A is

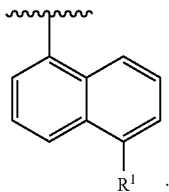

The Groups $R^1$ and $R^2$

In any of the formulae disclosed herein, unless otherwise specified, the definitions of $R^1$ and $R^2$ encompass situations wherein:
(a) each occurrence of $R^1$ and each occurrence of $R^2$ is a monovalent substituent as described elsewhere herein;
(b) when m=n, and each pair of $R^1$ and $R^2$ are on adjacent carbon atoms, each pair of $R^1$ and $R^2$ taken together with atom to which each is attached forms an independently selected carbocyclic or heterocyclic ring as described elsewhere herein; and
(c) one or more pairs of $R^1$ and $R^2$ on adjacent carbon atoms, taken together with the atom to which each is attached, form one or more independently selected carbocyclic or heterocyclic ring as described elsewhere herein; and each remaining occurrences of $R^1$ and $R^2$ (inclusive of pair(s) of $R^1$ and $R^2$ on adjacent atoms) is independently a monovalent substituent as described herein.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl);
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, and 5- to 10-membered heteroaryl are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$;

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$;
In some embodiments,
$R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, OCOC$_1$-C$_6$ alkyl, OCOC$_6$-C$_{10}$ aryl, OCO (5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, S(O$_2$)NR$^{11}$R$^{12}$, S(O)C$_1$-C$_6$ alkyl, C$_3$-C$_7$ cycloalkyl and 3- to 7-membered heterocycloalkyl, wherein the C$_3$-C$_7$ cycloalkyl, C$_1$-C$_6$ haloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein each C$_1$-C$_6$ alkyl substituent and each C$_1$-C$_6$ alkoxy substituent of the R$^1$ or R$^2$ C$_3$-C$_7$ cycloalkyl or of the R$^1$ or R$^2$ 3- to 7-membered heterocycloalkyl is further optionally independently substituted with one to three hydroxy, halo, NR$^8$R$^9$, or oxo;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^1$ and R$^2$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments,

R$^1$ and R$^2$ are each independently selected from C$_1$-C$_6$ alkyl, halo, CN, NO$_2$, COC$_1$-C$_6$ alkyl, CO—C$_6$-C$_{10}$ aryl, CO(5- to 10-membered heteroaryl), CO$_2$C$_1$-C$_6$ alkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)NR$^{11}$R$^{12}$, S(O$_2$)C$_1$-C$_6$ alkyl, S(O)C$_1$-C$_6$ alkyl, C$_3$-C$_7$ cycloalkyl and 3- to 7-membered heterocycloalkyl, wherein the C$_1$-C$_6$ alkyl, C$_1$-C$_6$ haloalkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein each C$_1$-C$_6$ alkyl substituent and each C$_1$-C$_6$ alkoxy substituent of the R$^1$ or R$^2$ C$_3$-C$_7$ cycloalkyl or of the R$^1$ or R$^2$ 3- to 7-membered heterocycloalkyl is further optionally independently substituted with one to three hydroxy, halo, or oxo;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^1$ and R$^2$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, NO$_2$, COC$_1$-C$_6$ alkyl, CO—C$_6$-C$_{10}$ aryl, CO(5- to 10-membered heteroaryl), CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, S(O$_2$)NR$^{11}$R$^{12}$, S(O$_2$)C$_1$-C$_6$ alkyl, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;
wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl.
In some embodiments,
$R^1$ and $R^2$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO—C$_6$-C$_{10}$ aryl, CO(5- to 10-membered heteroaryl), CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, S(O$_2$)NR$^{11}$R$^{12}$, S(O$_2$)C$_1$-C$_6$ alkyl, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl and 3- to 7-membered heterocycloalkyl are each unsubstituted;
or at least one pair of $R^1$ and $R^2$ on adjacent atoms, taken together with the atoms connecting them, independently form at least one C$_4$-C$_8$ carbocyclic ring or at least one 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$;
In some embodiments,
$R^1$ and $R^2$ are each independently selected from C$_1$-C$_6$ alkyl, halo, CN, COC$_1$-C$_6$ alkyl, CO$_2$C$_1$-C$_6$ alkyl, C$_6$-C$_{10}$ aryl, S(O)C$_1$-C$_6$ alkyl, 5- to 10-membered heteroaryl, and 3- to 7-membered heterocycloalkyl,
wherein the C$_1$-C$_6$ alkyl and 3- to 7-membered heterocycloalkyl is optionally substituted with one or more substituents each independently selected from hydroxy and oxo.

In some embodiments of any of the formulae herein, each of $R^1$ and $R^2$ is independently selected from the group consisting of C$_1$-C$_6$ alkyl optionally substituted with one or more hydroxy, halo, oxo, or C$_1$-C$_6$ alkoxy; C$_3$-C$_7$ cycloalkyl optionally substituted with one or more hydroxy, halo, oxo, C$_1$-C$_6$ alkoxy, or C$_1$-C$_6$ alkyl; wherein the C$_1$-C$_6$ alkoxy or C$_1$-C$_6$ alkyl is further optionally substituted with one to three hydroxy, halo, NR$^8$R$^9$, or oxo; 3- to 7-membered heterocycloalkyl optionally substituted with one or more hydroxy, halo, oxo, or C$_1$-C$_6$ alkyl wherein the C$_1$-C$_6$ alkoxy or C$_1$-C$_6$ alkyl is further optionally substituted with one to three hydroxy, halo, or oxo; C$_1$-C$_6$ haloalkyl; C$_1$-C$_6$ alkoxy; C$_1$-C$_6$ haloalkoxy; halo; CN; CO—C$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; S(O$_2$)NR$^{11}$R$^{12}$; S(O)C$_1$-C$_6$ alkyl; and S(O$_2$)C$_1$-C$_6$ alkyl.

In some embodiments of any of the formulae herein, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; ethoxycarbonyl; 2-methoxy-2-propyl; fluoro; chloro; phenyl; pyridyl; pyrazolyl; S(O$_2$)CH$_3$; and S(O$_2$)NR$^{11}$R$^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; COCH$_3$; COPh; 2-methoxy-2-propyl; ethox carbonyl; S(O$_2$)CH$_3$; and S(O$_2$)NR$^{11}$R$^{12}$.

In some embodiments, $R^1$ is selected from the group consisting of 2-hydroxy-2-propyl, ethoxy carbonyl, phenyl, methyl, ethyl, and isopropyl.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxy ethyl; 2-hydroxy ethyl; 1-hydroxy-2-propyl; 1-hydroxy-1-cyclopropyl; COCH$_3$; COPh; 2-methoxy-2-propyl; (dimethylamino)methyl; ethoxycarbonyl; S(O$_2$)CH$_3$; and S(O$_2$)NR$^{11}$R$^{12}$.

In some embodiments, $R^2$ is selected from the group consisting of 2-hydroxy-2-propyl, ethoxycarbonyl, phenyl, methyl, ethyl, and isopropyl.

In some embodiments, m=1; n=0; and
$R^1$ is selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO—C$_6$-C$_{10}$ aryl, CO(5- to 10-membered heteroaryl), CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, S(O$_2$)NR$^{11}$R$^{12}$, S(O)C$_1$-C$_6$ alkyl, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-

$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=0; and, $R^1$ is selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

In some embodiments, m=1; n=1; and, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are on adjacent atoms, and taken together with the atoms connecting them, form a $C_4$-$C_8$ carbocyclic ring or a 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_5$ carbocyclic ring or a 5- to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

Particular Embodiments Wherein m=1 and n=0:

In some embodiments, $R^1$ is $C_1$-$C_6$ alkyl optionally substituted with one or more hydroxy. In some embodiments, $R^1$ is 1-hydroxy-2-methylpropan-2-yl. In some embodiments, $R^1$ is 2-hydroxyethyl. In some embodiments, $R^1$ is $C_1$-$C_6$ alkyl. In some embodiments, $R^1$ is methyl. In some embodiments, $R^1$ is isopropyl. In some embodiments, $R^1$ is isopropyl. In some embodiments, $R^1$ is $C_1$-$C_6$ alkyl substituted with hydroxy at the carbon directly connected to ring A. In some embodiments, $R^1$ is 2-hydroxy-2-propyl. In some embodiments, $R^1$ is hydroxymethyl. In some embodiments, $R^1$ is 1-hydroxyethyl. In some embodiments, $R^1$ is 1-hydroxy-2-propyl. In some embodiments, $R^1$ is $C_1$-$C_6$ alkyl substituted with two or more hydroxy groups. In some embodiments, $R^1$ is $C_1$-$C_6$ alkyl substituted with two or more hydroxy groups, wherein one of the two or more hydroxy groups is bonded to the carbon directly connected to ring A. In some embodiments, $R^1$ is 1,2-dihydroxy-prop-2-yl. In some embodiments, $R^1$ is $C_3$-$C_7$ cycloalkyl optionally substituted with one or more hydroxy. In some embodiments, $R^1$ is $C_3$-$C_7$ cycloalkyl. In some embodiments, $R^1$ is $C_3$-$C_7$ cycloalkyl substituted with hydroxy at the carbon directly connected to ring A. In some embodiments, $R^1$ is 1-hydroxy-1-cyclopropyl. In some embodiments, $R^1$ is 1-hydroxy-1-cyclobutyl. In some embodiments, $R^1$ is 1-hydroxy-1-cyclopentyl. In some embodiments, $R^1$ is 1-hydroxy-1-cyclohexyl. In some embodiments, $R^1$ is 3- to 7-membered heterocycloalkyl optionally substituted with one or more hydroxy. In some embodiments, $R^1$ is 3- to 7-membered heterocycloalkyl. In some embodiments, $R^1$ is morpholinyl (e.g., 1-morpholinyl). In some embodiments, $R^1$ is 1,3-dioxolan-2-yl. In some embodiments, $R^1$ is 3- to 7-membered heterocycloalkyl optionally substituted with one or more $C_1$-$C_6$ alkyl. In some embodiments, $R^1$ is 1-methylpyrrolidin-2-yl. In some embodiments, $R^1$ is 3- to 7-membered heterocycloalkyl substituted with hydroxy at the carbon directly connected to ring A. In some embodiments, $R^1$ is $C_1$-$C_6$ alkyl optionally substituted with one or more oxo. In some embodiments, $R^1$ is $COCH_3$. In some embodiments, $R^1$ is $COCH_2CH_3$. In some embodiments, $R^1$ is $C_3$-$C_7$ cycloalkyl optionally substituted with one or more oxo. In some embodiments, $R^1$ is 3- to 7-membered heterocycloalkyl optionally substituted with one or more oxo. In some embodiments, $R^1$ is $C_1$-$C_6$ alkyl optionally substituted with one or more $C_1$-$C_6$ alkoxy. In some embodiments, $R^1$ is 2-methoxy-2-propyl. In some embodiments, $R^1$ is methoxymethyl. In some embodiments, $R^1$ is $C_3$-$C_7$ cycloalkyl optionally substituted with one or more $C_1$-$C_6$ alkoxy. In some embodiments, $R^1$ is 3- to 7-membered heterocycloalkyl optionally substituted with one or more $C_1$-$C_6$ alkoxy. In some embodiments, $R^1$ is $C_1$-$C_6$ alkyl optionally substituted with one or more $NR^8R^9$. In some embodiments, $R^1$ is $C_1$-$C_6$ alkyl substituted with $NR^8R^9$ at the carbon directly connected to ring A. In some embodiments, $R^1$ is (methylamino)methyl. In some embodiments, $R^1$ is (dimethylamino)methyl. In some embodiments, $R^1$ is aminomethyl. In some embodiments, $R^1$ is N-methylacetamidomethyl. In some embodiments, $R^1$ is 1-(dimethylamino)eth-1-yl. In some embodiments, $R^1$ is 2-(dimethylamino)prop-2-yl. In some embodiments, $R^1$ is (2-methoxy-eth-1-yl)(methyl)aminomethyl. In some embodiments, $R^1$ is (methyl)(acetyl)aminomethyl. In some embodiments, $R^1$ is (methyl)(cyclopropylmethyl)aminomethyl. In some embodiments, $R^1$ is (methyl)(2,2-difluoroeth-1-yl)aminomethyl. In some embodiments, $R^1$ is $C_3$-$C_7$ cycloalkyl optionally substituted with one or more $NR^8R^9$. In some embodiments, $R^1$ is 3- to 7-membered heterocycloalkyl optionally substituted with one or more $NR^8R^9$. In some embodiments, $R^1$ is $C_1$-$C_6$ haloalkyl optionally substituted with one or more hydroxy. In some embodiments, $R^1$ is $C_1$-$C_6$ alkoxy. In some embodiments, $R^1$ is $C_1$-$C_6$ haloalkoxy. In some embodiments, $R^1$ is $C_1$-$C_6$ alkyl optionally substituted with 3- to 7-membered heterocycloalkyl, wherein the 3- to 7-membered heterocycloalkyl is further optionally substituted as defined elsewhere herein. In some embodiments, $R^1$ is pyrrolidinylmethyl (e.g., pyrrolidin-1-ylmethyl). In some embodiments, $R^1$ is optionally substituted pyrrolidinylmethyl (e.g., 3,3-difluoropyrrolidin-1-ylmethyl). In some embodiments, $R^1$ is azetidinylmethyl (e.g., azetidin-1-ylmethyl). In some embodiments, $R^1$ is optionally substituted azetidinylmethyl (e.g., 3-methoxyazetidin-1-ylmethyl). In some embodiments, $R^1$ is morpholinylmethyl (e.g., morpholin-4-ylmethyl). In some embodiments, $R^1$ is halo. In some embodiments, $R^1$ is fluoro. In some embodiments, $R^1$ is chloro. In some embodiments, $R^1$ is CN. In some embodiments, $R^1$ is $NO_2$. In some embodiments, $R^1$ is $COC_1$-$C_6$ alkyl. In some embodiments, $R^1$ is CO—$C_6$-$C_{10}$ aryl. In some embodiments, $R^1$ is CO(5- to 10-membered heteroaryl). In some embodiments, $R^1$ is $CO_2C_1$-$C_6$ alkyl. In some embodiments, $R^1$ is $CO_2C_3$-$C_8$ cycloalkyl. In some embodiments, $R^1$ is $OCOC_1$-$C_6$ alkyl. In some embodiments, $R^1$ is $OCOC_6$-$C_{10}$ aryl. In some embodiments, $R^1$ is OCO(5- to 10-membered heteroaryl). In some embodiments, $R^1$ is OCO(3- to 7-membered heterocycloalkyl). In some embodiments, $R^1$ is $C_6$-$C_{10}$ aryl. In some embodiments, $R^1$ is phenyl. In some embodiments, $R^1$ is 5- to 10-membered heteroaryl. In some embodiments, $R^1$ is pyridyl (e.g., 4-pyridyl). In some embodiments, $R^1$ is pyrazolyl (e.g., 1-pyrazolyl). In some embodiments, $R^1$ is $NH_2$. In some embodiments, $R^1$ is $NHC_1$-$C_6$ alkyl. In some embodiments, $R^1$ is $N(C_1$-$C_6$ alkyl$)_2$. In some embodiments, $R^1$ is $CONR^8R^9$. In some embodiments, $R^1$ is $SF_5$. In some embodiments, $R^1$ is $SC_1$-$C_6$ alkyl, In some embodiments, $R^1$ is $S(O_2)C_1$-$C_6$ alkyl. In some embodiments, $R^1$ is $S(O_2)CH_3$. In some embodiments, $R^1$ is $S(O_2)NR^{11}R^{12}$. In some embodiments, $R^1$ is $S(O_2)N(CH_3)_2$. In some embodiments, $R^1$ is $S(O)C_1$-$C_6$ alkyl. In some embodiments, $R^1$ is $S(O)CH_3$. In some embodiments, $R^1$ is attached to a carbon of an aryl ring A. In some embodiments, $R^1$ is attached to a carbon of a heteroaryl ring A. In some embodiments, $R^1$ is attached to a nitrogen of a heteroaryl ring A.

Particular Embodiments Wherein m=1 and n=1:

In some embodiments, $R^1$ is $C_1$-$C_6$ alkyl optionally substituted with one or more hydroxy, and $R^2$ is $C_1$-$C_6$ alkyl optionally substituted with one or more hydroxy. In some embodiments, $R^1$ is 1-hydroxy-2-methylpropan-2-yl, and $R^2$ is methyl. In some embodiments, $R^1$ is 2-hydroxy-2-propyl and $R^2$ is methyl. In some embodiments, $R^1$ is 2-hydroxy-2-propyl and $R^2$ is isopropyl. In some embodiments, $R^1$ is 2-hydroxy-2-propyl and $R^2$ is 2-hydroxy-2-propyl. In some embodiments, $R^1$ is 2-hydroxy-2-propyl and $R^2$ is 1-hydroxyethyl. In some embodiments, $R^1$ is hydroxymethyl and $R^2$ is methyl. In some embodiments, $R^1$ is 1-hydroxyethyl and $R^2$ is methyl. In some embodiments, $R^1$ is 2-hydroxyethyl and $R^2$ is methyl. In some embodiments, $R^1$ is 1-hydroxy-2-propyl and $R^2$ is methyl. In some embodiments, $R^1$ is $C_1$-$C_6$ alkyl optionally substituted with one or more hydroxy, and $R^2$ is $C_6$-$C_{10}$ aryl. In some embodiments, $R^1$ is 2-hydroxy-2-propyl and $R^2$ is phenyl. In some embodiments, $R^1$ is $C_1$-$C_6$ alkyl optionally substituted with one or more hydroxy, and $R^2$ is 5- to 10-membered heteroaryl. In some embodiments, $R^1$ is 2-hydroxy-2-propyl and $R^2$ is pyridyl. In some embodiments, $R^1$ is 2-hydroxy-2-propyl and $R^2$ is pyrazolyl. In some embodiments, $R^1$ is $C_1$-$C_6$ alkyl optionally substituted with one or more hydroxy, and $R^2$ is $SF_5$. In some embodiments, $R^1$ is $C_1$-$C_6$ alkyl optionally substituted with one or more hydroxy, and $R^2$ is $SC_1$-$C_6$ alkyl, In some embodiments, $R^1$ is $C_1$-$C_6$ alkyl optionally substituted with one or more hydroxy, and $R^2$ is $S(O_2)C_1$-$C_6$ alkyl. In some embodiments, $R^1$ is $C_1$-$C_6$ alkyl optionally substituted with one or more hydroxy, and $R^2$ is $S(O_2)CH_3$. In some embodiments, $R^1$ is $C_1$-$C_6$ alkyl optionally substituted with one or more hydroxy, and $R^2$ is halo. In some embodiments, $R^1$ is 2-hydroxy-2-propyl and $R^2$ is chloro. In some embodiments, $R^1$ is 2-hydroxy-2-propyl and $R^2$ is fluoro. In some embodiments, $R^1$ is $C_3$-$C_7$ cycloalkyl optionally substituted with one or more hydroxy, and $R^2$ is $C_1$-$C_6$ alkyl. In some embodiments, $R^1$ is 1-hydroxy-1-cyclopropyl, and $R^2$ is methyl. In some embodiments, $R^1$ is 1-hydroxy-1-cyclobutyl, and $R^2$ is methyl. In some embodiments, $R^1$ is 1-hydroxy-1-cyclopentyl, and $R^2$ is methyl. In some embodiments, $R^1$ is 1-hydroxy-1-cyclohexyl, and $R^2$ is methyl. In some embodiments, $R^1$ is 3- to 7-membered heterocycloalkyl optionally substituted with one or more hydroxy, and $R^2$ is $C_1$-$C_6$ alkyl. In some embodiments, $R^1$ is morpholinyl, and $R^2$ is methyl. In some embodiments, $R^1$ is 1,3-dioxolan-2-yl, and $R^2$ is methyl. In some embodiments, $R^1$ is 3- to 7-membered heterocycloalkyl optionally substituted with one or more hydroxy, and $R^2$ is halo. In some embodiments, $R^1$ is 1,3-dioxolan-2-yl, and $R^2$ is fluoro. In some embodiments, $R^1$ is 1,3-dioxolan-2-yl, and $R^2$ is chloro. In some embodiments, $R^1$ is $C_1$-$C_6$ alkyl optionally substituted with one or more oxo, and $R^2$ is methyl. In some embodiments, $R^1$ is $COCH_3$, and $R^2$ is methyl. In some embodiments, $R^1$ is $C_1$-$C_6$ alkyl optionally substituted with one or more $C_1$-$C_6$ alkoxy, and $R^2$ is $C_1$-$C_6$ alkyl. In some embodiments, $R^1$ is 2-methoxy-2-propyl, and $R^2$ is methyl. In some embodiments, $R^1$ is $C_1$-$C_6$ alkyl optionally substituted with one or more $NR^8R^9$, and $R^2$ is $C_1$-$C_6$ alkyl. In some embodiments, $R^1$ is (dimethylamino)methyl, and $R^2$ is methyl. In some embodiments, $R^1$ is $C_1$-$C_6$ alkyl optionally substituted with one or more $NR^8R^9$, and $R^2$ is halo. In some embodiments, $R^1$ is (dimethylamino)methyl, and $R^2$ is fluoro. In some embodiments, $R^1$ is (dimethylamino)methyl, and $R^2$ is fluoro. In some embodiments, $R^1$ is (methylamino)methyl, and $R^2$ is fluoro. In some embodiments, $R^1$ is aminomethyl, and $R^2$ is fluoro. In some embodiments, $R^1$ is $C_1$-$C_6$ alkyl, and $R^2$ is $C_1$-$C_6$ alkyl. In some embodiments, $R^1$ is methyl, and $R^2$ is methyl.

In some embodiments, $R^2$ is 1-hydroxy-2-methylpropan-2-yl, and $R^1$ is methyl. In some embodiments, $R^2$ is 2-hydroxy-2-propyl and $R^1$ is methyl. In some embodiments, $R^2$ is 2-hydroxy-2-propyl and $R^1$ is isopropyl. In some embodiments, $R^2$ is 2-hydroxy-2-propyl and $R^1$ is 1-hydroxyethyl. In some embodiments, $R^2$ is hydroxymethyl and $R^1$ is methyl. In some embodiments, $R^2$ is 1-hydroxyethyl and $R^1$ is methyl. In some embodiments, $R^2$ is 2-hydroxyethyl and $R^1$ is methyl. In some embodiments, $R^2$ is 1-hydroxy-2-propyl and $R^1$ is methyl. In some embodiments, $R^2$ is $C_1$-$C_6$ alkyl optionally substituted with one or more hydroxy, and $R^1$ is $C_6$-$C_{10}$ aryl. In some embodiments, $R^2$ is 2-hydroxy-2-propyl and $R^1$ is phenyl. In some embodiments, $R^2$ is $C_1$-$C_6$ alkyl optionally substituted with one or more hydroxy, and $R^1$ is 5- to 10-membered heteroaryl. In some embodiments, $R^2$ is 2-hydroxy-2-propyl and $R^1$ is pyridyl. In some embodiments, $R^2$ is 2-hydroxy-2-propyl and $R^1$ is pyrazolyl. In some embodiments, $R^2$ is $C_1$-$C_6$ alkyl optionally substituted with one or more hydroxy, and $R^1$ is $SF_5$. In some embodiments, $R^2$ is $C_1$-$C_6$ alkyl optionally substituted with one or more hydroxy, and $R^1$ is $SC_1$-$C_6$ alkyl. In some embodiments, $R^2$ is $C_1$-$C_6$ alkyl optionally substituted with one or more hydroxy, and $R^1$ is $S(O_2)C_1$-$C_6$ alkyl. In some embodiments, $R^2$ is $C_1$-$C_6$ alkyl optionally substituted with one or more hydroxy, and $R^1$ is $S(O_2)CH_3$. In some embodiments, $R^2$ is $C_1$-$C_6$ alkyl optionally substituted with one or more hydroxy, and $R^1$ is halo. In some embodiments, $R^2$ is 2-hydroxy-2-propyl and $R^1$ is chloro. In some embodiments, $R^2$ is 2-hydroxy-2-propyl and $R^1$ is fluoro. In some embodiments, $R^2$ is $C_3$-$C_7$ cycloalkyl optionally substituted with one or more hydroxy, and $R^1$ is $C_1$-$C_6$ alkyl. In some embodiments, $R^2$ is 1-hydroxy-1-cyclopropyl, and $R^1$ is methyl. In some embodiments, $R^2$ is 1-hydroxy-1-cyclobutyl, and $R^1$ is methyl. In some embodiments, $R^2$ is 1-hydroxy-1-cyclopentyl, and $R^1$ is methyl. In some embodiments, $R^2$ is 1-hydroxy-1-cyclohexyl, and $R^1$ is methyl. In some embodiments, $R^2$ is 3- to 7-membered heterocycloalkyl optionally substituted with one or more hydroxy, and $R^1$ is $C_1$-$C_6$ alkyl. In some embodiments, $R^2$ is morpholinyl, and $R^1$ is methyl. In some embodiments, $R^2$ is 1,3-dioxolan-2-yl, and $R^1$ is methyl. In some embodiments, $R^2$ is 3- to 7-membered heterocycloalkyl optionally substituted with one or more hydroxy, and $R^1$ is halo. In some embodiments, $R^2$ is 1,3-dioxolan-2-yl, and $R^1$ is fluoro. In some embodiments, $R^2$ is 1,3-dioxolan-2-yl, and $R^1$ is chloro. In some embodiments, $R^2$ is $C_1$-$C_6$ alkyl optionally substituted with one or more oxo, and $R^1$ is methyl. In some embodiments, $R^2$ is $COCH_3$, and $R^1$ is methyl. In some embodiments, $R^2$ is $C_1$-$C_6$ alkyl optionally substituted with one or more $C_1$-$C_6$ alkoxy, and $R^1$ is $C_1$-$C_6$ alkyl. In some embodiments, $R^2$ is 2-methoxy-2-propyl, and $R^1$ is methyl. In some embodiments, $R^2$ is $C_1$-$C_6$ alkyl optionally substituted with one or more $NR^8R^9$, and $R^1$ is $C_1$-$C_6$ alkyl. In some embodiments, $R^2$ is (dimethylamino)methyl, and $R^1$ is methyl. In some embodiments, $R^2$ is $C_1$-$C_6$ alkyl optionally substituted with one or more $NR^8R^9$, and $R^1$ is halo. In some embodiments, $R^2$ is (dimethylamino)methyl, and $R^1$ is fluoro. In some embodiments, $R^2$ is (methylamino)methyl, and $R^1$ is fluoro. In some embodiments, $R^2$ is aminomethyl, and $R^1$ is fluoro.

In some embodiments, $R^2$ is $C_1$-$C_6$ alkoxy, and $R^1$ is $C_1$-$C_6$ alkyl optionally substituted with one or more $NR^8R^9$. In some embodiments, $R^2$ is methoxy, and $R^1$ is (dimethylamino)methyl.

In some embodiments, $R^1$ and $R^2$ are each attached to a carbon of an aryl ring A. In some embodiments, $R^1$ and $R^2$ are each attached to a carbon of a heteroaryl ring A. In some embodiments, $R^1$ is attached to a carbon and $R^2$ is attached to a nitrogen of a heteroaryl ring A. In some embodiments, $R^2$ is attached to a carbon and $R^1$ is attached to a nitrogen of a heteroaryl ring A.

In some embodiments, $R^1$ and $R^2$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_5$ aliphatic carbocyclic ring.

In some embodiments, $R^1$ and $R^2$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_6$ aliphatic carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 5-membered heteroaromatic ring containing 1 or 2 heteroatoms independently selected from O, N, and S.

In some embodiments, $R^1$ and $R^2$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 6-membered heteroaromatic ring containing 1 or 2 heteroatoms independently selected from O, N, and S.

In some embodiments, $R^1$ and $R^2$ are different. In some embodiments, $R^1$ and $R^2$ are different, and $R^2$ comprises a carbonyl group. In some embodiments, $R^1$ and $R^2$ are different, and $R^2$ comprises 1 or 2 (e.g., 1) nitrogen atoms. In some embodiments, $R^1$ and $R^2$ are different, and $R^2$ comprises 1 or 2 (e.g., 1) oxygen atoms. In some embodiments, $R^1$ and $R^2$ are different, and $R^2$ comprises a sulfur atom. In some embodiments, $R^2$ and $R^1$ are different, and $R^2$ comprises a carbonyl group. In some embodiments, $R^2$ and $R^1$ are different, and $R^2$ comprises 1 or 2 (e.g., 1) nitrogen atoms. In some embodiments, $R^2$ and $R^1$ are different, and $R^2$ comprises 1 or 2 (e.g., 1) oxygen atoms. In some embodiments, $R^2$ and $R^1$ are different, and $R^2$ comprises a sulfur atom. In some embodiments, $R^1$ and $R^2$ are the same. In some embodiments, $R^1$ is para or meta to $R^2$. In some embodiments, $R^1$ is para or ortho to $R^2$. In some embodiments, $R^1$ is ortho or meta to $R^2$. In some embodiments, $R^1$ is para to $R^2$. In some embodiments, $R^1$ is meta to $R^2$. In some embodiments, $R^1$ is ortho to $R^2$.

The Group X

In some embodiments, X is selected from the group consisting of —C(O)—, —S(O)$_q$—, —O—, —NR$^{14}$—, —S(O)(NH)—, —S(O)(NR$^{14}$), CHCH$_2$NHCOC$_1$-C$_6$ aryl, and CR$^3$NHR$^4$. In some embodiments, X is selected from the group consisting of —C(O)—, —S(O)$_q$—, —O—, —NR$^{14}$—, —S(O)(NH)—, CHCH$_2$NHCOC$_1$-C$_6$ aryl, and CR$^3$NHR$^4$. In some embodiments, X is selected from the group consisting of —C(O)—, —S—, —S(O)$_2$—, —NR$^{14}$—, —S(O)(NH)—, CHCH$_2$NHCOC$_1$-C$_6$ aryl, and CR$^3$NHR$^4$. In some embodiments, X is selected from the group consisting of —C(O)—, —S—, —S(O)$_2$—, —S(O)(NH)—, CHCH$_2$NHCOC$_1$-C$_6$ aryl, and CR$^3$NHR$^4$. In some embodiments, X is selected from the group consisting of —C(O)—, —S—, —S(O)$_2$—, —S(O)(NH)—, and CR$^3$NHR$^4$. In some embodiments, X is selected from the group consisting of —C(O)—, —S—, —S(O)$_2$—, —S(O)(NH)—, and CR$^3$NHR$^4$. In some embodiments, X is selected from the group consisting of —S—, —S(O)$_2$—, —S(O)(NH)—, and CR$^3$NHR$^4$. In some embodiments, X is selected from the group consisting of —C(O)—, —S(O)$_2$—, —S(O)(NH)—, and CR$^3$NHR$^4$. In some embodiments, X is selected from the group consisting of —C(O)—, —S—, —S(O)(NH)—, and CR$^3$NHR$^4$. In some embodiments, X is selected from the group consisting of —C(O)—, —S—, —S(O)$_2$—, and CR$^3$NHR$^4$. In some embodiments, X is selected from the group consisting of —C(O)—, —S—, —S(O)$_2$—, and —S(O)(NH)—. In some embodiments, X is selected from the group consisting of —C(O)—, —S—, —S(O)$_2$—, and —S(O)(NR$^{14}$)—. In some embodiments, X is selected from the group consisting of —S(O)$_2$—, —S(O)(NH)—, and CR$^3$NHR$^4$. In some embodiments, X is selected from the group consisting of —S—, —S(O)(NH)—, and CR$^3$NHR$^4$. In some embodiments, X is selected from the group consisting of —S—, —S(O)$_2$—, and CR$^3$NHR$^4$. In some embodiments, X is selected from the group consisting of —S—, —S(O)$_2$—, and —S(O)(NH)—. In some embodiments, X is selected from the group consisting of —S(O)(NH)— and CR$^3$NHR$^4$. In some embodiments, X is selected from the group consisting of —C(O)—, —S—, —S(O)$_2$—, —S(O)(NH)—, and CHNHCO$_2$CH$_2$Ph. In some embodiments, X is —C(O)—. In some embodiments, X is —S(O)$_q$—. In some embodiments, X is —O—. In some embodiments, X is —NR$^{14}$—. In some embodiments, X is —S(O)(NH)—. In some embodiments, the stereochemistry of the S of —S(O)(NH)— is (R). In some embodiments, the stereochemistry of the S of —S(O)(NH)— is (S). In some embodiments, X is CHCH$_2$NHCOC$_1$-C$_6$ aryl. In some embodiments, the stereochemistry of the CH of CHCH$_2$NHCOC$_1$-C$_6$ aryl is (R). In some embodiments, the stereochemistry of the CH of CHCH$_2$NHCOC$_1$-C$_6$ aryl is (S). In some embodiments, X is CR$^3$NHR$^4$. In some embodiments, X is CHNHCO$_2$CH$_2$Ph. In some embodiments, the stereochemistry of the CH of CHNHCO$_2$CH$_2$Ph is (R). In some embodiments, the stereochemistry of the CH of CHNHCO$_2$CH$_2$Ph is (S).

The Variable q

In some embodiments, q is 0, 1, or 2. In some embodiments, q is 1 or 2. In some embodiments, q is 0 or 2. In some embodiments, q is 0. In some embodiments, q is 1. In some embodiments, q is 2.

The Group $R^3$

In some embodiments, $R^3$ is selected from H and $C_1$-$C_6$ alkyl. In some embodiments, $R^3$ is H. In some embodiments, $R^3$ is $C_1$-$C_6$ alkyl. In some embodiments, $R^3$ is methyl.

The Group $R^4$

In some embodiments, $R^4$ is selected from H and COOC$_1$-C$_6$ alkyl optionally substituted with one or more C$_6$-C$_{10}$ aryl. In some embodiments, $R^4$ is H. In some embodiments, $R^4$ is COOC$_1$-C$_6$ alkyl optionally substituted with one or more C$_6$-C$_{10}$ aryl. In some embodiments, $R^4$ is COOCH$_2$Ph.

The Ring C and Substitutions on the Ring C

In some embodiments, C is a 5- to 10-membered monocyclic or bicyclic heteroarylene or a C$_6$-C$_{10}$ monocyclic or bicyclic arylene. In some embodiments, C is a 5- to 10-membered monocyclic heteroarylene or a C$_6$-C$_{10}$ monocyclic arylene. In some embodiments, C is a 5- to 10-membered monocyclic or bicyclic heteroarylene. In some embodiments, C is a 5- to 6-membered monocyclic heteroarylene. In some embodiments, C is a 5- to 10-membered C$_6$-C$_{10}$ monocyclic or bicyclic arylene. In some embodiments, C is a 5-membered monocyclic heteroarylene. In some embodiments, the optionally substituted ring C is

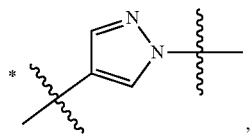 [SMILES: *c1cnn(*)c1]

and wherein the bond that is shown as being spatially closest to the asterisk connects to the X group.

In some embodiments, the optionally substituted ring C is

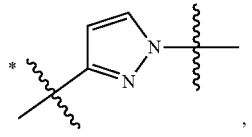 [SMILES: *c1ccn(*)n1]

and wherein the bond that is shown as being spatially closest to the asterisk connects to the X group. In some embodiments, the optionally substituted ring C is

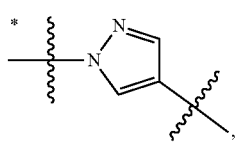 [SMILES: *c1cnn(*)c1]

and wherein the bond that is shown as being spatially closest to the asterisk connects to the X group. In some embodiments, the optionally substituted ring C is

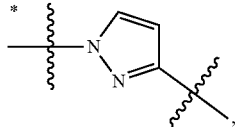 [SMILES: *c1ccn(*)n1]

and wherein the bond that is shown as being spatially closest to the asterisk connects to the X group. In some embodiments, the optionally substituted ring C is

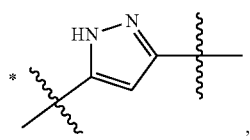

and wherein the bond that is shown as being spatially closest to the asterisk connects to the X group. In some embodiments, the optionally substituted ring C is

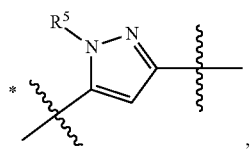

and wherein the bond that is shown as being spatially closest to the asterisk connects to the X group. In some embodiments, the optionally substituted ring C is

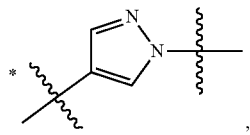 [SMILES: *c1cnn(*)c1]

and wherein the bond that is shown as being spatially closest to the asterisk connects to the X group. In some embodiments, the optionally substituted ring C is

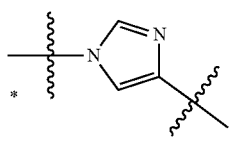 [SMILES: *c1cn(*)cn1]

and wherein the bond that is shown as being spatially closest to the asterisk connects to the X group. In some embodiments, the optionally substituted ring C is

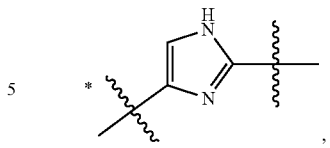

and wherein the bond that is shown as being spatially closest to the asterisk connects to the X group. In some embodiments, the optionally substituted ring C is

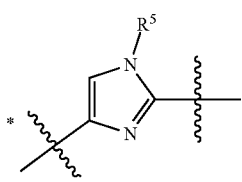

and wherein the bond that is shown as being spatially closest to the asterisk connects to the X group. In some embodiments, the optionally substituted ring C is

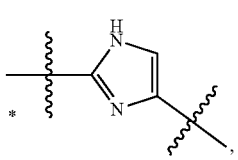

and wherein the bond that is shown as being spatially closest to the asterisk connects to the X group. In some embodiments, the optionally substituted ring C is

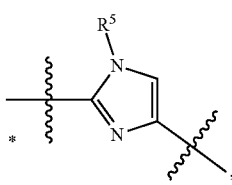

and wherein the bond that is shown as being spatially closest to the asterisk connects to the X group. In some embodiments, the optionally substituted ring C is

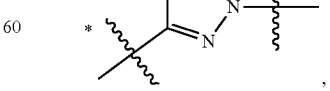

and wherein the bond that is shown as being spatially closest to the asterisk connects to the X group. In some embodiments, the optionally substituted ring C is

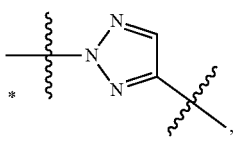 [SMILES: *c1cnn(*)n1]

and wherein the bond that is shown as being spatially closest to the asterisk connects to the X group. In some embodiments, the optionally substituted ring C is

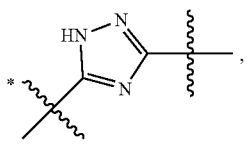 [SMILES: *c1n[nH]c(*)n1]

and wherein the bond that is shown as being spatially closest to the asterisk connects to the X group. In some embodiments, the optionally substituted ring C is

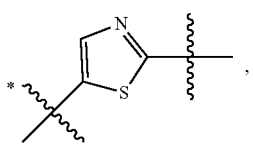 [SMILES: *c1cnc(*)s1]

and wherein the bond that is shown as being spatially closest to the asterisk connects to the X group. In some embodiments, the optionally substituted ring C is

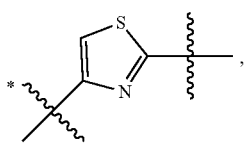 [SMILES: *c1csc(*)n1]

and wherein the bond that is shown as being spatially closest to the asterisk connects to the X group. In some embodiments, the optionally substituted ring C is

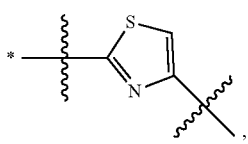

and wherein the bond that is shown as being spatially closest to the asterisk connects to the X group. In some embodiments, the optionally substituted ring C is

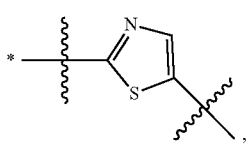 [SMILES: *c1cnc(*)s1]

and wherein the bond that is shown as being spatially closest to the asterisk connects to the X group. In some embodiments, the optionally substituted ring C is

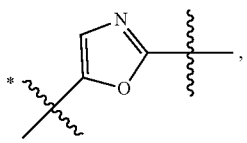 [SMILES: *c1cnc(*)o1]

and wherein the bond that is shown as being spatially closest to the asterisk connects to the X group. In some embodiments, the optionally substituted ring C is

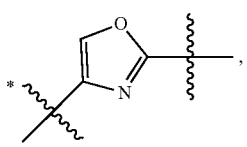 [SMILES: *c1coc(*)n1]

and wherein the bond that is shown as being spatially closest to the asterisk connects to the X group. In some embodiments, the optionally substituted ring C is

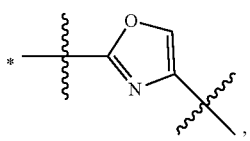 [SMILES: *c1coc(*)n1]

and wherein the bond that is shown as being spatially closest to the asterisk connects to the X group. In some embodiments, the optionally substituted ring C is

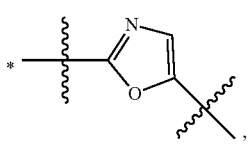 [SMILES: *c1cnc(*)o1]

and wherein the bond that is shown as being spatially closest to the asterisk connects to the X group. In some embodiments, the optionally substituted ring C is

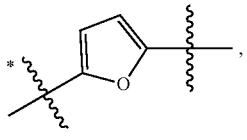 [SMILES: *c1ccc(*)o1]

and wherein the bond that is shown as being spatially closest to the asterisk connects to the X group. In some embodiments, the optionally substituted ring C is

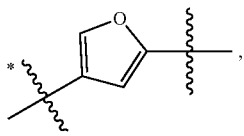 [SMILES: *c1coc(*)c1]

and wherein the bond that is shown as being spatially closest to the asterisk connects to the X group. In some embodiments, the optionally substituted ring C is

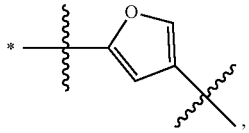 [SMILES: *c1coc(*)c1]

and wherein the bond that is shown as being spatially closest to the asterisk connects to the X group. In some embodiments, the optionally substituted ring C is

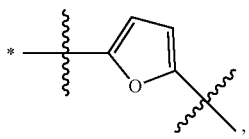 [SMILES: *c1ccc(*)o1]

and wherein the bond that is shown as being spatially closest to the asterisk connects to the X group. In some embodiments, the optionally substituted ring C is

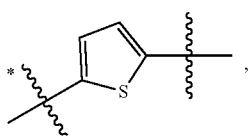 [SMILES: *c1ccc(*)s1]

and wherein the bond that is shown as being spatially closest to the asterisk connects to the X group. In some embodiments, the optionally substituted ring C is

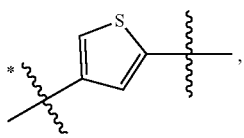 [SMILES: *c1csc(*)c1]

and wherein the bond that is shown as being spatially closest to the asterisk connects to the X group. In some embodiments, the optionally substituted ring C is

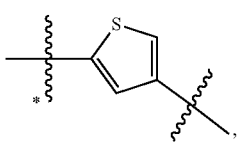 [SMILES: *c1csc(*)c1]

and wherein the bond that is shown as being spatially closest to the asterisk connects to the X group. In some embodiments, the optionally substituted ring C is

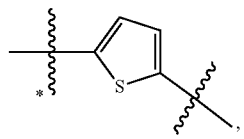 [SMILES: *c1ccc(*)s1]

and wherein the bond that is shown as being spatially closest to the asterisk connects to the X group. In some embodiments, C is a 6-membered monocyclic heteroarylene. In some embodiments, the optionally substituted ring C is

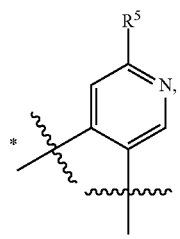

and wherein the bond that is shown as being spatially closest to the asterisk connects to the X group. In some embodiments, the optionally substituted ring C is

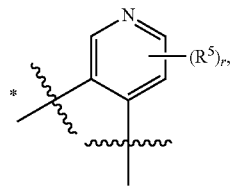

r is 0 or 1, and wherein the bond that is shown as being spatially closest to the asterisk connects to the X group. In some embodiments, the optionally substituted ring C is

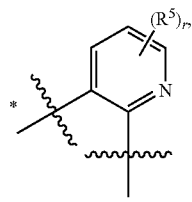

r is 0 or 1, and wherein the bond that is shown as being spatially closest to the asterisk connects to the X group. In some embodiments, the optionally substituted ring C is

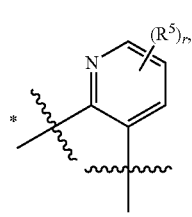

r is 0 or 1, and wherein the bond that is shown as being spatially closest to the asterisk connects to the X group. In some embodiments, the optionally substituted ring C is

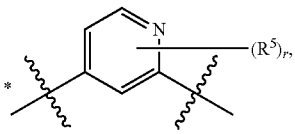

r is 0 or 1, and wherein the bond that is shown as being spatially closest to the asterisk connects to the X group. In some embodiments, the optionally substituted ring C is

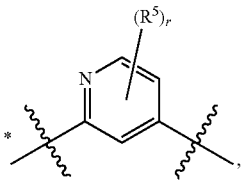

r is 0 or 1, and wherein the bond that is shown as being spatially closest to the asterisk connects to the X group. In some embodiments, the optionally substituted ring C is

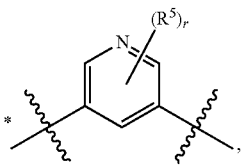

r is 0 or 1, and wherein the bond that is shown as being spatially closest to the asterisk connects to the X group. In some embodiments, the optionally substituted ring C is

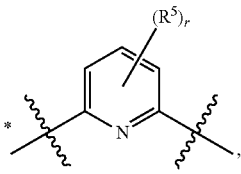

r is 0 or 1, and wherein the bond that is shown as being spatially closest to the asterisk connects to the X group. In some embodiments, the optionally substituted ring C is

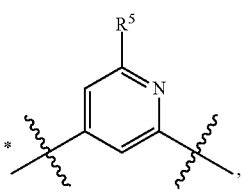

and wherein the bond that is shown as being spatially closest to the asterisk connects to the X group. In some embodiments, the optionally substituted ring C is

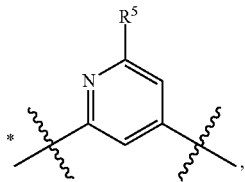

and wherein the bond that is shown as being spatially closest to the asterisk connects to the X group. In some embodiments, the optionally substituted ring C is

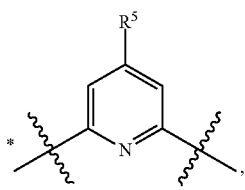

and wherein the bond that is shown as being spatially closest to the asterisk connects to the X group. In some embodiments, the optionally substituted ring C is

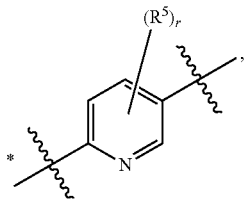

r is 0 or 1, and wherein the bond that is shown as being spatially closest to the asterisk connects to the X group. In some embodiments, the optionally substituted ring C is

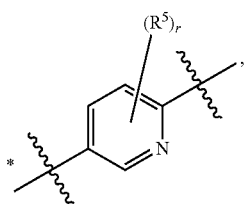

r is 0 or 1, and wherein the bond that is shown as being spatially closest to the asterisk connects to the X group. In some embodiments, the optionally substituted ring C is

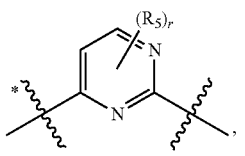

r is 0 or 1, and wherein the bond that is shown as being spatially closest to the asterisk connects to the X group. In some embodiments, the optionally substituted ring C is

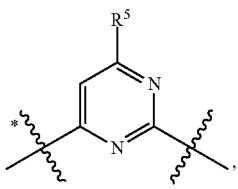

and wherein the bond that is shown as being spatially closest to the asterisk connects to the X group. In some embodiments, the optionally substituted ring C is

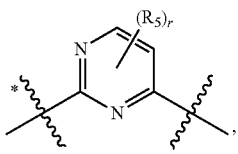

r is 0 or 1, and wherein the bond that is shown as being spatially closest to the asterisk connects to the X group. In some embodiments, the optionally substituted ring C is

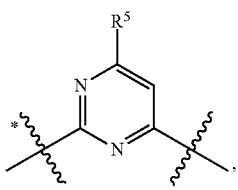

and wherein the bond that is shown as being spatially closest to the asterisk connects to the X group. In some embodiments, the optionally substituted ring C is

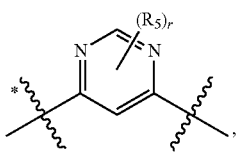

r is 0 or 1, and wherein the bond that is shown as being spatially closest to the asterisk connects to the X group. In some embodiments, the optionally substituted ring C is

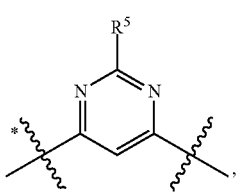

and wherein the bond that is shown as being spatially closest to the asterisk connects to the X group. In some embodiments, the optionally substituted ring C is

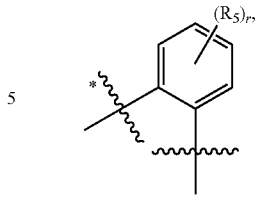

r is 0 or 1, and wherein the bond that is shown as being spatially closest to the asterisk connects to the X group. In some embodiments, the optionally substituted ring C is

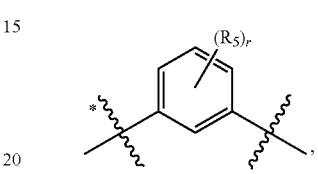

r is 0 or 1, and wherein the bond that is shown as being spatially closest to the asterisk connects to the X group. In some embodiments, the optionally substituted ring C is

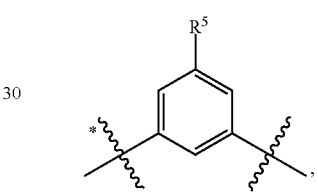

and wherein the bond that is shown as being spatially closest to the asterisk connects to the X group. In some embodiments, the optionally substituted ring C is

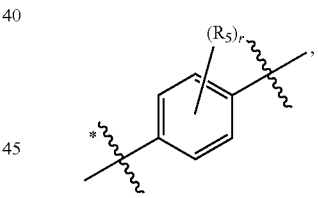

r is 0 or 1, and wherein the bond that is shown as being spatially closest to the asterisk connects to the X group.

The Group $R^5$

In some embodiments, each occurrence of $R^5$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, $OC_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^5$ $C_3$-$C_7$ cycloalkyl or of the $R^5$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, each occurrence of $R^5$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCO_2$-$C_6$ alkynyl, $NHCOOC_1$-$C_6$ alkyl, $CONR^8R^9$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, $OC_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^5$ $C_3$-$C_7$ cycloalkyl or of the $R^5$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, each occurrence of $R^5$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_8$ cycloalkyl, $NH_2$, $NHC_1$-$C_6$ alkyl, $N(C_1$-$C_6$ alkyl$)_2$, $NHCOC_1$-$C_6$ alkyl, $NHCOOC_1$-$C_6$ alkyl, $CONR^8R^9$, $SC_1$-$C_6$ alkyl, $S(O_2)C_1$-$C_6$ alkyl, $S(O_2)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl is optionally substituted with one or more substituents each independently selected from hydroxy, halo, CN, oxo, $C_1$-$C_6$ alkyl, $C_1$-$C_6$ alkoxy, $NR^8R^9$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, and $NHCOC_1$-$C_6$ alkyl.

Particular Embodiments Wherein r=1

In some embodiments, $R^5$ is $C_1$-$C_6$ alkyl optionally substituted with one or more hydroxy. In some embodiments, $R^5$ is 1-hydroxy-2-methylpropan-2-yl. In some embodiments, $R^5$ is 2-hydroxyethyl. In some embodiments, $R^5$ is $C_1$-$C_6$ alkyl. In some embodiments, $R^5$ is methyl. In some embodiments, $R^5$ is isopropyl. In some embodiments, $R^5$ is isopropyl. In some embodiments, $R^5$ is $C_1$-$C_6$ alkyl substituted with hydroxy at the carbon directly connected to ring A. In some embodiments, $R^5$ is 2-hydroxy-2-propyl. In some embodiments, $R^5$ is hydroxymethyl. In some embodiments, $R^5$ is 1-hydroxyethyl. In some embodiments, $R^5$ is 1-hydroxy-2-propyl. In some embodiments, $R^5$ is $C_1$-$C_6$ alkyl substituted with two or more hydroxy groups. In some embodiments, $R^5$ is $C_1$-$C_6$ alkyl substituted with two or more hydroxy groups, wherein one of the two or more hydroxy groups is bonded to the carbon directly connected to ring A. In some embodiments, $R^5$ is 1,2-dihydroxy-prop-2-yl. In some embodiments, $R^5$ is $C_3$-$C_7$ cycloalkyl optionally substituted with one or more hydroxy. In some embodiments, $R^5$ is $C_3$-$C_7$ cycloalkyl. In some embodiments, $R^5$ is $C_3$-$C_7$ cycloalkyl substituted with hydroxy at the carbon directly connected to ring A. In some embodiments, $R^5$ is 1-hydroxy-1-cyclopropyl. In some embodiments, $R^5$ is 1-hydroxy-1-cyclobutyl. In some embodiments, $R^5$ is 1-hydroxy-1-cyclopentyl. In some embodiments, $R^5$ is 1-hydroxy-1-cyclohexyl. In some embodiments, $R^5$ is 3- to 7-membered heterocycloalkyl optionally substituted with one or more hydroxy. In some embodiments, $R^5$ is 3- to 7-membered heterocycloalkyl. In some embodiments, $R^5$ is morpholinyl (e.g., 1-morpholinyl). In some embodiments, $R^5$ is 1,3-dioxolan-2-yl. In some embodiments, $R^5$ is 3- to 7-membered heterocycloalkyl optionally substituted with one or more $C_1$-$C_6$ alkyl. In some embodiments, $R^5$ is 1-methylpyrrolidin-2-yl. In some embodiments, $R^5$ is 3- to 7-membered heterocycloalkyl substituted with hydroxy at the carbon directly connected to ring A. In some embodiments, $R^5$ is $C_1$-$C_6$ alkyl optionally substituted with one or more oxo. In some embodiments, $R^5$ is $COCH_3$. In some embodiments, $R^5$ is $COCH_2CH_3$. In some embodiments, $R^5$ is $C_3$-$C_7$ cycloalkyl optionally substituted with one or more oxo. In some embodiments, $R^5$ is 3- to 7-membered heterocycloalkyl optionally substituted with one or more oxo. In some embodiments, $R^5$ is $C_1$-$C_6$ alkyl optionally substituted with one or more $C_1$-$C_6$ alkoxy. In some embodiments, $R^5$ is 2-methoxy-2-propyl. In some embodiments, $R^5$ is methoxymethyl. In some embodiments, $R^5$ is $C_3$-$C_7$ cycloalkyl optionally substituted with one or more $C_1$-$C_6$ alkoxy. In some embodiments, $R^5$ is 3- to 7-membered heterocycloalkyl optionally substituted with one or more $C_1$-$C_6$ alkoxy. In some embodiments, $R^5$ is $C_1$-$C_6$ alkyl optionally substituted with one or more $NR^8R^9$. In some embodiments, $R^5$ is $C_1$-$C_6$ alkyl substituted with $NR^8R^9$ at the carbon directly connected to ring A. In some embodiments, $R^5$ is (methylamino)methyl. In some embodiments, $R^5$ is (dimethylamino)methyl. In some embodiments, $R^5$ is aminomethyl. In some embodiments, $R^5$ is N-methylacetamidomethyl. In some embodiments, $R^5$ is 1-(dimethylamino)eth-1-yl. In some embodiments, $R^5$ is 2-(dimethylamino)prop-2-yl. In some embodiments, $R^5$ is (2-methoxy-eth-1-yl)(methyl)aminomethyl. In some embodiments, $R^5$ is (methyl)(acetyl)aminomethyl. In some embodiments, $R^5$ is (methyl)(cyclopropylmethyl)aminomethyl. In some embodiments, $R^5$ is (methyl)(2,2-difluoroeth-1-yl)aminomethyl. In some embodiments, $R^5$ is $C_3$-$C_7$ cycloalkyl optionally substituted with one or more $NR^8R^9$. In some embodiments, $R^5$ is 3- to 7-membered heterocycloalkyl optionally substituted with one or more $NR^8R^9$. In some embodiments, $R^5$ is $C_1$-$C_6$ haloalkyl optionally substituted with one or more hydroxy. In some embodiments, $R^5$ is $C_1$-$C_6$ alkoxy. In some embodiments, $R^5$ is $C_1$-$C_6$ haloalkoxy. In some embodiments, $R^5$ is $C_1$-$C_6$ alkyl optionally substituted with 3- to 7-membered heterocycloalkyl, wherein the 3- to 7-membered heterocycloalkyl is further optionally substituted as defined elsewhere herein. In some embodiments, $R^5$ is pyrrolidinylmethyl (e.g., pyrrolidin-1-ylmethyl). In some embodiments, $R^5$ is optionally substituted pyrrolidinylmethyl (e.g., 3,3-difluoropyrrolidin-1-ylmethyl). In some embodiments, $R^5$ is azetidinylmethyl (e.g., azetidin-1-ylmethyl). In some embodiments, $R^5$ is optionally substituted azetidinylmethyl (e.g., 3-methoxyazetidin-1-ylmethyl). In some embodiments, $R^5$ is morpholinylmethyl (e.g., morpholin-4-ylmethyl). In some embodiments, $R^5$ is halo. In some embodiments, $R^5$ is fluoro. In some embodiments, $R^5$ is chloro. In some embodiments, $R^5$ is CN. In some embodiments, $R^5$ is $NO_2$. In some embodiments, $R^5$ is $COC_1$-$C_6$ alkyl. In some embodiments, $R^5$ is CO—$C_6$-$C_{10}$ aryl. In some embodiments, $R^5$ is CO(5- to 10-membered heteroaryl). In some embodiments, $R^5$ is $CO_2C_1$-$C_6$ alkyl. In some embodiments, $R^5$ is $CO_2C_3$-$C_8$ cycloalkyl. In some embodiments, $R^5$ is $OCOC_1$-$C_6$ alkyl. In some embodiments, $R^5$ is $OCOC_6$-$C_{10}$ aryl. In some embodiments, $R^5$ is OCO(5- to 10-membered heteroaryl). In some embodiments, $R^5$ is OCO(3- to 7-membered heterocycloalkyl). In some embodiments, $R^5$ is $C_6$-$C_{10}$ aryl. In some embodiments, $R^5$ is phenyl. In some embodiments, $R^5$ is 5- to 10-membered heteroaryl. In some embodiments, $R^5$ is pyridyl (e.g., 4-pyridyl). In some embodiments, $R^5$ is pyrazolyl (e.g., 1-pyrazolyl). In some embodiments, $R^5$ is $NH_2$. In some embodiments, $R^5$ is $NHC_1$-$C_6$ alkyl. In some embodiments, $R^5$ is $N(C_1$-$C_6$ alkyl$)_2$. In some embodiments, $R^5$ is $CONR^8R^9$. In some embodiments, $R^5$ is $SF_5$. In some embodiments, $R^5$ is $SC_1$-$C_6$ alkyl, In some embodiments, $R^5$ is $S(O_2)C_1$-$C_6$ alkyl. In some embodiments, $R^5$ is $S(O_2)CH_3$. In some embodiments, $R^5$ is $S(O_2)NR^{51}R^{52}$. In some embodiments, $R^5$ is $S(O_2)N(CH_3)_2$. In some embodiments, $R^5$ is $S(O)C_1$-$C_6$ alkyl. In some embodiments, $R^5$ is $S(O)CH_3$. In some embodiments, $R^5$ is attached to a carbon of an aryl ring A. In some embodiments, $R^5$ is attached to a carbon of a heteroaryl ring A. In some embodiments, $R^5$ is attached to a nitrogen of a heteroaryl ring A.

Particular Embodiments Wherein r=2:

In some embodiments, one $R^5$ is $C_1$-$C_6$ alkyl optionally substituted with one or more hydroxy, and the other $R^5$ is $C_1$-$C_6$ alkyl optionally substituted with one or more hydroxy. In some embodiments, one $R^5$ is 1-hydroxy-2-methylpropan-2-yl, and the other $R^5$ is methyl. In some embodiments, one $R^5$ is 2-hydroxy-2-propyl and the other $R^5$ is methyl. In some embodiments, one $R^5$ is 2-hydroxy-2-propyl and the other $R^5$ is isopropyl. In some embodiments, one $R^5$ is 2-hydroxy-2-propyl and the other $R^5$ is 2-hydroxy-2-propyl. In some embodiments, one $R^5$ is 2-hydroxy-2-propyl and the other $R^5$ is 1-hydroxyethyl. In some embodiments, one $R^5$ is hydroxymethyl and the other $R^5$ is methyl. In some embodiments, one $R^5$ is 1-hydroxyethyl and the other $R^5$ is methyl. In some embodiments, one $R^5$ is 2-hydroxyethyl and the other $R^5$ is methyl. In some embodiments, one $R^5$ is 1-hydroxy-2-propyl and the other $R^5$ is methyl. In some embodiments, one $R^5$ is $C_1$-$C_6$ alkyl optionally substituted with one or more hydroxy, and the other $R^5$ is $C_6$-$C_{10}$ aryl. In some embodiments, one $R^5$ is 2-hydroxy-2-propyl and the other $R^5$ is phenyl. In some embodiments, one $R^5$ is $C_1$-$C_6$ alkyl optionally substituted with one or more hydroxy, and the other $R^5$ is 5- to 10-membered heteroaryl. In some embodiments, one $R^5$ is 2-hydroxy-2-propyl and the other $R^5$ is pyridyl. In some embodiments, one $R^5$ is 2-hydroxy-2-propyl and the other $R^5$ is pyrazolyl. In some embodiments, one $R^5$ is $C_1$-$C_6$ alkyl optionally substituted with one or more hydroxy, and the other $R^5$ is $SF_5$. In some embodiments, one $R^5$ is $C_1$-$C_6$ alkyl optionally substituted with one or more hydroxy, and the other $R^5$ is $SC_1$-$C_6$ alkyl. In some embodiments, one $R^5$ is $C_1$-$C_6$ alkyl optionally substituted with one or more hydroxy, and the other $R^5$ is $S(O_2)C_1$-$C_6$ alkyl. In some embodiments, one $R^5$ is $C_1$-$C_6$ alkyl optionally substituted with one or more hydroxy, and the other $R^5$ is $S(O_2)CH_3$. In some embodiments, one $R^5$ is $C_1$-$C_6$ alkyl optionally substituted with one or more hydroxy, and the other $R^5$ is halo. In some embodiments, one $R^5$ is 2-hydroxy-2-propyl and the other $R^5$ is chloro. In some embodiments, one $R^5$ is 2-hydroxy-2-propyl and the other $R^5$ is fluoro. In some embodiments, one $R^5$ is $C_3$-$C_7$ cycloalkyl optionally substituted with one or more hydroxy, and the other $R^5$ is $C_1$-$C_6$ alkyl. In some embodiments, one $R^5$ is 1-hydroxy-1-cyclopropyl, and the other $R^5$ is methyl. In some embodiments, one $R^5$ is 1-hydroxy-1-cyclobutyl, and the other $R^5$ is methyl. In some embodiments, one $R^5$ is 1-hydroxy-1-cyclopentyl, and the other $R^5$ is methyl. In some embodiments, one $R^5$ is 1-hydroxy-1-cyclohexyl, and the other $R^5$ is methyl. In some embodiments, one $R^5$ is 3- to 7-membered heterocycloalkyl optionally substituted with one or more hydroxy, and the other $R^5$ is $C_1$-$C_6$ alkyl. In some embodiments, one $R^5$ is morpholinyl, and the other $R^5$ is methyl. In some embodiments, one $R^5$ is 1,3-dioxolan-2-yl, and the other $R^5$ is methyl. In some embodiments, one $R^5$ is 3- to 7-membered heterocycloalkyl optionally substituted with one or more hydroxy, and the other $R^5$ is halo. In some embodiments, one $R^5$ is 1,3-dioxolan-2-yl, and the other $R^5$ is fluoro. In some embodiments, one $R^5$ is 1,3-dioxolan-2-yl, and the other $R^5$ is chloro. In some embodiments, one $R^5$ is $C_1$-$C_6$ alkyl optionally substituted with one or more oxo, and the other $R^5$ is methyl. In some embodiments, one $R^5$ is $COCH_3$, and the other $R^5$ is methyl. In some embodiments, one $R^5$ is $C_1$-$C_6$ alkyl optionally substituted with one or more $C_1$-$C_6$ alkoxy, and the other $R^5$ is $C_1$-$C_6$ alkyl. In some embodiments, one $R^5$ is 2-methoxy-2-propyl, and the other $R^5$ is methyl. In some embodiments, one $R^5$ is $C_1$-$C_6$ alkyl optionally substituted with one or more $NR^8R^9$, and the other $R^5$ is $C_1$-$C_6$ alkyl. In some embodiments, one $R^5$ is (dimethylamino)methyl, and the other $R^5$ is methyl. In some embodiments, one $R^5$ is $C_1$-$C_6$ alkyl optionally substituted with one or more $NR^8R^9$, and the other $R^5$ is halo. In some embodiments, one $R^5$ is (dimethylamino)methyl, and the other $R^5$ is fluoro. In some embodiments, one $R^5$ is (dimethylamino)methyl, and the other $R^5$ is fluoro. In some embodiments, one $R^5$ is (methylamino)methyl, and the other $R^5$ is fluoro. In some embodiments, one $R^5$ is aminomethyl, and the other $R^5$ is fluoro. In some embodiments, one $R^5$ is $C_1$-$C_6$ alkyl, and the other $R^5$ is $C_1$-$C_6$ alkyl. In some embodiments, one $R^5$ is methyl, and the other $R^5$ is methyl.

In some embodiments, one $R^5$ is 1-hydroxy-2-methylpropan-2-yl, and the other $R^5$ is methyl. In some embodiments, one $R^5$ is 2-hydroxy-2-propyl and the other $R^5$ is methyl. In some embodiments, one $R^5$ is 2-hydroxy-2-propyl and the other $R^5$ is isopropyl. In some embodiments, one $R^5$ is 2-hydroxy-2-propyl and the other $R^5$ is 1-hydroxyethyl. In some embodiments, one $R^5$ is hydroxymethyl and the other $R^5$ is methyl. In some embodiments, one $R^5$ is 1-hydroxyethyl and the other $R^5$ is methyl. In some embodiments, one $R^5$ is 2-hydroxyethyl and the other $R^5$ is methyl. In some embodiments, one $R^5$ is 1-hydroxy-2-propyl and the other $R^5$ is methyl. In some embodiments, one $R^5$ is $C_1$-$C_6$ alkyl optionally substituted with one or more hydroxy, and the other $R^5$ is $C_6$-$C_{10}$ aryl. In some embodiments, one $R^5$ is 2-hydroxy-2-propyl and the other $R^5$ is phenyl. In some embodiments, one $R^5$ is $C_1$-$C_6$ alkyl optionally substituted with one or more hydroxy, and the other $R^5$ is 5- to 10-membered heteroaryl. In some embodiments, one $R^5$ is 2-hydroxy-2-propyl and the other $R^5$ is pyridyl. In some embodiments, one $R^5$ is 2-hydroxy-2-propyl and the other $R^5$ is pyrazolyl. In some embodiments, one $R^5$ is $C_1$-$C_6$ alkyl optionally substituted with one or more hydroxy, and the other $R^5$ is $SF_5$. In some embodiments, one $R^5$ is $C_1$-$C_6$ alkyl optionally substituted with one or more hydroxy, and the other $R^5$ is $SC_1$-$C_6$ alkyl. In some embodiments, one $R^5$ is $C_1$-$C_6$ alkyl optionally substituted with one or more hydroxy, and the other $R^5$ is $S(O_2)C_1$-$C_6$ alkyl. In some embodiments, one $R^5$ is $C_1$-$C_6$ alkyl optionally substituted with one or more hydroxy, and the other $R^5$ is $S(O_2)CH_3$. In some embodiments, one $R^5$ is $C_1$-$C_6$ alkyl optionally substituted with one or more hydroxy, and the other $R^5$ is halo. In some embodiments, one $R^5$ is 2-hydroxy-2-propyl and the other $R^5$ is chloro. In some embodiments, one $R^5$ is 2-hydroxy-2-propyl and the other $R^5$ is fluoro. In some embodiments, one $R^5$ is $C_3$-$C_7$ cycloalkyl optionally substituted with one or more hydroxy, and the other $R^5$ is $C_1$-$C_6$ alkyl. In some embodiments, one $R^5$ is 1-hydroxy-1-cyclopropyl, and the other $R^5$ is methyl. In some embodiments, one $R^5$ is 1-hydroxy-1-cyclobutyl, and the other $R^5$ is methyl. In some embodiments, one $R^5$ is 1-hydroxy-1-cyclopentyl, and the other $R^5$ is methyl. In some embodiments, one $R^5$ is 1-hydroxy-1-cyclohexyl, and the other $R^5$ is methyl. In some embodiments, one $R^5$ is 3- to 7-membered heterocycloalkyl optionally substituted with one or more hydroxy, and the other $R^5$ is $C_1$-$C_6$ alkyl. In some embodiments, one $R^5$ is morpholinyl, and the other $R^5$ is methyl. In some embodiments, one $R^5$ is 1,3-dioxolan-2-yl, and the other $R^5$ is methyl. In some embodiments, one $R^5$ is 3- to 7-membered heterocycloalkyl optionally substituted with one or more hydroxy, and the other $R^5$ is halo. In some embodiments, one $R^5$ is 1,3-dioxolan-2-yl, and the other $R^5$ is fluoro. In some embodiments, one $R^5$ is 1,3-dioxolan-2-yl, and the other $R^5$ is chloro. In some embodiments, one $R^5$ is $C_1$-$C_6$ alkyl optionally substituted with one or more oxo, and the other $R^5$ is methyl. In some embodiments, one $R^5$ is $COCH_3$, and the other $R^5$ is methyl. In some embodiments, one $R^5$ is $C_1$-$C_6$ alkyl optionally substituted with one or more $C_1$-$C_6$ alkoxy, and the other $R^5$ is $C_1$-$C_6$ alkyl. In some embodiments, one $R^5$ is 2-methoxy-2-propyl, and the other $R^5$ is methyl. In some embodiments, one $R^5$ is $C_1$-$C_6$ alkyl optionally substituted with one or more $NR^8R^9$, and the other $R^5$ is $C_1$-$C_6$ alkyl. In some embodiments, one $R^5$ is (dimethylamino)methyl, and the other $R^5$ is methyl. In some embodiments, one $R^5$ is $C_1$-$C_6$ alkyl optionally substituted with one or more $NR^8R^9$, and the other $R^5$ is halo. In some embodiments, one $R^5$ is (dimethylamino)methyl, and the other $R^5$ is fluoro. In some embodiments, one $R^5$ is (methylamino)methyl, and the other $R^5$ is fluoro. In some embodiments, one $R^5$ is aminomethyl, and the other $R^5$ is fluoro.

In some embodiments, one $R^5$ is $C_1$-$C_6$ alkoxy, and the other $R^5$ is $C_1$-$C_6$ alkyl optionally substituted with one or more $NR^8R^9$. In some embodiments, one $R^5$ is methoxy, and the other $R^5$ is (dimethylamino)methyl. In some embodiments, $R^5$ and $R^5$ are each attached to a carbon of an aryl ring A. In some embodiments, $R^5$ and $R^5$ are each attached to a carbon of a heteroaryl ring A. In some embodiments, one $R^5$ is attached to a carbon and the other $R^5$ is attached to a nitrogen of a heteroaryl ring A. In some embodiments, one $R^5$ is attached to a carbon and the other $R^5$ is attached to a nitrogen of a heteroaryl ring A.

In some embodiments, each $R^5$ is different. In some embodiments, each $R^5$ is different, and at least one $R^5$ comprises a carbonyl group. In some embodiments, each $R^5$ is different, and at least one $R^5$ comprises 1 or 2 (e.g., 1) nitrogen atoms. In some embodiments, each $R^5$ is different, and at least one $R^5$ comprises 1 or 2 (e.g., 1) oxygen atoms. In some embodiments, each $R^5$ is different, and at least one $R^5$ comprises a sulfur atom. In some embodiments, each $R^5$ is different, and at least one $R^5$ comprises a carbonyl group. In some embodiments, each $R^5$ is different, and at least one $R^5$ comprises 1 or 2 (e.g., 1) nitrogen atoms. In some embodiments, each $R^5$ is different, and at least one $R^5$ comprises 1 or 2 (e.g., 1) oxygen atoms. In some embodiments, each $R^5$ is different, and at least one $R^5$ comprises a sulfur atom. In some embodiments, each $R^5$ is the same. In some embodiments, one $R^5$ is para or meta to the other $R^5$. In some embodiments, one $R^5$ is para or ortho to the other $R^5$. In some embodiments, one $R^5$ is ortho or meta to the other $R^5$. In some embodiments, one $R^5$ is para to the other $R^5$. In some embodiments, one $R^5$ is meta to the other $R^5$. In some embodiments, one $R^5$ is ortho to the other $R^5$.

The Variables o and p

In some embodiments, o=1 or 2. In some embodiments, o=1. In some embodiments, o=2. In some embodiments, p=0, 1, 2, or 3. In some embodiments, p=0. In some embodiments, p=1. In some embodiments, p=2. In some embodiments, o=1 and p=0. In some embodiments, o=2 and p=0. In some embodiments, o=1 and p=1. In some embodiments, o=1 and p=2. In some embodiments, o=2 and p=1. In some embodiments, o=2 and p=2. In some embodiments, o=2 and p=3.

The Ring B and Substitutions on the Ring B

In some embodiments, B is a 5- to 10-membered monocyclic or bicyclic heteroaryl or a $C_6$-$C_{10}$ monocyclic or bicyclic aryl, such as phenyl. In some embodiments, B is a 5- to 6-membered monocyclic heteroaryl or a $C_6$ monocyclic aryl. In some embodiments, B is a 5- to 10-membered monocyclic or bicyclic heteroaryl. In some embodiments, B is a $C_6$-$C_{10}$ monocyclic or bicyclic aryl. In some embodiments, B is a 5-membered heteroaryl. In some embodiments, B is a 7-10 membered monocyclic or bicyclic heteroaryl. In some embodiments, B is phenyl substituted with 1 or 2 $R^6$ and optionally substituted with 1, 2, or 3 $R^7$. In some embodiments, B is pyridyl substituted with 1 or 2 $R^6$ and optionally substituted with 1, 2, or 3 $R^7$. In some embodiments, B is indazolyl substituted with 1 or 2 $R^6$ and optionally substituted with 1, 2, or 3 $R^7$. In some embodiments, B is pyrazolyl substituted with 1 or 2 $R^6$ and optionally substituted with 1 or 2 $R^7$. In some embodiments, B is phenyl, o is 1 or 2, and p is 0, 1, 2, or 3. In some embodiments, B is phenyl, o is 1, and p is 0, 1, 2, or 3. In some embodiments, B is phenyl, o is 2, and p is 0, 1, 2, or 3.

In some embodiments, B is one of the rings disclosed hereinbelow, substituted as disclosed hereinbelow, wherein in each case the bond that is shown as being broken by the wavy line ∕ connects B to the ring C of Formula AA.

In some embodiments, the substituted ring B

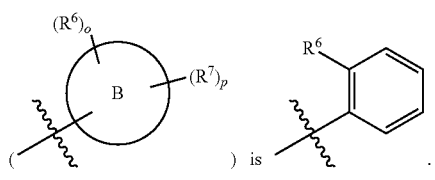 ) is 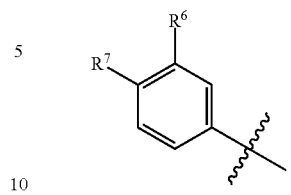 .

In some embodiments, the substituted ring B

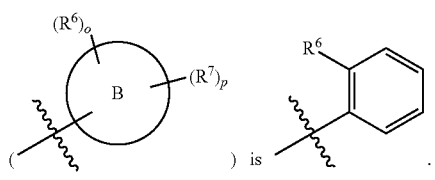 ) is 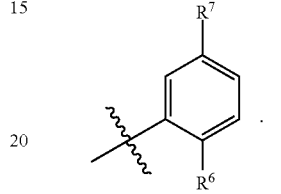 .

In some embodiments, the substituted ring B is

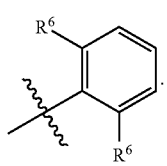 .

In some embodiments, the substituted ring B is

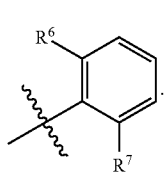 .

In some embodiments, the substituted ring B is

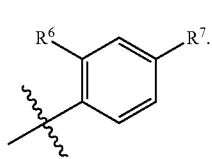 .

In some embodiments, the substituted ring B is

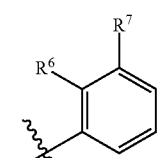 .

In some embodiments, the substituted ring B is

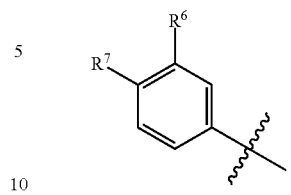 .

In some embodiments, the substituted ring B is

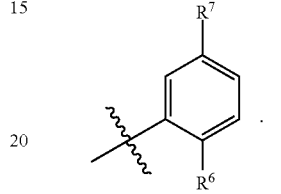 .

In some embodiments, the substituted ring B is

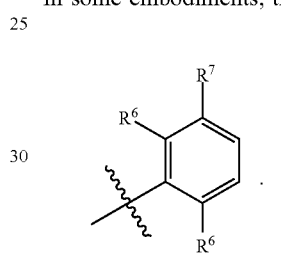 .

In some embodiments, the substituted ring B is

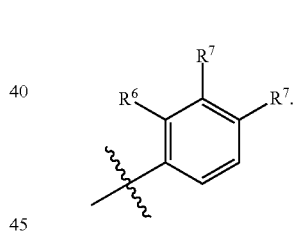 .

In some embodiments, the substituted ring B is

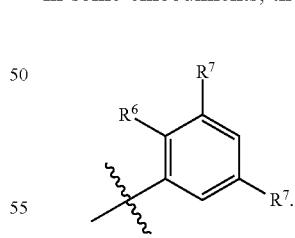 .

In some embodiments, the substituted ring B is

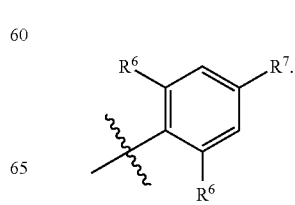 .

In some embodiments, the substituted ring B is

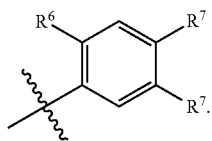

In some embodiments, the substituted ring B is

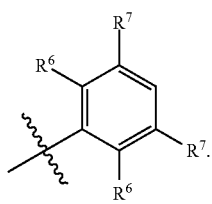

In some embodiments, the substituted ring B is

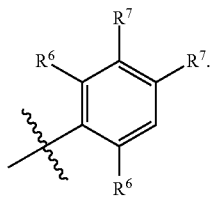

In some embodiments, the substituted ring B is

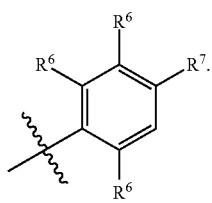

In some embodiments, the substituted ring B is

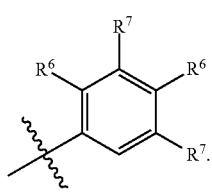

In some embodiments, the substituted ring B is

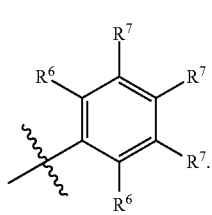

In some embodiments, the substituted ring B is

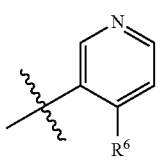

In some embodiments, the substituted ring B is

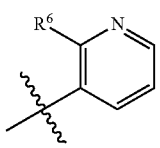

In some embodiments, the substituted ring B is

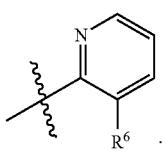

In some embodiments, the substituted ring B is

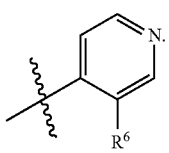

In some embodiments, the substituted ring B is

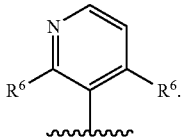

In some embodiments, the substituted ring B is

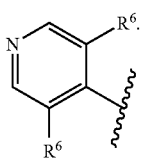

In some embodiments, the substituted ring B is

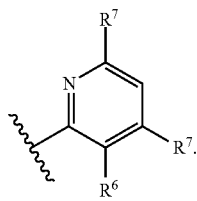

In some embodiments, the substituted ring B is

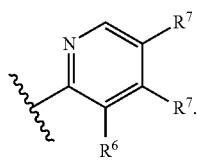

In some embodiments, the substituted ring B is

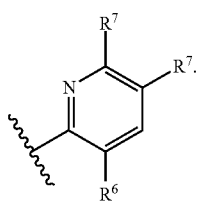

In some embodiments, the substituted ring B is

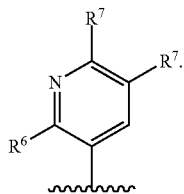

In some embodiments, the substituted ring B is

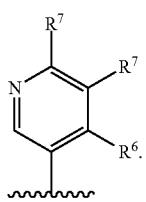

In some embodiments, the substituted ring B is

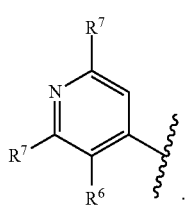

In some embodiments, the substituted ring B is

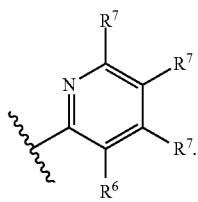

In some embodiments, the substituted ring B is

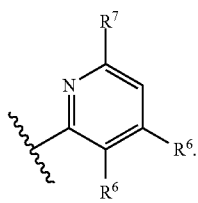

In some embodiments, the substituted ring B is

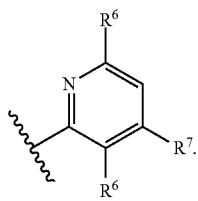

In some embodiments, the substituted ring B is

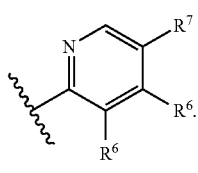

In some embodiments, the substituted ring B is

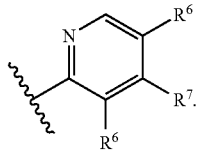

In some embodiments, the substituted ring B is

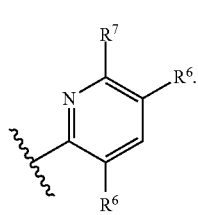

In some embodiments, the substituted ring B is

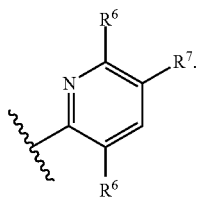

In some embodiments, the substituted ring B is

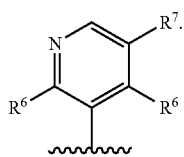

In some embodiments, the substituted ring B is

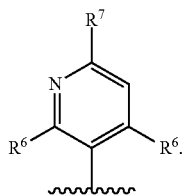

In some embodiments, the substituted ring B is

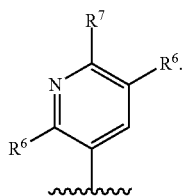

In some embodiments, the substituted ring B is

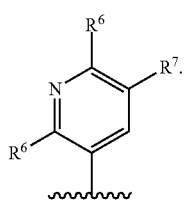

In some embodiments, the substituted ring B is

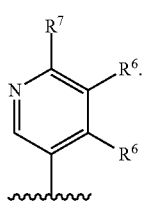

In some embodiments, the substituted ring B is

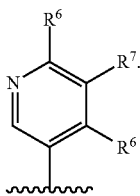

In some embodiments, the substituted ring B is

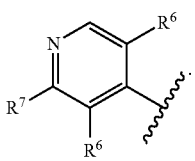

In some embodiments, the substituted ring B is

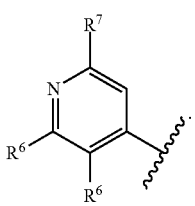

In some embodiments, the substituted ring B is

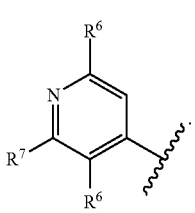

In some embodiments, the substituted ring B is

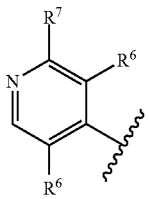

In some embodiments, the substituted ring B is

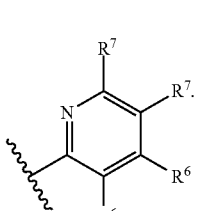

In some embodiments, the substituted ring B is

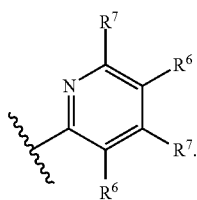

In some embodiments, the substituted ring B is

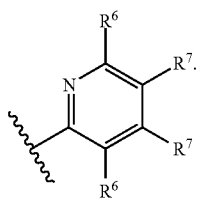

In some embodiments, the substituted ring B is

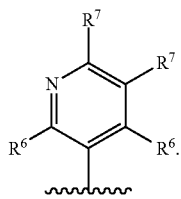

In some embodiments, the substituted ring B is

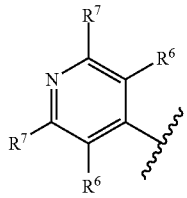

In some embodiments, the substituted ring B is

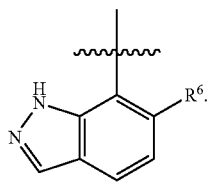

In some embodiments, the substituted ring B is

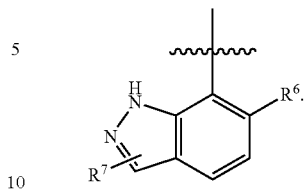

In some embodiments, the substituted ring B is

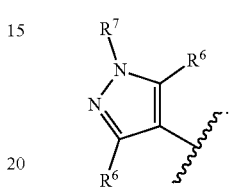

In some embodiments, the substituted ring B is

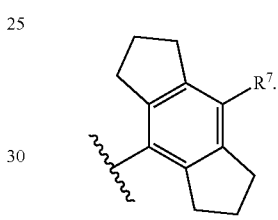

In some embodiments, the substituted ring B is

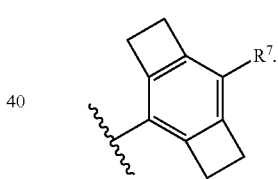

In some embodiments, the substituted ring B is

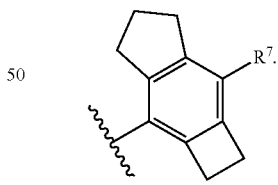

In some embodiments, the substituted ring B is

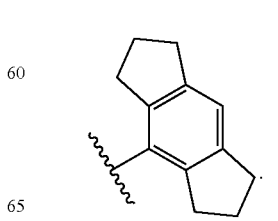

In some embodiments, the substituted ring B is


In some embodiments, the substituted ring B is

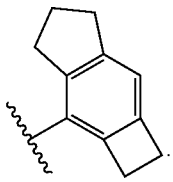

In some embodiments, the substituted ring B is

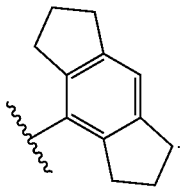 [SMILES: *c1c2c(cc3c1CCC3)CCC2]

In some embodiments, the substituted ring B is

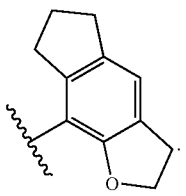 [SMILES: *c1c2c(cc3c1OCC3)CCC2]

In some embodiments, the substituted ring B is

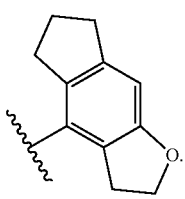 [SMILES: *c1c2c(cc3c1CCO3)CCC2]

In some embodiments, the substituted ring B is

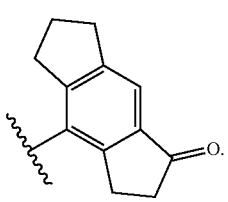 [SMILES: *c1c2c(cc3c1CCC3=O)CCC2]

In some embodiments, the substituted ring B is

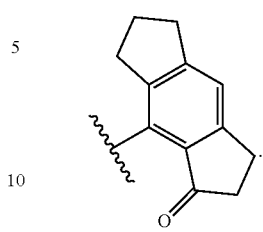

In some embodiments, the substituted ring B is

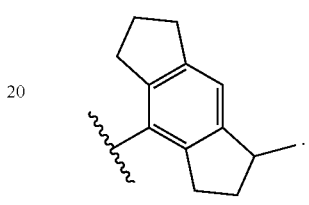

In some embodiments, the substituted ring B is

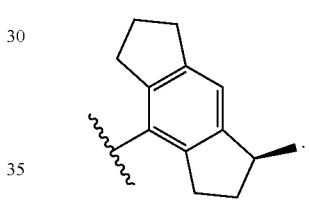

In some embodiments, the substituted ring B is

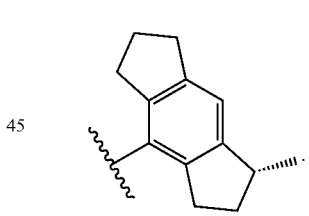

In some embodiments, the substituted ring B is

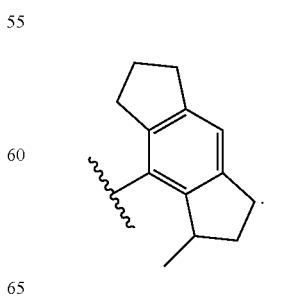

In some embodiments, the substituted ring B is

In some embodiments, the substituted ring B is

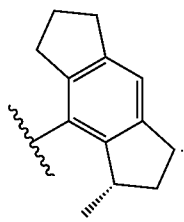 [SMILES: *c1c2c(cc3c1[C@@H](C)CC3)CCC2]

In some embodiments, the substituted ring B is

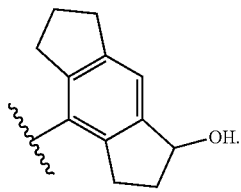 [SMILES: *c1c2c(cc3c1CCC3O)CCC2]

In some embodiments, the substituted ring B is

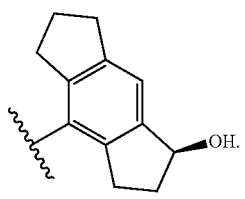 [SMILES: *c1c2c(cc3c1CC[C@@H]3O)CCC2]

In some embodiments, the substituted ring B is

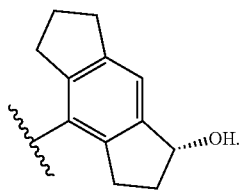 [SMILES: *c1c2c(cc3c1CC[C@H]3O)CCC2]

In some embodiments, the substituted ring B is

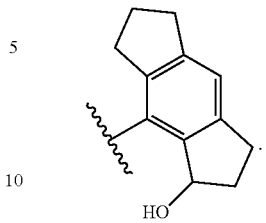

In some embodiments, the substituted ring B is

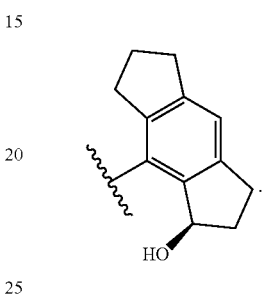

In some embodiments, the substituted ring B is

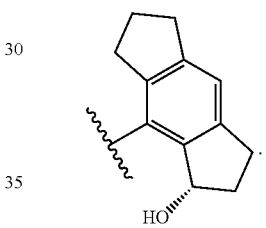

In some embodiments, the substituted ring B is

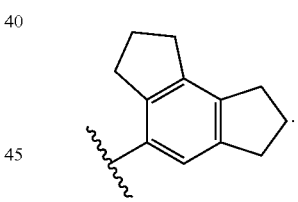

In some embodiments, the substituted ring B is

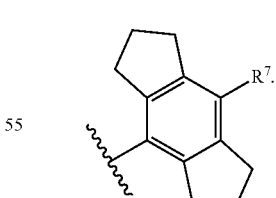

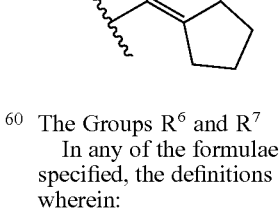

The Groups $R^6$ and $R^7$

In any of the formulae disclosed herein, unless otherwise specified, the definitions of $R^6$ and $R^7$ encompass situations wherein:
  (a) each occurrence of $R^6$ and each occurrence of $R^7$ is a monovalent substituent as described elsewhere herein;
  (b) when o=p, and each pair of $R^6$ and $R^7$ are on adjacent carbon atoms, each pair of $R^6$ and $R^7$ taken together with atom to which each is attached forms an independently selected carbocyclic or heterocyclic ring as described elsewhere herein;
and
(c) one or more pairs of $R^6$ and $R^7$ on adjacent carbon atoms, taken together with the atom to which each is attached, form one or more independently selected carbocyclic or heterocyclic ring as described elsewhere herein; and each remaining occurrences of $R^6$ and $R^7$ (inclusive of pair(s) of $R^6$ and $R^7$ on adjacent atoms) is independently a monovalent substituent as described herein.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl,
$C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to -seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl,
$C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to -seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_6$ aliphatic carbocyclic ring or at least one 5- to 6-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)$ $C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,

R$^6$ and R$^7$ are each independently selected from C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO (5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, C$_3$-C$_7$ cycloalkyl and 3- to 7-membered heterocycloalkyl, wherein the C$_3$-C$_7$ cycloalkyl, C$_1$-C$_6$ haloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,

R$^6$ and R$^7$ are each independently selected from C$_1$-C$_6$ alkyl, halo, CN, NO$_2$, COC$_1$-C$_6$ alkyl, CO$_2$C$_1$-C$_6$ alkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, C$_3$-C$_7$ cycloalkyl and 3- to 7-membered heterocycloalkyl, wherein the C$_1$-C$_6$ alkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments,

R$^6$ and R$^7$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, C$_3$-C$_7$ cycloalkyl and 3- to 7-membered heterocycloalkyl, wherein the C$_1$-C$_6$ alkyl, C$_1$-C$_6$ haloalkyl, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are unsubstituted;

or at least one pair of R$^6$ and R$^7$ on adjacent atoms, taken together with the atoms connecting them, independently form at least one C$_4$-C$_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more $C_1$-$C_6$ alkyl.

In some embodiments, two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of these embodiments, one pair of $R^6$ and $R^7$ on adjacent atoms, taken together with the atoms connecting them, form one $C_4$-$C_7$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain embodiments, one pair of $R^6$ and $R^7$ on adjacent atoms, taken together with the atoms connecting them, form one $C_4$-$C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of the foregoing embodiments, a second pair of $R^6$ and $R^7$ on adjacent atoms, taken together with the atoms connecting them, form one $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=0; and $R^6$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, o=1; p=1; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, o=1 or 2; p=1, 2, or 3; and $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, o=2; p=1; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ (e.g., $C_4$-$C_6$) carbocyclic ring (e.g., aliphatic carbocyclic ring) or at least one 5-to-7-membered (e.g., 5-to-6-membered) heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_1$-$C_{10}$ aryl, and $CONR^8R^9$.

In some embodiments, o=1 or 2; p=1, 2, or 3; and
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_1$-$C_6$ carbocyclic ring, wherein the carbocyclic ring is optionally independently substituted with one or more hydroxy or oxo.

In some embodiments, o=1 or 2; p=1, 2, or 3; and
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo.

In some embodiments, o=1 or 2; p=1, 2, or 3; and
one $R^6$ and one $R^7$ are on adjacent atoms, and taken together with the atoms connecting them, form a $C_1$-$C_6$ carbocyclic ring or a 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and
one $R^6$ and one $R^7$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and
one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, one pair of one $R^6$ and one $R^7$ taken together with the atoms connecting them independently form a $C_4$ carbocyclic ring, and the other pair of one $R^6$ and one $R^7$ taken together with the atoms connecting them independently form a $C_5$ carbocyclic ring, wherein each of $C_4$ and $C_5$ carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, one pair of one $R^6$ and one $R^7$ taken together with the atoms connecting them independently form a $C_5$ carbocyclic ring, and the other pair of one $R^6$ and one $R^7$ taken together with the atoms connecting them independently form a 5- to 8-membered heterocyclic ring containing 1 or 2 heteroatoms independently selected from O, N, and S (e.g., a 5-membered heterocyclic ring, e.g., 5-membered heterocyclic ring containing 1 heteroatom), wherein each of carbocyclic and heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

In some embodiments, o=2; and p=2 or 3; and two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of these embodiments, one pair of $R^6$ and $R^7$ on adjacent atoms, taken together with the atoms connecting them, form one $C_4$-$C_7$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain embodiments, one pair of $R^6$ and $R^7$ on adjacent atoms, taken together with the atoms connecting them, form one $C_4$-$C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of the foregoing embodiments, a second pair of $R^6$ and $R^7$ on adjacent atoms, taken together with the atoms connecting them, form one $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

Particular Embodiments Wherein o=1; p=0:

In some embodiments, $R^6$ is $C_1$-$C_6$ alkyl. In some embodiments, $R^6$ is isopropyl. In some embodiments, $R^6$ is ethyl. In some embodiments, $R^6$ is methyl. In some embodiments, $R^6$ is $C_1$-$C_6$ alkyl substituted with one or more halo. In some embodiments, $R^6$ is trifluoromethyl. In some embodiments, $R^6$ is trifluoromethoxy. In some embodiments, $R^6$ is $C_3$-$C_7$ cycloalkyl. In some embodiments, $R^6$ is cyclopropyl. In some embodiments, $R^6$ is halo. In some embodiments, $R^6$ is chloro. In some embodiments, $R^6$ is fluoro. In some embodiments, $R^6$ is cyano. In some embodiments, $R^6$ is attached to a carbon of an aryl ring B. In some embodiments, $R^6$ is attached to a carbon of a heteroaryl ring B. In some embodiments, $R^6$ is attached to a nitrogen of a heteroaryl ring B.

Particular Embodiments Wherein o=1 or 2; p=1, 2, or 3:

In some embodiments, at least one $R^6$ is $C_1$-$C_6$ alkyl, and at least one $R^7$ is $C_1$-$C_6$ alkyl optionally substituted with one or more halo. In some embodiments, at least one $R^6$ is $C_1$-$C_6$ alkyl and at least one $R^7$ is $C_1$-$C_6$ alkyl. In some embodiments, at least one $R^6$ is isopropyl and at least one $R^7$ is methyl. In some embodiments, at least one $R^6$ is isopropyl and at least one $R^7$ is isopropyl. In some embodiments, o=1; p=1; $R^6$ is isopropyl; and $R^7$ is isopropyl. In some embodiments, at least one $R^6$ is $C_1$-$C_6$ alkyl, and at least one $R^7$ is $C_1$-$C_6$ alkyl substituted with one or more halo. In some embodiments, at least one $R^6$ is isopropyl and at least one $R^7$ is trifluoromethyl. In some embodiments, at least one $R^6$ is $C_1$-$C_6$ alkyl, and at least one $R^7$ is $C_3$-$C_7$ cycloalkyl. In some embodiments, at least one $R^6$ is isopropyl and at least one $R^7$ is cyclopropyl. In some embodiments, o=1; p=1; $R^6$ is isopropyl; and $R^7$ is cyclopropyl. In some embodiments, at least one $R^6$ is $C_1$-$C_6$ alkyl, and at least one $R^7$ is halo. In some embodiments, at least one $R^6$ is isopropyl and at least one $R^7$ is halo. In some embodiments, at least one $R^6$ is isopropyl and at least one $R^7$ is chloro. In some embodiments, at least one $R^6$ is isopropyl and at least one $R^7$ is fluoro. In some embodiments, o=1; p=1; $R^6$ is isopropyl; and $R^7$ is chloro. In some embodiments, o=2; p=1; at least one $R^6$ is isopropyl; and $R^7$ is chloro.

In some embodiments, o=1; p=1; $R^6$ is isopropyl; and $R^7$ is fluoro. In some embodiments, o=2; p=1; at least one $R^6$ is isopropyl; and $R^7$ is fluoro. In some embodiments, o=2; p=2; at least one $R^6$ is isopropyl; and at least one $R^7$ is fluoro. In some embodiments, o=2; p=2; at least one $R^6$ is isopropyl; one $R^7$ is fluoro; and the other $R^7$ is cyano. In some embodiments, o=2; p=3; at least one $R^6$ is isopropyl; two $R^7$ are fluoro; and one $R^7$ is chloro. In some embodiments, o=2; p=1; at least one $R^6$ is ethyl; and $R^7$ is fluoro. In some embodiments, o=2; p=1; one $R^6$ is isopropyl; the other $R^6$ is trifluoromethyl; and $R^7$ is chloro. In some embodiments, at least one $R^6$ is $C_1$-$C_6$ alkyl, and at least one $R^7$ is cyano. In some embodiments, at least one $R^6$ is isopropyl and at least one $R^7$ is cyano. In some embodiments, o=1; p=1; $R^6$ is isopropyl; and $R^7$ is cyano. In some embodiments, o=2; p=1; at least one $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl. In some embodiments, at least one $R^6$ is cyclopropyl, and at least one $R^7$ is cyclopropyl. In some embodiments, at least one $R^6$ is $C_3$-$C_7$ cycloalkyl, and at least one $R^7$ is halo. In some embodiments, at least one $R^6$ is cyclopropyl and at least one $R^7$ is halo. In some embodiments, at least one $R^6$ is cyclopropyl and at least one $R^7$ is chloro. In some embodiments, at least one $R^6$ is cyclopropyl and at least one $R^7$ is fluoro. In some embodiments, o=1; p=1; $R^6$ is cyclopropyl; and $R^7$ is chloro. In some embodiments, o=1; p=1; $R^6$ is cyclopropyl; and $R^7$ is fluoro. In some embodiments, at least one $R^6$ is $C_1$-$C_6$ alkyl, and at least one $R^7$ is $C_1$-$C_6$ alkoxy optionally substituted with one or more halo. In some embodiments, at least one $R^6$ is isopropyl, and at least one $R^7$ is $C_1$-$C_6$ alkoxy. In some embodiments, at least one $R^6$ is isopropyl, and at least one $R^7$ is methoxy. In some embodiments, o=1; p=1; $R^6$ is isopropyl, and $R^7$ is methoxy. In some embodiments, o=2; p=1; at least one $R^6$ is isopropyl, and $R^7$ is methoxy. In some embodiments, at least one $R^6$ is $C_1$-$C_6$ alkyl, and at least one $R^7$ is $C_1$-$C_6$ alkoxy substituted with one or more halo. In some embodiments, at least one $R^6$ is isopropyl, and at least one $R^7$ is trifluoromethoxy. In some embodiments, at least one $R^6$ is isopropyl, and at least one $R^7$ is difluoromethoxy. In some embodiments, at least one $R^6$ is halo, and at least one $R^7$ is $C_1$-$C_6$ haloalkyl optionally substituted with hydroxy. In some embodiments, o=1; p=1; $R^6$ is chloro, and $R^7$ is trifluoromethyl. In some embodiments, at least one $R^6$ is halo, and at least one $R^7$ is $C_1$-$C_6$ haloalkoxy. In some embodiments, at least one $R^6$ is chloro, and at least one $R^7$ is trifluoromethoxy. In some embodiments, o=1; p=1; $R^6$ is chloro, and $R^7$ is trifluoromethoxy. In some embodiments, at least one $R^6$ is $C_1$-$C_6$ alkoxy; and at least one $R^7$ is halo. In some embodiments, o=1; p=2; $R^6$ is $C_1$-$C_6$ alkoxy; and at least one $R^7$ is chloro. In some embodiments, at least one $R^7$ is $C_1$-$C_6$ alkyl, and at least one $R^6$ is $C_1$-$C_6$ alkyl optionally substituted with one or more halo. In some embodiments, at least one $R^7$ is isopropyl and at least one $R^6$ is methyl. In some embodiments, at least one $R^7$ is $C_1$-$C_6$ alkyl, and at least one $R^6$ is $C_1$-$C_6$ alkyl substituted with one or more halo. In some embodiments, at least one $R^7$ is isopropyl and at least one $R^6$ is trifluoromethyl. In some embodiments, at least one $R^7$ is $C_1$-$C_6$ alkyl, and at least one $R^6$ is $C_3$-$C_7$ cycloalkyl. In some embodiments, at least one $R^7$ is isopropyl and at least one $R^6$ is cyclopropyl. In some embodiments, o=1; p=1; $R^7$ is isopropyl; and $R^6$ is cyclopropyl. In some embodiments, at least one $R^7$ is $C_1$-$C_6$ alkyl, and at least one $R^6$ is halo. In some embodiments, at least one $R^7$ is isopropyl and at least one $R^6$ is halo. In some embodiments, at least one $R^7$ is isopropyl and at least one $R^6$ is chloro. In some embodiments, at least one $R^7$ is isopropyl and at least one $R^6$ is fluoro. In some embodiments, o=1; p=1; $R^7$ is isopropyl; and $R^6$ is chloro. In some embodiments, o=2; p=1; $R^7$ is isopropyl; and at least one $R^6$ is chloro. In some embodiments, o=1; p=1; $R^7$ is isopropyl; and $R^6$ is fluoro. In some embodiments, o=2; p=1; $R^7$ is isopropyl; and at least one $R^6$ is fluoro. In some embodiments, o=2; p=2; $R^7$ is isopropyl; and at least one $R^6$ is fluoro. In some embodiments, o=2; p=2; at least one $R^7$ is isopropyl; one $R^6$ is fluoro; and the other $R^6$ is cyano. In some embodiments, o=2; p=1; $R^7$ is ethyl; and at least one $R^6$ is fluoro. In some embodiments, o=1; p=2; one $R^7$ is isopropyl; the other $R^7$ is trifluoromethyl; and $R^6$ is chloro. In some embodiments, at least one $R^7$ is $C_1$-$C_6$ alkyl, and at least one $R^6$ is cyano. In some embodiments, at least one $R^7$ is isopropyl and at least one $R^6$ is cyano. In some embodiments, o=1; p=1; $R^7$ is isopropyl; and $R^6$ is cyano. In some embodiments, o=2; p=1; $R^7$ is isopropyl; and at least one $R^6$ is cyano. In some embodiments, at least one $R^7$ is $C_3$-$C_7$ cycloalkyl, and at least one $R^6$ is $C_3$-$C_7$ cycloalkyl. In some embodiments, at least one $R^7$ is cyclopropyl, and at least one $R^6$ is cyclopropyl. In some embodiments, at least one $R^7$ is $C_3$-$C_7$ cycloalkyl, and at least one $R^6$ is halo. In some embodiments, at least one $R^7$ is cyclopropyl and at least one $R^6$ is halo. In some embodiments, at least one $R^7$ is cyclopropyl and at least one $R^6$ is chloro. In some embodiments, at least one $R^7$ is cyclopropyl and at least one $R^6$ is fluoro. In some embodiments, o=1; p=1; $R^7$ is cyclopropyl; and $R^6$ is chloro. In some embodiments, o=1; p=1; $R^7$ is cyclopropyl; and $R^6$ is fluoro. In some embodiments, at least one $R^7$ is $C_1$-$C_6$ alkyl, and at least one $R^6$ is $C_1$-$C_6$ alkoxy optionally substituted with one or more halo. In some embodiments, at least one $R^7$ is isopropyl, and at least one $R^6$ is $C_1$-$C_6$ alkoxy. In some embodiments, at least one $R^7$ is isopropyl, and at least one $R^6$ is methoxy. In some embodiments, o=1; p=1; $R^7$ is isopropyl, and $R^6$ is methoxy. In some embodiments, o=2; p=1; $R^7$ is isopropyl, and at least one $R^6$ is methoxy. In some embodiments, at least one $R^7$ is $C_1$-$C_6$ alkyl, and at least one $R^6$ is $C_1$-$C_6$ alkoxy substituted with one or more halo. In some embodiments, at least one $R^7$ is isopropyl, and at least one $R^6$ is trifluoromethoxy. In some embodiments, at least one $R^7$ is halo, and at least one $R^6$ is $C_1$-$C_6$ haloalkyl optionally substituted with one or more hydroxy. In some embodiments, o=1; p=1; $R^7$ is chloro, and $R^6$ is trifluoromethyl. In some embodiments, at least one $R^7$ is halo, and at least one $R^6$ is $C_1$-$C_6$ haloalkoxy. In some embodiments, at least one $R^7$ is chloro, and at least one $R^6$ is trifluoromethoxy. In some embodiments, o=1; p=1; $R^7$ is chloro, and $R^6$ is trifluoromethoxy. In some embodiments, at least one $R^7$ is $C_1$-$C_6$ alkoxy; and at least one $R^6$ is halo. In some embodiments, o=1; p=2; at least one $R^7$ is $C_1$-$C_6$ alkoxy; and $R^6$ is chloro. In some embodiments, $R^6$ and $R^7$ are each attached to a carbon of an aryl ring B. In some embodiments, $R^6$ and $R^7$ are each attached to a carbon of a heteroaryl ring B. In some embodiments, $R^6$ is attached to a carbon and $R^7$ is attached to a nitrogen of a heteroaryl ring B. In some embodiments, $R^7$ is attached to a carbon and $R^6$ is attached to a nitrogen of a heteroaryl ring B.

In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_5$ aliphatic carbocyclic ring.

In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_6$ aliphatic carbocyclic ring.

In some embodiments, $R^6$ and $R^7$ are on adjacent atoms, and taken together with the atoms connecting them, form a $C_6$ aromatic carbocyclic ring.

In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 5-membered heteroaromatic ring containing 1 or 2 heteroatoms independently selected from O, N, and S.

In some embodiments, $R^6$ and $R^7$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 6-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 6-membered heteroaromatic ring containing 1 or 2 heteroatoms independently selected from O, N, and S.

In some embodiments, one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S,
   wherein the ring is fused to the B ring at the 2- and 3-positions relative to the bond connecting the B ring to the NH(CO)group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring or a 5- to 8-membered heterocyclic ring containing 1 or 2 heteroatoms independently selected from O, N, and S,
   wherein the ring is fused to the B ring at the 2- and 3-positions relative to the bond connecting the B ring to the $NR^3$(CO) group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ aliphatic carbocyclic ring and the other pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_{4-8}$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 5- to 8-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3(CO)$ group, and the other of the two rings is fused to the B ring at the 5- and 6-positions relative to the bond connecting the B ring to the NH(CO) group.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3(CO)$ group, and the other of the two rings is fused to the B ring at the 4- and 5-positions relative to the bond connecting the B ring to the NH(CO) group.

In some embodiments, o=2; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_4$ aliphatic carbocyclic ring, and the other pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, and each pair of one $R^6$ and one $R^7$ taken together with the atoms connecting them form a $C_4$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_5$ aliphatic carbocyclic ring, and the other pair of one $R^6$ and one $R^7$ taken together with the atoms connecting them form a 5-membered heterocyclic ring containing 1 or 2 heteroatoms independently selected from O, N, and S.

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., Cl or F).

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

In some embodiments, one $R^7$ is pyrazolyl and is para to the bond connecting the B ring to the ring C of Formula AA. In some embodiments, one $R^7$ is 3-pyrazolyl and is para to the bond connecting the B ring to the ring C of Formula AA. In some embodiments, one $R^7$ is 4-pyrazolyl and is para to the bond connecting the B ring to the ring C of Formula AA. In some embodiments, one $R^7$ is 5-pyrazolyl and is para to the bond connecting the B ring to the ring C of Formula AA. In some embodiments, one $R^7$ is thiazolyl and is para to the bond connecting the B ring to the ring C of Formula AA. In some embodiments, one $R^7$ is 4-thiazolyl and is para to the bond connecting the B ring to the ring C of Formula AA. In some embodiments, one $R^7$ is 5-thiazolyl and is para to the bond connecting the B ring to the ring C of Formula AA. In some embodiments, one $R^7$ is furyl and is para to the bond connecting the B ring to the ring C of Formula AA. In some embodiments, one $R^7$ is 2-furyl and is para to the bond connecting the B ring to the ring C of Formula AA. In some embodiments, one $R^7$ is thiophenyl and is para to the bond connecting the B ring to the ring C of Formula AA. In some embodiments, one $R^7$ is 2-thiophenyl and is para to the bond connecting the B ring to ring C of Formula AA. In some embodiments, one $R^7$ is phenyl and is para to the bond connecting the B ring to the ring C of Formula AA. In some embodiments, one $R^7$ is cycloalkenyl (e.g., cyclopentenyl, e.g., 1-cyclopentenyl) and is para to the bond connecting the B ring to the ring C of Formula AA.

In some embodiments, one $R^7$ is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the ring C of Formula AA.

In some embodiments, one $R^7$ is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the ring C of Formula AA.

In some embodiments, one $R^7$ is phenyl optionally substituted with one or more $C_6$-$C_{10}$ aryloxy (e.g., phenoxy) and is para to the bond connecting the B ring to the ring C of Formula AA.

In some embodiments, one $R^7$ is phenyl optionally substituted with one or more CN and is para to the bond connecting the B ring to the ring C of Formula AA.

In some embodiments, one $R^7$ is phenyl optionally substituted with one or more halo (e.g., F, Cl) and is para to the bond connecting the B ring to the ring C of Formula AA and is para to the bond connecting the B ring to the ring C of Formula AA.

In some embodiments, one $R^7$ is phenyl optionally substituted with one or more $COOC_1$-$C_6$ alkyl (e.g., $CO_2$t-Bu) and is para to the bond connecting the B ring to the ring C of Formula AA.

In some embodiments, one $R^7$ is phenyl optionally substituted with one or more $S(O_2)C_1$-$C_6$ alkyl (e.g., $S(O_2)$ methyl) and is para to the bond connecting the B ring to the ring C of Formula AA.

In some embodiments, one $R^7$ is phenyl optionally substituted with one or more 3- to 7-membered heterocycloalkyl (e.g., morpholinyl) and is para to the bond connecting the B ring to the ring C of Formula AA.

In some embodiments, one $R^7$ is phenyl optionally substituted with one or more $CONR^8R^9$ (e.g., unsubstituted amido) and is para to the bond connecting the B ring to the ring C of Formula AA.

In some embodiments, one $R^7$ is phenyl optionally substituted with one or more $C_1$-$C_6$ alkyl (e.g., methyl or propyl, e.g., 2-propyl) and with one or more halo (e.g., F, Cl) and is para to the bond connecting the B ring to the ring C of Formula AA and is para to the bond connecting the B ring to the ring C of Formula AA.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

— In some embodiments, the substituted ring B is

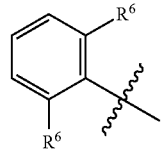

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl.

In some embodiments, the substituted ring B is

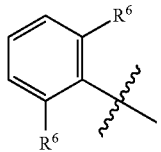

and each R⁶ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

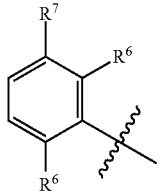

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC₁-$C_6$ alkyl, CONR⁸R⁹, 4- to 6-membered heterocycloalkyl, $C_6$-$C_{10}$ aryl, 5- to 10-membered heteroaryl, OCOC₁-$C_6$ alkyl, OCOC₆-$C_{10}$ aryl, OCO(5- to 10-membered heteroaryl), OCO(4- to 6-membered heterocycloalkyl), NHCOC₁-$C_6$ alkyl, NHCOC₆-$C_{10}$ aryl, NHCO(5- to 10-membered heteroaryl), NHCO(4- to 6-membered heterocycloalkyl), and NHCOC₂-$C_6$ alkynyl;
  wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC₁-$C_6$ alkyl, CO₂C₁-$C_6$ alkyl, CO₂C₃-$C_6$ cycloalkyl, OCOC₁-$C_6$ alkyl, OCOC₆-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C₁-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC₁-$C_6$ alkyl, $C_6$-$C_{10}$ aryl, and CONR⁸R⁹.

In some embodiments, the substituted ring B is

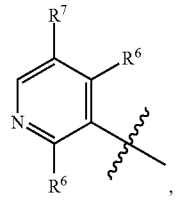

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC₁-$C_6$ alkyl, CONR⁸R⁹, 4- to 6-membered heterocycloalkyl, $C_6$-$C_{10}$ aryl, 5- to 10-membered heteroaryl, OCOC₁-$C_6$ alkyl, OCOC₆-$C_{10}$ aryl, OCO(5- to 10-membered heteroaryl), OCO(4- to 6-membered heterocycloalkyl), NHCOC₁-$C_6$ alkyl, NHCOC₆-$C_{10}$ aryl, NHCO(5- to 10-membered heteroaryl), NHCO(4- to 6-membered heterocycloalkyl), and NHCOC₂-$C_6$ alkynyl;
  wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC₁-$C_6$ alkyl, CO₂C₁-$C_6$ alkyl, CO₂C₃-$C_6$ cycloalkyl, OCOC₁-$C_6$ alkyl, OCOC₆-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C₁-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC₁-$C_6$ alkyl, $C_6$-$C_{10}$ aryl, and CONR⁸R⁹.

In some embodiments, the substituted ring B is

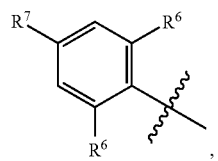

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In some embodiments, $R^6$ is isopropyl. In some embodiments, $R^7$ is halo (e.g., F).

In some embodiments, the substituted ring B is

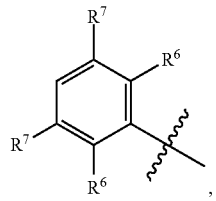

, wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, the substituted ring B is

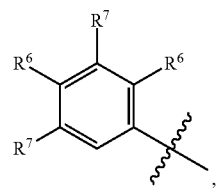

, wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, the substituted ring B is

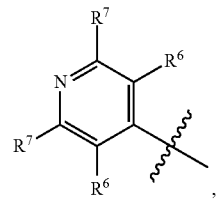

, wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, the substituted ring B is

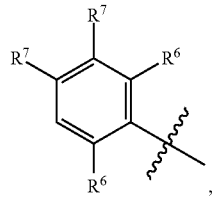

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form a $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, the substituted ring B is

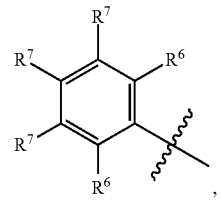

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;

The Group $R^{14}$

In some embodiments, $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$. In some embodiments, $R^{14}$ is hydrogen or $C_1$-$C_6$ alkyl. In some embodiments, $R^{14}$ is hydrogen, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$. In some embodiments, $R^{14}$ is hydrogen. In some embodiments, $R^{14}$ is $C_1$-$C_6$ alkyl. In some embodiments, $R^{14}$ is methyl. In some embodiments, $R^{14}$ is 5- to 10-membered monocyclic or bicyclic heteroaryl optionally independently substituted with 1 or 2 $R^6$. In some embodiments, $R^{14}$ is $C_6$-$C_{10}$ monocyclic or bicyclic aryl optionally independently substituted with 1 or 2 $R^6$.

The Group $R^{10}$

In some embodiments, $R^{10}$ is $C_1$-$C_6$ alkyl. In some embodiments, $R^{10}$ is methyl. In some embodiments, $R^{10}$ is ethyl.

The Groups $R^8$ and $R^9$

In some embodiments, each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is hydrogen, In some embodiments, each $R^8$ at each occurrence is hydrogen and each $R^9$ at each occurrence is $C_1$-$C_6$ alkyl. In some embodiments, each $R^8$ at each occurrence is hydrogen and each $R^9$ at each occurrence is methyl. In some embodiments, each $R^8$ at each occurrence is hydrogen and each $R^9$ at each occurrence is ethyl. In some embodiments, each of $R^8$ and $R^9$ at each occurrence is methyl. In some embodiments, each of $R^8$ and $R^9$ at each occurrence is ethyl. In some embodiments, $R^8$ and $R^9$ taken together with the nitrogen they are attached to form a 3-membered ring. In some embodiments, $R^8$ and $R^9$ taken together with the nitrogen they are attached to form a 4-membered ring. In some embodiments, $R^8$ and $R^9$ taken together with the nitrogen they are attached to form a 5-membered ring. In some embodiments, $R^8$ and $R^9$ taken together with the nitrogen they are attached to form a 6-membered ring optionally containing one or more oxygen atoms in addition to the nitrogen they are attached to. In some embodiments, $R^8$ and $R^9$ taken together with the nitrogen they are attached to form a 6-membered ring optionally containing one or more nitrogen atoms in addition to the nitrogen they are attached to. In some embodiments, $R^8$ and $R^9$ taken together with the nitrogen they are attached to form a 7-membered ring.

The Group $R^{13}$

In some embodiments, $R^{13}$ is $C_1$-$C_6$ alkyl. In some embodiments, $R^{13}$ is methyl. In some embodiments, $R^{13}$ is ethyl. In some embodiments, $R^{13}$ is $C_6$-$C_{10}$ aryl. In some embodiments, $R^{13}$ is phenyl. In some embodiments, $R^{13}$ is 5- to 10-membered heteroaryl.

The Groups $R^{11}$ and $R^{12}$

In some embodiments, each of $R^{11}$ and $R^{12}$ at each occurrence is independently selected from hydrogen and $C_1$-$C_6$ alkyl. In some embodiments, each of $R^{11}$ and $R^{12}$ at each occurrence is hydrogen, In some embodiments, each $R^{11}$ at each occurrence is hydrogen and each $R^{12}$ at each occurrence is $C_1$-$C_6$ alkyl. In some embodiments, each $R^{11}$ at each occurrence is hydrogen and each $R^{12}$ at each occurrence is methyl. In some embodiments, each $R^{11}$ at each occurrence is hydrogen and each $R^{12}$ at each occurrence is ethyl. In some embodiments, each of $R^{11}$ and $R^{12}$ at each occurrence is methyl. In some embodiments, each of $R^{11}$ and $R^{12}$ at each occurrence is ethyl.

In some embodiments of the compound of formula AA, the substituted ring A is

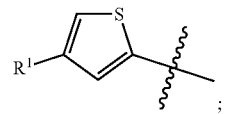

and R is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

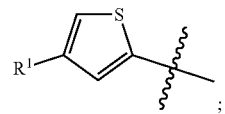

and R¹ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

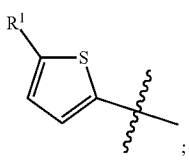

and R¹ is selected from:
  C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

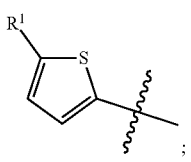

and R¹ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

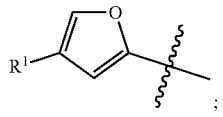

and R¹ is selected from:
  C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

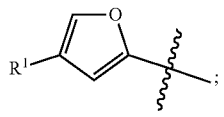

and R¹ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

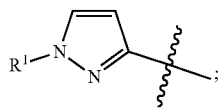

and R¹ is selected from:
  C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; $C_1$-$C_6$ haloalkyl; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; CONR⁸R⁹; $SF_5$; and $S(O_2)C_1$-$C_6$ alkyl.

In some embodiments of the compound of formula AA, the substituted ring A is

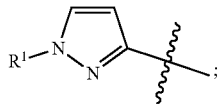

and $R^1$ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

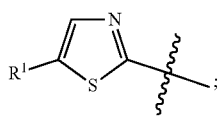

and $R^1$ is selected from:
  $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more NR⁸R⁹; 3- to 7-membered heterocycloalkyl substituted with one or more NR⁸R⁹; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; CONR⁸R⁹; $SF_5$; and $S(O_2)C_1$-$C_6$ alkyl.

In some embodiments of the compound of formula AA, the substituted ring A is

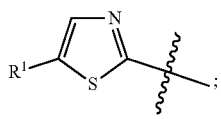

and $R^1$ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

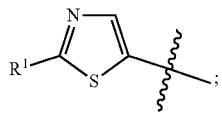

and $R^1$ is selected from:
  $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more NR⁸R⁹; 3- to 7-membered heterocycloalkyl substituted with one or more NR⁸R⁹; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; CONR⁸R⁹; $SF_5$; and $S(O_2)C_1$-$C_6$ alkyl.

In some embodiments of the compound of formula AA, the substituted ring A is

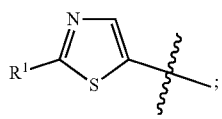

and $R^1$ is selected from:
  1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

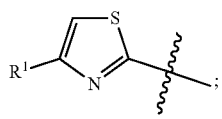

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

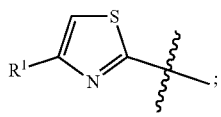

and R¹ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

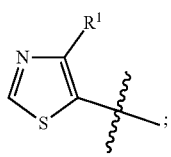

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

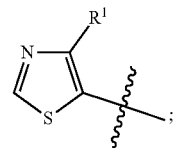

and R¹ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

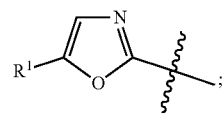

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

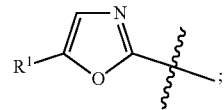

and R¹ is selected from:
1-hydroxy-2-methylpropan-2-yl; methyl; isopropyl; 2-hydroxy-2-propyl; hydroxymethyl; 1-hydroxy ethyl;

2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

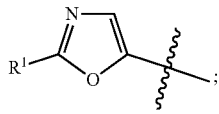

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

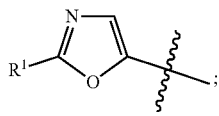

and $R^1$ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

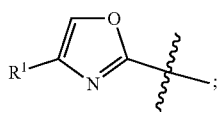

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

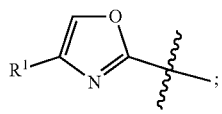

and $R^1$ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

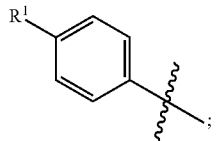

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl;

5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

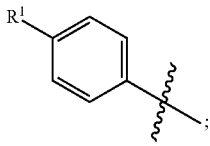

and $R^1$ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

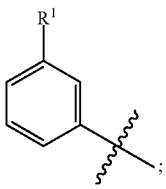

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

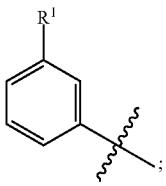

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

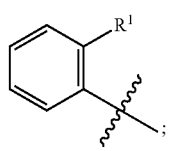

and $R^1$ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

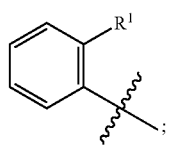

and $R^1$ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

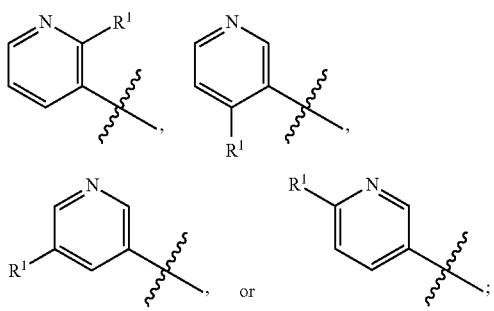

and R¹ is selected from:

C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

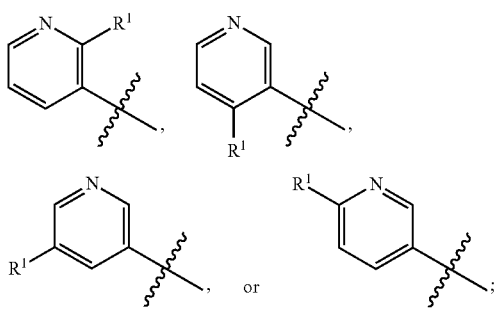

and R¹ is selected from:

1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino) ethyl; fluoro; chloro; phenyl; pyridyl; pyrazolyl; and S(O₂)CH₃.

In some embodiments of the compound of formula AA, the substituted ring A is

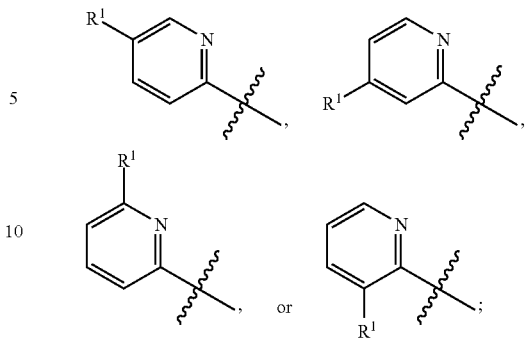

and R is selected from:

C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

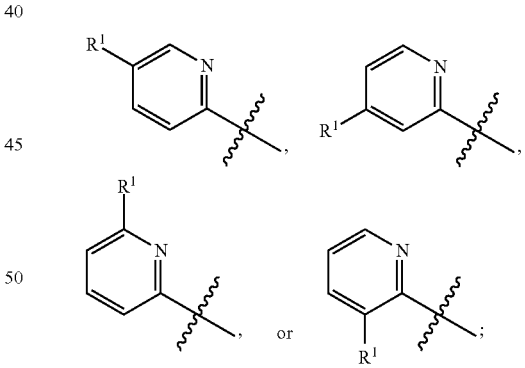

and R¹ is selected from:

1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino) ethyl; fluoro; chloro; phenyl; pyridyl; pyrazolyl; and S(O₂)CH₃.

In some embodiments of the compound of formula AA, the substituted ring A is

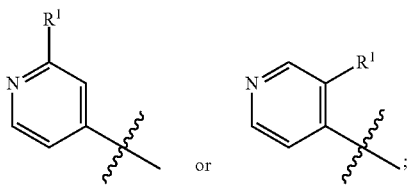

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

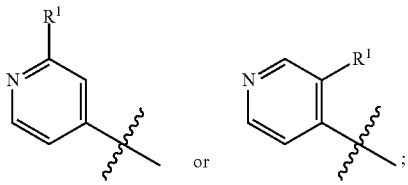

and R¹ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

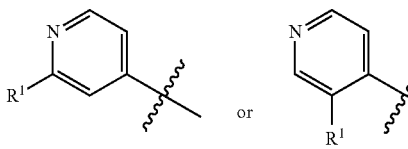

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

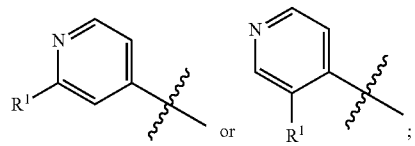

and R¹ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

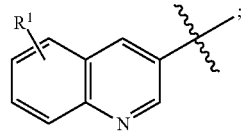

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; C₁-C₆ alkyl substituted with one or more NR⁸R⁹; and S(O₂)C₁-C₆ alkyl.

In some embodiments of the compound of formula AA, the substituted ring A is

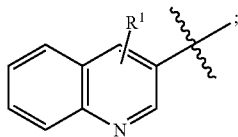

and R¹ is selected from:
1-hydroxy-2-methyl propan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; (dimethylamino)methyl; 1,3-dioxolan-2-yl; $COCH_3$; $COCH_2CH_3$; 2-methoxy-2-propyl; fluoro; chloro; phenyl; pyridyl; pyrazolyl; and $S(O_2)CH_3$.

In some embodiments of the compound of formula AA, the substituted ring A is

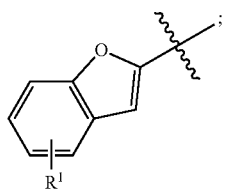

and R¹ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $C_1$-$C_6$ alkyl substituted with one or more $NR^8R^9$; and $S(O_2)C_1$-$C_6$ alkyl.

In some embodiments of the compound of formula AA, the substituted ring A is

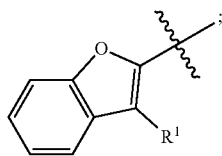

and R¹ is selected from:
1-hydroxy-2-methylpropan-2-yl; methyl; isopropyl; 2-hydroxy-2-propyl; hydroxymethyl; 1-hydroxy ethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; (dimethylamino)methyl; and $S(O_2)CH_3$.

In some embodiments of the compound of formula AA, the substituted ring A is

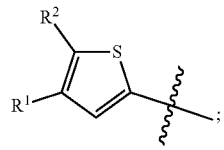

and R¹ and R² are one following combinations:
R¹ is $C_1$-$C_6$ alkyl optionally substituted with one or more hydroxy, and R² is $C_1$-$C_6$ alkyl optionally substituted with one or more hydroxy; R¹ is $C_1$-$C_6$ alkyl optionally substituted with one or more hydroxy, and R² is $C_6$-$C_{10}$ aryl; R¹ is $C_1$-$C_6$ alkyl optionally substituted with one or more hydroxy, and R² is 5- to 10-membered heteroaryl; R¹ is $C_1$-$C_6$ alkyl optionally substituted with one or more hydroxy, and R² is $SF_5$; R¹ is $C_1$-$C_6$ alkyl optionally substituted with one or more hydroxy, and R² is $S(O_2)C_1$-$C_6$ alkyl; R¹ is $C_1$-$C_6$ alkyl optionally substituted with one or more hydroxy, and R² is halo; R¹ is $C_3$-$C_7$ cycloalkyl optionally substituted with one or more hydroxy, and R² is $C_1$-$C_6$ alkyl; R¹ is 3- to 7-membered heterocycloalkyl optionally substituted with one or more hydroxy, and R² is $C_1$-$C_6$ alkyl; R¹ is 3- to 7-membered heterocycloalkyl optionally substituted with one or more hydroxy, and R² is halo; R¹ is $C_1$-$C_6$ alkyl optionally substituted with one or more oxo, and R² is methyl; R¹ is $C_1$-$C_6$ alkyl optionally substituted with one or more $C_1$-$C_6$ alkoxy, and R² is $C_1$-$C_6$ alkyl; R¹ is $C_1$-$C_6$ alkyl optionally substituted with one or more $NR^8R^9$, and R² is $C_1$-$C_6$ alkyl; R¹ is $C_1$-$C_6$ alkyl optionally substituted with one or more $NR^8R^9$, and R² is halo; R² is $C_1$-$C_6$ alkyl optionally substituted with one or more hydroxy, and R¹ is $C_6$-$C_{10}$ aryl; R² is $C_1$-$C_6$ alkyl optionally substituted with one or more hydroxy, and R¹ is 5- to 10-membered heteroaryl; R² is $C_1$-$C_6$ alkyl optionally substituted with one or more hydroxy, and R¹ is $SF_5$. R² is $C_1$-$C_6$ alkyl optionally substituted with one or more hydroxy, and R¹ is $S(O_2)C_1$-$C_6$ alkyl; R² is $C_1$-$C_6$ alkyl optionally substituted with one or more hydroxy, and R¹ is halo; R² is $C_3$-$C_7$ cycloalkyl optionally substituted with one or more hydroxy, and R¹ is $C_1$-$C_6$ alkyl; R² is 3- to 7-membered heterocycloalkyl optionally substituted with one or more hydroxy, and R¹ is $C_1$-$C_6$ alkyl; R² is 3- to 7-membered heterocycloalkyl optionally substituted with one or more hydroxy, and R¹ is halo; R² is $C_1$-$C_6$ alkyl optionally substituted with one or more oxo, and R¹ is methyl; R² is $C_1$-$C_6$ alkyl optionally substituted with one or more $C_1$-$C_6$ alkoxy, and R¹ is $C_1$-$C_6$ alkyl; R² is $C_1$-$C_6$ alkyl optionally substituted with one or more $NR^8R^9$, and R¹ is $C_1$-$C_6$ alkyl; R² is $C_1$-$C_6$ alkyl optionally substituted with one or more $NR^8R^9$, and R¹ is halo.

In some embodiments of the compound of formula AA, the substituted ring A is

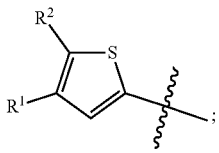

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^2$ is (dimethylamino)methyl, and $R^1$ is methyl; $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

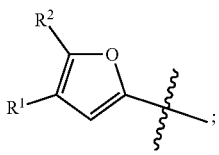

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl. $R^2$ is $C_1$-$C_6$ alkyl optionally substituted with one or more $NR^8R^9$, and $R^1$ is $C_1$-$C_6$ alkyl; or $R^2$ is $C_1$-$C_6$ alkyl optionally substituted with one or more $NR^8R^9$, and $R^1$ is halo.

In some embodiments, of the compound of formula AA, the substituted ring A is

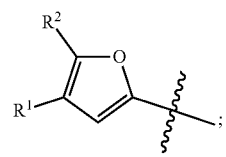

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxy ethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

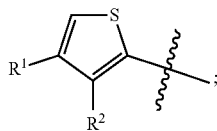

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

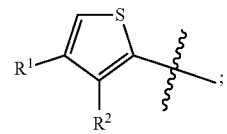

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl; $R^2$ is 1-hydroxy-2-methylpropan-2-yl, and $R^1$ is methyl; $R^2$ is 2-hydroxy-2-propyl and $R^1$ is methyl;

$R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

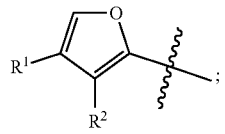

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

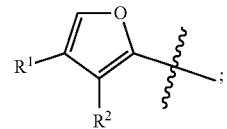

and $R^1$ and $R^2$ are one of the following combinations:

$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1- cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

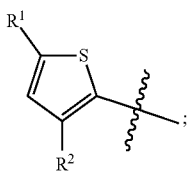

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

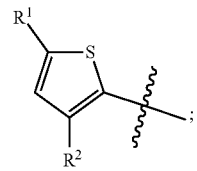

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

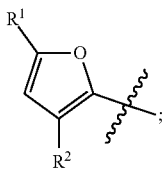

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

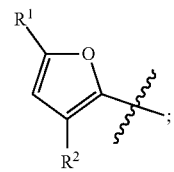

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

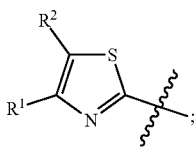

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

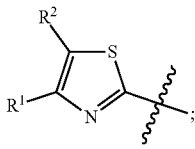

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

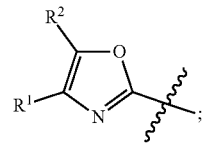

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

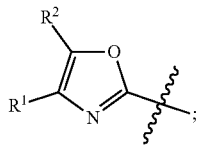

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxyethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxy ethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

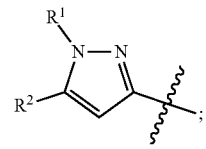

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and R² is methyl; R¹ is 2-methoxy-2-propyl, and R² is methyl; R¹ is (dimethylamino)methyl, and R² is methyl. R² is 1-hydroxy-2-methylpropan-2-yl, and R¹ is methyl; R² is 2-hydroxy-2-propyl and R¹ is methyl; R² is 2-hydroxy-2-propyl and R¹ is isopropyl; R² is 2-hydroxy-2-propyl and R¹ is 1-hydroxyethyl; R² is hydroxymethyl and R¹ is methyl; R² is 1-hydroxyethyl and R¹ is methyl; R² is 2-hydroxyethyl and R¹ is methyl; R² is 1-hydroxy-2-propyl and R¹ is methyl; R² is 2-hydroxy-2-propyl and R¹ is phenyl; R² is $C_1$-$C_6$ alkyl optionally substituted with one or more hydroxy, and R¹ is 5- to 10-membered heteroaryl; R² is 2-hydroxy-2-propyl and R¹ is pyridyl; R² is 2-hydroxy-2-propyl and R¹ is pyrazolyl; R² is $C_1$-$C_6$ alkyl optionally substituted with one or more hydroxy, and R¹ is $S(O_2)CH_3$; R² is 2-hydroxy-2-propyl and R¹ is chloro; R² is 2-hydroxy-2-propyl and R¹ is fluoro; R² is $C_3$-$C_7$ cycloalkyl optionally substituted with one or more hydroxy, and R¹ is $C_1$-$C_6$ alkyl; R² is 1-hydroxy-1-cyclopropyl, and R¹ is methyl; R² is 1-hydroxy-1-cyclobutyl, and R¹ is methyl; R² is 1-hydroxy-1-cyclopentyl, and R¹ is methyl; R² is 1-hydroxy-1-cyclohexyl, and R¹ is methyl; R² is morpholinyl, and R¹ is methyl; R² is 1,3-dioxolan-2-yl, and R¹ is methyl; R² is 1,3-dioxolan-2-yl, and R¹ is fluoro; R² is 1,3-dioxolan-2-yl, and R¹ is chloro; R² is $C_1$-$C_6$ alkyl optionally substituted with one or more oxo, and R¹ is methyl; R² is (dimethylamino)methyl, and R¹ is methyl; R² is $COCH_3$, and R¹ is methyl; or R² is 2-methoxy-2-propyl, and R¹ is methyl.

In some embodiments, of the compound of formula AA, the substituted ring A is

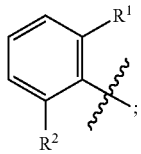

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy; R¹ is $C_1$-$C_6$ alkyl optionally substituted with one or more hydroxy, and R² is $C_6$-$C_{10}$ aryl; R¹ is $C_1$-$C_6$ alkyl optionally substituted with one or more hydroxy, and R² is 5- to 10-membered heteroaryl; R¹ is $C_1$-$C_6$ alkyl optionally substituted with one or more hydroxy, and R² is $SF_5$; R¹ is $C_1$-$C_6$ alkyl optionally substituted with one or more hydroxy, and R² is $S(O_2)C_1$-$C_6$ alkyl; R¹ is $C_1$-$C_6$ alkyl optionally substituted with one or more hydroxy, and R² is halo; R¹ is $C_3$-$C_7$ cycloalkyl optionally substituted with one or more hydroxy, and R² is $C_1$-$C_6$ alkyl; R¹ is 3- to 7-membered heterocycloalkyl optionally substituted with one or more hydroxy, and R² is $C_1$-$C_6$ alkyl; R¹ is 3- to 7-membered heterocycloalkyl optionally substituted with one or more hydroxy, and R² is halo; R¹ is $C_1$-$C_6$ alkyl optionally substituted with one or more oxo, and R² is methyl; R¹ is $C_1$-$C_6$ alkyl optionally substituted with one or more $C_1$-$C_6$ alkoxy, and R² is $C_1$-$C_6$ alkyl; R¹ is $C_1$-$C_6$ alkyl optionally substituted with one or more $NR^8R^9$, and R² is $C_1$-$C_6$ alkyl; R¹ is $C_1$-$C_6$ alkyl optionally substituted with one or more $NR^8R^9$, and R² is halo; R² is $C_1$-$C_6$ alkyl optionally substituted with one or more hydroxy, and R¹ is $C_6$-$C_{10}$ aryl; R² is $C_1$-$C_6$ alkyl optionally substituted with one or more hydroxy, and R¹ is 5- to 10-membered heteroaryl; R² is $C_1$-$C_6$ alkyl optionally substituted with one or more hydroxy, and R¹ is $SF_5$. R² is $C_1$-$C_6$ alkyl optionally substituted with one or more hydroxy, and R¹ is $S(O_2)C_1$-$C_6$ alkyl; R² is $C_1$-$C_6$ alkyl optionally substituted with one or more hydroxy, and R¹ is halo; R² is $C_3$-$C_7$ cycloalkyl optionally substituted with one or more hydroxy, and R¹ is $C_1$-$C_6$ alkyl; R² is 3- to 7-membered heterocycloalkyl optionally substituted with one or more hydroxy, and R¹ is $C_1$-$C_6$ alkyl; R² is 3- to 7-membered heterocycloalkyl optionally substituted with one or more hydroxy, and R¹ is halo; R² is $C_1$-$C_6$ alkyl optionally substituted with one or more $NR^8R^9$, and R¹ is $C_1$-$C_6$ alkyl; R² is $C_1$-$C_6$ alkyl optionally substituted with one or more $NR^8R^9$, and R¹ is halo; R² is $C_1$-$C_6$ alkyl optionally substituted with one or more oxo, and R¹ is methyl; or R² is $C_1$-$C_6$ alkyl optionally substituted with one or more $C_1$-$C_6$ alkoxy, and R¹ is $C_1$-$C_6$ alkyl.

In some embodiments, of the compound of formula AA, the substituted ring A is

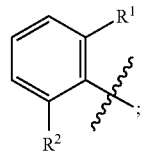

and R¹ and R² are one of the following combinations:
R¹ is 1-hydroxy-2-methylpropan-2-yl, and R² is methyl; R¹ is 2-hydroxy-2-propyl and R² is methyl; R¹ is 2-hydroxy-2-propyl and R² is isopropyl; R¹ is 2-hydroxy-2-propyl and R² is 2-hydroxy-2-propyl; R¹ is 2-hydroxy-2-propyl and R² is 1-hydroxyethyl; R¹ is hydroxymethyl and R² is methyl; R¹ is 1-hydroxyethyl and R² is methyl; R¹ is 2-hydroxyethyl and R² is methyl; R¹ is 1-hydroxy-2-propyl and R² is methyl; R¹ is 2-hydroxy-2-propyl and R² is phenyl; R¹ is 2-hydroxy-2-propyl and R² is pyridyl; R¹ is 2-hydroxy-2-propyl and R² is pyrazolyl; R¹ is 2-hydroxy-2-propyl, and R² is $S(O_2)CH_3$; R¹ is 2-hydroxy-2-propyl and R² is chloro; R¹ is 2-hydroxy-2-propyl and R² is fluoro; R¹ is 1-hydroxy-1-cyclopropyl, and R² is methyl; R¹ is 1-hydroxy-1-cyclobutyl, and R² is methyl; R¹ is 1-hydroxy-1-cyclopentyl, and R² is methyl; R¹ is 1-hydroxy-1-cyclohexyl, and R² is methyl; R¹ is morpholinyl, and R² is methyl; R¹ is 1,3-dioxolan-2-yl, and R² is methyl; R¹ is 1,3-dioxolan-2-yl, and R² is fluoro; R¹ is 1,3-dioxolan-2-yl, and R² is chloro; R¹ is $COCH_3$, and R² is methyl; R¹ is 2-methoxy-2-propyl, and R² is methyl; R¹ is (dimethylamino)methyl, and R² is methyl. R² is 1-hydroxy-2-methylpropan-2-yl, and R¹ is methyl; R² is 2-hydroxy-2-propyl and R¹ is methyl; R² is 2-hydroxy-2-propyl and R¹ is isopropyl; R² is 2-hydroxy-2-propyl and R¹ is 1-hydroxyethyl; R² is hydroxymethyl and R¹ is methyl; R² is 1-hydroxyethyl and R¹ is methyl; R² is 2-hydroxyethyl and R¹ is methyl; R² is 1-hydroxy-2-propyl and R¹ is methyl; R² is 2-hydroxy-2-propyl and R¹ is phenyl; R² is $C_1$-$C_6$ alkyl optionally substituted with one or more hydroxy, and R¹ is 5- to 10-membered heteroaryl; R² is 2-hydroxy-2-propyl and R¹ is pyridyl; R² is 2-hydroxy-2- propyl and R¹ is pyrazolyl; R² is $C_1$-$C_6$ alkyl optionally substituted with one or more hydroxy, and R¹ is $S(O_2)CH_3$; R² is 2-hydroxy-2-propyl and R¹ is chloro; R² is 2-hydroxy-2-propyl and R¹ is fluoro; R² is $C_3$-$C_7$ cycloalkyl optionally substituted with one or more hydroxy, and R¹ is $C_1$-$C_6$ alkyl; R² is 1-hydroxy-1-cyclopropyl, and R¹ is methyl; R² is 1-hydroxy-1-cyclobutyl, and R¹ is methyl; R² is 1-hydroxy-1-cyclopentyl, and R¹ is methyl; R² is 1-hydroxy-1-cyclohexyl, and R¹ is methyl; R² is morpholinyl, and R¹ is methyl; R² is 1,3-dioxolan-2-yl, and R¹ is methyl; R² is 1,3-dioxolan-2-yl, and R¹ is fluoro; R² is 1,3-dioxolan-2-yl, and R¹ is chloro; R² is $C_1$-$C_6$ alkyl optionally substituted with one or more oxo, and R¹ is methyl; R² is (dimethylamino)methyl, and R¹ is methyl; R² is $COCH_3$, and R¹ is methyl; or R² is 2-methoxy-2-propyl, and R¹ is methyl.

In some embodiments, of the compound of formula AA, the substituted ring A is

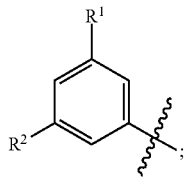

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy; R¹ is $C_1$-$C_6$ alkyl optionally substituted with one or more hydroxy, and R² is $C_6$-$C_{10}$ aryl; R¹ is $C_1$-$C_6$ alkyl optionally substituted with one or more hydroxy, and R² is 5- to 10-membered heteroaryl; R¹ is $C_1$-$C_6$ alkyl optionally substituted with one or more hydroxy, and R² is $SF_5$; R¹ is $C_1$-$C_6$ alkyl optionally substituted with one or more hydroxy, and R² is $S(O_2)C_1$-$C_6$ alkyl; R¹ is $C_1$-$C_6$ alkyl optionally substituted with one or more hydroxy, and R² is halo; R¹ is $C_3$-$C_7$ cycloalkyl optionally substituted with one or more hydroxy, and R² is $C_1$-$C_6$ alkyl; R¹ is 3- to 7-membered heterocycloalkyl optionally substituted with one or more hydroxy, and R² is $C_1$-$C_6$ alkyl; R¹ is 3- to 7-membered heterocycloalkyl optionally substituted with one or more hydroxy, and R² is halo; R¹ is $C_1$-$C_6$ alkyl optionally substituted with one or more oxo, and R² is methyl; R¹ is $C_1$-$C_6$ alkyl optionally substituted with one or more $C_1$-$C_6$ alkoxy, and R² is $C_1$-$C_6$ alkyl; R¹ is $C_1$-$C_6$ alkyl optionally substituted with one or more $NR^8R^9$, and R² is $C_1$-$C_6$ alkyl; R¹ is $C_1$-$C_6$ alkyl optionally substituted with one or more $NR^8R^9$, and R² is halo; R² is $C_1$-$C_6$ alkyl optionally substituted with one or more hydroxy, and R¹ is $C_6$-$C_{10}$ aryl; R² is $C_1$-$C_6$ alkyl optionally substituted with one or more hydroxy, and R¹ is 5- to 10-membered heteroaryl; R² is $C_1$-$C_6$ alkyl optionally substituted with one or more hydroxy, and R¹ is $SF_5$. R² is $C_1$-$C_6$ alkyl optionally substituted with one or more hydroxy, and R¹ is $S(O_2)C_1$-$C_6$ alkyl; R² is $C_1$-$C_6$ alkyl optionally substituted with one or more hydroxy, and R¹ is halo; R² is $C_3$-$C_7$ cycloalkyl optionally substituted with one or more hydroxy, and R¹ is $C_1$-$C_6$ alkyl; R² is 3- to 7-membered heterocycloalkyl optionally substituted with one or more hydroxy, and R¹ is $C_1$-$C_6$ alkyl; R² is 3- to 7-membered heterocycloalkyl optionally substituted with one or more hydroxy, and R¹ is halo; R² is $C_1$-$C_6$ alkyl optionally substituted with one or more $NR^8R^9$, and R¹ is $C_1$-$C_6$ alkyl; R² is $C_1$-$C_6$ alkyl optionally substituted with one or more $NR^8R^9$, and R¹ is halo; R² is $C_1$-$C_6$ alkyl optionally substituted with one or more oxo, and R¹ is methyl; or R² is $C_1$-$C_6$ alkyl optionally substituted with one or more $C_1$-$C_6$ alkoxy, and R¹ is $C_1$-$C_6$ alkyl.

In some embodiments, of the compound of formula AA, the substituted ring A is

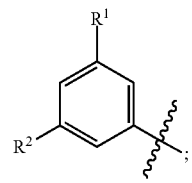

and R¹ and R² are one of the following combinations:
R¹ is 1-hydroxy-2-methylpropan-2-yl, and R² is methyl; R¹ is 2-hydroxy-2-propyl and R² is methyl; R¹ is 2-hydroxy-2-propyl and R² is isopropyl; R¹ is 2-hydroxy-2-propyl and R² is 2-hydroxy-2-propyl; R¹ is 2-hydroxy-2-propyl and R² is 1-hydroxyethyl; R¹ is hydroxymethyl and R² is methyl; R¹ is 1-hydroxyethyl and R² is methyl; R¹ is 2-hydroxyethyl and R² is methyl; R¹ is 1-hydroxy-2-propyl and R² is methyl; R¹ is 2-hydroxy-2-propyl and R² is phenyl; R¹ is 2-hydroxy-2-propyl and R² is pyridyl; R¹ is 2-hydroxy-2-propyl and R² is pyrazolyl; R¹ is 2-hydroxy-2-propyl, and R² is $S(O_2)CH_3$; R¹ is 2-hydroxy-2-propyl and R² is chloro; R¹ is 2-hydroxy-2-propyl and R² is fluoro; R¹ is 1-hydroxy-1-cyclopropyl, and R² is methyl; R¹ is 1-hydroxy-1-cyclobutyl, and R² is methyl; R¹ is 1-hydroxy-1-cyclopentyl, and R² is methyl; R¹ is 1-hydroxy-1-cyclohexyl, and R² is methyl; R¹ is morpholinyl, and R² is methyl; R¹ is 1,3-dioxolan-2-yl, and R² is methyl; R¹ is 1,3-dioxolan-2-yl, and R² is fluoro; R¹ is 1,3-dioxolan-2-yl, and R² is chloro; R¹ is $COCH_3$, and R² is methyl; R¹ is 2-methoxy-2-propyl, and R² is methyl; R¹ is (dimethylamino)methyl, and R² is methyl. R² is 1-hydroxy-2-methylpropan-2-yl, and R¹ is methyl; R² is 2-hydroxy-2-propyl and R¹ is methyl; R² is 2-hydroxy-2-propyl and R¹ is isopropyl; R² is 2-hydroxy-2-propyl and R¹ is 1-hydroxyethyl; R² is hydroxymethyl and R¹ is methyl; R² is 1-hydroxyethyl and R¹ is methyl; R² is 2-hydroxyethyl and R¹ is methyl; R² is 1-hydroxy-2-propyl and R¹ is methyl; R² is 2-hydroxy-2-propyl and R¹ is phenyl; R² is $C_1$-$C_6$ alkyl optionally substituted with one or more hydroxy, and R¹ is 5- to 10-membered heteroaryl; R² is 2-hydroxy-2-propyl and R¹ is pyridyl; R² is 2-hydroxy-2-propyl and R¹ is pyrazolyl; R² is $C_1$-$C_6$ alkyl optionally substituted with one or more hydroxy, and R¹ is $S(O_2)CH_3$; R² is 2-hydroxy-2-propyl and R¹ is chloro; R² is 2-hydroxy-2-propyl and R¹ is fluoro; R² is $C_3$-$C_7$ cycloalkyl optionally substituted with one or more hydroxy, and R¹ is $C_1$-$C_6$ alkyl; R² is 1-hydroxy-1-cyclopropyl, and R¹ is methyl; R² is 1-hydroxy-1-cyclobutyl, and R¹ is methyl; R² is 1-hydroxy-1-cyclopentyl, and R¹ is methyl; R² is 1-hydroxy-1-cyclohexyl, and R¹ is methyl; R² is morpholinyl, and R¹ is methyl; R² is 1,3-dioxolan-2-yl, and R¹ is methyl; R² is 1,3- dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

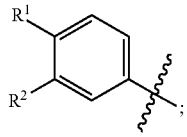

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

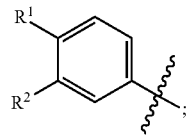

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxy ethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments, of the compound of formula AA, the substituted ring A is

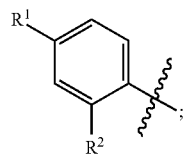

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

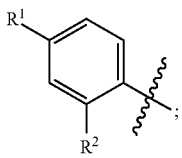

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxy ethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is (dimethylamino)methyl, and $R^1$ is methyl; $R^2$ is $C_1$-$C_6$ alkyl optionally substituted with one or more oxo, and $R^1$ is methyl; or $R^2$ is $COCH_3$, and $R^1$ is methyl.

In some embodiments, of the compound of formula AA, the substituted ring A is

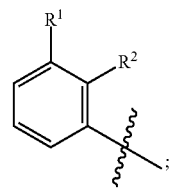

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

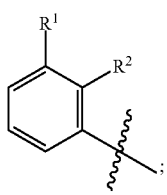

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxyethyl and $R^1$ is methyl; $R^2$ is 2-hydroxyethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $COCH_3$, and $R^1$ is methyl; or $R^2$ is 2-methoxy-2-propyl, and $R^1$ is methyl.

In some embodiments, of the compound of formula AA, the substituted ring A is

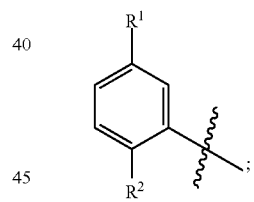

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy; $R^1$ is $C_1$-$C_6$ alkyl optionally substituted with one or more hydroxy, and $R^2$ is $C_6$-$C_{10}$ aryl; $R^1$ is $C_1$-$C_6$ alkyl optionally substituted with one or more hydroxy, and $R^2$ is 5- to 10-membered heteroaryl; $R^1$ is $C_1$-$C_6$ alkyl optionally substituted with one or more hydroxy, and $R^2$ is $SF_5$; $R^1$ is $C_1$-$C_6$ alkyl optionally substituted with one or more hydroxy, and $R^2$ is $S(O_2)C_1$-$C_6$ alkyl; $R^1$ is $C_1$-$C_6$ alkyl optionally substituted with one or more hydroxy, and $R^2$ is halo; $R^1$ is $C_3$-$C_7$ cycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is $C_1$-$C_6$ alkyl; $R^1$ is 3- to 7-membered heterocycloalkyl optionally substituted with one or more hydroxy, and $R^2$ is halo; $R^1$ is $C_1$-$C_6$ alkyl optionally substituted with one or more oxo, and $R^2$ is methyl; $R^1$ is $C_1$-$C_6$ alkyl optionally substituted with one or more $C_1$-$C_6$ alkoxy, and $R^2$ is $C_1$-$C_6$ alkyl; $R^1$ is $C_1$-$C_6$ alkyl optionally substituted with one or more $NR^8R^9$, and $R^2$ is $C_1$-$C_6$ alkyl; $R^1$ is $C_1$-$C_6$ alkyl optionally substituted with one or more $NR^8R^9$, and $R^2$ is halo; $R^2$ is $C_1$-$C_6$ alkyl optionally substituted with one or more hydroxy, and $R^1$ is $C_6$-$C_{10}$ aryl; $R^2$ is $C_1$-$C_6$ alkyl optionally substituted with one or more hydroxy, and $R^1$ is 5- to 10-membered heteroaryl; $R^2$ is $C_1$-$C_6$ alkyl optionally substituted with one or more hydroxy, and $R^1$ is $SF_5$. $R^2$ is $C_1$-$C_6$ alkyl optionally substituted with one or more hydroxy, and $R^1$ is $S(O_2)C_1$-$C_6$ alkyl; $R^2$ is $C_1$-$C_6$ alkyl optionally substituted with one or more hydroxy, and $R^1$ is halo; $R^2$ is $C_3$-$C_7$ cycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is $C_1$-$C_6$ alkyl; $R^2$ is 3- to 7-membered heterocycloalkyl optionally substituted with one or more hydroxy, and $R^1$ is halo; $R^2$ is $C_1$-$C_6$ alkyl optionally substituted with one or more $NR^8R^9$, and $R^1$ is $C_1$-$C_6$ alkyl; $R^2$ is $C_1$-$C_6$ alkyl optionally substituted with one or more $NR^8R^9$, and $R^1$ is halo; $R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

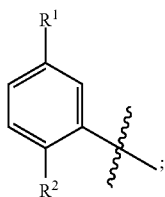

and $R^1$ and $R^2$ are one of the following combinations:
$R^1$ is 1-hydroxy-2-methylpropan-2-yl, and $R^2$ is methyl; $R^1$ is 2-hydroxy-2-propyl and $R^2$ is methyl; $R^1$ is 2-hydroxy-2-propyl and $R^2$ is isopropyl; $R^1$ is 2-hydroxy-2-propyl and $R^2$ is 2-hydroxy-2-propyl; $R^1$ is 2-hydroxy-2-propyl and $R^2$ is 1-hydroxyethyl; $R^1$ is hydroxymethyl and $R^2$ is methyl; $R^1$ is 1-hydroxyethyl and $R^2$ is methyl; $R^1$ is 2-hydroxy ethyl and $R^2$ is methyl; $R^1$ is 1-hydroxy-2-propyl and $R^2$ is methyl; $R^1$ is 2-hydroxy-2-propyl and $R^2$ is phenyl; $R^1$ is 2-hydroxy-2-propyl and $R^2$ is pyridyl; $R^1$ is 2-hydroxy-2-propyl and $R^2$ is pyrazolyl; $R^1$ is 2-hydroxy-2-propyl, and $R^2$ is $S(O_2)CH_3$; $R^1$ is 2-hydroxy-2-propyl and $R^2$ is chloro; $R^1$ is 2-hydroxy-2-propyl and $R^2$ is fluoro; $R^1$ is 1-hydroxy-1-cyclopropyl, and $R^2$ is methyl; $R^1$ is 1-hydroxy-1-cyclobutyl, and $R^2$ is methyl; $R^1$ is 1-hydroxy-1-cyclopentyl, and $R^2$ is methyl; $R^1$ is 1-hydroxy-1-cyclohexyl, and $R^2$ is methyl; $R^1$ is morpholinyl, and $R^2$ is methyl; $R^1$ is 1,3-dioxolan-2-yl, and $R^2$ is methyl; $R^1$ is 1,3-dioxolan-2-yl, and $R^2$ is fluoro; $R^1$ is 1,3-dioxolan-2-yl, and $R^2$ is chloro; $R^1$ is $COCH_3$, and $R^2$ is methyl; $R^1$ is 2-methoxy-2-propyl, and $R^2$ is methyl; $R^1$ is (dimethylamino)methyl, and $R^2$ is methyl. $R^2$ is 1-hydroxy-2-methylpropan-2-yl, and $R^1$ is methyl; $R^2$ is 2-hydroxy-2-propyl and $R^1$ is methyl; $R^2$ is 2-hydroxy-2-propyl and $R^1$ is isopropyl; $R^2$ is 2-hydroxy-2-propyl and $R^1$ is 1-hydroxyethyl; $R^2$ is hydroxymethyl and $R^1$ is methyl; $R^2$ is 1-hydroxy ethyl and $R^1$ is methyl; $R^2$ is 2-hydroxy ethyl and $R^1$ is methyl; $R^2$ is 1-hydroxy-2-propyl and $R^1$ is methyl; $R^2$ is 2-hydroxy-2-propyl and $R^1$ is phenyl; $R^2$ is $C_1$-$C_6$ alkyl optionally substituted with one or more hydroxy, and $R^1$ is 5- to 10-membered heteroaryl; $R^2$ is 2-hydroxy-2-propyl and $R^1$ is pyridyl; $R^2$ is 2-hydroxy-2-propyl and $R^1$ is pyrazolyl; $R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro; $R^2$ is 2-hydroxy-2-propyl and $R^1$ is fluoro; $R^2$ is $C_3$-$C_7$ cycloalkyl optionally substituted with one or more hydroxy, and $R^1$ is $C_1$-$C_6$ alkyl; $R^2$ is 1-hydroxy-1-cyclopropyl, and $R^1$ is methyl; $R^2$ is 1-hydroxy-1-cyclobutyl, and $R^1$ is methyl; $R^2$ is 1-hydroxy-1-cyclopentyl, and $R^1$ is methyl; $R^2$ is 1-hydroxy-1-cyclohexyl, and $R^1$ is methyl; $R^2$ is morpholinyl, and $R^1$ is methyl; $R^2$ is 1,3-dioxolan-2-yl, and $R^1$ is methyl; $R^2$ is 1,3-dioxolan-2-yl, and $R^1$ is fluoro; $R^2$ is 1,3-dioxolan-2-yl, and $R^1$ is chloro; $R^2$ is $C_1$-$C_6$ alkyl optionally substituted with one or more oxo, and $R^1$ is methyl; $R^2$ is (dimethylamino)methyl, and $R^1$ is methyl; $R^2$ is $COCH_3$, and $R^1$ is methyl; or $R^2$ is 2-methoxy-2-propyl, and $R^1$ is methyl.

In some embodiments of the compound of formula AA, the substituted ring B is

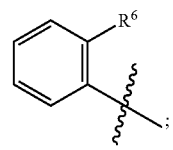

and $R^6$ is selected from: $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

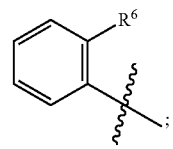

and $R^6$ is selected from: isopropyl, ethyl, methyl, trifluoromethyl, trifluoromethoxy, cyclopropyl, halo, chloro, and fluoro.

In some embodiments of the compound of formula AA, the substituted ring B is

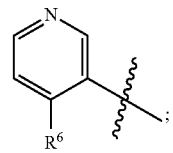

and $R^6$ is selected from: $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

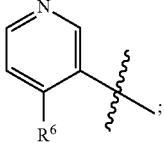

and $R^6$ is selected from: isopropyl, ethyl, methyl, trifluoromethyl, trifluoromethoxy, cyclopropyl, halo, chloro, and fluoro.

In some embodiments of the compound of formula AA, the substituted ring B is

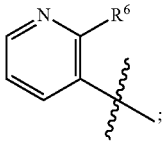

and $R^6$ is selected from: $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

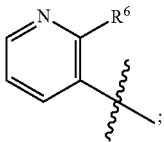

and $R^6$ is selected from: isopropyl, ethyl, methyl, trifluoromethyl, trifluoromethoxy, cyclopropyl, halo, chloro, and fluoro.

In some embodiments of the compound of formula AA, the substituted ring B is

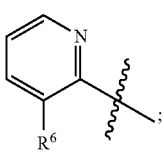

and $R^6$ is selected from: $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

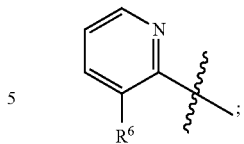

and $R^6$ is selected from: isopropyl, ethyl, methyl, trifluoromethyl, trifluoromethoxy, cyclopropyl, halo, chloro, and fluoro.

In some embodiments of the compound of formula AA, the substituted ring B is

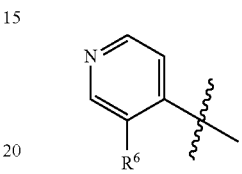

and $R^6$ is selected from: $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

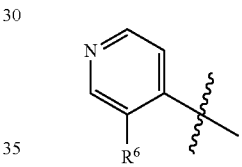

and $R^6$ is selected from: isopropyl, ethyl, methyl, trifluoromethyl, trifluoromethoxy, cyclopropyl, halo, chloro, and fluoro.

In some embodiments, of the compound of formula AA, the substituted ring B is

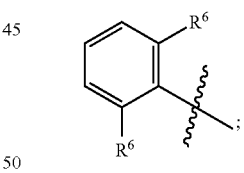

and the two $R^6$ are one of the following combinations:
One $R^6$ is $C_1$-$C_6$ alkyl, and the other $R^6$ is $C_1$-$C_6$ alkyl optionally substituted with one or more halo; One $R^6$ is $C_1$-$C_6$ alkyl and the other $R^6$ is $C_1$-$C_6$ alkyl; One $R^6$ is $C_1$-$C_6$ alkyl, and the other $R^6$ is $C_1$-$C_6$ alkyl substituted with one or more halo; One $R^6$ is $C_1$-$C_6$ alkyl, and the other $R^6$ is $C_3$-$C_7$ cycloalkyl; One $R^6$ is $C_1$-$C_6$ alkyl, and the other $R^6$ is halo; One $R^6$ is $C_1$-$C_6$ alkyl, and the other $R^6$ is cyano; One $R^6$ is $C_3$-$C_7$ cycloalkyl, and the other $R^6$ is $C_3$-$C_7$ cycloalkyl; One $R^6$ is $C_3$-$C_7$ cycloalkyl, and the other $R^6$ is halo; One $R^6$ is cyclopropyl and the other $R^6$ is halo; One $R^6$ is $C_1$-$C_6$ alkyl, and the other $R^6$ is $C_1$-$C_6$ alkoxy optionally substituted with one or more halo; One $R^6$ is $C_1$-$C_6$ alkyl, and the other $R^6$ is $C_1$-$C_6$ alkoxy; One $R^6$ is $C_1$-$C_6$ alkyl, and the other $R^6$ is $C_1$-$C_6$ alkoxy substituted with one or more halo;

One $R^6$ is halo, and the other $R^6$ is $C_1$-$C_6$ haloalkyl; One $R^6$ is halo, and the other $R^6$ is $C_1$-$C_6$ haloalkoxy; One $R^6$ is $C_1$-$C_6$ alkoxy; and the other $R^6$ is halo; One $R^6$ is $C_1$-$C_6$ alkoxy; and the other $R^6$ is chloro.

In some embodiments, of the compound of formula AA, the substituted ring B is

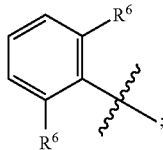

and the two $R^6$ are one of the following combinations:
One $R^6$ is isopropyl; and the other $R^6$ is methyl; One $R^6$ is isopropyl; and the other $R^6$ is n-propyl; One $R^6$ is isopropyl; and the other $R^6$ is isopropyl; One $R^6$ is isopropyl; and the other $R^6$ is trifluoromethyl; One $R^6$ is isopropyl; and the other $R^6$ is cyclopropyl; One $R^6$ is isopropyl; and the other $R^6$ is chloro; One $R^6$ is isopropyl; and the other $R^6$ is fluoro; One $R^6$ is ethyl; and the other $R^6$ is fluoro; One $R^6$ is isopropyl; and the other $R^6$ is cyano; One $R^6$ is cyclopropyl; and the other $R^6$ is cyclopropyl; One $R^6$ is cyclopropyl; and the other $R^6$ is chloro; One $R^6$ is cyclopropyl; and the other $R^6$ is fluoro; One $R^6$ is isopropyl; and the other $R^6$ is methoxy; One $R^6$ is isopropyl; and the other $R^6$ is methoxy; or One $R^6$ is isopropyl; and the other $R^6$ is trifluoromethoxy.

In some embodiments, of the compound of formula AA, the substituted ring B is

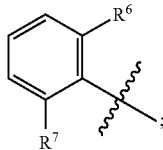

and $R^6$ and $R^7$ are one of the following combinations:
$R^6$ is $C_1$-$C_6$ alkyl, and $R^7$ is $C_1$-$C_6$ alkyl optionally substituted with one or more halo; $R^6$ is $C_1$-$C_6$ alkyl and $R^7$ is $C_1$-$C_6$ alkyl; $R^6$ is $C_1$-$C_6$ alkyl, and $R^7$ is $C_1$-$C_6$ alkyl substituted with one or more halo; $R^6$ is $C_1$-$C_6$ alkyl, and $R^7$ is $C_3$-$C_7$ cycloalkyl; $R^6$ is $C_1$-$C_6$ alkyl, and $R^7$ is halo; $R^6$ is $C_1$-$C_6$ alkyl, and $R^7$ is cyano; $R^6$ is $C_3$-$C_7$ cycloalkyl, and $R^7$ is $C_3$-$C_7$ cycloalkyl; $R^6$ is $C_3$-$C_7$ cycloalkyl, and $R^7$ is halo; $R^6$ is cyclopropyl and $R^7$ is halo; $R^6$ is $C_1$-$C_6$ alkyl, and $R^7$ is $C_1$-$C_6$ alkoxy optionally substituted with one or more halo; $R^6$ is $C_1$-$C_6$ alkyl, and $R^7$ is $C_1$-$C_6$ alkoxy; $R^6$ is $C_1$-$C_6$ alkyl, and $R^7$ is $C_1$-$C_6$ alkoxy substituted with one or more halo; $R^6$ is halo, and $R^7$ is $C_1$-$C_6$ haloalkyl; $R^6$ is halo, and $R^7$ is $C_1$-$C_6$ haloalkoxy; $R^6$ is $C_1$-$C_6$ alkoxy; and $R^7$ is halo; $R^6$ is $C_1$-$C_6$ alkoxy; and $R^7$ is chloro; $R^7$ is $C_1$-$C_6$ alkyl, and $R^6$ is $C_1$-$C_6$ alkyl optionally substituted with one or more halo; $R^7$ is $C_1$-$C_6$ alkyl, and $R^6$ is $C_1$-$C_6$ alkyl substituted with one or more halo; $R^7$ is $C_1$-$C_6$ alkyl, and $R^6$ is $C_3$-$C_7$ cycloalkyl; $R^7$ is $C_1$-$C_6$ alkyl, and $R^6$ is halo; $R^7$ is $C_1$-$C_6$ alkyl and $R^6$ is halo; $R^7$ is $C_1$-$C_6$ alkyl, and $R^6$ is cyano; $R^7$ is $C_3$-$C_7$ cycloalkyl, and $R^6$ is $C_3$-$C_7$ cycloalkyl; $R^7$ is $C_3$-$C_7$ cycloalkyl, and $R^6$ is halo; $R^7$ is $C_3$-$C_7$ cycloalkyl and $R^6$ is halo; $R^7$ is $C_1$-$C_6$ alkyl, and $R^6$ is $C_1$-$C_6$ alkoxy optionally substituted with one or more halo; $R^7$ is $C_1$-$C_6$ alkyl, and $R^6$ is $C_1$-$C_6$ alkoxy; $R^7$ is $C_1$-$C_6$ alkyl, and $R^6$ is $C_1$-$C_6$ alkoxy substituted with one or more halo; $R^7$ is halo, and $R^6$ is $C_1$-$C_6$ haloalkyl; $R^7$ is halo, and $R^6$ is $C_1$-$C_6$ haloalkoxy; $R^7$ is $C_1$-$C_6$ alkoxy; and $R^6$ is halo; or $R^7$ is $C_1$-$C_6$ alkoxy; and $R^6$ is chloro.

In some embodiments, of the compound of formula AA, the substituted ring B is

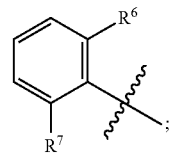

and $R^6$ and $R^7$ are one of the following combinations:
$R^6$ is isopropyl; and $R^7$ is methyl; $R^6$ is isopropyl; and $R^7$ is isopropyl; $R^6$ is isopropyl; and $R^7$ is trifluoromethyl; $R^6$ is isopropyl; and $R^7$ is cyclopropyl; $R^6$ is isopropyl; and $R^7$ is chloro; $R^6$ is isopropyl; and $R^7$ is fluoro; $R^6$ is ethyl; and $R^7$ is fluoro; $R^6$ is isopropyl; and $R^7$ is cyano; $R^6$ is cyclopropyl; and $R^7$ is cyclopropyl; $R^6$ is cyclopropyl; and $R^7$ is chloro; $R^6$ is cyclopropyl; and $R^7$ is fluoro; $R^6$ is isopropyl; and $R^7$ is methoxy; $R^6$ is isopropyl; and $R^7$ is trifluoromethoxy; $R^6$ is chloro; and $R^7$ is trifluoromethyl; $R^6$ is chloro; and $R^7$ is trifluoromethoxy; $R^7$ is isopropyl; and $R^6$ is methyl; $R^7$ is isopropyl; and $R^6$ is trifluoromethyl; $R^7$ is isopropyl; and $R^6$ is cyclopropyl; $R^7$ is isopropyl; and $R^6$ is chloro; $R^7$ ethyl; and $R^6$ is fluoro; $R^7$ is isopropyl; and $R^6$ is cyano; $R^7$ is cyclopropyl; and $R^6$ is cyclopropyl; $R^7$ is cyclopropyl; and $R^6$ is chloro; $R^7$ is cyclopropyl; and $R^6$ is fluoro; $R^7$ is isopropyl; and $R^6$ is methoxy; $R^7$ is isopropyl; and $R^6$ is trifluoromethoxy; $R^7$ is chloro; and $R^6$ is trifluoromethyl; or $R^7$ is chloro; and $R^6$ is trifluoromethoxy.

In some embodiments, of the compound of formula AA, the substituted ring B is

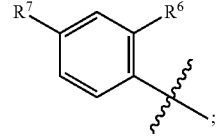

and $R^6$ and $R^7$ are one of the following combinations:
$R^6$ is $C_1$-$C_6$ alkyl, and $R^7$ is $C_1$-$C_6$ alkyl optionally substituted with one or more halo; $R^6$ is $C_1$-$C_6$ alkyl and $R^7$ is $C_1$-$C_6$ alkyl; $R^6$ is $C_1$-$C_6$ alkyl, and $R^7$ is $C_1$-$C_6$ alkyl substituted with one or more halo; $R^6$ is $C_1$-$C_6$ alkyl, and $R^7$ is $C_3$-$C_7$ cycloalkyl; $R^6$ is $C_1$-$C_6$ alkyl, and $R^7$ is halo; $R^6$ is $C_1$-$C_6$ alkyl, and $R^7$ is cyano; $R^6$ is $C_3$-$C_7$ cycloalkyl, and $R^7$ is $C_3$-$C_7$ cycloalkyl; $R^6$ is $C_3$-$C_7$ cycloalkyl, and $R^7$ is halo; $R^6$ is cyclopropyl and $R^7$ is halo; $R^6$ is $C_1$-$C_6$ alkyl, and $R^7$ is $C_1$-$C_6$ alkoxy optionally substituted with one or more halo; $R^6$ is $C_1$-$C_6$ alkyl, and $R^7$ is $C_1$-$C_6$ alkoxy; $R^6$ is $C_1$-$C_6$ alkyl, and $R^7$ is $C_1$-$C_6$ alkoxy substituted with one or more halo; $R^6$ is halo, and $R^7$ is $C_1$-$C_6$ haloalkyl; $R^6$ is halo, and $R^7$ is $C_1$-$C_6$ haloalkoxy; $R^6$ is $C_1$-$C_6$ alkoxy; and $R^7$ is halo; $R^6$ is $C_1$-$C_6$ alkoxy; and $R^7$ is chloro; $R^7$ is $C_1$-$C_6$ alkyl, and $R^6$ is $C_1$-$C_6$ alkyl optionally substituted with one or more halo; $R^7$ is $C_1$-$C_6$ alkyl, and $R^6$ is $C_1$-$C_6$ alkyl substituted with one or more halo; $R^7$ is $C_1$-$C_6$ alkyl, and $R^6$ is $C_3$-$C_7$ cycloalkyl; $R^7$ is $C_1$-$C_6$ alkyl, and $R^6$ is halo; $R^7$ is $C_1$-$C_6$ alkyl and $R^6$ is halo; $R^7$ is $C_1$-$C_6$ alkyl, and $R^6$ is cyano; $R^7$ is $C_3$-$C_7$ cycloalkyl, and $R^6$ is $C_3$-$C_7$ cycloalkyl; $R^7$ is $C_3$-$C_7$ cycloalkyl, and $R^6$ is halo; $R^7$ is $C_3$-$C_7$ cycloalkyl and $R^6$ is halo; $R^7$ is $C_1$-$C_6$ alkyl, and $R^6$ is $C_1$-$C_6$ alkoxy optionally substituted with one or more halo; $R^7$ is $C_1$-$C_6$ alkyl, and $R^6$ is $C_1$-$C_6$ alkoxy; $R^7$ is $C_1$-$C_6$ alkyl, and $R^6$ is $C_1$-$C_6$ alkoxy substituted with one or more halo; $R^7$ is halo, and $R^6$ is $C_1$-$C_6$ haloalkyl; $R^7$ is halo, and $R^6$ is $C_1$-$C_6$ haloalkoxy; $R^7$ is $C_1$-$C_6$ alkoxy; and $R^6$ is halo; or $R^7$ is $C_1$-$C_6$ alkoxy; and $R^6$ is chloro.

In some embodiments, of the compound of formula AA, the substituted ring B is

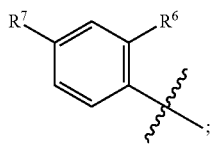

and $R^6$ and $R^7$ are one of the following combinations:
$R^6$ is isopropyl; and $R^7$ is methyl; $R^6$ is isopropyl; and $R^7$ is isopropyl; $R^6$ is isopropyl; and $R^7$ is trifluoromethyl; $R^6$ is isopropyl; and $R^7$ is cyclopropyl; $R^6$ is isopropyl; and $R^7$ is chloro; $R^6$ is isopropyl; and $R^7$ is fluoro; $R^6$ is ethyl; and $R^7$ is fluoro; $R^6$ is isopropyl; and $R^7$ is cyano; $R^6$ is cyclopropyl; and $R^7$ is cyclopropyl; $R^6$ is cyclopropyl; and $R^7$ is chloro; $R^6$ is cyclopropyl; and $R^7$ is fluoro; $R^6$ is isopropyl; and $R^7$ is methoxy; $R^6$ is isopropyl; and $R^7$ is trifluoromethoxy; $R^6$ is chloro; and $R^7$ is trifluoromethyl; $R^6$ is chloro; and $R^7$ is trifluoromethoxy; $R^7$ is isopropyl; and $R^6$ is methyl; $R^7$ is isopropyl; and $R^6$ is trifluoromethyl; $R^7$ is isopropyl; and $R^6$ is cyclopropyl; $R^7$ is isopropyl; and $R^6$ is chloro; $R^7$ is ethyl; and $R^6$ is fluoro; $R^7$ is isopropyl; and $R^6$ is cyano; $R^7$ is cyclopropyl; and $R^6$ is cyclopropyl; $R^7$ is cyclopropyl; and $R^6$ is chloro; $R^7$ is cyclopropyl; and $R^6$ is fluoro; $R^7$ is isopropyl; and $R^6$ is methoxy; $R^7$ is isopropyl; and $R^6$ is trifluoromethoxy; $R^7$ is chloro; and $R^6$ is trifluoromethyl; or $R^7$ is chloro; and $R^6$ is trifluoromethoxy.

In some embodiments, of the compound of formula AA, the substituted ring B is

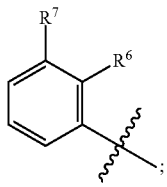

and $R^6$ and $R^7$ are one of the following combinations:
$R^6$ is $C_1$-$C_6$ alkyl, and $R^7$ is $C_1$-$C_6$ alkyl optionally substituted with one or more halo; $R^6$ is $C_1$-$C_6$ alkyl and $R^7$ is $C_1$-$C_6$ alkyl; $R^6$ is $C_1$-$C_6$ alkyl, and $R^7$ is $C_1$-$C_6$ alkyl substituted with one or more halo; $R^6$ is $C_1$-$C_6$ alkyl, and $R^7$ is $C_3$-$C_7$ cycloalkyl; $R^6$ is $C_1$-$C_6$ alkyl, and $R^7$ is halo; $R^6$ is $C_1$-$C_6$ alkyl, and $R^7$ is cyano; $R^6$ is $C_3$-$C_7$ cycloalkyl, and $R^7$ is $C_3$-$C_7$ cycloalkyl; $R^6$ is $C_3$-$C_7$ cycloalkyl, and $R^7$ is halo; $R^6$ is cyclopropyl and $R^7$ is halo; $R^6$ is $C_1$-$C_6$ alkyl, and $R^7$ is $C_1$-$C_6$ alkoxy optionally substituted with one or more halo; $R^6$ is $C_1$-$C_6$ alkyl, and $R^7$ is $C_1$-$C_6$ alkoxy; $R^6$ is $C_1$-$C_6$ alkyl, and $R^7$ is $C_1$-$C_6$ alkoxy substituted with one or more halo; $R^6$ is halo, and $R^7$ is $C_1$-$C_6$ haloalkyl; $R^6$ is halo, and $R^7$ is $C_1$-$C_6$ haloalkoxy; $R^6$ is $C_1$-$C_6$ alkoxy; and $R^7$ is halo; $R^6$ is $C_1$-$C_6$ alkoxy; and $R^7$ is chloro; $R^7$ is $C_1$-$C_6$ alkyl, and $R^6$ is $C_1$-$C_6$ alkyl optionally substituted with one or more halo; $R^7$ is $C_1$-$C_6$ alkyl, and $R^6$ is $C_1$-$C_6$ alkyl substituted with one or more halo; $R^7$ is $C_1$-$C_6$ alkyl, and $R^6$ is $C_3$-$C_7$ cycloalkyl; $R^7$ is $C_1$-$C_6$ alkyl, and $R^6$ is halo; $R^7$ is $C_1$-$C_6$ alkyl and $R^6$ is halo; $R^7$ is $C_1$-$C_6$ alkyl, and $R^6$ is cyano; $R^7$ is $C_3$-$C_7$ cycloalkyl, and $R^6$ is $C_3$-$C_7$ cycloalkyl; $R^7$ is $C_3$-$C_7$ cycloalkyl, and $R^6$ is halo; $R^7$ is $C_3$-$C_7$ cycloalkyl and $R^6$ is halo; $R^7$ is $C_1$-$C_6$ alkyl, and $R^6$ is $C_1$-$C_6$ alkoxy optionally substituted with one or more halo; $R^7$ is $C_1$-$C_6$ alkyl, and $R^6$ is $C_1$-$C_6$ alkoxy; $R^7$ is $C_1$-$C_6$ alkyl, and $R^6$ is $C_1$-$C_6$ alkoxy substituted with one or more halo; $R^7$ is halo, and $R^6$ is $C_1$-$C_6$ haloalkyl; $R^7$ is halo, and $R^6$ is $C_1$-$C_6$ haloalkoxy; $R^7$ is $C_1$-$C_6$ alkoxy; and $R^6$ is halo; or $R^7$ is $C_1$-$C_6$ alkoxy; and $R^6$ is chloro; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

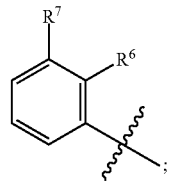

and $R^6$ and $R^7$ are one of the following combinations:
$R^6$ is isopropyl; and $R^7$ is methyl; $R^6$ is isopropyl; and $R^7$ is isopropyl; $R^6$ is isopropyl; and $R^7$ is trifluoromethyl; $R^6$ is isopropyl; and $R^7$ is cyclopropyl; $R^6$ is isopropyl; and $R^7$ is chloro; $R^6$ is isopropyl; and $R^7$ is fluoro; $R^6$ is ethyl; and $R^7$ is fluoro; $R^6$ is isopropyl; and $R^7$ is cyano; $R^6$ is cyclopropyl; and $R^7$ is cyclopropyl; $R^6$ is cyclopropyl; and $R^7$ is chloro; $R^6$ is cyclopropyl; and $R^7$ is fluoro; $R^6$ is isopropyl; and $R^7$ is methoxy; $R^6$ is isopropyl; and $R^7$ is trifluoromethoxy; $R^6$ is chloro; and $R^7$ is trifluoromethyl; $R^6$ is chloro; and $R^7$ is trifluoromethoxy; $R^7$ is isopropyl; and $R^6$ is methyl; $R^7$ is isopropyl; and $R^6$ is trifluoromethyl; $R^7$ is isopropyl; and $R^6$ is cyclopropyl; $R^7$ is isopropyl; and $R^6$ is chloro; $R^7$ is ethyl; and $R^6$ is fluoro; $R^7$ is isopropyl; and $R^6$ is cyano; $R^7$ is cyclopropyl; and $R^6$ is cyclopropyl; $R^7$ is cyclopropyl; and $R^6$ is chloro; $R^7$ is cyclopropyl; and $R^6$ is fluoro; $R^7$ is isopropyl; and $R^6$ is methoxy; $R^7$ is isopropyl; and $R^6$ is trifluoromethoxy; $R^7$ is chloro; and $R^6$ is trifluoromethyl; $R^7$ is chloro; and $R^6$ is trifluoromethoxy; $R^6$ and $R^7$ on adjacent atoms taken together with the atoms connecting them form a $C_4$ aliphatic carbocyclic ring; $R^6$ and $R^7$ on adjacent atoms taken together with the atoms connecting them form a $C_5$ aliphatic carbocyclic ring; $R^6$ and $R^7$ on adjacent atoms taken together with the atoms connecting them form a $C_6$ aliphatic carbocyclic ring; $R^6$ and $R^7$ on adjacent atoms taken together with the atoms connecting them form a 5-membered heterocyclic ring containing 1 heteroatoms independently selected from O, N, and S; $R^6$ and $R^7$ on adjacent atoms taken together with the atoms connecting them form a 6-membered heterocyclic ring containing 1 heteroatoms independently selected from O, N, and S; or $R^6$ and $R^7$ on adjacent atoms taken together with the atoms connecting them form a $C_5$ aliphatic carbocyclic ring.

In some embodiments, of the compound of formula AA, the substituted ring B is

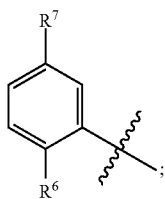

and $R^6$ and $R^7$ are one of the following combinations:
$R^6$ is $C_1$-$C_6$ alkyl, and $R^7$ is $C_1$-$C_6$ alkyl optionally substituted with one or more halo; $R^6$ is $C_1$-$C_6$ alkyl and $R^7$ is $C_1$-$C_6$ alkyl; $R^6$ is $C_1$-$C_6$ alkyl, and $R^7$ is $C_1$-$C_6$ alkyl substituted with one or more halo; $R^6$ is $C_1$-$C_6$ alkyl, and $R^7$ is $C_3$-$C_7$ cycloalkyl; $R^6$ is $C_1$-$C_6$ alkyl, and $R^7$ is halo; $R^6$ is $C_1$-$C_6$ alkyl, and $R^7$ is cyano; $R^6$ is $C_3$-$C_7$ cycloalkyl, and $R^7$ is $C_3$-$C_7$ cycloalkyl; $R^6$ is $C_3$-$C_7$ cycloalkyl, and $R^7$ is halo; $R^6$ is cyclopropyl and $R^7$ is halo; $R^6$ is $C_1$-$C_6$ alkyl, and $R^7$ is $C_1$-$C_6$ alkoxy optionally substituted with one or more halo; $R^6$ is $C_1$-$C_6$ alkyl, and $R^7$ is $C_1$-$C_6$ alkoxy; $R^6$ is $C_1$-$C_6$ alkyl, and $R^7$ is $C_1$-$C_6$ alkoxy substituted with one or more halo; $R^6$ is halo, and $R^7$ is $C_1$-$C_6$ haloalkyl; $R^6$ is halo, and $R^7$ is $C_1$-$C_6$ haloalkoxy; $R^6$ is $C_1$-$C_6$ alkoxy; and $R^7$ is halo; $R^6$ is $C_1$-$C_6$ alkoxy; and $R^7$ is chloro; $R^7$ is $C_1$-$C_6$ alkyl, and $R^6$ is $C_1$-$C_6$ alkyl optionally substituted with one or more halo; $R^7$ is $C_1$-$C_6$ alkyl, and $R^6$ is $C_1$-$C_6$ alkyl substituted with one or more halo; $R^7$ is $C_1$-$C_6$ alkyl, and $R^6$ is $C_3$-$C_7$ cycloalkyl; $R^7$ is $C_1$-$C_6$ alkyl, and $R^6$ is halo; $R^7$ is $C_1$-$C_6$ alkyl and $R^6$ is halo; $R^7$ is $C_1$-$C_6$ alkyl, and $R^6$ is cyano; $R^7$ is $C_3$-$C_7$ cycloalkyl, and $R^6$ is $C_3$-$C_7$ cycloalkyl; $R^7$ is $C_3$-$C_7$ cycloalkyl, and $R^6$ is halo; $R^7$ is $C_3$-$C_7$ cycloalkyl and $R^6$ is halo; $R^7$ is $C_1$-$C_6$ alkyl, and $R^6$ is $C_1$-$C_6$ alkoxy optionally substituted with one or more halo; $R^7$ is $C_1$-$C_6$ alkyl, and $R^6$ is $C_1$-$C_6$ alkoxy; $R^7$ is $C_1$-$C_6$ alkyl, and $R^6$ is $C_1$-$C_6$ alkoxy substituted with one or more halo; $R^7$ is halo, and $R^6$ is $C_1$-$C_6$ haloalkyl; $R^7$ is halo, and $R^6$ is $C_1$-$C_6$ haloalkoxy; $R^7$ is $C_1$-$C_6$ alkoxy; and $R^6$ is halo; or $R^7$ is $C_1$-$C_6$ alkoxy; and $R^6$ is chloro.

In some embodiments, of the compound of formula AA, the substituted ring B is

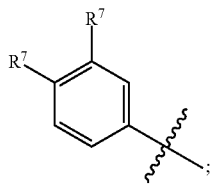

and $R^6$ and $R^7$ are one of the following combinations:
$R^6$ is $C_1$-$C_6$ alkyl, and $R^7$ is $C_1$-$C_6$ alkyl optionally substituted with one or more halo; $R^6$ is $C_1$-$C_6$ alkyl and $R^7$ is $C_1$-$C_6$ alkyl; $R^6$ is $C_1$-$C_6$ alkyl, and $R^7$ is $C_1$-$C_6$ alkyl substituted with one or more halo; $R^6$ is $C_1$-$C_6$ alkyl, and $R^7$ is $C_3$-$C_7$ cycloalkyl; $R^6$ is $C_1$-$C_6$ alkyl, and $R^7$ is halo; $R^6$ is $C_1$-$C_6$ alkyl, and $R^7$ is cyano; $R^6$ is $C_3$-$C_7$ cycloalkyl, and $R^7$ is $C_3$-$C_7$ cycloalkyl; $R^6$ is $C_3$-$C_7$ cycloalkyl, and $R^7$ is halo; $R^6$ is cyclopropyl and $R^7$ is halo; $R^6$ is $C_1$-$C_6$ alkyl, and $R^7$ is $C_1$-$C_6$ alkoxy optionally substituted with one or more halo; $R^6$ is $C_1$-$C_6$ alkyl, and $R^7$ is $C_1$-$C_6$ alkoxy; $R^6$ is $C_1$-$C_6$ alkyl, and $R^7$ is $C_1$-$C_6$ alkoxy substituted with one or more halo; $R^6$ is halo, and $R^7$ is $C_1$-$C_6$ haloalkyl; $R^6$ is halo, and $R^7$ is $C_1$-$C_6$ haloalkoxy; $R^6$ is $C_1$-$C_6$ alkoxy; and $R^7$ is halo; $R^6$ is $C_1$-$C_6$ alkoxy; and $R^7$ is chloro; $R^7$ is $C_1$-$C_6$ alkyl, and $R^6$ is $C_1$-$C_6$ alkyl optionally substituted with one or more halo; $R^7$ is $C_1$-$C_6$ alkyl, and $R^6$ is $C_1$-$C_6$ alkyl substituted with one or more halo; $R^7$ is $C_1$-$C_6$ alkyl, and $R^6$ is $C_3$-$C_7$ cycloalkyl; $R^7$ is $C_1$-$C_6$ alkyl, and $R^6$ is halo; $R^7$ is $C_1$-$C_6$ alkyl and $R^6$ is halo; $R^7$ is $C_1$-$C_6$ alkyl, and $R^6$ is cyano; $R^7$ is $C_3$-$C_7$ cycloalkyl, and $R^6$ is $C_3$-$C_7$ cycloalkyl; $R^7$ is $C_3$-$C_7$ cycloalkyl, and $R^6$ is halo; $R^7$ is $C_3$-$C_7$ cycloalkyl and $R^6$ is halo; $R^7$ is $C_1$-$C_6$ alkyl, and $R^6$ is $C_1$-$C_6$ alkoxy optionally substituted with one or more halo; $R^7$ is $C_1$-$C_6$ alkyl, and $R^6$ is $C_1$-$C_6$ alkoxy; $R^7$ is $C_1$-$C_6$ alkyl, and $R^6$ is $C_1$-$C_6$ alkoxy substituted with one or more halo; $R^7$ is halo, and $R^6$ is $C_1$-$C_6$ haloalkyl; $R^7$ is halo, and $R^6$ is $C_1$-$C_6$ haloalkoxy; $R^7$ is $C_1$-$C_6$ alkoxy; and $R^6$ is halo; $R^7$ is $C_1$-$C_6$ alkoxy; and $R^6$ is chloro; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

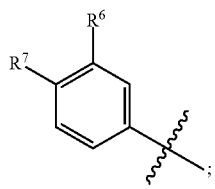

and $R^6$ and $R^7$ are one of the following combinations:
$R^6$ is isopropyl; and $R^7$ is methyl; $R^6$ is isopropyl; and $R^7$ is isopropyl; $R^6$ is isopropyl; and $R^7$ is trifluoromethyl; $R^6$ is isopropyl; and $R^7$ is cyclopropyl; $R^6$ is isopropyl; and $R^7$ is chloro; $R^6$ is isopropyl; and $R^7$ is fluoro; $R^6$ is ethyl; and $R^7$ is fluoro; $R^6$ is isopropyl; and $R^7$ is cyano; $R^6$ is cyclopropyl; and $R^7$ is cyclopropyl; $R^6$ is cyclopropyl; and $R^7$ is chloro; $R^6$ is cyclopropyl; and $R^7$ is fluoro; $R^6$ is isopropyl; and $R^7$ is methoxy; $R^6$ is isopropyl; and $R^7$ is trifluoromethoxy; $R^6$ is chloro; and $R^7$ is trifluoromethyl; $R^6$ is chloro; and $R^7$ is trifluoromethoxy; $R^7$ is isopropyl; and $R^6$ is methyl; $R^7$ is isopropyl; and $R^6$ is trifluoromethyl; $R^7$ is isopropyl; and $R^6$ is cyclopropyl; $R^7$ is isopropyl; and $R^6$ is chloro;

$R^7$ is ethyl; and $R^6$ is fluoro; $R^7$ is isopropyl; and $R^6$ is cyano; $R^7$ is cyclopropyl; and $R^6$ is cyclopropyl; $R^7$ is cyclopropyl; and $R^6$ is chloro; $R^7$ is cyclopropyl; and $R^6$ is fluoro; $R^7$ is isopropyl; and $R^6$ is methoxy; $R^7$ is isopropyl; and $R^6$ is trifluoromethoxy; $R^7$ is chloro; and $R^6$ is trifluoromethyl; $R^7$ is chloro; and $R^6$ is trifluoromethoxy; $R^6$ and $R^7$ on adjacent atoms taken together with the atoms connecting them form a $C_4$ aliphatic carbocyclic ring; $R^6$ and $R^7$ on adjacent atoms taken together with the atoms connecting them form a $C_5$ aliphatic carbocyclic ring; $R^6$ and $R^7$ on adjacent atoms taken together with the atoms connecting them form a $C_6$ aliphatic carbocyclic ring; $R^6$ and $R^7$ on adjacent atoms taken together with the atoms connecting them form a 5-membered heterocyclic ring containing 1 heteroatoms independently selected from O, N, and S; $R^6$ and $R^7$ on adjacent atoms taken together with the atoms connecting them form a 6-membered heterocyclic ring containing 1 heteroatoms independently selected from O, N, and S; or $R^6$ and $R^7$ on adjacent atoms taken together with the atoms connecting them form a $C_5$ aliphatic carbocyclic ring.

In some embodiments, of the compound of formula AA, the substituted ring B is

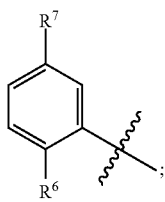

and $R^6$ and $R^7$ are one of the following combinations:
$R^6$ is isopropyl; and $R^7$ is methyl; $R^6$ is isopropyl; and $R^7$ is isopropyl; $R^6$ is isopropyl; and $R^7$ is trifluoromethyl; $R^6$ is isopropyl; and $R^7$ is cyclopropyl; $R^6$ is isopropyl; and $R^7$ is chloro; $R^6$ is isopropyl; and $R^7$ is fluoro; $R^6$ is ethyl; and $R^7$ is fluoro; $R^6$ is isopropyl; and $R^7$ is cyano; $R^6$ is cyclopropyl; and $R^7$ is cyclopropyl; $R^6$ is cyclopropyl; and $R^7$ is chloro; $R^6$ is cyclopropyl; and $R^7$ is fluoro; $R^6$ is isopropyl; and $R^7$ is methoxy; $R^6$ is isopropyl; and $R^7$ is trifluoromethoxy; $R^6$ is chloro; and $R^7$ is trifluoromethyl; $R^6$ is chloro; and $R^7$ is trifluoromethoxy; $R^7$ is isopropyl; and $R^6$ is methyl; $R^7$ is isopropyl; and $R^6$ is trifluoromethyl; $R^7$ is isopropyl; and $R^6$ is cyclopropyl; $R^7$ is isopropyl; and $R^6$ is chloro; $R^7$ is ethyl; and $R^6$ is fluoro; $R^7$ is isopropyl; and $R^6$ is cyano; $R^7$ is cyclopropyl; and $R^6$ is cyclopropyl; $R^7$ is cyclopropyl; and $R^6$ is chloro; $R^7$ is cyclopropyl; and $R^6$ is fluoro; $R^7$ is isopropyl; and $R^6$ is methoxy; $R^7$ is isopropyl; and $R^6$ is trifluoromethoxy; $R^7$ is chloro; and $R^6$ is trifluoromethyl; or $R^7$ is chloro; and $R^6$ is trifluoromethoxy.

In some embodiments, of the compound of formula AA, the substituted ring B is

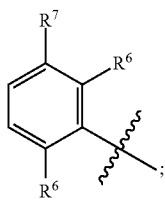

and $R^6$ and $R^7$ are one of the following combinations:
each $R^6$ is independently $C_1$-$C_6$ alkyl, and $R^7$ is $C_1$-$C_6$ alkyl optionally substituted with one or more halo; each $R^6$ is independently $C_1$-$C_6$ alkyl and $R^7$ is $C_1$-$C_6$ alkyl; each $R^6$ is independently $C_1$-$C_6$ alkyl, and $R^7$ is $C_1$-$C_6$ alkyl substituted with one or more halo; each $R^6$ is independently $C_1$-$C_6$ alkyl, and $R^7$ is $C_3$-$C_7$ cycloalkyl; each $R^6$ is independently $C_1$-$C_6$ alkyl, and $R^7$ is halo; each $R^6$ is independently $C_1$-$C_6$ alkyl, and $R^7$ is cyano; each $R^6$ is independently $C_3$-$C_7$ cycloalkyl, and $R^7$ is $C_3$-$C_7$ cycloalkyl; each $R^6$ is independently $C_3$-$C_7$ cycloalkyl, and $R^7$ is halo; each $R^6$ is independently cyclopropyl and $R^7$ is halo; each $R^6$ is independently $C_1$-$C_6$ alkyl, and $R^7$ is $C_1$-$C_6$ alkoxy optionally substituted with one or more halo; each $R^6$ is independently $C_1$-$C_6$ alkyl, and $R^7$ is $C_1$-$C_6$ alkoxy; each $R^6$ is independently $C_1$-$C_6$ alkyl, and $R^7$ is $C_1$-$C_6$ alkoxy substituted with one or more halo; each $R^6$ is independently halo, and $R^7$ is $C_1$-$C_6$ haloalkyl; each $R^6$ is independently halo, and $R^7$ is $C_1$-$C_6$ haloalkoxy; each $R^6$ is independently $C_1$-$C_6$ alkoxy; and $R^7$ is halo; each $R^6$ is independently $C_1$-$C_6$ alkoxy; and $R^7$ is chloro; $R^7$ is $C_1$-$C_6$ alkyl, and each $R^6$ is independently $C_1$-$C_6$ alkyl optionally substituted with one or more halo; $R^7$ is $C_1$-$C_6$ alkyl, and each $R^6$ is independently $C_1$-$C_6$ alkyl substituted with one or more halo; $R^7$ is $C_1$-$C_6$ alkyl, and each $R^6$ is independently $C_3$-$C_7$ cycloalkyl; $R^7$ is $C_1$-$C_6$ alkyl, and each $R^6$ is independently halo; $R^7$ is $C_1$-$C_6$ alkyl and each $R^6$ is independently halo; $R^7$ is $C_1$-$C_6$ alkyl, and $R^6$ is cyano; $R^7$ is $C_3$-$C_7$ cycloalkyl, and each $R^6$ is independently $C_3$-$C_7$ cycloalkyl; $R^7$ is $C_3$-$C_7$ cycloalkyl, and each $R^6$ is independently halo; $R^7$ is $C_3$-$C_7$ cycloalkyl and each $R^6$ is independently halo; $R^7$ is $C_1$-$C_6$ alkyl, and each $R^6$ is independently $C_1$-$C_6$ alkoxy optionally substituted with one or more halo; $R^7$ is $C_1$-$C_6$ alkyl, and each $R^6$ is independently $C_1$-$C_6$ alkoxy; $R^7$ is $C_1$-$C_6$ alkyl, and each $R^6$ is independently $C_1$-$C_6$ alkoxy substituted with one or more halo; $R^7$ is halo, and each $R^6$ is independently $C_1$-$C_6$ haloalkyl; $R^7$ is halo, and each $R^6$ is independently $C_1$-$C_6$ haloalkoxy; $R^7$ is $C_1$-$C_6$ alkoxy; and each $R^6$ is independently halo; $R^7$ is $C_1$-$C_6$ alkoxy; and $R^6$ is chloro; $R^6$ and $R^7$ on adjacent atoms taken together with the atoms connecting them form a $C_5$ aliphatic carbocyclic ring; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

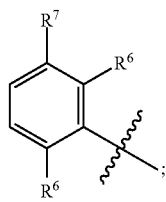

and $R^6$ and $R^7$ are one of the following combinations:
each $R^6$ is isopropyl; and $R^7$ is methyl; each $R^6$ is isopropyl; and $R^7$ is isopropyl; each $R^6$ is isopropyl; and $R^7$ is trifluoromethyl; each $R^6$ is isopropyl; and $R^7$ is cyclopropyl; each $R^6$ is isopropyl; and $R^7$ is chloro; each $R^6$ is isopropyl; and $R^7$ is fluoro; each $R^6$ is ethyl; and $R^7$ is fluoro; each $R^6$ is isopropyl; and $R^7$ is cyano; each $R^6$ is cyclopropyl; and $R^7$ is cyclopropyl; each $R^6$ is cyclopropyl; and $R^7$ is chloro; each $R^6$ is cyclopropyl; and $R^7$ is fluoro; each $R^6$ is isopropyl; and $R^7$ is methoxy; each $R^6$ is isopropyl; and $R^7$ is trifluoromethoxy; each $R^6$ is chloro; and $R^7$ is trifluoromethyl; each $R^6$ is chloro; and $R^7$ is trifluoromethoxy; $R^7$ is isopropyl; and each $R^6$ is methyl; $R^7$ is isopropyl; and each $R^6$ is trifluoromethyl; $R^7$ is isopropyl; and each $R^6$ is cyclopropyl; $R^7$ is isopropyl; and each $R^6$ is chloro; $R^7$ is ethyl; and each $R^6$ is fluoro; $R^7$ is isopropyl; and each $R^6$ is cyano; $R^7$ is cyclopropyl; and each $R^6$ is cyclopropyl; $R^7$ is cyclopropyl; and each $R^6$ is chloro; $R^7$ is cyclopropyl; and each $R^6$ is fluoro; $R^7$ is isopropyl; and each $R^6$ is methoxy; $R^7$ is isopropyl; and each $R^6$ is trifluoromethoxy; $R^7$ is chloro; and each $R^6$ is trifluoromethyl; $R^7$ is chloro; and each $R^6$ is trifluoromethoxy; one $R^6$ is isopropyl; the other $R^6$ is trifluoromethyl; and $R^7$ is chloro; $R^6$ and $R^7$ on adjacent atoms taken together with the atoms connecting them form a $C_4$ aliphatic carbocyclic ring; and one $R^6$ is fluoro, chloro, or cyano; $R^6$ and $R^7$ on adjacent atoms taken together with the atoms connecting them form a $C_5$ aliphatic carbocyclic ring; and one $R^6$ is fluoro, chloro, or cyano; $R^6$ and $R^7$ on adjacent atoms taken together with the atoms connecting them form a $C_6$ aliphatic carbocyclic ring; and one $R^6$ is fluoro, chloro, or cyano; $R^6$ and $R^7$ on adjacent atoms taken together with the atoms connecting them form a 5-membered heterocyclic ring containing 1 heteroatoms independently selected from O, N, and S; and one $R^6$ is fluoro, chloro, or cyano; or $R^6$ and $R^7$ on adjacent atoms taken together with the atoms connecting them form a 6-membered heterocyclic ring containing 1 heteroatoms independently selected from O, N, and S; and one $R^6$ is fluoro, chloro, or cyano.

In some embodiments, of the compound of formula AA, the substituted ring B is

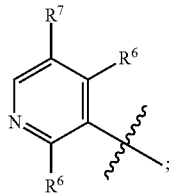

and $R^6$ and $R^7$ are one of the following combinations:
each $R^6$ is independently $C_1$-$C_6$ alkyl, and $R^7$ is $C_1$-$C_6$ alkyl optionally substituted with one or more halo; each $R^6$ is independently $C_1$-$C_6$ alkyl and $R^7$ is $C_1$-$C_6$ alkyl; each $R^6$ is independently $C_1$-$C_6$ alkyl, and $R^7$ is $C_1$-$C_6$ alkyl substituted with one or more halo; each $R^6$ is independently $C_1$-$C_6$ alkyl, and $R^7$ is $C_3$-$C_7$ cycloalkyl; each $R^6$ is independently $C_1$-$C_6$ alkyl, and $R^7$ is halo; each $R^6$ is independently $C_1$-$C_6$ alkyl, and $R^7$ is cyano; each $R^6$ is independently $C_3$-$C_7$ cycloalkyl, and $R^7$ is $C_3$-$C_7$ cycloalkyl; each $R^6$ is independently $C_3$-$C_7$ cycloalkyl, and $R^7$ is halo; each $R^6$ is independently cyclopropyl and $R^7$ is halo; each $R^6$ is independently $C_1$-$C_6$ alkyl, and $R^7$ is $C_1$-$C_6$ alkoxy optionally substituted with one or more halo; each $R^6$ is independently $C_1$-$C_6$ alkyl, and $R^7$ is $C_1$-$C_6$ alkoxy; each $R^6$ is independently $C_1$-$C_6$ alkyl, and $R^7$ is $C_1$-$C_6$ alkoxy substituted with one or more halo; each $R^6$ is independently halo, and $R^7$ is $C_1$-$C_6$ haloalkyl; each $R^6$ is independently halo, and $R^7$ is $C_1$-$C_6$ haloalkoxy; each $R^6$ is independently $C_1$-$C_6$ alkoxy; and $R^7$ is halo; each $R^6$ is independently $C_1$-$C_6$ alkoxy; and $R^7$ is chloro; $R^7$ is $C_1$-$C_6$ alkyl, and each $R^6$ is independently $C_1$-$C_6$ alkyl optionally substituted with one or more halo; $R^7$ is $C_1$-$C_6$ alkyl, and each $R^6$ is independently $C_1$-$C_6$ alkyl substituted with one or more halo; $R^7$ is $C_1$-$C_6$ alkyl, and each $R^6$ is independently $C_3$-$C_7$ cycloalkyl; $R^7$ is $C_1$-$C_6$ alkyl, and each $R^6$ is independently halo; $R^7$ is $C_1$-$C_6$ alkyl and each $R^6$ is independently halo; $R^7$ is $C_1$-$C_6$ alkyl, and $R^6$ is cyano; $R^7$ is $C_3$-$C_7$ cycloalkyl, and each $R^6$ is independently $C_3$-$C_7$ cycloalkyl; $R^7$ is $C_3$-$C_7$ cycloalkyl, and each $R^6$ is independently halo; $R^7$ is $C_3$-$C_7$ cycloalkyl and each $R^6$ is independently halo; $R^7$ is $C_1$-$C_6$ alkyl, and each $R^6$ is independently $C_1$-$C_6$ alkoxy optionally substituted with one or more halo; $R^7$ is $C_1$-$C_6$ alkyl, and each $R^6$ is independently $C_1$-$C_6$ alkoxy; $R^7$ is $C_1$-$C_6$ alkyl, and each $R^6$ is independently $C_1$-$C_6$ alkoxy substituted with one or more halo; $R^7$ is halo, and each $R^6$ is independently $C_1$-$C_6$ haloalkyl; $R^7$ is halo, and each $R^6$ is independently $C_1$-$C_6$ haloalkoxy; $R^7$ is $C_1$-$C_6$ alkoxy; and each $R^6$ is independently halo; or $R^7$ is $C_1$-$C_6$ alkoxy; and $R^6$ is chloro.

In some embodiments, of the compound of formula AA, the substituted ring B is

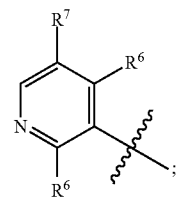

and $R^6$ and $R^7$ are one of the following combinations:
each $R^6$ is isopropyl; and $R^7$ is methyl; each $R^6$ is isopropyl; and $R^7$ is isopropyl; each $R^6$ is isopropyl; and $R^7$ is trifluoromethyl; each $R^6$ is isopropyl; and $R^7$ is cyclopropyl; each $R^6$ is isopropyl; and $R^7$ is chloro; each $R^6$ is isopropyl; and $R^7$ is fluoro; each $R^6$ is ethyl; and $R^7$ is fluoro; each $R^6$ is isopropyl; and $R^7$ is cyano; each $R^6$ is cyclopropyl; and $R^7$ is cyclopropyl; each $R^6$ is cyclopropyl; and $R^7$ is chloro; each $R^6$ is cyclopropyl; and $R^7$ is fluoro; each $R^6$ is isopropyl; and $R^7$ is methoxy; each $R^6$ is isopropyl; and $R^7$ is trifluoromethoxy; each $R^6$ is chloro; and $R^7$ is trifluoromethyl; each $R^6$ is chloro; and $R^7$ is trifluoromethoxy; $R^7$ is isopropyl; and each $R^6$ is methyl; $R^7$ is isopropyl; and each $R^6$ is trifluoromethyl; $R^7$ is isopropyl; and each $R^6$ is cyclopropyl; $R^7$ is isopropyl; and each $R^6$ is chloro; $R^7$ is ethyl; and each $R^6$ is fluoro; $R^7$ is isopropyl; and each $R^6$ is cyano; $R^7$ is cyclopropyl; and each $R^6$ is cyclopropyl; $R^7$ is cyclopropyl; and each $R^6$ is chloro; $R^7$ is cyclopropyl; and each $R^6$ is fluoro; $R^7$ is isopropyl; and each $R^6$ is methoxy; $R^7$ is isopropyl; and each $R^6$ is trifluoromethoxy; $R^7$ is chloro; and each $R^6$ is trifluoromethyl; $R^7$ is chloro; and each $R^6$ is trifluoromethoxy; or one $R^6$ is isopropyl; the other $R^6$ is trifluoromethyl; and $R^7$ is chloro.

In some embodiments, of the compound of formula AA, the substituted ring B is

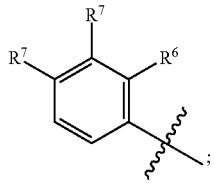

and $R^6$ and $R^7$ are one of the following combinations:
$R^6$ is $C_1$-$C_6$ alkyl, and each $R^7$ is independently $C_1$-$C_6$ alkyl optionally substituted with one or more halo; $R^6$ is $C_1$-$C_6$ alkyl and each $R^7$ is independently $C_1$-$C_6$ alkyl; $R^6$ is $C_1$-$C_6$ alkyl, and each $R^7$ is independently $C_1$-$C_6$ alkyl substituted with one or more halo; $R^6$ is $C_1$-$C_6$ alkyl, and each $R^7$ is independently $C_3$-$C_7$ cycloalkyl; $R^6$ is $C_1$-$C_6$ alkyl, and each $R^7$ is independently halo; $R^6$ is $C_1$-$C_6$ alkyl, and $R^7$ is cyano; $R^6$ is $C_3$-$C_7$ cycloalkyl, and each $R^7$ is independently $C_3$-$C_7$ cycloalkyl; $R^6$ is $C_3$-$C_7$ cycloalkyl, and each $R^7$ is independently halo; $R^6$ is cyclopropyl and each $R^7$ is independently halo; $R^6$ is $C_1$-$C_6$ alkyl, and each $R^7$ is independently $C_1$-$C_6$ alkoxy optionally substituted with one or more halo; $R^6$ is $C_1$-$C_6$ alkyl, and each $R^7$ is independently $C_1$-$C_6$ alkoxy; $R^6$ is $C_1$-$C_6$ alkyl, and each $R^7$ is independently $C_1$-$C_6$ alkoxy substituted with one or more halo; $R^6$ is halo, and each $R^7$ is independently $C_1$-$C_6$ haloalkyl; $R^6$ is halo, and each $R^7$ is independently $C_1$-$C_6$ haloalkoxy; $R^6$ is $C_1$-$C_6$ alkoxy; and each $R^7$ is independently halo; $R^6$ is $C_1$-$C_6$ alkoxy; and $R^7$ is chloro; each $R^7$ is independently $C_1$-$C_6$ alkyl, and $R^6$ is $C_1$-$C_6$ alkyl optionally substituted with one or more halo; each $R^7$ is independently $C_1$-$C_6$ alkyl, and $R^6$ is $C_1$-$C_6$ alkyl substituted with one or more halo; each $R^7$ is independently $C_1$-$C_6$ alkyl, and $R^6$ is $C_3$-$C_7$ cycloalkyl; each $R^7$ is independently $C_1$-$C_6$ alkyl, and $R^6$ is halo; each $R^7$ is independently $C_1$-$C_6$ alkyl and $R^6$ is halo; each $R^7$ is independently $C_1$-$C_6$ alkyl, and $R^6$ is cyano; each $R^7$ is independently $C_3$-$C_7$ cycloalkyl, and $R^6$ is $C_3$-$C_7$ cycloalkyl, each $R^7$ is independently $C_3$-$C_7$ cycloalkyl, and $R^6$ is halo; each $R^7$ is independently $C_3$-$C_7$ cycloalkyl and $R^6$ is halo; each $R^7$ is independently $C_1$-$C_6$ alkyl, and $R^6$ is $C_1$-$C_6$ alkoxy optionally substituted with one or more halo; each $R^7$ is independently $C_1$-$C_6$ alkyl, and $R^6$ is $C_1$-$C_6$ alkoxy; each $R^7$ is independently $C_1$-$C_6$ alkyl, and $R^6$ is $C_1$-$C_6$ alkoxy substituted with one or more halo; each $R^7$ is independently halo, and $R^6$ is $C_1$-$C_6$ haloalkyl; each $R^7$ is independently halo, and $R^6$ is $C_1$-$C_6$ haloalkoxy; each $R^7$ is independently $C_1$-$C_6$ alkoxy; and $R^6$ is halo; each $R^7$ is independently $C_1$-$C_6$ alkoxy; and $R^6$ is chloro; $R^6$ and $R^7$ on adjacent atoms taken together with the atoms connecting them form a $C_5$ aliphatic carbocyclic ring; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

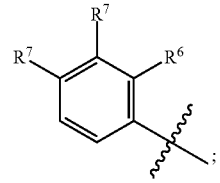

and $R^6$ and $R^7$ are one of the following combinations:
$R^6$ is isopropyl; and each $R^7$ is methyl; $R^6$ is isopropyl; and each $R^7$ is isopropyl; $R^6$ is isopropyl; and each $R^7$ is trifluoromethyl; $R^6$ is isopropyl; and each $R^7$ is cyclopropyl; $R^6$ is isopropyl; and each $R^7$ is chloro; $R^6$ is isopropyl; and each $R^7$ is fluoro; $R^6$ is ethyl; and each $R^7$ is fluoro; $R^6$ is isopropyl; and each $R^7$ is cyano; $R^6$ is cyclopropyl; and each $R^7$ is cyclopropyl; $R^6$ is cyclopropyl; and each $R^7$ is chloro; $R^6$ is cyclopropyl; and each $R^7$ is fluoro; $R^6$ is isopropyl; and $R^7$ is methoxy; $R^6$ is isopropyl; and each $R^7$ is trifluoromethoxy; $R^6$ is chloro; and each $R^7$ is trifluoromethyl; $R^6$ is chloro; and each $R^7$ is trifluoromethoxy; each $R^7$ is isopropyl; and $R^6$ is methyl; each $R^7$ is isopropyl; and $R^6$ is trifluoromethyl; each $R^7$ is isopropyl; and $R^6$ is cyclopropyl; each $R^7$ is isopropyl; and $R^6$ is chloro; each $R^7$ is ethyl; and $R^6$ is fluoro; each $R^7$ is isopropyl; and $R^6$ is cyano; each $R^7$ is cyclopropyl; and $R^6$ is cyclopropyl; each $R^7$ is cyclopropyl; and $R^6$ is chloro; each $R^7$ is cyclopropyl; and $R^6$ is fluoro; each $R^7$ is isopropyl; and $R^6$ is methoxy; each $R^7$ is isopropyl; and $R^6$ is trifluoromethoxy; each $R^7$ is chloro; and $R^6$ is trifluoromethyl; each $R^7$ is chloro; and $R^6$ is trifluoromethoxy; $R^6$ and $R^7$ on adjacent atoms taken together with the atoms connecting them form a $C_5$ aliphatic carbocyclic ring; and one $R^7$ is fluoro, chloro, or cyano; $R^6$ and $R^7$ on adjacent atoms taken together with the atoms connecting them form a $C_4$ aliphatic carbocyclic ring; and one $R^7$ is fluoro, chloro, or cyano; $R^6$ and $R^7$ on adjacent atoms taken together with the atoms connecting them form a $C_6$ aliphatic carbocyclic ring; and one $R^7$ is fluoro, chloro, or cyano; $R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

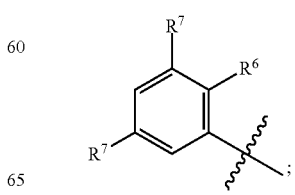

and $R^6$ and $R^7$ are one of the following combinations:
$R^6$ is $C_1$-$C_6$ alkyl, and each $R^7$ is independently $C_1$-$C_6$ alkyl optionally substituted with one or more halo; $R^6$ is $C_1$-$C_6$ alkyl and each $R^7$ is independently $C_1$-$C_6$ alkyl; $R^6$ is $C_1$-$C_6$ alkyl, and each $R^7$ is independently $C_1$-$C_6$ alkyl substituted with one or more halo; $R^6$ is $C_1$-$C_6$ alkyl, and each $R^7$ is independently $C_3$-$C_7$ cycloalkyl; $R^6$ is $C_1$-$C_6$ alkyl, and each $R^7$ is independently halo; $R^6$ is $C_1$-$C_6$ alkyl, and $R^7$ is cyano; $R^6$ is $C_3$-$C_7$ cycloalkyl, and each $R^7$ is independently $C_3$-$C_7$ cycloalkyl; $R^6$ is $C_3$-$C_7$ cycloalkyl, and each $R^7$ is independently halo; $R^6$ is cyclopropyl and each $R^7$ is independently halo; $R^6$ is $C_1$-$C_6$ alkyl, and each $R^7$ is independently $C_1$-$C_6$ alkoxy optionally substituted with one or more halo; $R^6$ is $C_1$-$C_6$ alkyl, and each $R^7$ is independently $C_1$-$C_6$ alkoxy; $R^6$ is $C_1$-$C_6$ alkyl, and each $R^7$ is independently $C_1$-$C_6$ alkoxy substituted with one or more halo; $R^6$ is halo, and each $R^7$ is independently $C_1$-$C_6$ haloalkyl; $R^6$ is halo, and each $R^7$ is independently $C_1$-$C_6$ haloalkoxy; $R^6$ is $C_1$-$C_6$ alkoxy; and each $R^7$ is independently halo; $R^6$ is $C_1$-$C_6$ alkoxy; and $R^7$ is chloro; each $R^7$ is independently $C_1$-$C_6$ alkyl, and $R^6$ is $C_1$-$C_6$ alkyl optionally substituted with one or more halo; each $R^7$ is independently $C_1$-$C_6$ alkyl, and $R^6$ is $C_1$-$C_6$ alkyl substituted with one or more halo; each $R^7$ is independently $C_1$-$C_6$ alkyl, and $R^6$ is $C_3$-$C_7$ cycloalkyl; each $R^7$ is independently $C_1$-$C_6$ alkyl, and $R^6$ is halo; each $R^7$ is independently $C_1$-$C_6$ alkyl and $R^6$ is halo; each $R^7$ is independently $C_1$-$C_6$ alkyl, and $R^6$ is cyano; each $R^7$ is independently $C_3$-$C_7$ cycloalkyl, and $R^6$ is $C_3$-$C_7$ cycloalkyl; each $R^7$ is independently $C_3$-$C_7$ cycloalkyl, and $R^6$ is halo; each $R^7$ is independently $C_3$-$C_7$ cycloalkyl and $R^6$ is halo; each $R^7$ is independently $C_1$-$C_6$ alkyl, and $R^6$ is $C_1$-$C_6$ alkoxy optionally substituted with one or more halo; each $R^7$ is independently $C_1$-$C_6$ alkyl, and $R^6$ is $C_1$-$C_6$ alkoxy; each $R^7$ is independently $C_1$-$C_6$ alkyl, and $R^6$ is $C_1$-$C_6$ alkoxy substituted with one or more halo; each $R^7$ is independently halo, and $R^6$ is $C_1$-$C_6$ haloalkyl; each $R^7$ is independently halo, and $R^6$ is $C_1$-$C_6$ haloalkoxy; each $R^7$ is independently $C_1$-$C_6$ alkoxy; and $R^6$ is halo; each $R^6$ is independently $C_1$-$C_6$ alkoxy; and $R^6$ is chloro; $R^6$ and $R^7$ on adjacent atoms taken together with the atoms connecting them form a $C_5$ aliphatic carbocyclic ring; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

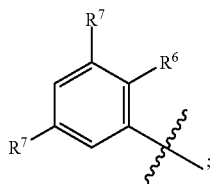

and $R^6$ and $R^7$ are one of the following combinations:
$R^6$ is isopropyl; and each $R^7$ is methyl; $R^6$ is isopropyl; and each $R^7$ is isopropyl; $R^6$ is isopropyl; and each $R^7$ is trifluoromethyl; $R^6$ is isopropyl; and each $R^7$ is cyclopropyl; $R^6$ is isopropyl; and each $R^7$ is chloro; $R^6$ is isopropyl; and each $R^7$ is fluoro; $R^6$ is ethyl; and each $R^7$ is fluoro; $R^6$ is isopropyl; and each $R^7$ is cyano; $R^6$ is cyclopropyl; and each $R^7$ is cyclopropyl; $R^6$ is cyclopropyl; and each $R^7$ is chloro; $R^6$ is cyclopropyl; and each $R^7$ is fluoro; $R^6$ is isopropyl; and each $R^7$ is methoxy; $R^6$ is isopropyl; and each $R^7$ is trifluoromethoxy; $R^6$ is chloro; and each $R^7$ is trifluoromethyl; $R^6$ is chloro; and each $R^7$ is trifluoromethoxy; each $R^7$ is isopropyl; and $R^6$ is methyl; each $R^7$ is isopropyl; and $R^6$ is trifluoromethyl; each $R^7$ is isopropyl; and $R^6$ is cyclopropyl; each $R^7$ is isopropyl; and $R^6$ is chloro; each $R^7$ is ethyl; and $R^6$ is fluoro; each $R^7$ is isopropyl; and $R^6$ is cyano; each $R^7$ is cyclopropyl; and $R^6$ is cyclopropyl; each $R^7$ is cyclopropyl; and $R^6$ is chloro; each $R^7$ is cyclopropyl; and $R^6$ is fluoro; each $R^7$ is isopropyl; and $R^6$ is methoxy; each $R^7$ is isopropyl; and $R^6$ is trifluoromethoxy; each $R^7$ is chloro; and $R^6$ is trifluoromethyl; each $R^7$ is chloro; and $R^6$ is trifluoromethoxy; $R^6$ and $R^7$ on adjacent atoms taken together with the atoms connecting them form a $C_5$ aliphatic carbocyclic ring; and one $R^7$ is fluoro, chloro, or cyano; $R^6$ and $R^7$ on adjacent atoms taken together with the atoms connecting them form a $C_4$ aliphatic carbocyclic ring; and one $R^7$ is fluoro, chloro, or cyano; $R^6$ and $R^7$ on adjacent atoms taken together with the atoms connecting them form a $C_6$ aliphatic carbocyclic ring; and one $R^7$ is fluoro, chloro, or cyano; $R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

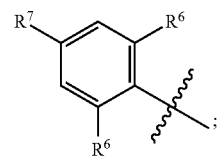

and $R^6$ and $R^7$ are one of the following combinations:
each $R^6$ is independently $C_1$-$C_6$ alkyl, and $R^7$ is $C_1$-$C_6$ alkyl optionally substituted with one or more halo; each $R^6$ is independently $C_1$-$C_6$ alkyl and $R^7$ is $C_1$-$C_6$ alkyl; each $R^6$ is independently $C_1$-$C_6$ alkyl, and $R^7$ is $C_1$-$C_6$ alkyl substituted with one or more halo; each $R^6$ is independently $C_1$-$C_6$ alkyl, and $R^7$ is $C_3$-$C_7$ cycloalkyl; each $R^6$ is independently $C_1$-$C_6$ alkyl, and $R^7$ is halo; each $R^6$ is independently $C_1$-$C_6$ alkyl, and $R^7$ is cyano; each $R^6$ is independently $C_3$-$C_7$ cycloalkyl, and $R^7$ is $C_3$-$C_7$ cycloalkyl; each $R^6$ is independently $C_3$-$C_7$ cycloalkyl, and $R^7$ is halo; each $R^6$ is independently cyclopropyl and $R^7$ is halo; each $R^6$ is independently $C_1$-$C_6$ alkyl, and $R^7$ is $C_1$-$C_6$ alkoxy optionally substituted with one or more halo; each $R^6$ is independently $C_1$-$C_6$ alkyl, and $R^7$ is $C_1$-$C_6$ alkoxy; each $R^6$ is independently $C_1$-$C_6$ alkyl, and $R^7$ is $C_1$-$C_6$ alkoxy substituted with one or more halo; each $R^6$ is independently halo, and $R^7$ is $C_1$-$C_6$ haloalkyl; each $R^6$ is independently halo, and $R^7$ is $C_1$-$C_6$ haloalkoxy; each $R^6$ is independently $C_1$-$C_6$ alkoxy; and $R^7$ is halo; each $R^6$ is independently $C_1$-$C_6$ alkoxy; and $R^7$ is chloro; $R^7$ is $C_1$-$C_6$ alkyl, and each $R^6$ is independently $C_1$-$C_6$ alkyl optionally substituted with one or more halo; $R^7$ is $C_1$-$C_6$ alkyl, and each $R^6$ is independently $C_1$-$C_6$ alkyl substituted with one or more halo; $R^7$ is $C_1$-$C_6$ alkyl, and each $R^6$ is independently $C_3$-$C_7$ cycloalkyl; $R^7$ is $C_1$-$C_6$ alkyl, and each $R^6$ is independently halo; $R^7$ is $C_1$-$C_6$ alkyl and each $R^6$ is independently halo; $R^7$ is $C_1$-$C_6$ alkyl, and $R^6$ is cyano; $R^7$ is $C_3$-$C_7$ cycloalkyl, and each $R^6$ is independently $C_3$-$C_7$ cycloalkyl; $R^7$ is $C_3$-$C_7$ cycloalkyl, and each $R^6$ is independently halo; $R^7$ is $C_3$-$C_7$ cycloalkyl and each $R^6$ is independently halo; $R^7$ is $C_1$-$C_6$ alkyl, and each $R^6$ is independently $C_1$-$C_6$ alkoxy optionally substituted with one or more halo; $R^7$ is $C_1$-$C_6$ alkyl, and each $R^6$ is independently $C_1$-$C_6$ alkoxy; $R^7$ is $C_1$-$C_6$ alkyl, and each $R^6$ is independently $C_1$-$C_6$ alkoxy substituted with one or more halo; $R^7$ is halo, and each $R^6$ is independently $C_1$-$C_6$ haloalkyl; $R^7$ is halo, and each $R^6$ is independently $C_1$-$C_6$ haloalkoxy; $R^7$ is $C_1$-$C_6$ alkoxy; and each $R^6$ is independently halo; or $R^7$ is $C_1$-$C_6$ alkoxy; and $R^6$ is chloro.

In some embodiments, of the compound of formula AA, the substituted ring B is

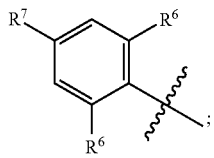

and $R^6$ and $R^7$ are one of the following combinations:
each $R^6$ is isopropyl; and $R^7$ is methyl; each $R^6$ is isopropyl; and $R^7$ is isopropyl; each $R^6$ is isopropyl; and $R^7$ is trifluoromethyl; each $R^6$ is isopropyl; and $R^7$ is cyclopropyl; each $R^6$ is isopropyl; and $R^7$ is chloro; each $R^6$ is isopropyl; and $R^7$ is fluoro; each $R^6$ is ethyl; and $R^7$ is fluoro; each $R^6$ is isopropyl; and $R^7$ is cyano; each $R^6$ is cyclopropyl; and $R^7$ is cyclopropyl; each $R^6$ is cyclopropyl; and $R^7$ is chloro; each $R^6$ is cyclopropyl; and $R^7$ is fluoro; each $R^6$ is isopropyl; and $R^7$ is methoxy; each $R^6$ is isopropyl; and $R^7$ is trifluoromethoxy; each $R^6$ is chloro; and $R^7$ is trifluoromethyl; each $R^6$ is chloro; and $R^7$ is trifluoromethoxy; $R^7$ is isopropyl; and each $R^6$ is methyl; $R^7$ is isopropyl; and each $R^6$ is trifluoromethyl; $R^7$ is isopropyl; and each $R^6$ is cyclopropyl; $R^7$ is isopropyl; and each $R^6$ is chloro; $R^7$ is ethyl; and each $R^6$ is fluoro; $R^7$ is isopropyl; and each $R^6$ is cyano; $R^7$ is cyclopropyl; and each $R^6$ is cyclopropyl; $R^7$ is cyclopropyl; and each $R^6$ is chloro; $R^7$ is cyclopropyl; and each $R^6$ is fluoro; $R^7$ is isopropyl; and each $R^6$ is methoxy; $R^7$ is isopropyl; and each $R^6$ is trifluoromethoxy; $R^7$ is chloro; and each $R^6$ is trifluoromethyl; $R^7$ is chloro; and each $R^6$ is trifluoromethoxy; or one $R^6$ is isopropyl; the other $R^6$ is trifluoromethyl; and $R^7$ is chloro.

In some embodiments, of the compound of formula AA, the substituted ring B is

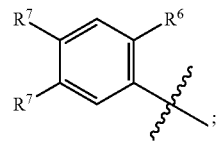

and $R^6$ and $R^7$ are one of the following combinations:
$R^6$ is $C_1$-$C_6$ alkyl, and each $R^7$ is independently $C_1$-$C_6$ alkyl optionally substituted with one or more halo; $R^6$ is $C_1$-$C_6$ alkyl and each $R^7$ is independently $C_1$-$C_6$ alkyl; $R^6$ is $C_1$-$C_6$ alkyl, and each $R^7$ is independently $C_1$-$C_6$ alkyl substituted with one or more halo; $R^6$ is $C_1$-$C_6$ alkyl, and each $R^7$ is independently $C_3$-$C_7$ cycloalkyl; $R^6$ is $C_1$-$C_6$ alkyl, and each $R^7$ is independently halo; $R^6$ is $C_1$-$C_6$ alkyl, and $R^7$ is cyano; $R^6$ is $C_3$-$C_7$ cycloalkyl, and each $R^7$ is independently $C_3$-$C_7$ cycloalkyl; $R^6$ is $C_3$-$C_7$ cycloalkyl, and each $R^7$ is independently halo; $R^6$ is cyclopropyl and each $R^7$ is independently halo; $R^6$ is $C_1$-$C_6$ alkyl, and each $R^7$ is independently $C_1$-$C_6$ alkoxy optionally substituted with one or more halo; $R^6$ is $C_1$-$C_6$ alkyl, and each $R^7$ is independently $C_1$-$C_6$ alkoxy; $R^6$ is $C_1$-$C_6$ alkyl, and each $R^7$ is independently $C_1$-$C_6$ alkoxy substituted with one or more halo; $R^6$ is halo, and each $R^7$ is independently $C_1$-$C_6$ haloalkyl; $R^6$ is halo, and each $R^7$ is independently $C_1$-$C_6$ haloalkoxy; $R^6$ is $C_1$-$C_6$ alkoxy; and each $R^7$ is independently halo; $R^6$ is $C_1$-$C_6$ alkoxy; and $R^7$ is chloro; each $R^7$ is independently $C_1$-$C_6$ alkyl, and $R^6$ is $C_1$-$C_6$ alkyl optionally substituted with one or more halo; each $R^7$ is independently $C_1$-$C_6$ alkyl, and $R^6$ is $C_1$-$C_6$ alkyl substituted with one or more halo; each $R^7$ is independently $C_1$-$C_6$ alkyl, and $R^6$ is $C_3$-$C_7$ cycloalkyl; each $R^7$ is independently $C_1$-$C_6$ alkyl, and $R^6$ is halo; each $R^7$ is independently $C_1$-$C_6$ alkyl and $R^6$ is halo; each $R^7$ is independently $C_1$-$C_6$ alkyl, and $R^6$ is cyano; each $R^7$ is independently $C_3$-$C_7$ cycloalkyl, and $R^6$ is $C_3$-$C_7$ cycloalkyl; each $R^7$ is independently $C_3$-$C_7$ cycloalkyl, and $R^6$ is halo; each $R^7$ is independently $C_3$-$C_7$ cycloalkyl and $R^6$ is halo; each $R^7$ is independently $C_1$-$C_6$ alkyl, and $R^6$ is $C_1$-$C_6$ alkoxy optionally substituted with one or more halo; each $R^7$ is independently $C_1$-$C_6$ alkyl, and $R^6$ is $C_1$-$C_6$ alkoxy; each $R^7$ is independently $C_1$-$C_6$ alkyl, and $R^6$ is $C_1$-$C_6$ alkoxy substituted with one or more halo; each $R^7$ is independently halo, and $R^6$ is $C_1$-$C_6$ haloalkyl; each $R^7$ is independently halo, and $R^6$ is $C_1$-$C_6$ haloalkoxy; each $R^7$ is independently $C_1$-$C_6$ alkoxy; and $R^6$ is halo; or each $R^7$ is independently $C_1$-$C_6$ alkoxy; and $R^6$ is chloro.

In some embodiments, of the compound of formula AA, the substituted ring B is

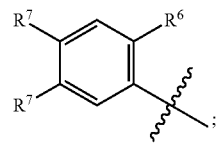

and $R^6$ and $R^7$ are one of the following combinations:
$R^6$ is isopropyl; and each $R^7$ is methyl; $R^6$ is isopropyl; and each $R^7$ is isopropyl; $R^6$ is isopropyl; and each $R^7$ is trifluoromethyl; $R^6$ is isopropyl; and each $R^7$ is cyclopropyl; $R^6$ is isopropyl; and each $R^7$ is chloro; $R^6$ is isopropyl; and each $R^7$ is fluoro; $R^6$ is ethyl; and each $R^7$ is fluoro; $R^6$ is isopropyl; and each $R^7$ is cyano; $R^6$ is cyclopropyl; and each $R^7$ is cyclopropyl; $R^6$ is cyclopropyl; and each $R^7$ is chloro; $R^6$ is cyclopropyl; and each $R^7$ is fluoro; $R^6$ is isopropyl; and each $R^7$ is methoxy; $R^6$ is isopropyl; and each $R^7$ is trifluoromethoxy; $R^6$ is chloro; and each $R^7$ is trifluoromethyl; $R^6$ is chloro; and each $R^7$ is trifluoromethoxy; each $R^7$ is isopropyl; and $R^6$ is methyl; each $R^7$ is isopropyl; and $R^6$ is trifluoromethyl; each $R^7$ is isopropyl; and $R^6$ is cyclopropyl; each $R^7$ is isopropyl; and $R^6$ is chloro; each $R^7$ is ethyl; and $R^6$ is fluoro; each $R^7$ is isopropyl; and $R^6$ is cyano; each $R^7$ is cyclopropyl; and $R^6$ is cyclopropyl; each $R^7$ is cyclopropyl; and $R^6$ is chloro; each $R^7$ is cyclopropyl; and $R^6$ is fluoro; each $R^7$ is isopropyl; and $R^6$ is methoxy; each $R^7$ is isopropyl; and $R^6$ is trifluoromethoxy; each $R^7$ is chloro; and $R^6$ is trifluoromethyl; or each $R^7$ is chloro; and $R^6$ is trifluoromethoxy.

In some embodiments, of the compound of formula AA, the substituted ring B is

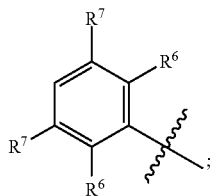

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo; each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo; each $R^6$ is independently $C_1$-$C_6$ alkyl, and each $R^7$ is independently $C_3$-$C_7$ cycloalkyl; each $R^6$ is independently $C_1$-$C_6$ alkyl, and each $R^7$ is independently halo; each $R^6$ is independently $C_1$-$C_6$ alkyl, and $R^7$ is cyano; each $R^6$ is independently $C_3$-$C_7$ cycloalkyl, and each $R^7$ is independently $C_3$-$C_7$ cycloalkyl; each $R^6$ is independently $C_3$-$C_7$ cycloalkyl, and each $R^7$ is independently halo; each $R^6$ is independently cyclopropyl and each $R^7$ is independently halo; each $R^6$ is independently $C_1$-$C_6$ alkyl, and each $R^7$ is independently $C_1$-$C_6$ alkoxy optionally substituted with one or more halo; each $R^6$ is independently $C_1$-$C_6$ alkyl, and each $R^7$ is independently $C_1$-$C_6$ alkoxy; each $R^6$ is independently $C_1$-$C_6$ alkyl, and each $R^7$ is independently $C_1$-$C_6$ alkoxy substituted with one or more halo; each $R^6$ is independently halo, and each $R^7$ is independently $C_1$-$C_6$ haloalkyl; each $R^6$ is independently halo, and each $R^7$ is independently $C_1$-$C_6$ haloalkoxy; each $R^6$ is independently $C_1$-$C_6$ alkoxy; and each $R^7$ is independently halo; each $R^6$ is independently $C_1$-$C_6$ alkoxy; and $R^7$ is chloro; each $R^7$ is independently $C_1$-$C_6$ alkyl, and each $R^6$ is independently $C_1$-$C_6$ alkyl optionally substituted with one or more halo; each $R^7$ is independently $C_1$-$C_6$ alkyl, and each $R^6$ is independently $C_1$-$C_6$ alkyl substituted with one or more halo; each $R^7$ is independently $C_1$-$C_6$ alkyl, and each $R^6$ is independently $C_3$-$C_7$ cycloalkyl; each $R^7$ is independently $C_1$-$C_6$ alkyl, and each $R^6$ is independently halo; each $R^7$ is independently $C_1$-$C_6$ alkyl and each $R^6$ is independently halo; each $R^7$ is independently $C_1$-$C_6$ alkyl, and $R^6$ is cyano; each $R^7$ is independently $C_3$-$C_7$ cycloalkyl, and each $R^6$ is independently $C_3$-$C_7$ cycloalkyl each $R^7$ is independently $C_3$-$C_7$ cycloalkyl, and each $R^6$ is independently halo; each $R^7$ is independently $C_3$-$C_7$ cycloalkyl and each $R^6$ is independently halo; each $R^7$ is independently $C_1$-$C_6$ alkyl, and each $R^6$ is independently $C_1$-$C_6$ alkoxy optionally substituted with one or more halo; each $R^7$ is independently $C_1$-$C_6$ alkyl, and each $R^6$ is independently $C_1$-$C_6$ alkoxy; each $R^7$ is independently $C_1$-$C_6$ alkyl, and each $R^6$ is independently $C_1$-$C_6$ alkoxy substituted with one or more halo; each $R^7$ is independently halo, and each $R^6$ is independently $C_1$-$C_6$ haloalkyl; each $R^7$ is independently halo, and each $R^6$ is independently $C_1$-$C_6$ haloalkoxy; each $R^7$ is independently $C_1$-$C_6$ alkoxy; and each $R^6$ is independently halo; each $R^7$ is independently $C_1$-$C_6$ alkoxy; and $R^6$ is chloro; two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; two pairs, each of one $R^6$ and one $R^7$, are on adjacent atoms, and one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring is optionally substituted with one or more hydroxy, oxo, or $C_1$-$C_6$ alkyl; or two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

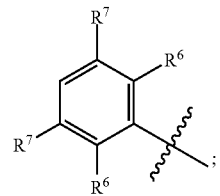

and $R^6$ and $R^7$ are one of the following combinations:
each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each R⁷ is fluoro; each R⁶ is isopropyl; and each R⁷ is methoxy; each R⁶ is isopropyl; and each R⁷ is trifluoromethoxy; each R⁶ is chloro; and each R⁷ is trifluoromethyl; each R⁶ is chloro; and each R⁷ is trifluoromethoxy; each R⁷ is isopropyl; and each R⁶ is methyl; each R⁷ is isopropyl; and each R⁶ is trifluoromethyl; each R⁷ is isopropyl; and each R⁶ is cyclopropyl; each R⁷ is isopropyl; and each R⁶ is chloro; each R⁷ is ethyl; and each R⁶ is fluoro; each R⁷ is isopropyl; and each R⁶ is cyano; each R⁷ is cyclopropyl; and each R⁶ is cyclopropyl; each R⁷ is cyclopropyl; and each R⁶ is chloro; each R⁷ is cyclopropyl; and each R⁶ is fluoro; each R⁷ is isopropyl; and each R⁶ is methoxy; each R⁷ is isopropyl; and each R⁶ is trifluoromethoxy; each R⁷ is chloro; and each R⁶ is trifluoromethyl; each R⁷ is chloro; and each R⁶ is trifluoromethoxy; one R⁶ is isopropyl; the other R⁶ is trifluoromethyl; and each R⁷ is chloro; each R⁶ is isopropyl; one R⁷ is fluoro; and the other R⁷ is cyano; two pairs, each of one R⁶ and one R⁷, are on adjacent atoms, and each pair of one R⁶ and one R⁷ taken together with the atoms connecting them form a C₅ aliphatic carbocyclic ring; two pairs, each of one R⁶ and one R⁷, are on adjacent atoms, and each pair of one R⁶ and one R⁷ taken together with the atoms connecting them form a C₄ aliphatic carbocyclic ring optionally substituted with one or more hydroxy, oxo, or methyl; two pairs, each of one R⁶ and one R⁷, are on adjacent atoms, and each pair of one R⁶ and one R⁷ taken together with the atoms connecting them form a C₅ aliphatic carbocyclic ring optionally substituted with one or more hydroxy, oxo, or methyl; two pairs, each of one R⁶ and one R⁷, are on adjacent atoms, and each pair of one R⁶ and one R⁷ taken together with the atoms connecting them form a C₆ aliphatic carbocyclic ring optionally substituted with one or more hydroxy, oxo, or methyl; two pairs, each of one R⁶ and one R⁷, are on adjacent atoms, and each pair of one R⁶ and one R⁷ taken together with the atoms connecting them form a 5-membered heterocyclic ring containing 1 heteroatom independently selected from O, N, and S, wherein the heterocyclic ring is optionally substituted with one or more hydroxy, oxo, or methyl; two pairs, each of one R⁶ and one R⁷, are on adjacent atoms, and each pair of one R⁶ and one R⁷ taken together with the atoms connecting them form a 6-membered heterocyclic ring containing 1 heteroatom independently selected from O, N, and S, wherein the heterocyclic ring is optionally substituted with one or more hydroxy, oxo, or methyl; or two pairs, each of one R⁶ and one R⁷, are on adjacent atoms, one pair of one R⁶ and one R⁷ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one R⁶ and one R⁷ taken together with the atoms connecting them form a C₅ aliphatic carbocyclic ring optionally substituted with one or more hydroxy, oxo, or methyl.

In some embodiments, of the compound of formula AA, the substituted ring B is

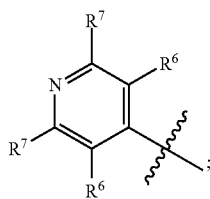

and R⁶ and R⁷ are one of the following combinations:
each R⁶ is independently C₁-C₆ alkyl, and each R⁷ is independently C₁-C₆ alkyl optionally substituted with one or more halo; each R⁶ is independently C₁-C₆ alkyl and each R⁷ is independently C₁-C₆ alkyl; each R⁶ is independently C₁-C₆ alkyl, and each R⁷ is independently C₁-C₆ alkyl substituted with one or more halo; each R⁶ is independently C₁-C₆ alkyl, and each R⁷ is independently C₃-C₇ cycloalkyl; each R⁶ is independently C₁-C₆ alkyl, and each R⁷ is independently halo; each R⁶ is independently C₁-C₆ alkyl, and R⁷ is cyano; each R⁶ is independently C₃-C₇ cycloalkyl, and each R⁷ is independently C₃-C₇ cycloalkyl; each R⁶ is independently C₃-C₇ cycloalkyl, and each R⁷ is independently halo; each R⁶ is independently cyclopropyl and each R⁷ is independently halo; each R⁶ is independently C₁-C₆ alkyl, and each R⁷ is independently C₁-C₆ alkoxy optionally substituted with one or more halo; each R⁶ is independently C₁-C₆ alkyl, and each R⁷ is independently C₁-C₆ alkoxy; each R⁶ is independently C₁-C₆ alkyl, and each R⁷ is independently C₁-C₆ alkoxy substituted with one or more halo; each R⁶ is independently halo, and each R⁷ is independently C₁-C₆ haloalkyl; each R⁶ is independently halo, and each R⁷ is independently C₁-C₆ haloalkoxy; each R⁶ is independently C₁-C₆ alkoxy; and each R⁷ is independently halo; each R⁶ is independently C₁-C₆ alkoxy; and R⁷ is chloro; each R⁷ is independently C₁-C₆ alkyl, and each R⁶ is independently C₁-C₆ alkyl optionally substituted with one or more halo; each R⁷ is independently C₁-C₆ alkyl, and each R⁶ is independently C₁-C₆ alkyl substituted with one or more halo; each R⁷ is independently C₁-C₆ alkyl, and each R⁶ is independently C₃-C₇ cycloalkyl; each R⁷ is independently C₁-C₆ alkyl, and each R⁶ is independently halo; each R⁷ is independently C₁-C₆ alkyl and each R⁶ is independently halo; each R⁷ is independently C₁-C₆ alkyl, and R⁶ is cyano; each R⁷ is independently C₃-C₇ cycloalkyl, and each R⁶ is independently C₃-C₇ cycloalkyl; each R⁷ is independently C₃-C₇ cycloalkyl, and each R⁶ is independently halo; each R⁷ is independently C₃-C₇ cycloalkyl and each R⁶ is independently halo; each R⁷ is independently C₁-C₆ alkyl, and each R⁶ is independently C₁-C₆ alkoxy optionally substituted with one or more halo; each R⁷ is independently C₁-C₆ alkyl, and each R⁶ is independently C₁-C₆ alkoxy; each R⁷ is independently C₁-C₆ alkyl, and each R⁶ is independently C₁-C₆ alkoxy substituted with one or more halo; each R⁷ is independently halo, and each R⁶ is independently C₁-C₆ haloalkyl; each R⁷ is independently halo, and each R⁶ is independently C₁-C₆ haloalkoxy; each R⁷ is independently C₁-C₆ alkoxy; and each R⁶ is independently halo; each R⁷ is independently C₁-C₆ alkoxy; and R⁶ is chloro; two pairs, each of one R⁶ and one R⁷, are on adjacent atoms, and each pair of one R⁶ and one R⁷ taken together with the atoms connecting them form a C₄-C₈ aliphatic carbocyclic ring; two pairs, each of one R⁶ and one R⁷ on adjacent atoms taken together with the atoms connecting them form a C₄-C₆ aliphatic carbocyclic ring optionally substituted with one or more hydroxy, oxo, or C₁-C₆ alkyl; or two pairs, each of one R⁶ and one R⁷ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or C₁-C₆ alkyl.

In some embodiments, of the compound of formula AA, the substituted ring B is

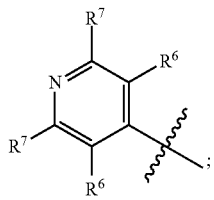

and $R^6$ and $R^7$ are one of the following combinations:
each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; each $R^7$ is chloro; and each $R^6$ is trifluoromethyl; each $R^7$ is chloro; and each $R^6$ is trifluoromethoxy; one $R^6$ is isopropyl; the other $R^6$ is trifluoromethyl; and each $R^7$ is chloro; each $R^6$ is isopropyl; one $R^7$ is fluoro; and the other $R^7$ is cyano; or two pairs, each of one $R^6$ and one $R^7$ on adjacent atoms taken together with the atoms connecting them form a $C_4$ aliphatic carbocyclic ring optionally substituted with one or more hydroxy, oxo, or methyl; two pairs, each of one $R^6$ and one $R^7$ on adjacent atoms taken together with the atoms connecting them form a $C_5$ aliphatic carbocyclic ring optionally substituted with one or more hydroxy, oxo, or methyl; two pairs, each of one $R^6$ and one $R^7$ on adjacent atoms taken together with the atoms connecting them form a $C_6$ aliphatic carbocyclic ring optionally substituted with one or more hydroxy, oxo, or methyl; two pairs, each of one $R^6$ and one $R^7$ on adjacent atoms taken together with the atoms connecting them form a 5-membered heterocyclic ring containing 1 heteroatom independently selected from O, N, and S, wherein the heterocyclic ring is optionally substituted with one or more hydroxy, oxo, or methyl; two pairs, each of one $R^6$ and one $R^7$ on adjacent atoms taken together with the atoms connecting them form a 6-membered heterocyclic ring containing 1 heteroatom independently selected from O, N, and S, wherein the heterocyclic ring is optionally substituted with one or more hydroxy, oxo, or methyl; or two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, of the compound of formula AA, the substituted ring B is

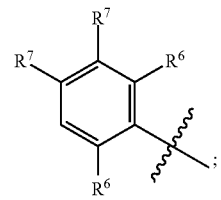

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo; each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo; each $R^6$ is independently $C_1$-$C_6$ alkyl, and each $R^7$ is independently $C_3$-$C_7$ cycloalkyl; each $R^6$ is independently $C_1$-$C_6$ alkyl, and each $R^7$ is independently halo; each $R^6$ is independently $C_1$-$C_6$ alkyl, and $R^7$ is cyano; each $R^6$ is independently $C_3$-$C_7$ cycloalkyl, and each $R^7$ is independently $C_3$-$C_7$ cycloalkyl; each $R^6$ is independently $C_3$-$C_7$ cycloalkyl, and each $R^7$ is independently halo; each $R^6$ is independently cyclopropyl and each $R^7$ is independently halo; each $R^6$ is independently $C_1$-$C_6$ alkyl, and each $R^7$ is independently $C_1$-$C_6$ alkoxy optionally substituted with one or more halo; each $R^6$ is independently $C_1$-$C_6$ alkyl, and each $R^7$ is independently $C_1$-$C_6$ alkoxy; each $R^6$ is independently $C_1$-$C_6$ alkyl, and each $R^7$ is independently $C_1$-$C_6$ alkoxy substituted with one or more halo; each $R^6$ is independently halo, and each $R^7$ is independently $C_1$-$C_6$ haloalkyl; each $R^6$ is independently halo, and each $R^7$ is independently $C_1$-$C_6$ haloalkoxy; each $R^6$ is independently $C_1$-$C_6$ alkoxy; and each $R^7$ is independently halo; each $R^6$ is independently $C_1$-$C_6$ alkoxy; and $R^7$ is chloro; each $R^7$ is independently $C_1$-$C_6$ alkyl, and each $R^6$ is independently $C_1$-$C_6$ alkyl optionally substituted with one or more halo; each $R^7$ is independently $C_1$-$C_6$ alkyl, and each $R^6$ is independently $C_1$-$C_6$ alkyl substituted with one or more halo; each $R^7$ is independently $C_1$-$C_6$ alkyl, and each $R^6$ is independently $C_3$-$C_7$ cycloalkyl; each $R^7$ is independently $C_1$-$C_6$ alkyl, and each $R^6$ is independently halo; each $R^7$ is independently $C_1$-$C_6$ alkyl and each $R^6$ is independently halo; each $R^7$ is independently $C_1$-$C_6$ alkyl, and $R^6$ is cyano; each $R^7$ is independently $C_3$-$C_7$ cycloalkyl, and each $R^6$ is independently $C_3$-$C_7$ cycloalkyl; each $R^7$ is independently $C_3$-$C_7$ cycloalkyl, and each $R^6$ is independently halo; each $R^7$ is independently $C_3$-$C_7$ cycloalkyl and each $R^6$ is independently halo; each $R^7$ is independently $C_1$-$C_6$ alkyl, and each $R^6$ is independently $C_1$-$C_6$ alkoxy optionally substituted with one or more halo; each $R^7$ is independently $C_1$-$C_6$ alkyl, and each $R^6$ is independently $C_1$-$C_6$ alkoxy; each $R^7$ is independently $C_1$-$C_6$ alkyl, and each $R^6$ is independently $C_1$-$C_6$ alkoxy substituted with one or more halo; each $R^7$ is independently halo, and each $R^6$ is independently $C_1$-$C_6$ haloalkyl; each $R^7$ is independently halo, and each $R^6$ is independently $C_1$-$C_6$ haloalkoxy; each $R^7$ is independently $C_1$-$C_6$ alkoxy; and each $R^6$ is independently halo; or each $R^7$ is independently $C_1$-$C_6$ alkoxy; and $R^6$ is chloro.

In some embodiments of the compound of formula AA, the substituted ring B is

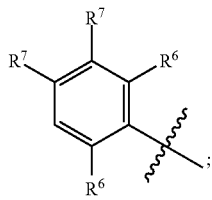

and $R^6$ and $R^7$ are one of the following combinations:
each R is isopropyl; and each R is methyl; each R is isopropyl; and each R is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; each $R^7$ is chloro; and each $R^6$ is trifluoromethyl; each $R^7$ is chloro; and each $R^6$ is trifluoromethoxy; one $R^6$ is isopropyl; the other $R^6$ is trifluoromethyl; and $R^7$ is chloro; or $R^6$ is isopropyl; one $R^7$ is fluoro; and the other $R^7$ is cyano.

In some embodiments, of the compound of formula AA, the substituted ring B is

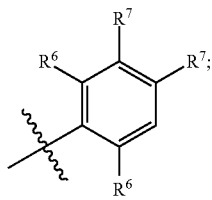

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo; each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo; each $R^6$ is independently $C_1$-$C_6$ alkyl, and each $R^7$ is independently $C_3$-$C_7$ cycloalkyl; each $R^6$ is independently $C_1$-$C_6$ alkyl, and each $R^7$ is independently halo; each $R^6$ is independently $C_1$-$C_6$ alkyl, and each $R^7$ is cyano; each $R^6$ is independently $C_3$-$C_7$ cycloalkyl, and each $R^7$ is independently $C_3$-$C_7$ cycloalkyl; each $R^6$ is independently $C_3$-$C_7$ cycloalkyl, and each $R^7$ is independently halo; each $R^6$ is independently cyclopropyl and each $R^7$ is independently halo; each $R^6$ is independently $C_1$-$C_6$ alkyl, and each $R^7$ is independently $C_1$-$C_6$ alkoxy optionally substituted with one or more halo; each $R^6$ is independently $C_1$-$C_6$ alkyl, and each $R^7$ is independently $C_1$-$C_6$ alkoxy; each $R^6$ is independently $C_1$-$C_6$ alkyl, and each $R^7$ is independently $C_1$-$C_6$ alkoxy substituted with one or more halo; each $R^6$ is independently halo, and each $R^7$ is independently $C_1$-$C_6$ haloalkyl; each $R^6$ is independently halo, and each $R^7$ is independently $C_1$-$C_6$ haloalkoxy; each $R^6$ is independently $C_1$-$C_6$ alkoxy; and each $R^7$ is independently halo; each $R^6$ is independently $C_1$-$C_6$ alkoxy; and each $R^7$ is chloro; each $R^7$ is independently $C_1$-$C_6$ alkyl, and each $R^6$ is independently $C_1$-$C_6$ alkyl optionally substituted with one or more halo; each $R^7$ is independently $C_1$-$C_6$ alkyl, and each $R^6$ is independently $C_1$-$C_6$ alkyl substituted with one or more halo; each $R^7$ is independently $C_1$-$C_6$ alkyl, and each $R^6$ is independently $C_3$-$C_7$ cycloalkyl; each $R^7$ is independently $C_1$-$C_6$ alkyl, and each $R^6$ is independently halo; each $R^7$ is independently $C_1$-$C_6$ alkyl, and each $R^6$ is cyano; each $R^7$ is independently $C_3$-$C_7$ cycloalkyl, and each $R^6$ is independently $C_3$-$C_7$ cycloalkyl; each $R^7$ is independently $C_3$-$C_7$ cycloalkyl, and each $R^6$ is independently halo; each $R^7$ is independently $C_3$-$C_7$ cycloalkyl and each $R^6$ is independently halo; each $R^7$ is independently $C_1$-$C_6$ alkyl, and each $R^6$ is independently $C_1$-$C_6$ alkoxy optionally substituted with one or more halo; each $R^7$ is independently $C_1$-$C_6$ alkyl, and each $R^6$ is independently $C_1$-$C_6$ alkoxy; each $R^7$ is independently $C_1$-$C_6$ alkyl, and each $R^6$ is independently $C_1$-$C_6$ alkoxy substituted with one or more halo; each $R^7$ is independently halo, and each $R^6$ is independently $C_1$-$C_6$ haloalkyl; each $R^7$ is independently halo, and each $R^6$ is independently $C_1$-$C_6$ haloalkoxy; each $R^7$ is independently $C_1$-$C_6$ alkoxy; and each $R^6$ is independently halo; each $R^7$ is independently $C_1$-$C_6$ alkoxy; and each $R^6$ is chloro; $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

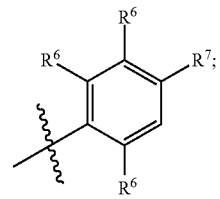

and $R^6$ and $R^7$ are one of the following combinations:

each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; each $R^7$ is chloro; and each $R^6$ is trifluoromethyl; each $R^7$ is chloro; and each $R^6$ is trifluoromethoxy; one $R^6$ is isopropyl; the other $R^6$ is trifluoromethyl; and each $R^7$ is chloro; each $R^6$ is isopropyl; one $R^7$ is fluoro; and the other $R^7$ is cyano; $R^6$ and $R^7$ on adjacent atoms taken together with the atoms connecting them form a $C_4$ aliphatic carbocyclic ring; and one $R^6$ is chloro, fluoro, or cyano; $R^6$ and $R^7$ on adjacent atoms taken together with the atoms connecting them form a $C_5$ aliphatic carbocyclic ring; and one $R^6$ is chloro, fluoro, or cyano; $R^6$ and $R^7$ on adjacent atoms taken together with the atoms connecting them form a $C_6$ aliphatic carbocyclic ring; and one $R^6$ is chloro, fluoro, or cyano; $R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano; $R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or $R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

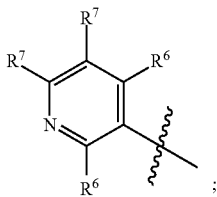

;

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo; each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo; each $R^6$ is independently $C_1$-$C_6$ alkyl, and each $R^7$ is independently $C_3$-$C_7$ cycloalkyl; each $R^6$ is independently $C_1$-$C_6$ alkyl, and each $R^7$ is independently halo; each $R^6$ is independently $C_1$-$C_6$ alkyl, and $R^7$ is cyano; each $R^6$ is independently $C_3$-$C_7$ cycloalkyl, and each $R^7$ is independently $C_3$-$C_7$ cycloalkyl; each $R^6$ is independently $C_3$-$C_7$ cycloalkyl, and each $R^7$ is independently halo; each $R^6$ is independently cyclopropyl and each $R^7$ is independently halo; each $R^6$ is independently $C_1$-$C_6$ alkyl, and each $R^7$ is independently $C_1$-$C_6$ alkoxy optionally substituted with one or more halo; each $R^6$ is independently $C_1$-$C_6$ alkyl, and each $R^7$ is independently $C_1$-$C_6$ alkoxy; each $R^6$ is independently $C_1$-$C_6$ alkyl, and each $R^7$ is independently $C_1$-$C_6$ alkoxy substituted with one or more halo; each $R^6$ is independently halo, and each $R^7$ is independently $C_1$-$C_6$ haloalkyl; each $R^6$ is independently halo, and each $R^7$ is independently $C_1$-$C_6$ haloalkoxy; each $R^6$ is independently $C_1$-$C_6$ alkoxy; and each $R^7$ is independently halo; each $R^6$ is independently $C_1$-$C_6$ alkoxy; and $R^7$ is chloro; each $R^7$ is independently $C_1$-$C_6$ alkyl, and each $R^6$ is independently $C_1$-$C_6$ alkyl optionally substituted with one or more halo; each $R^7$ is independently $C_1$-$C_6$ alkyl, and each $R^6$ is independently $C_1$-$C_6$ alkyl substituted with one or more halo; each $R^7$ is independently $C_1$-$C_6$ alkyl, and each $R^6$ is independently $C_3$-$C_7$ cycloalkyl; each $R^7$ is independently $C_1$-$C_6$ alkyl, and each $R^6$ is independently halo; each $R^7$ is independently $C_1$-$C_6$ alkyl and each $R^6$ is independently halo; each $R^7$ is independently $C_1$-$C_6$ alkyl, and $R^6$ is cyano; each $R^7$ is independently $C_3$-$C_7$ cycloalkyl, and each $R^6$ is independently $C_3$-$C_7$ cycloalkyl; each $R^7$ is independently $C_3$-$C_7$ cycloalkyl, and each $R^6$ is independently halo; each $R^7$ is independently $C_3$-$C_7$ cycloalkyl and each $R^6$ is independently halo; each $R^7$ is independently $C_1$-$C_6$ alkyl, and each $R^6$ is independently $C_1$-$C_6$ alkoxy optionally substituted with one or more halo; each $R^7$ is independently $C_1$-$C_6$ alkyl, and each $R^6$ is independently $C_1$-$C_6$ alkoxy; each $R^7$ is independently $C_1$-$C_6$ alkyl, and each $R^6$ is independently $C_1$-$C_6$ alkoxy substituted with one or more halo; each $R^7$ is independently halo, and each $R^6$ is independently $C_1$-$C_6$ haloalkyl; each $R^7$ is independently halo, and each $R^6$ is independently $C_1$-$C_6$ haloalkoxy; each $R^7$ is independently $C_1$-$C_6$ alkoxy; and each $R^6$ is independently halo; or each $R^7$ is independently $C_1$-$C_6$ alkoxy; and $R^6$ is chloro.

In some embodiments, of the compound of formula AA, the substituted ring B is

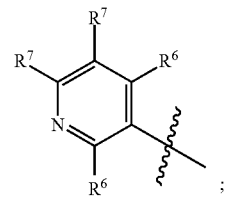

;

and $R^6$ and $R^7$ are one of the following combinations:
each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl;

and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; each $R^7$ is chloro; and each $R^6$ is trifluoromethyl; each $R^7$ is chloro; and each $R^6$ is trifluoromethoxy; one $R^6$ is isopropyl; the other $R^6$ is trifluoromethyl; and each $R^7$ is chloro; or each $R^6$ is isopropyl; one $R^7$ is fluoro; and the other $R^7$ is cyano.

In some embodiments, of the compound of formula AA, the substituted ring B is

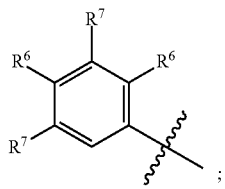

and $R^6$ and $R^7$ are one of the following combinations:

each $R^6$ is independently $C_1$-$C_6$ alkyl, and each $R^7$ is independently $C_1$-$C_6$ alkyl optionally substituted with one or more halo; each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo; each $R^6$ is independently $C_1$-$C_6$ alkyl, and each $R^7$ is independently $C_3$-$C_7$ cycloalkyl; each $R^6$ is independently $C_1$-$C_6$ alkyl, and each $R^7$ is independently halo; each $R^6$ is independently $C_1$-$C_6$ alkyl, and $R^7$ is cyano; each $R^6$ is independently $C_3$-$C_7$ cycloalkyl, and each $R^7$ is independently $C_3$-$C_7$ cycloalkyl; each $R^6$ is independently $C_3$-$C_7$ cycloalkyl, and each $R^7$ is independently halo; each $R^6$ is independently cyclopropyl and each $R^7$ is independently halo; each $R^6$ is independently $C_1$-$C_6$ alkyl, and each $R^7$ is independently $C_1$-$C_6$ alkoxy optionally substituted with one or more halo; each $R^6$ is independently $C_1$-$C_6$ alkyl, and each $R^7$ is independently $C_1$-$C_6$ alkoxy; each $R^6$ is independently $C_1$-$C_6$ alkyl, and each $R^7$ is independently $C_1$-$C_6$ alkoxy substituted with one or more halo; each $R^6$ is independently halo, and each $R^7$ is independently $C_1$-$C_6$ haloalkyl; each $R^6$ is independently halo, and each $R^7$ is independently $C_1$-$C_6$ haloalkoxy; each $R^6$ is independently $C_1$-$C_6$ alkoxy; and $R^7$ is independently halo; each $R^6$ is independently $C_1$-$C_6$ alkoxy; and $R^7$ is chloro; each $R^7$ is independently $C_1$-$C_6$ alkyl, and each $R^6$ is independently $C_1$-$C_6$ alkyl optionally substituted with one or more halo; each $R^7$ is independently $C_1$-$C_6$ alkyl, and each $R^6$ is independently $C_1$-$C_6$ alkyl, and each $R^6$ is independently $C_1$-$C_6$ alkyl substituted with one or more halo; each $R^7$ is independently $C_1$-$C_6$ alkyl, and each $R^6$ is independently $C_3$-$C_7$ cycloalkyl; each $R^7$ is independently $C_1$-$C_6$ alkyl, and each $R^6$ is independently halo; each $R^7$ is independently $C_1$-$C_6$ alkyl and each $R^6$ is independently halo; each $R^7$ is independently $C_1$-$C_6$ alkyl, and $R^6$ is cyano; each $R^7$ is independently $C_3$-$C_7$ cycloalkyl, and each $R^6$ is independently $C_3$-$C_7$ cycloalkyl; each $R^7$ is independently $C_3$-$C_7$ cycloalkyl, and each $R^6$ is independently halo; each $R^7$ is independently $C_3$-$C_7$ cycloalkyl and each $R^6$ is independently halo; each $R^7$ is independently $C_1$-$C_6$ alkyl, and each $R^6$ is independently $C_1$-$C_6$ alkoxy optionally substituted with one or more halo; each $R^7$ is independently $C_1$-$C_6$ alkyl, and each $R^6$ is independently $C_1$-$C_6$ alkoxy; each $R^7$ is independently $C_1$-$C_6$ alkyl, and each $R^6$ is independently $C_1$-$C_6$ alkoxy substituted with one or more halo; each $R^7$ is independently halo, and each $R^6$ is independently $C_1$-$C_6$ haloalkyl; each $R^7$ is independently halo, and each $R^6$ is independently $C_1$-$C_6$ haloalkoxy; each $R^7$ is independently $C_1$-$C_6$ alkoxy; and each $R^6$ is independently halo; each $R^7$ is independently $C_1$-$C_6$ alkoxy; and $R^6$ is chloro; two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; or two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

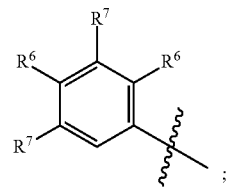

and $R^6$ and $R^7$ are one of the following combinations:

each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; $R^7$ is chloro; and each $R^6$ is trifluoromethyl; $R^7$ is chloro; and each $R^6$ is trifluoromethoxy; one $R^6$ is isopropyl; the other $R^6$ is trifluoromethyl; and $R^7$ is chloro; $R^6$ is isopropyl; one $R^7$ is fluoro; and the other $R^7$ is cyano; two pairs, each of one $R^6$ and one $R^7$, are on adjacent atoms, and each pair of one $R^6$ and one $R^7$ taken together with the atoms connecting them form a $C_5$ aliphatic carbocyclic ring; two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl; two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

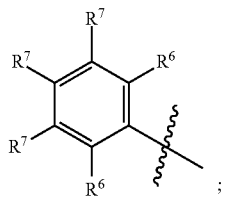

;

and $R^6$ and $R^7$ are one of the following combinations:
$R^6$ is independently $C_1$-$C_6$ alkyl, and $R^7$ is $C_1$-$C_6$ alkyl optionally substituted with one or more halo; each $R^6$ is independently $C_1$-$C_6$ alkyl and $R^7$ is $C_1$-$C_6$ alkyl; each $R^6$ is independently $C_1$-$C_6$ alkyl, and $R^7$ is $C_1$-$C_6$ alkyl substituted with one or more halo; each $R^6$ is independently $C_1$-$C_6$ alkyl, and $R^7$ is $C_3$-$C_7$ cycloalkyl; each $R^6$ is independently $C_1$-$C_6$ alkyl, and $R^7$ is halo; each $R^6$ is independently $C_1$-$C_6$ alkyl, and $R^7$ is cyano; each $R^6$ is independently $C_3$-$C_7$ cycloalkyl, and $R^7$ is $C_3$-$C_7$ cycloalkyl; each $R^6$ is independently $C_3$-$C_7$ cycloalkyl, and $R^7$ is halo; each $R^6$ is independently cyclopropyl and $R^7$ is halo; each $R^6$ is independently $C_1$-$C_6$ alkyl, and $R^7$ is $C_1$-$C_6$ alkoxy optionally substituted with one or more halo; each $R^6$ is independently $C_1$-$C_6$ alkyl, and $R^7$ is $C_1$-$C_6$ alkoxy; each $R^6$ is independently $C_1$-$C_6$ alkyl, and $R^7$ is $C_1$-$C_6$ alkoxy substituted with one or more halo; each $R^6$ is independently halo, and $R^7$ is $C_1$-$C_6$ haloalkyl; each $R^6$ is independently halo, and $R^7$ is $C_1$-$C_6$ haloalkoxy; each $R^6$ is independently $C_1$-$C_6$ alkoxy; and $R^7$ is halo; each $R^6$ is independently $C_1$-$C_6$ alkoxy; and $R^7$ is chloro; $R^7$ is $C_1$-$C_6$ alkyl, and each $R^6$ is independently $C_1$-$C_6$ alkyl optionally substituted with one or more halo; $R^7$ is $C_1$-$C_6$ alkyl, and each $R^6$ is independently $C_1$-$C_6$ alkyl substituted with one or more halo; $R^7$ is $C_1$-$C_6$ alkyl, and each $R^6$ is independently $C_3$-$C_7$ cycloalkyl; $R^7$ is $C_1$-$C_6$ alkyl, and each $R^6$ is independently halo; $R^7$ is $C_1$-$C_6$ alkyl and each $R^6$ is independently halo; $R^7$ is $C_1$-$C_6$ alkyl, and $R^6$ is cyano; $R^7$ is $C_3$-$C_7$ cycloalkyl, and each $R^6$ is independently $C_3$-$C_7$ cycloalkyl; $R^7$ is $C_3$-$C_7$ cycloalkyl, and each $R^6$ is independently halo; $R^7$ is $C_3$-$C_7$ cycloalkyl and each $R^6$ is independently halo; $R^7$ is $C_1$-$C_6$ alkyl, and each $R^6$ is independently $C_1$-$C_6$ alkoxy optionally substituted with one or more halo; $R^7$ is $C_1$-$C_6$ alkyl, and each $R^6$ is independently $C_1$-$C_6$ alkoxy; $R^7$ is $C_1$-$C_6$ alkyl, and each $R^6$ is independently $C_1$-$C_6$ alkoxy substituted with one or more halo; $R^7$ is halo, and each $R^6$ is independently $C_1$-$C_6$ haloalkyl; $R^7$ is halo, and each $R^6$ is independently $C_1$-$C_6$ haloalkoxy; $R^7$ is $C_1$-$C_6$ alkoxy; and each $R^6$ is independently halo; $R^7$ is $C_1$-$C_6$ alkoxy; and $R^6$ is chloro; two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is halo; two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is cyano; two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; and one $R^7$ is halo or cyano; two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano; or two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano.

In some embodiments, of the compound of formula AA, the substituted ring B is

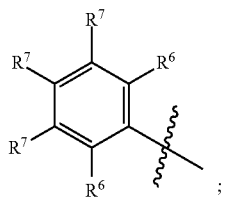

and $R^6$ and $R^7$ are one of the following combinations:
(i) each $R^6$ is isopropyl; and each $R^7$ is methyl; each $R^6$ is isopropyl; and each $R^7$ is isopropyl; each $R^6$ is isopropyl; and each $R^7$ is trifluoromethyl; each $R^6$ is isopropyl; and each $R^7$ is cyclopropyl; each $R^6$ is isopropyl; and each $R^7$ is chloro; each $R^6$ is isopropyl; and each $R^7$ is fluoro; each $R^6$ is ethyl; and each $R^7$ is fluoro; each $R^6$ is isopropyl; and each $R^7$ is cyano; each $R^6$ is cyclopropyl; and each $R^7$ is cyclopropyl; each $R^6$ is cyclopropyl; and each $R^7$ is chloro; each $R^6$ is cyclopropyl; and each $R^7$ is fluoro; each $R^6$ is isopropyl; and each $R^7$ is methoxy; each $R^6$ is isopropyl; and each $R^7$ is trifluoromethoxy; each $R^6$ is chloro; and each $R^7$ is trifluoromethyl; each $R^6$ is chloro; and each $R^7$ is trifluoromethoxy; each $R^7$ is isopropyl; and each $R^6$ is methyl; each $R^7$ is isopropyl; and each $R^6$ is trifluoromethyl; each $R^7$ is isopropyl; and each $R^6$ is cyclopropyl; each $R^7$ is isopropyl; and each $R^6$ is chloro; each $R^7$ is ethyl; and each $R^6$ is fluoro; each $R^7$ is isopropyl; and each $R^6$ is cyano; each $R^7$ is cyclopropyl; and each $R^6$ is cyclopropyl; each $R^7$ is cyclopropyl; and each $R^6$ is chloro; each $R^7$ is cyclopropyl; and each $R^6$ is fluoro; each $R^7$ is isopropyl; and each $R^6$ is methoxy; each $R^7$ is isopropyl; and each $R^6$ is trifluoromethoxy; each $R^7$ is chloro; and each $R^6$ is trifluoromethyl; each $R^7$ is chloro; and each $R^6$ is trifluoromethoxy; each $R^6$ is isopropyl; two $R^7$ are fluoro; and one $R^7$ is chloro; two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is chloro; two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is fluoro; two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; and one $R^7$ is fluoro or chloro; two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro; two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl; and one $R^7$ is fluoro or chloro; two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; and one $R^7$ is fluoro or chloro; two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; and one $R^7$ is fluoro or chloro; or two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro.

Additional Subgenera

In some embodiments, the compound of Formula AA is a compound of Formula AA-1

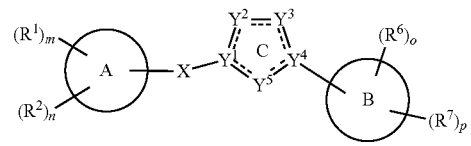

(Formula AA-1)

wherein ring C is a charge neutral heteroaromatic ring; and $Y^2$, $Y^3$, and $Y^5$ are each independently selected from O, S, N, NH, $NR^5$, C, CH, and $CR^5$; and $Y^1$ and $Y^4$ are independently selected from N or C;

wherein A, B, $R^1$, $R^2$, m, n, X, $R^5$, $R^6$, $R^7$, o, and p are as defined anywhere herein.

In some embodiments,

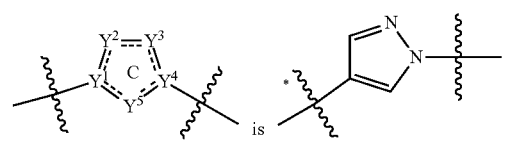

and wherein the broken bond closest to the asterisk is bonded to X.

In some embodiments,

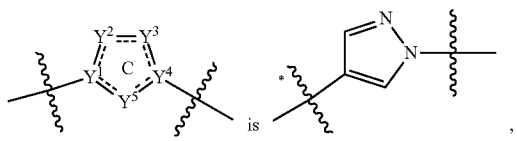, and wherein the bond that is shown as being spatially closest to the asterisk connects to the X group.

In some embodiments,

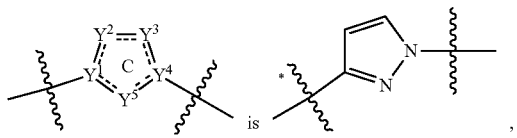, and wherein the bond that is shown as being spatially closest to the asterisk connects to the X group.

In some embodiments,

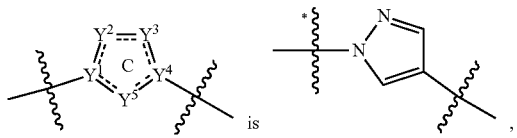, and wherein the bond that is shown as being spatially closest to the asterisk connects to the X group.

In some embodiments,

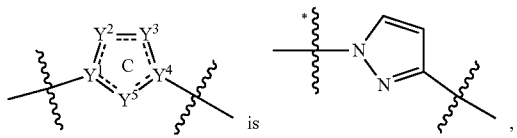, and wherein the bond that is shown as being spatially closest to the asterisk connects to the X group.

In some embodiments,

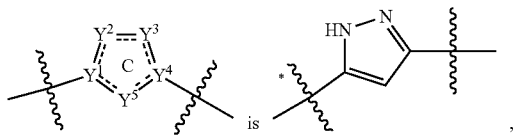, and wherein the bond that is shown as being spatially closest to the asterisk connects to the X group.

In some embodiments,

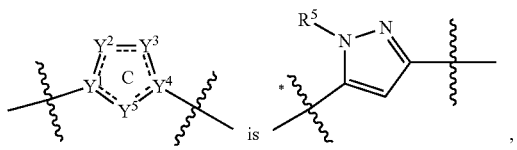, and wherein the bond that is shown as being spatially closest to the asterisk connects to the X group.

In some embodiments,

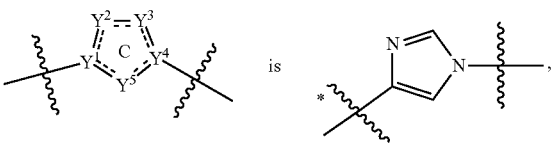, and wherein the bond that is shown as being spatially closest to the asterisk connects to the X group.

In some embodiments,

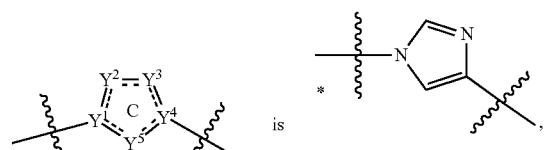, and wherein the bond that is shown as being spatially closest to the asterisk connects to the X group.

In some embodiments,

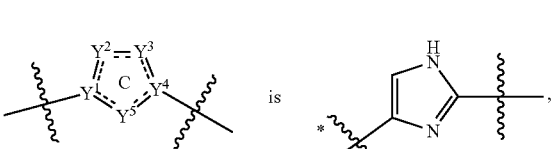
, and wherein the bond that is shown as being spatially closest to the asterisk connects to the X group.

In some embodiments,

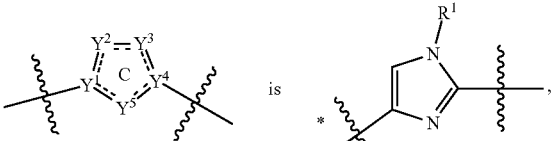
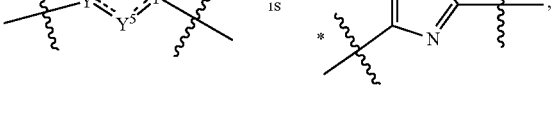, and wherein the bond that is shown as being spatially closest to the asterisk connects to the X group.

In some embodiments,

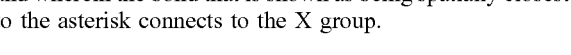, and wherein the bond that is shown as being spatially closest to the asterisk connects to the X group.

In some embodiments,

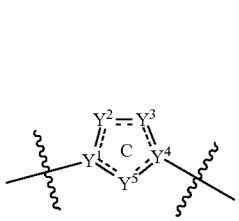 is 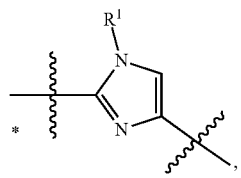, and wherein the bond that is shown as being spatially closest to the asterisk connects to the X group.

In some embodiments,

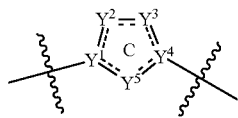 is 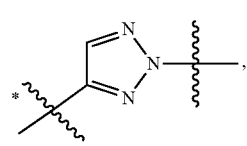, and wherein the bond that is shown as being spatially closest to the asterisk connects to the X group.

In some embodiments,

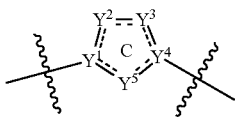 is 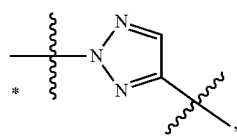, and wherein the bond that is shown as being spatially closest to the asterisk connects to the X group.

In some embodiments,

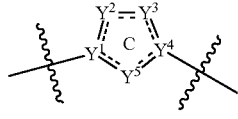 is 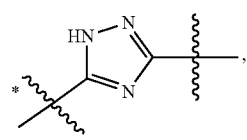, and wherein the bond that is shown as being spatially closest to the asterisk connects to the X group.

In some embodiments,

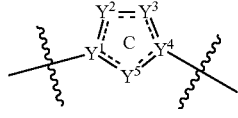 is 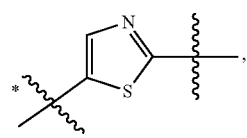, and wherein the bond that is shown as being spatially closest to the asterisk connects to the X group.

In some embodiments,

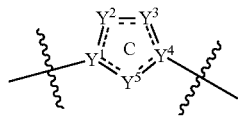 is 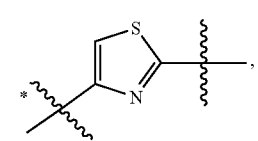, and wherein the bond that is shown as being spatially closest to the asterisk connects to the X group.

In some embodiments,

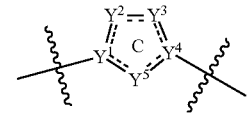 is 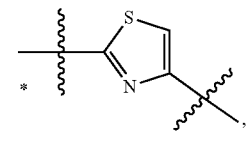, and wherein the bond that is shown as being spatially closest to the asterisk connects to the X group.

In some embodiments,

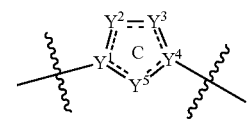 is 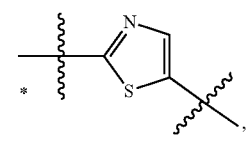, and wherein the bond that is shown as being spatially closest to the asterisk connects to the X group.

In some embodiments,

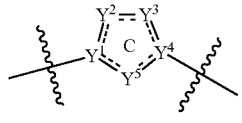 is 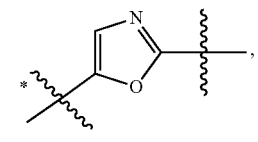, and wherein the bond that is shown as being spatially closest to the asterisk connects to the X group.

In some embodiments,

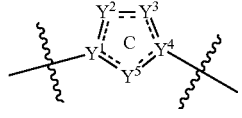 is 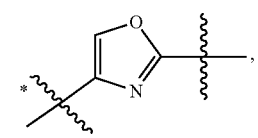, and wherein the bond that is shown as being spatially closest to the asterisk connects to the X group.

In some embodiments,

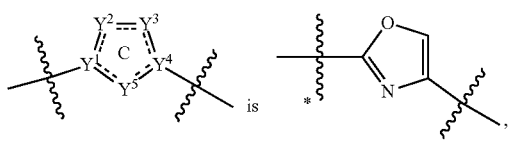

and wherein the bond that is shown as being spatially closest to the asterisk connects to the X group.

In some embodiments,

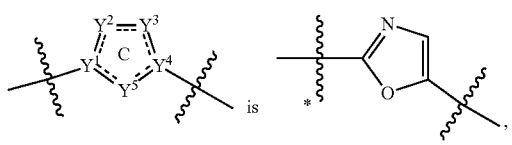

and wherein the bond that is shown as being spatially closest to the asterisk connects to the X group.

In some embodiments,

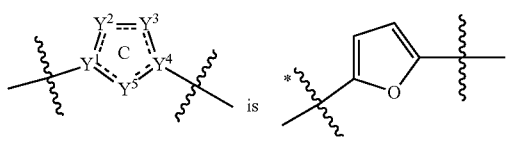

and wherein the bond that is shown as being spatially closest to the asterisk connects to the X group.

In some embodiments,

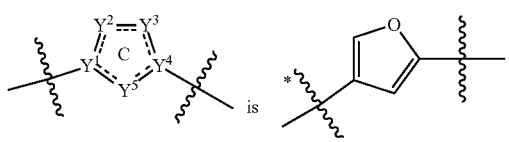

and wherein the bond that is shown as being spatially closest to the asterisk connects to the X group.

In some embodiments,

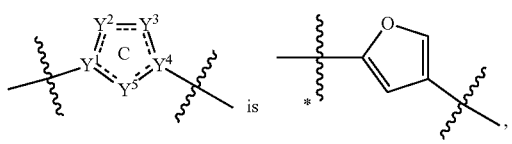

and wherein the bond that is shown as being spatially closest to the asterisk connects to the X group.

In some embodiments,

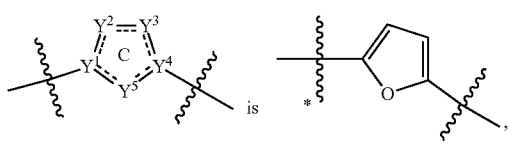

and wherein the bond that is shown as being spatially closest to the asterisk connects to the X group.

In some embodiments,

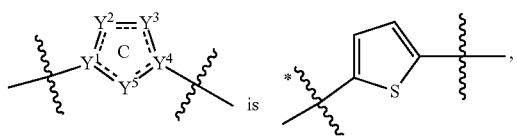

and wherein the bond that is shown as being spatially closest to the asterisk connects to the X group.

In some embodiments,

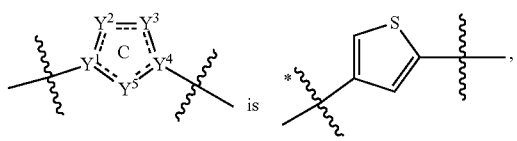

and wherein the bond that is shown as being spatially closest to the asterisk connects to the X group.

In some embodiments,

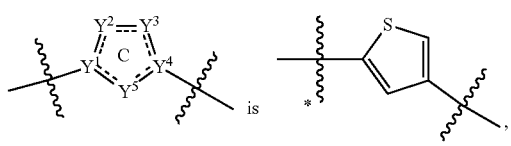

and wherein the bond that is shown as being spatially closest to the asterisk connects to the X group.

In some embodiments,

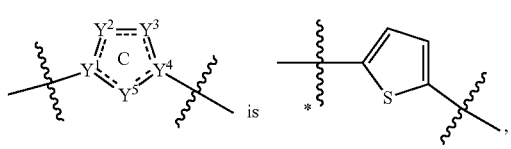

and wherein the bond that is shown as being spatially closest to the asterisk connects to the X group.

In some embodiments, the compound of Formula AA is a compound of Formula AA-2

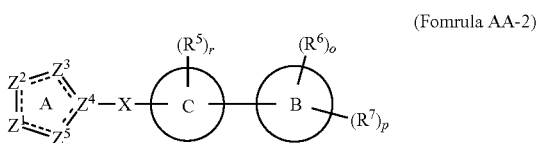

(Fomrula AA-2)

wherein
ring A is a charge neutral heteroaromatic ring; and
$Z^1, Z^2, Z^3$, and $Z^5$ are each independently selected from O, S, N, NH, $NR^1$, C, CH, and $CR^1$; and
$Z^4$ is selected from N and C;
wherein A, B, $R^1$, $R^2$, m, n, X, $R^5$, $R^6$, $R^7$, o, and p are as defined anywhere herein.

In some embodiments, 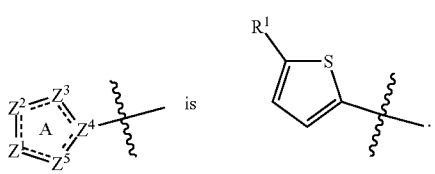 is 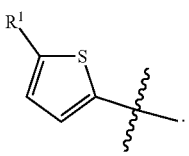.
In some embodiments, 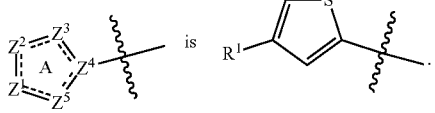 is 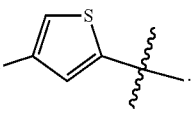.
In some embodiments, 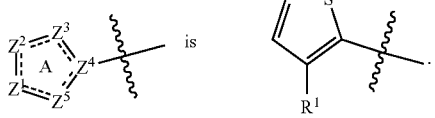 is 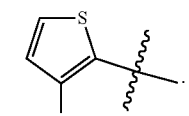.
In some embodiments, 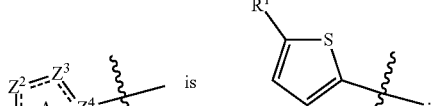 is 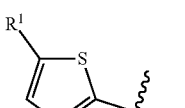.
In some embodiments, 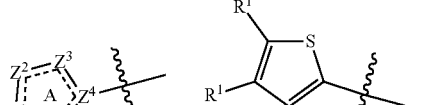 is 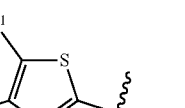.
In some embodiments, 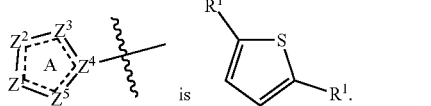 is 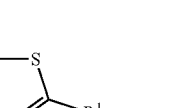.
In some embodiments, 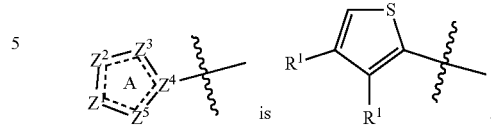 is 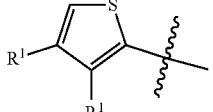.
In some embodiments,  is 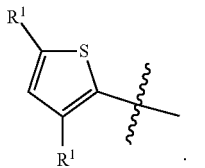.
In some embodiments, 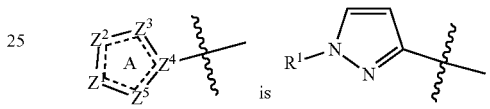 is 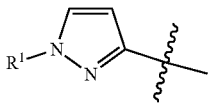.
In some embodiments, 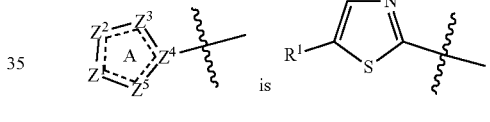 is 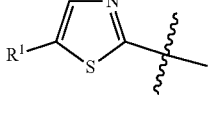.
In some embodiments, 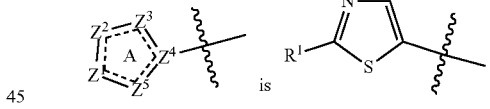 is 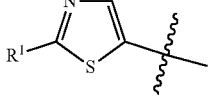.
In some embodiments, 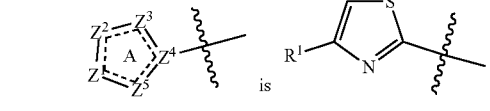 is 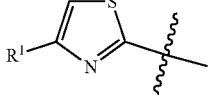.
In some embodiments, 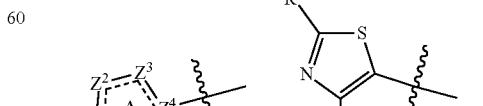 is 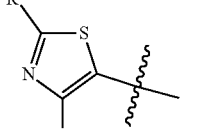.

In some embodiments,

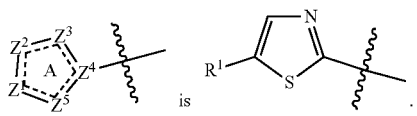 is .

In some embodiments,

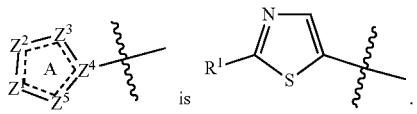 is .

In some embodiments,

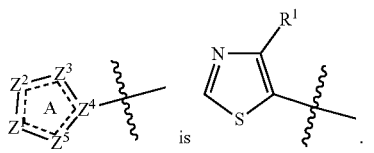 is .

In some embodiments,

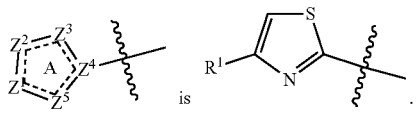 is .

In some embodiments,

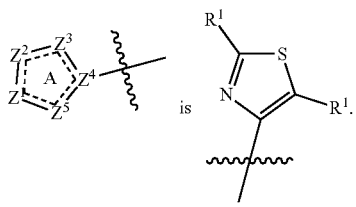 is .

In some embodiments,

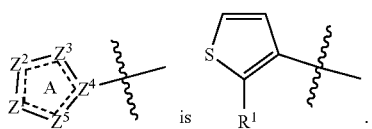 is .

In some embodiments,

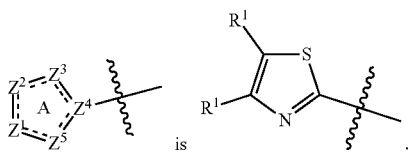 is .

In some embodiments, the compound of Formula AA is a compound of Formula AA-3

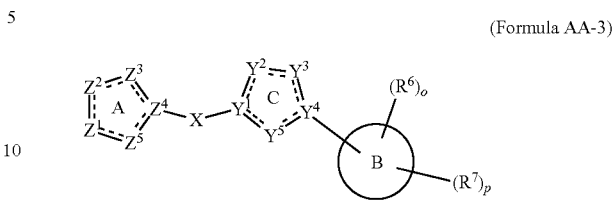

(Formula AA-3)

wherein ring A is a charge neutral heteroaromatic ring;

ring C is a charge neutral heteroaromatic ring;

$Y^1$, $Y^2$, $Y^3$, $Y^4$ and $Y^5$ are each independently selected from O, S, N, NH, $NR^5$, C, CH, and $CR^5$;

$Z^1$, $Z^2$, $Z^3$, $Z^4$, and $Z^5$ are each independently selected from O, S, N, NH, Nit % C, CH, and $CR^1$; and wherein A, B, $R^1$, $R^2$, m, n, X, $R^5$, $R^6$, $R^7$, o, and p are as defined anywhere herein.

In some embodiments,

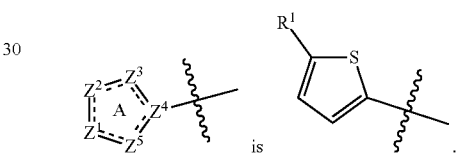 is .

In some embodiments,

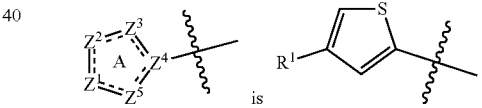 is .

In some embodiments,

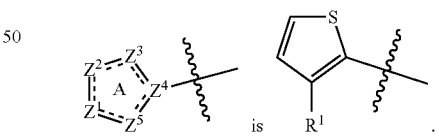 is .

In some embodiments,

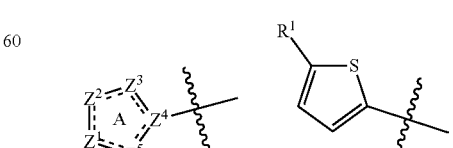 is .

In some embodiments, 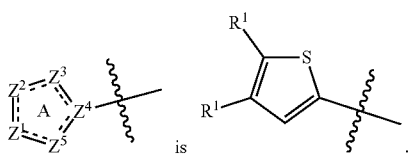 is .
In some embodiments, 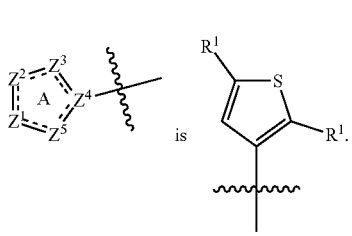 is .
In some embodiments, 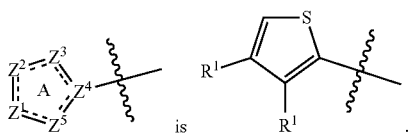 is .
In some embodiments, 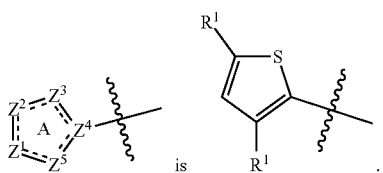 is .
In some embodiments, 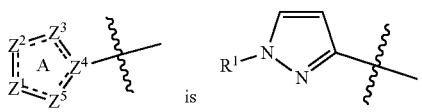 is .
In some embodiments, 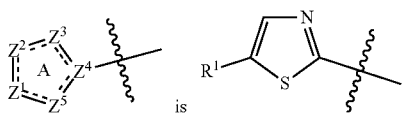 is .
In some embodiments, 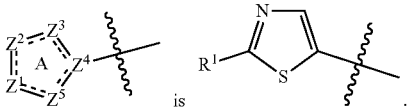 is .
In some embodiments, 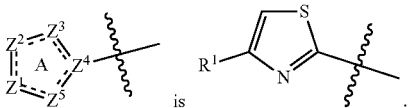 is .
In some embodiments, 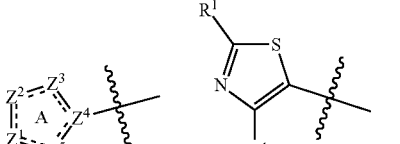 is .
In some embodiments, 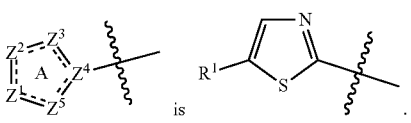 is .
In some embodiments, 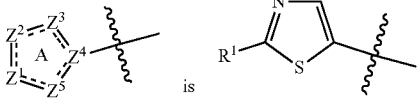 is .
In some embodiments, 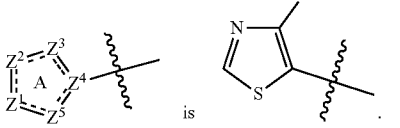 is .
In some embodiments, 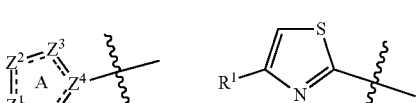 is .

In some embodiments,

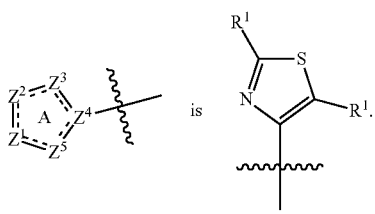 is 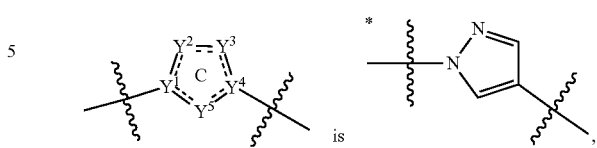

In some embodiments,

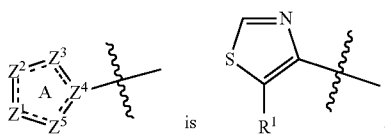 is 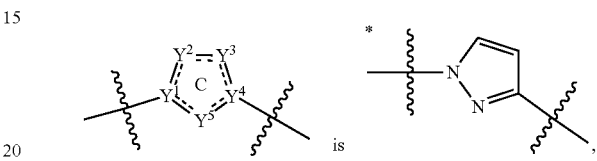.

In some embodiments,

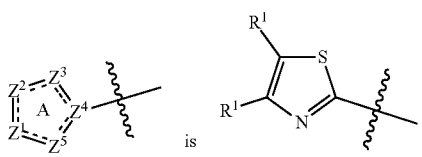 is .

In some embodiments,

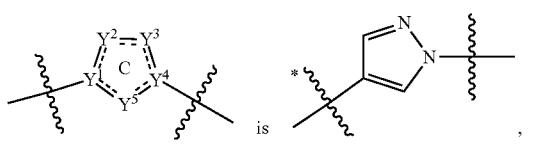 is , and wherein the broken bond closest to the asterisk is bonded to X.

In some embodiments,

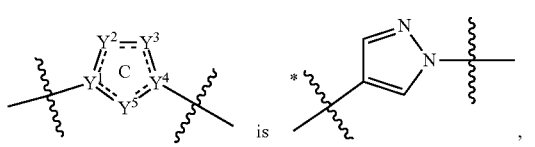 is , and wherein the bond that is shown as being spatially closest to the asterisk connects to the X group.

In some embodiments,

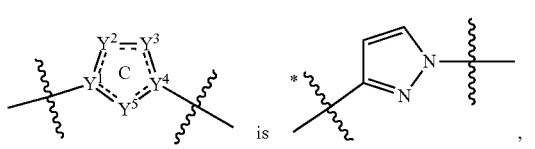 is , and wherein the bond that is shown as being spatially closest to the asterisk connects to the X group.

In some embodiments,

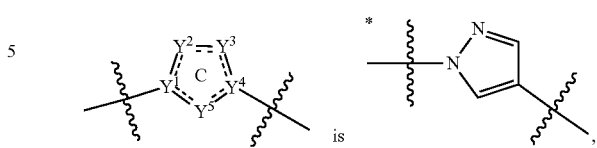 is , and wherein the bond that is shown as being spatially closest to the asterisk connects to the X group.

In some embodiments,

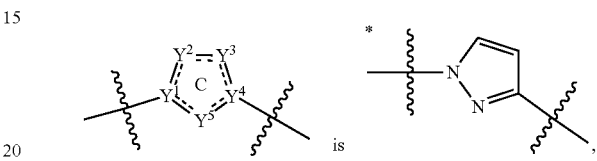 is , and wherein the bond that is shown as being spatially closest to the asterisk connects to the X group.

In some embodiments,

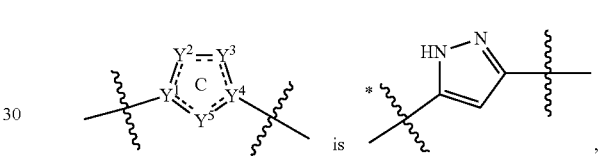 is , and wherein the bond that is shown as being spatially closest to the asterisk connects to the X group.

In some embodiments,

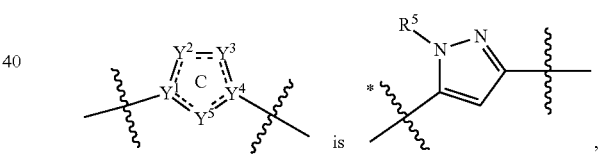 is , and wherein the bond that is shown as being spatially closest to the asterisk connects to the X group.

In some embodiments,

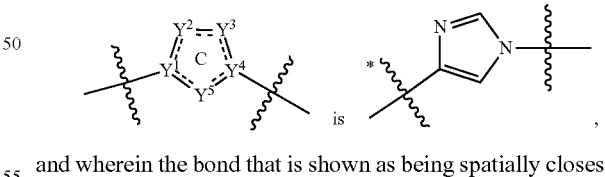 is , and wherein the bond that is shown as being spatially closest to the asterisk connects to the X group.

In some embodiments,

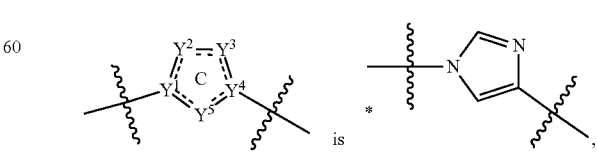 is , and wherein the bond that is shown as being spatially closest to the asterisk connects to the X group.

In some embodiments,

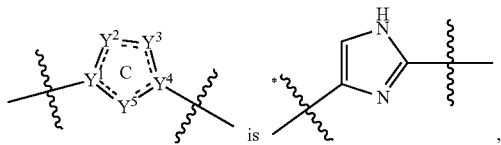

and wherein the bond that is shown as being spatially closest to the asterisk connects to the X group.

In some embodiments,

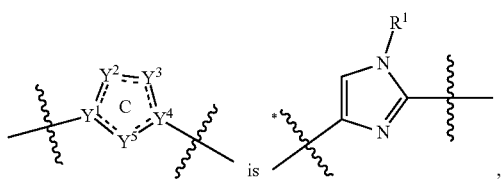

and wherein the bond that is shown as being spatially closest to the asterisk connects to the X group.

In some embodiments,

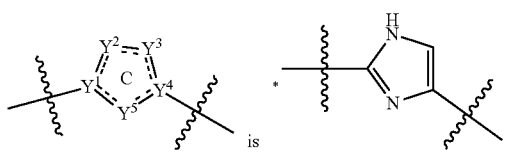

and wherein the bond that is shown as being spatially closest to the asterisk connects to the X group.

In some embodiments,

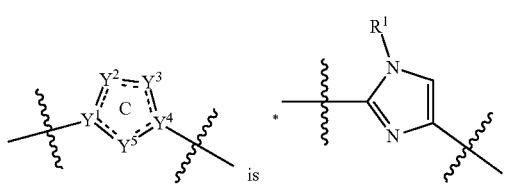

and wherein the bond that is shown as being spatially closest to the asterisk connects to the X group.

In some embodiments,

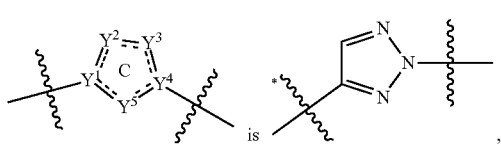

and wherein the bond that is shown as being spatially closest to the asterisk connects to the X group.

In some embodiments,

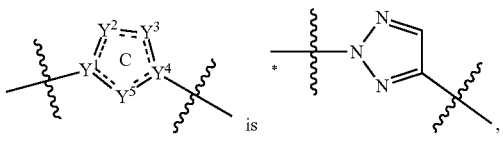

and wherein the bond that is shown as being spatially closest to the asterisk connects to the X group.

In some embodiments,

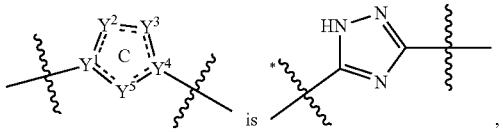

and wherein the bond that is shown as being spatially closest to the asterisk connects to the X group.

In some embodiments,

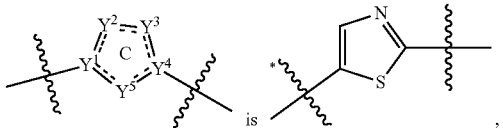

and wherein the bond that is shown as being spatially closest to the asterisk connects to the X group.

In some embodiments,

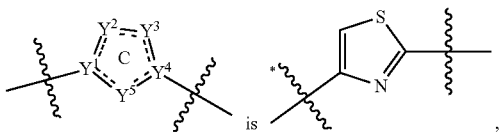

and wherein the bond that is shown as being spatially closest to the asterisk connects to the X group.

In some embodiments,

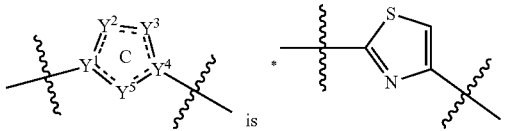

and wherein the bond that is shown as being spatially closest to the asterisk connects to the X group.

In some embodiments,

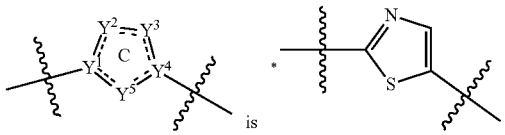

and wherein the bond that is shown as being spatially closest to the asterisk connects to the X group.

In some embodiments,

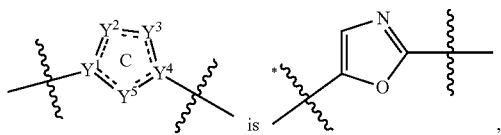

and wherein the bond that is shown as being spatially closest to the asterisk connects to the X group.

In some embodiments,

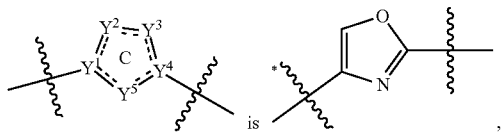

and wherein the bond that is shown as being spatially closest to the asterisk connects to the X group.

In some embodiments,

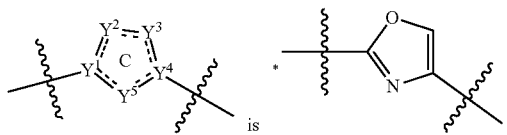

and wherein the bond that is shown as being spatially closest to the asterisk connects to the X group.

In some embodiments,

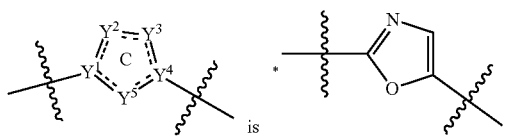

and wherein the bond that is shown as being spatially closest to the asterisk connects to the X group.

In some embodiments,

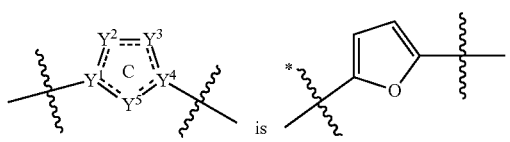

and wherein the bond that is shown as being spatially closest to the asterisk connects to the X group.

In some embodiments,

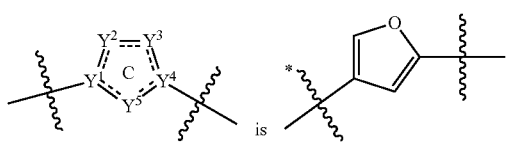

and wherein the bond that is shown as being spatially closest to the asterisk connects to the X group.

In some embodiments,

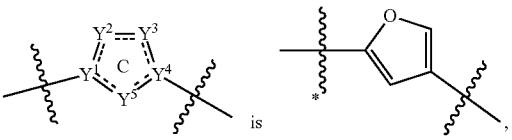

and wherein the bond that is shown as being spatially closest to the asterisk connects to the X group.

In some embodiments,

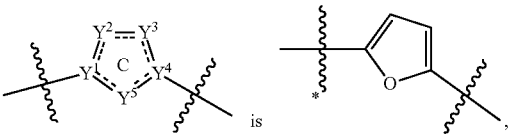

and wherein the bond that is shown as being spatially closest to the asterisk connects to the X group.

In some embodiments,

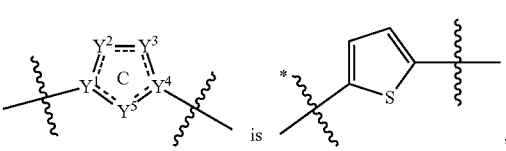

and wherein the bond that is shown as being spatially closest to the asterisk connects to the X group.

In some embodiments,

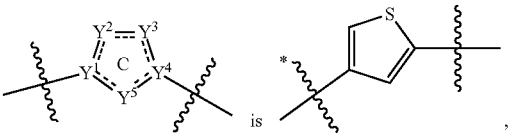

and wherein the bond that is shown as being spatially closest to the asterisk connects to the X group.

In some embodiments,

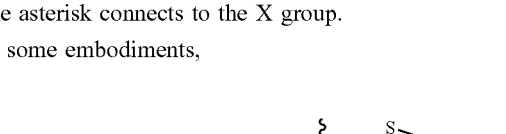

and wherein the bond that is shown as being spatially closest to the asterisk connects to the X group.

In some embodiments,

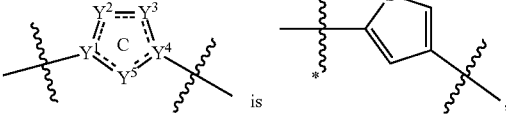

and wherein the bond that is shown as being spatially closest to the asterisk connects to the X group.

In some embodiments,

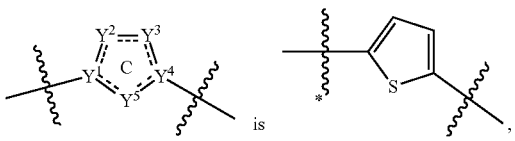

is and wherein the bond that is shown as being spatially closest to the asterisk connects to the X group.

Embodiments of $Y^1$, $Y^2$, $Y^3$, $Y^4$, and $Y^5$ in Formula AA-1 and AA-3

In some embodiments of Formula AA-1 and/or AA-3, $Y^2$, $Y^3$, and $Y^5$ are each independently selected from O, S, N, NH, $NR^5$, C, CH, and $CR^5$; and $Y^4$ and $Y^1$ are each independently selected from N and C.

In some embodiments of Formula AA-1 and/or AA-3, $Y^2$, $Y^3$, and $Y^5$ are each independently selected from S, N, NH, $NR^5$, C, CH, and $CR^5$; and $Y^4$ and $Y^1$ are each independently selected from N and C.

In some embodiments of Formula AA-1 and/or AA-3, $Y^2$, $Y^3$, and $Y^5$ are each independently selected from O, N, NH, $NR^5$, C, CH, and $CR^5$; and $Y^4$ and $Y^1$ are each independently selected from N and C.

In some embodiments of Formula AA-1 and/or AA-3, $Y^2$, $Y^3$, and $Y^5$ are each independently selected from N, NH, $NR^5$, C, CH, and $CR^5$; and $Y^4$ and $Y^1$ are each independently selected from N and C.

In some embodiments of Formula AA-1 and/or AA-3, $Y^2$, $Y^3$, and $Y^5$ are each independently selected from N, NH, $NR^5$, C, and CH; and $Y^4$ and $Y^1$ are each independently selected from N and C.

In some embodiments of Formula AA-1 and/or AA-3, $Y^2$, $Y^3$, and $Y^5$ are each independently selected from O, S, N, NH, C, CH, and $CR^5$; and $Y^4$ and $Y^1$ are each independently selected from N and C.

In some embodiments of Formula AA-1 and/or AA-3, $Y^1$ is N; $Y^4$ is C; and $Y^2$, $Y^3$, and $Y^5$ are each independently selected from NH, $NR^5$, CH, and $CR^5$.

In some embodiments of Formula AA-1 and/or AA-3, $Y^1$ is C; $Y^4$ is N; and $Y^2$, $Y^3$, and $Y^5$ are each independently selected from NH, $NR^5$, CH, and $CR^5$.

In some embodiments of Formula AA-1 and/or AA-3, $Y^1$ is C; $Y^4$ is C; and $Y^2$, $Y^3$, and $Y^5$ are each independently selected from NH, $NR^5$, CH, and $CR^5$.

In some embodiments of Formula AA-1 and/or AA-3, $Y^1$ is N; $Y^4$ is C; and $Y^2$, $Y^3$, and $Y^5$ are each independently selected from NH, CH, and $CR^5$.

In some embodiments of Formula AA-1 and/or AA-3, $Y^1$ is C; $Y^4$ is N; and $Y^2$, $Y^3$, and $Y^5$ are each independently selected from NH, CH, and $CR^5$.

In some embodiments of Formula AA-1 and/or AA-3, $Y^1$ is C; $Y^4$ is C; and $Y^2$, $Y^3$, and $Y^5$ are each independently selected from NH, CH, and $CR^5$.

In some embodiments of Formula AA-1 and/or AA-3, $Y^1$ is N; $Y^4$ is C; and $Y^2$, $Y^3$, and $Y^5$ are each independently selected from NH, $NR^5$, and CH.

In some embodiments of Formula AA-1 and/or AA-3, $Y^1$ is C; $Y^4$ is N; and $Y^2$, $Y^3$, and $Y^5$ are each independently selected from NH, $NR^5$, and CH.

In some embodiments of Formula AA-1 and/or AA-3, $Y^1$ is C; $Y^4$ is C; and $Y^2$, $Y^3$, and $Y^5$ are each independently selected from NH, $NR^5$, and CH.

Embodiments of $Z^1$, $Z^2$, $Z^3$, $Z^4$, and $Z^5$ in Formula AA-2 and AA-3

In some embodiments of Formula AA-2 and/or AA-3, $Z^1$, $Z^2$, $Z^3$, and $Z^5$ are each independently selected from O, S, N, NH, $NR^5$, C, CH, and $CR^5$; and $Z^4$ is N or C.

In some embodiments of Formula AA-2 and/or AA-3, $Z^1$, $Z^2$, $Z^3$, and $Z^5$ are each independently selected from S, N, NH, $NR^5$, C, CH, and $CR^5$; and $Z^4$ is N or C.

In some embodiments of Formula AA-2 and/or AA-3, $Z^1$, $Z^2$, $Z^3$, and $Z^5$ are each independently selected from O, N, NH, $NR^5$, C, CH, and $CR^5$; and $Z^4$ is N or C.

In some embodiments of Formula AA-2 and/or AA-3, $Z^1$, $Z^2$, $Z^3$, and $Z^5$ are each independently selected from N, NH, $NR^5$, C, CH, and $CR^5$; and $Z^4$ is N or C.

In some embodiments of Formula AA-2 and/or AA-3, $Z^1$, $Z^2$, $Z^3$, and $Z^5$ are each independently selected from N, NH, $NR^5$, C, and CH; and $Z^4$ is N or C.

In some embodiments of Formula AA-2 and/or AA-3, $Z^1$, $Z^2$, $Z^3$, and $Z^5$ are each independently selected from O, S, N, NH, C, CH, and $CR^5$; and $Z^4$ is N or C.

In some embodiments of Formula AA-2 and/or AA-3, $Z^4$ is C; and $Z^1$, $Z^2$, $Z^3$, and $Z^5$ are each independently selected from O, S, N, NH, CH, and $CR^5$.

In some embodiments of Formula AA-2 and/or AA-3, $Z^4$ is N; and $Z^1$, $Z^2$, $Z^3$, and $Z^5$ are each independently selected from O, S, N, NH, CH, and $CR^5$.

In some embodiments of Formula AA-2 and/or AA-3, $Z^4$ is C; and $Z^1$, $Z^2$, $Z^3$, and $Z^5$ are each independently selected from S, N, NH, CH, and $CR^5$.

In some embodiments of Formula AA-2 and/or AA-3, $Z^4$ is N; and $Z^1$, $Z^2$, $Z^3$, and $Z^5$ are each independently selected from S, N, NH, CH, and $CR^5$.

In some embodiments of Formula AA-1, Formula AA-2, or Formula AA-3, X is selected from the group consisting of —C(O)—, —S(O)$_2$—, —S(O)(NH)—, and CHNHCO$_2$CH$_2$Ph.

In some embodiments of Formula AA-1, Formula AA-2, or Formula AA-3, X is CHNHCO$_2$CH$_2$Ph. In certain of these embodiments, the stereochemistry of the CH of CHNHCO$_2$CH$_2$Ph is (R). In other embodiments, the stereochemistry of the CH of CHNHCO$_2$CH$_2$Ph is (S).

In some embodiments of Formula AA-1, Formula AA-2, or Formula AA-3, B is phenyl substituted with 1 or 2 $R^6$ and optionally substituted with 1, 2, or 3 $R^7$.

In some embodiments of Formula AA-1, Formula AA-2, or Formula AA-3, o=2 and p=1.

In some embodiments of Formula AA-1, Formula AA-2, or Formula AA-3, B is

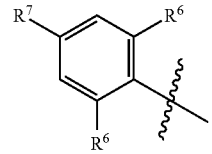

In certain embodiments, each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl; wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

As a non-limiting example of the foregoing, $R^6$ can be isopropyl. As a non-limiting example of the foregoing, $R^7$ can be halo (e.g., F).

In some embodiments of Formula AA-1, Formula AA-2, or Formula AA-3, o=2 and p=2.

In some embodiments of Formula AA-1, Formula AA-2, or Formula AA-3, B is

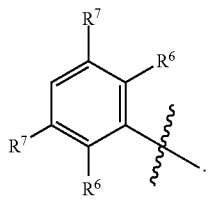

In some embodiments of Formula AA-1, Formula AA-2, or Formula AA-3, each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl; wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In certain of these embodiments, two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments of Formula AA-1, Formula AA-2, or Formula AA-3, B is

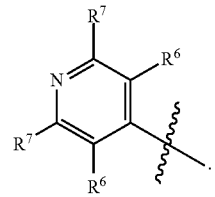

In certain embodiments, each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl; wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In certain of these embodiments, two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, the compound of Formula AA is a compound of Formula AA-4:

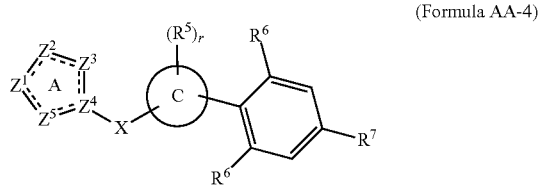

(Formula AA-4)

wherein
ring A is a charge neutral heteroaromatic ring;
ring C is a 5- to 6-membered monocyclic heteroarylene;
$Z^1$, $Z^2$, $Z^3$, and $Z^5$ are each independently selected from O, S, N, NH, $NR^1$, C, CH, and $CR^1$;
$Z^4$ is selected from N and C;
each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl; and
$R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In some embodiments of Formula AA-4,

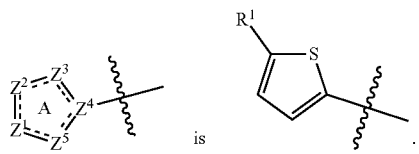

is

In some embodiments of Formula AA-4,

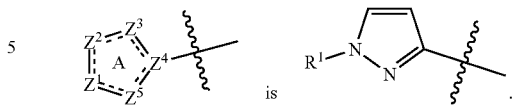

In some embodiments of Formula AA-4,

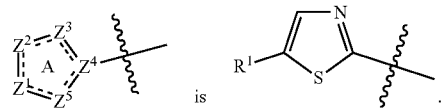

In some embodiments of Formula AA-4,

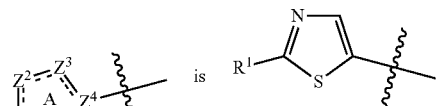

In some embodiments of Formula AA-4,

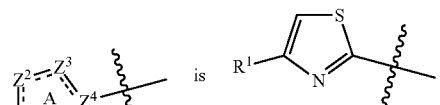

In some embodiments of Formula AA-4,

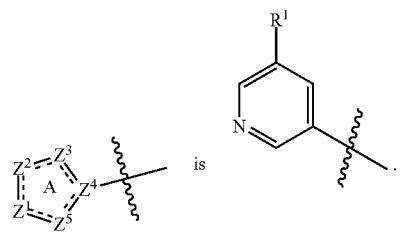

In some embodiments of Formula AA-4, $R^1$, when present, is independently selected from the group consisting of $C_1$-$C_6$ alkyl optionally substituted with one or more hydroxy, halo, oxo, $C_1$-$C_6$ alkoxy, or $NR^8R^9$; $C_3$-$C_7$ cycloalkyl optionally substituted with one or more hydroxy, halo, oxo, $C_1$-$C_6$ alkoxy, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of Formula AA-4, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; ethoxy carbonyl; 2-methoxy-2-propyl; (dimethylamino)methyl; 1-(dimethylamino)ethyl; fluoro; chloro; phenyl; pyridyl; pyrazolyl; $S(O_2)CH_3$; and $S(O_2)NR^{11}R^{12}$.

In some embodiments of Formula AA-4, $R^1$ is selected from the group consisting of 2-hydroxy-2-propyl, ethoxycarbonyl, phenyl, methyl, ethyl, and isopropyl.

In some embodiments of Formula AA-4, $R^6$ is isopropyl.

In some embodiments of Formula AA-4, $R^7$ is halo (e.g., F).

In some embodiments, the compound of Formula AA is a compound of Formula AA-5:

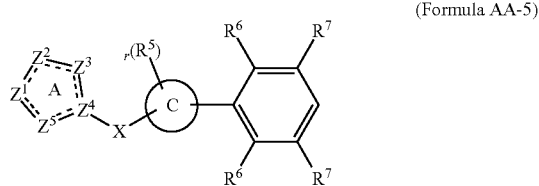

(Formula AA-5)

wherein ring A is a charge neutral heteroaromatic ring;

ring C is a 5- to 6-membered monocyclic heteroarylene;

$Z^1$, $Z^2$, $Z^3$, and $Z^5$ are each independently selected from O, S, N, NH, $NR^1$, C, CH, and $CR^1$;

$Z^4$ is selected from N and C; and two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments of Formula AA-5,

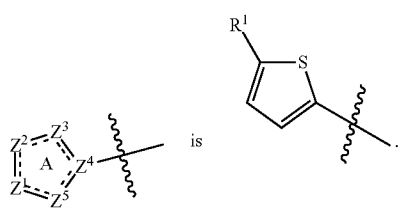

In some embodiments of Formula AA-5,

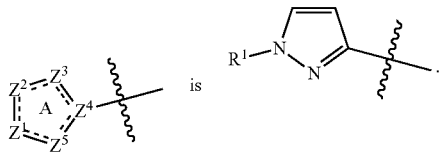

In some embodiments of Formula AA-5,

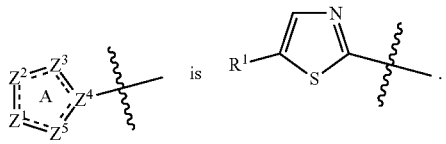

In some embodiments of Formula AA-5,

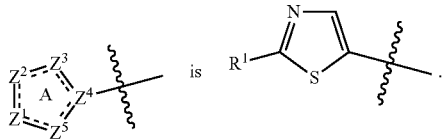

In some embodiments of Formula AA-5,

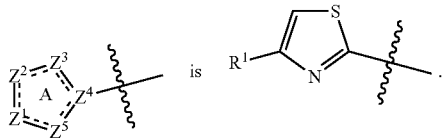

In some embodiments of Formula AA-5.

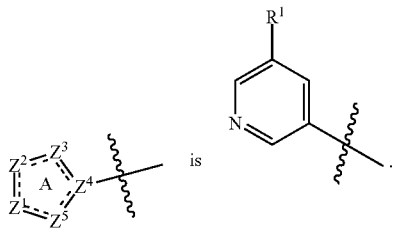

In some embodiments of Formula AA-5, $R^1$, when present, is independently selected from the group consisting of $C_1$-$C_6$ alkyl optionally substituted with one or more hydroxy, halo, oxo, $C_1$-$C_6$ alkoxy, or $NR^8R^9$; $C_3$-$C_7$ cycloalkyl optionally substituted with one or more hydroxy, halo, oxo, $C_1$-$C_6$ alkoxy, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of Formula AA-5, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; ethoxycarbonyl; 2-methoxy-2-propyl; (dimethylamino)methyl; 1-(dimethylamino)ethyl; fluoro; chloro; phenyl; pyridyl; pyrazolyl; $S(O_2)CH_3$; and $S(O_2)NR^{11}R^{12}$.

In some embodiments of Formula AA-5, $R^1$ is selected from the group consisting of 2-hydroxy-2-propyl, ethoxycarbonyl, phenyl, methyl, ethyl, and isopropyl.

In some embodiments of Formula AA-5, one pair of $R^6$ and $R^7$ on adjacent atoms, taken together with the atoms connecting them, form one $C_4$-$C_7$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of these embodiments, one pair of $R^6$ and $R^7$ on adjacent atoms, taken together with the atoms connecting them, form one $C_4$-$C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of the foregoing embodiments, a second pair of $R^6$ and $R^7$ on adjacent atoms, taken together with the atoms connecting them, form one $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the compound of Formula AA is a compound of Formula AA-6:

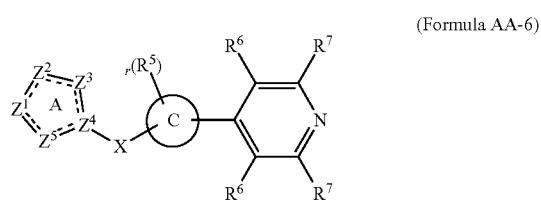

(Formula AA-6)

wherein
ring A is a charge neutral heteroaromatic ring;
ring C is a 5- to 6-membered monocyclic heteroarylene;
$Z^1$, $Z^2$, $Z^3$, and $Z^5$ are each independently selected from O, S, N, NH, $NR^1$, C, CH, and $CR^1$;

$Z^4$ is selected from N and C; and two pairs of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments of Formula AA-6,

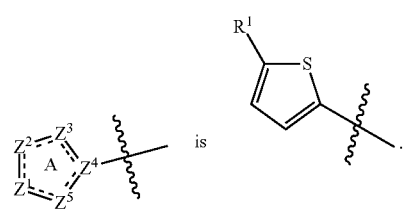

In some embodiments of Formula AA-6,

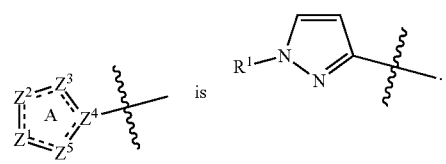

In some embodiments of Formula AA-6,

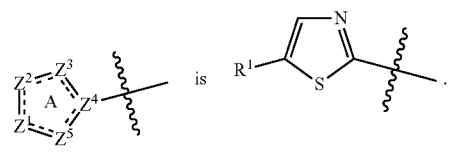

In some embodiments of Formula AA-6,

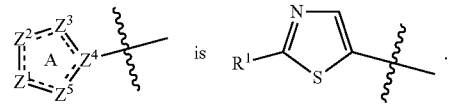

In some embodiments of Formula AA-6,

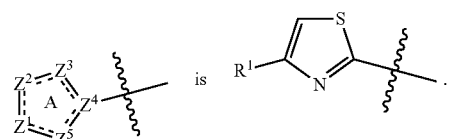

In some embodiments of Formula AA-6,

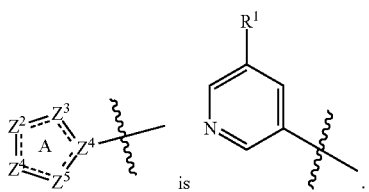

is

In some embodiments of Formula AA-6, $R^1$, when present, is independently selected from the group consisting of $C_1$-$C_6$ alkyl optionally substituted with one or more hydroxy, halo, oxo, $C_1$-$C_6$ alkoxy, or $NR^8R^9$; $C_3$-$C_7$ cycloalkyl optionally substituted with one or more hydroxy, halo, oxo, $C_1$-$C_6$ alkoxy, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of Formula AA-6, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxy ethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; ethoxycarbonyl; 2-methoxy-2-propyl; (dimethylamino)methyl; 1-(dimethylamino)ethyl; fluoro; chloro; phenyl; pyridyl; pyrazolyl; $S(O_2)CH_3$; and $S(O_2)NR^{11}R^{12}$.

In some embodiments of Formula AA-6, $R^1$ is selected from the group consisting of 2-hydroxy-2-propyl, ethoxycarbonyl, phenyl, methyl, ethyl, and isopropyl.

In some embodiments of Formula AA-6, one pair of $R^6$ and $R^7$ on adjacent atoms, taken together with the atoms connecting them, form one $C_4$-$C_7$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of these embodiments, one pair of $R^6$ and $R^7$ on adjacent atoms, taken together with the atoms connecting them, form one $C_4$-$C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain of the foregoing embodiments, a second pair of $R^6$ and $R^7$ on adjacent atoms, taken together with the atoms connecting them, form one $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain other of the foregoing embodiments, a second pair of $R^6$ and $R^7$ on adjacent atoms, taken together with the atoms connecting them, form one $C_6$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments of Formula AA-4, Formula AA-5, or Formula AA-6, the optionally substituted ring C is

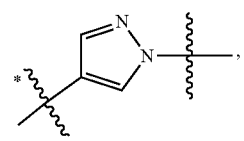 [SMILES: *c1cnn(*)c1]

and wherein the bond that is shown as being spatially closest to the asterisk connects to the X group.

In some embodiments of Formula AA-4, Formula AA-5, or Formula AA-6, the optionally substituted ring C is

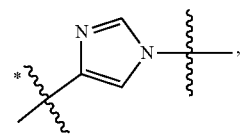 [SMILES: *c1cn(*)cn1]

and wherein the bond that is shown as being spatially closest to the asterisk connects to the X group.

In some embodiments of Formula AA-4, Formula AA-5, or Formula AA-6, the optionally substituted ring C is

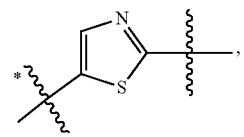 [SMILES: *c1cnc(*)s1]

and wherein the bond that is shown as being spatially closest to the asterisk connects to the X group.

In some embodiments of Formula AA-4, Formula AA-5, or Formula AA-6, the optionally substituted ring C is

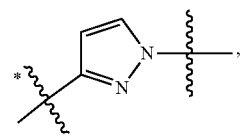 [SMILES: *c1ccn(*)n1]

and wherein the bond that is shown as being spatially closest to the asterisk connects to the X group.

In some embodiments of Formula AA-4, Formula AA-5, or Formula AA-6, the optionally substituted ring C is

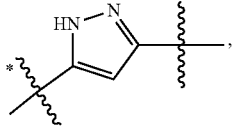 [SMILES: *c1cc(*)[nH]n1]

and wherein the bond that is shown as being spatially closest to the asterisk connects to the X group.

In some embodiments of Formula AA-4, Formula AA-5, or Formula AA-6, the optionally substituted ring C is

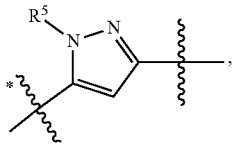

and wherein the bond that is shown as being spatially closest to the asterisk connects to the X group.

In some embodiments of Formula AA-4, Formula AA-5, or Formula AA-6, the optionally substituted ring C is

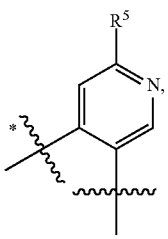

and wherein the bond that is shown as being spatially closest to the asterisk connects to the X group.

In some embodiments of Formula AA-4, Formula AA-5, or Formula AA-6, the optionally substituted ring C is

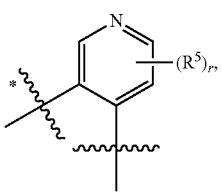

r is 0 or 1, and wherein the bond that is shown as being spatially closest to the asterisk connects to the X group.

In some embodiments of Formula AA-4, Formula AA-5, or Formula AA-6, the optionally substituted ring C is

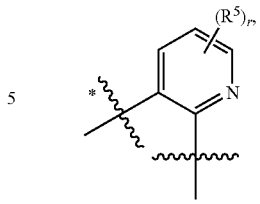

r is 0 or 1, and wherein the bond that is shown as being spatially closest to the asterisk connects to the X group.

In some embodiments of Formula AA-4, Formula AA-5, or Formula AA-6, the optionally substituted ring C is

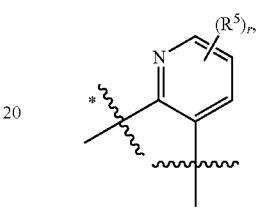

r is 0 or 1, and wherein the bond that is shown as being spatially closest to the asterisk connects to the X group.

In some embodiments of Formula AA-4, Formula AA-5, or Formula AA-6, the optionally substituted ring C is

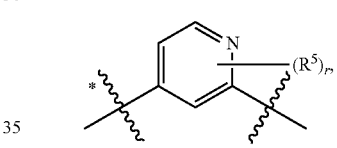

r is 0 or 1, and wherein the bond that is shown as being spatially closest to the asterisk connects to the X group.

In some embodiments of Formula AA-4, Formula AA-5, or Formula AA-6, the optionally substituted ring C is

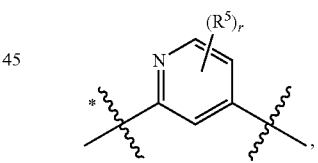

r is 0 or 1, and wherein the bond that is shown as being spatially closest to the asterisk connects to the X group.

In some embodiments of Formula AA-4, Formula AA-5, or Formula AA-6, the optionally substituted ring C is

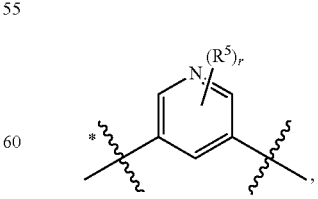

r is 0 or 1, and wherein the bond that is shown as being spatially closest to the asterisk connects to the X group.

In some embodiments of Formula AA-4, Formula AA-5, or Formula AA-6, the optionally substituted ring C is

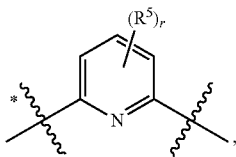

r is 0 or 1, and wherein the bond that is shown as being spatially closest to the asterisk connects to the X group.

In some embodiments of Formula AA-4, Formula AA-5, or Formula AA-6, the optionally substituted ring C is

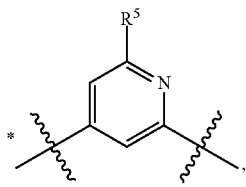

and wherein the bond that is shown as being spatially closest to the asterisk connects to the X group.

In some embodiments of Formula AA-4, Formula AA-5, or Formula AA-6, the optionally substituted ring C is

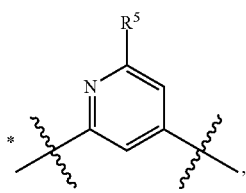

and wherein the bond that is shown as being spatially closest to the asterisk connects to the X group.

In some embodiments of Formula AA-4, Formula AA-5, or Formula AA-6, the optionally substituted ring C is

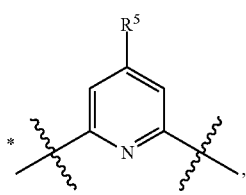

and wherein the bond that is shown as being spatially closest to the asterisk connects to the X group.

In some embodiments of Formula AA-4, Formula AA-5, or Formula AA-6, the optionally substituted ring C is

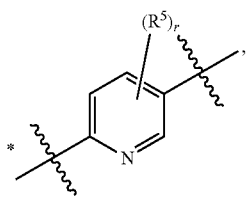

r is 0 or 1, and wherein the bond that is shown as being spatially closest to the asterisk connects to the X group.

In some embodiments of Formula AA-4, Formula AA-5, or Formula AA-6, the optionally substituted ring C is

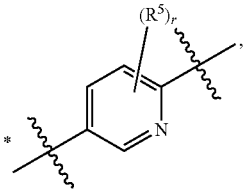

r is 0 or 1, and wherein the bond that is shown as being spatially closest to the asterisk connects to the X group.

In some embodiments of Formula AA-4, Formula AA-5, or Formula AA-6, the optionally substituted ring C is

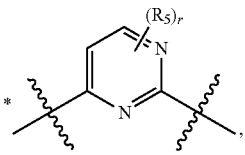

r is 0 or 1, and wherein the bond that is shown as being spatially closest to the asterisk connects to the X group.

In some embodiments of Formula AA-4, Formula AA-5, or Formula AA-6, the optionally substituted ring C is

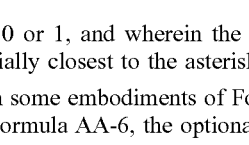

and wherein the bond that is shown as being spatially closest to the asterisk connects to the X group.

In some embodiments of Formula AA-4, Formula AA-5, or Formula AA-6, the optionally substituted ring C is

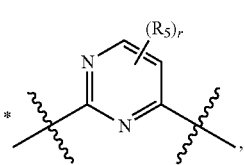

r is 0 or 1, and wherein the bond that is shown as being spatially closest to the asterisk connects to the X group.

In some embodiments of Formula AA-4, Formula AA-5, or Formula AA-6, the optionally substituted ring C is

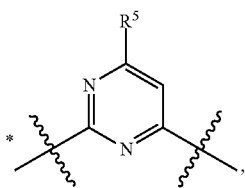

and wherein the bond that is shown as being spatially closest to the asterisk connects to the X group.

In some embodiments of Formula AA-4, Formula AA-5, or Formula AA-6, the optionally substituted ring C is

r is 0 or 1, and wherein the bond that is shown as being spatially closest to the asterisk connects to the X group.

In some embodiments of Formula AA-4, Formula AA-5, or Formula AA-6, the optionally substituted ring C is

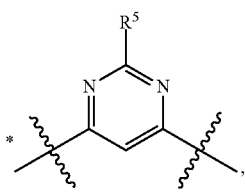

and wherein the bond that is shown as being spatially closest to the asterisk connects to the X group.

In some embodiments of Formula AA-4, Formula AA-5, or Formula AA-6, the optionally substituted ring C is

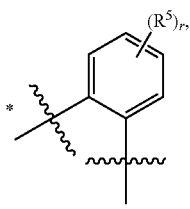

r is 0 or 1, and wherein the bond that is shown as being spatially closest to the asterisk connects to the X group.

In some embodiments of Formula AA-4, Formula AA-5, or Formula AA-6, the optionally substituted ring C is

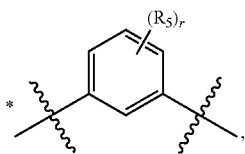

r is 0 or 1, and wherein the bond that is shown as being spatially closest to the asterisk connects to the X group.

In some embodiments of Formula AA-4, Formula AA-5, or Formula AA-6, the optionally substituted ring C is

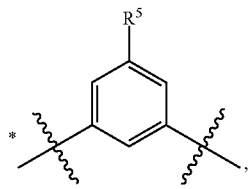

and wherein the bond that is shown as being spatially closest to the asterisk connects to the X group.

In some embodiments of Formula AA-4, Formula AA-5, or Formula AA-6, the optionally substituted ring C is

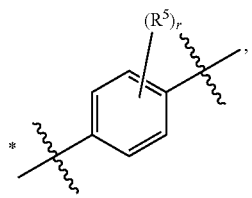

r is 0 or 1, and wherein the bond that is shown as being spatially closest to the asterisk connects to the X group.

In some embodiments of Formula AA-4, Formula AA-5, or Formula AA-6, X is selected from the group consisting of —C(O)—, —S(O)$_2$—, —S(O)(NH)—, and CHNHCO$_2$CH$_2$Ph.

In some embodiments of Formula AA-4, Formula AA-5, or Formula AA-6, X is CHNHCO$_2$CH$_2$Ph. In certain of these embodiments, the stereochemistry of the CH of CHNHCO$_2$CH$_2$Ph is (R). In certain other embodiments, the stereochemistry of the CH of CHNHCO$_2$CH$_2$Ph is (S).

In one embodiment, provided herein is a combination of a compound of any preceding embodiment, for use in the treatment or the prevention of a condition mediated by TNF-α, in a patient in need thereof, wherein the compound is administered to said patient at a therapeutically effective amount. Preferably, the subject is resistant to treatment with an anti-TNFα agent. Preferably, the condition is a gut disease or disorder.

In one embodiment, provided herein is a pharmaceutical composition of comprising a compound of any preceding embodiment, and an anti-TNFα agent disclosed herein. Preferably wherein the anti-TNFα agent is Infliximab, Etanercept, Certolizumab pegol, Golimumab or Adalimumab, more preferably wherein the anti-TNFα agent is Adalimumab.

In one embodiment, provided herein is a pharmaceutical combination of a compound of any preceding embodiment, and an anti-TNFα agent Preferably wherein the anti-TNFα agent is Infliximab, Etanercept, Certolizumab pegol, Golimumab or Adalimumab, more preferably wherein the anti-TNFα agent is Adalimumab.

In one embodiment, the present invention relates to an NLRP3 antagonist for use in the treatment or the prevention of a condition mediated by TNF-α, in particular a gut disease or disorder, in a patient in need thereof, wherein the NLRP3 antagonist is administered to said patient at a therapeutically effective amount.

In one embodiment, the present invention relates to an NLRP3 antagonist for use in the treatment or the prevention of a condition, in particular a gut disease or disorder, in a patient in need thereof wherein the NLRP3 antagonist is administered to said patient at a therapeutically effective amount.

In one embodiment, the present invention relates to an NLRP3 antagonist for use in the treatment, stabilization or lessening the severity or progression of gut disease or disorder, in a patient in need thereof wherein the NLRP3 antagonist is administered to said patient at a therapeutically effective amount.

In one embodiment, the present invention relates to an NLRP3 antagonist for use in the slowing, arresting, or reducing the development of a gut disease or disorder, in a patient in need thereof wherein the NLRP3 antagonist is administered to said patient at a therapeutically effective amount.

In one embodiment, the present invention relates to an NLRP3 antagonist for use according to above listed embodiments wherein the NLRP3 antagonist is a gut-targeted NLRP3 antagonist.

In one embodiment, the present invention relates ton NLRP3 antagonist for use according to any of the above embodiments, wherein the gut disease is IBD.

In one embodiment, the present invention relates to an NLRP3 antagonist for use according to any of the above embodiments, wherein the gut disease is US or CD.

In one embodiment, the present invention relates to a method for the treatment or the prevention of a condition mediated by TNF-α, in particular a gut disease or disorder, in a patient in need thereof, comprising administering to said patient a therapeutically effective amount of a gut-targeted NLRP3 antagonist.

In one embodiment, the present invention relates to a method for the treatment or the prevention of a condition, in particular a gut disease or disorder, in a patient in need thereof, comprising administering to said patient a therapeutically effective amount of a gut-targeted NLRP3 antagonist.

In one embodiment, the present invention relates to a method for the treatment, stabilization or lessening the severity or progression of gut disease or disorder, in a patient in need thereof comprising administering to said patient a therapeutically effective amount of a gut-targeted NLRP3 antagonist.

In one embodiment, the present invention relates to a method for slowing, arresting, or reducing the development of a gut disease or disorder, in a patient in need thereof comprising administering to said patient a therapeutically effective amount of a gut-targeted NLRP3 antagonist.

In one embodiment, the present invention relates to a method according to any of the above embodiments, wherein the gut disease is IBD.

In one embodiment, the present invention relates to a method according to any of the above embodiments x to xx, wherein the gut disease is UC or CD.

In one embodiment, the present invention relates to a method for the treatment or the prevention of a condition mediated by TNF-α, in particular a gut disease or disorder, in a patient in need thereof, comprising administering to said patient a therapeutically effective amount of a gut-targeted NLRP3 antagonist.

Additional Features of the Embodiments Herein

It is understood that the combination of variables in the formulae herein is such that the compounds are stable.

In some embodiments, provided herein is a compound that is selected from the group consisting of the compounds in Table 1:

TABLE 1

| Compound # | Structure |
|---|---|
| 101 | 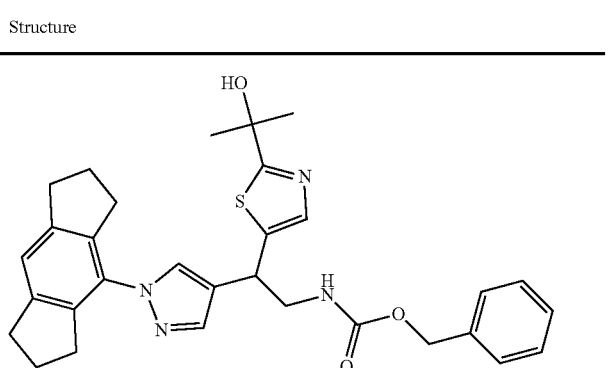 |
| 102 | |
| 103 | 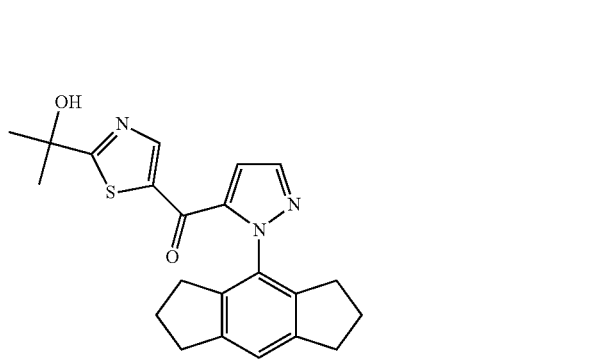 [SMILES: CC(C)(O)c1ncc(C(=O)c2ccnn2-c2c3c(cc4c2CCC4)CCC3)s1] |

TABLE 1-continued
| Compound # | Structure |
|---|---|
| 104 | 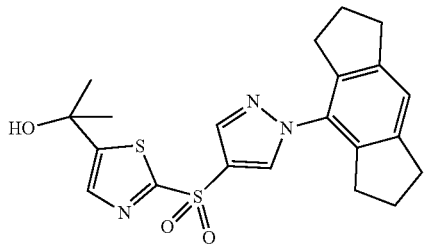 [SMILES: CC(C)(O)c1cnc(S(=O)(=O)c2cnn(-c3c4c(cc5c3CCC5)CCC4)c2)s1] |
| 105 | |
| 106 | |
| 107 | 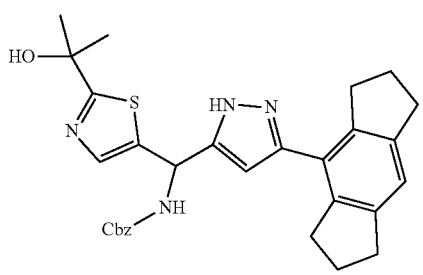 [SMILES: CC(C)(O)c1ncc(C(NC(=O)OCc2ccccc2)c2cc(-c3c4c(cc5c3CCC5)CCC4)n[nH]2)s1] |
| 108 | 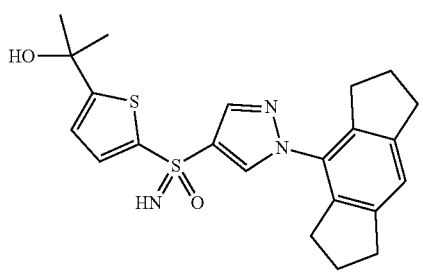 [SMILES: CC(C)(O)c1ccc(S(=N)(=O)c2cnn(-c3c4c(cc5c3CCC5)CCC4)c2)s1] |
| 109 | 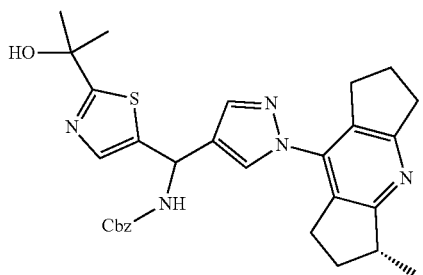 [SMILES: C[C@@H]1CCc2c1nc1c(c2-n2cc(C(NC(=O)OCc3ccccc3)c3cnc(C(C)(C)O)s3)cn2)CCC1] |
| 110 | 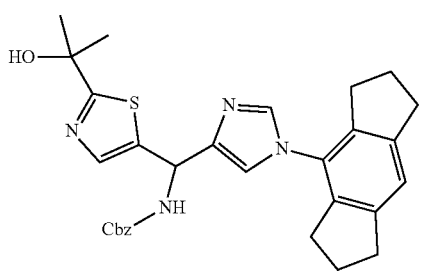 [SMILES: CC(C)(O)c1ncc(C(NC(=O)OCc2ccccc2)c2cn(-c3c4c(cc5c3CCC5)CCC4)cn2)s1] |

TABLE 1-continued
| Compound # | Structure |
|---|---|
| 111 | 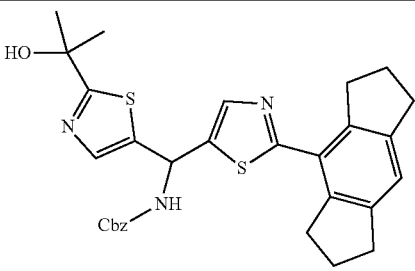 |
| 112 | 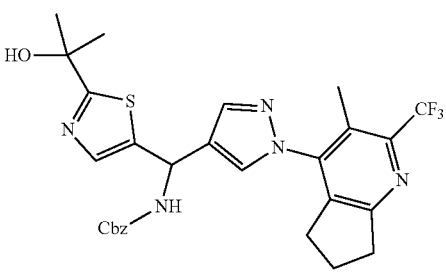 [SMILES: Cc1c(C(F)(F)F)nc2c(c1-n1cc(C(NC(=O)OCc3ccccc3)c3cnc(C(C)(C)O)s3)cn1)CCC2] |
| 113 | 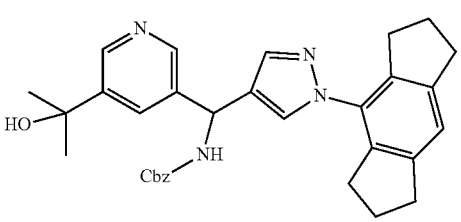 [SMILES: CC(C)(O)c1cncc(C(NC(=O)OCc2ccccc2)c2cnn(-c3c4c(cc5c3CCC5)CCC4)c2)c1] |
| 114 | 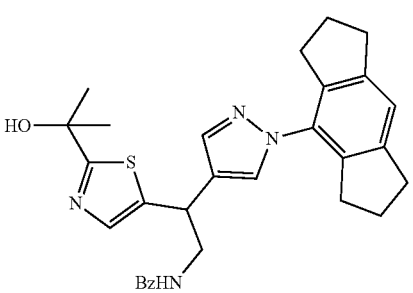 |
| 115 | 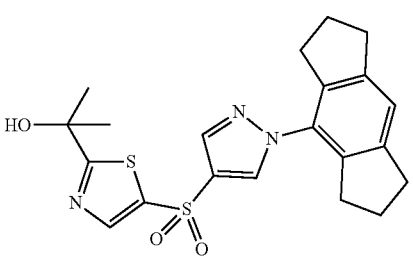 [SMILES: CC(C)(O)c1ncc(S(=O)(=O)c2cnn(-c3c4c(cc5c3CCC5)CCC4)c2)s1] |
| 116 | 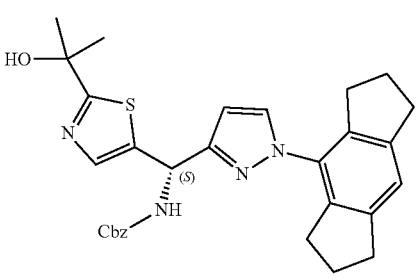 |

TABLE 1-continued
| Compound # | Structure |
|---|---|
| 117 | 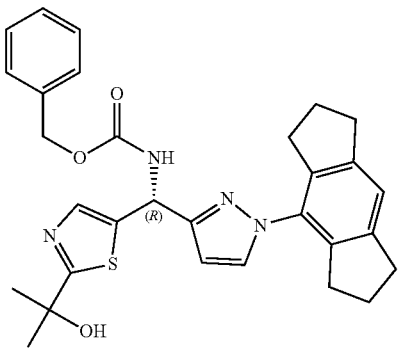 |
| 118 | 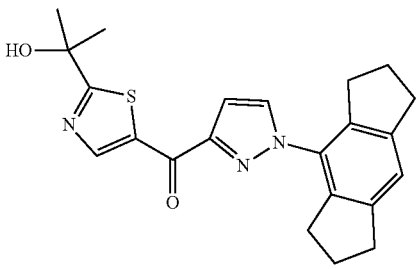 [SMILES: CC(C)(O)c1ncc(C(=O)c2ccn(-c3c4c(cc5c3CCC5)CCC4)n2)s1] |
| 119 | 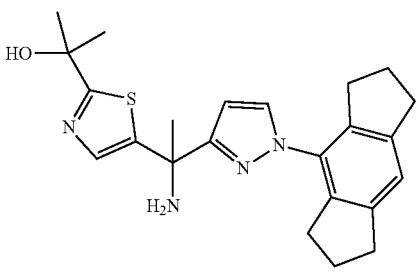 [SMILES: CC(C)(O)c1ncc(C(C)(N)c2ccn(-c3c4c(cc5c3CCC5)CCC4)n2)s1] |
| 120 | 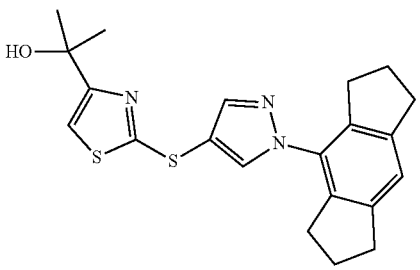 [SMILES: CC(C)(O)c1csc(Sc2cnn(-c3c4c(cc5c3CCC5)CCC4)c2)n1] |
| 121 | 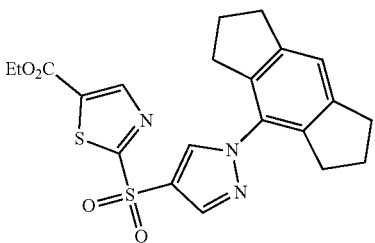 [SMILES: CCOC(=O)c1cnc(S(=O)(=O)c2cnn(-c3c4c(cc5c3CCC5)CCC4)c2)s1] |

TABLE 1-continued
| Compound # | Structure |
|---|---|
| 122 | 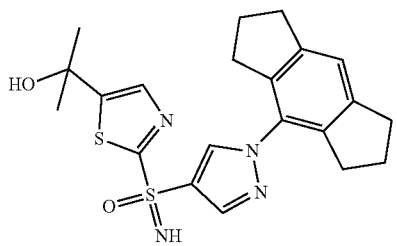 [SMILES: CC(C)(O)c1cnc(S(=N)(=O)c2cnn(-c3c4c(cc5c3CCC5)CCC4)c2)s1] |
| 123 | 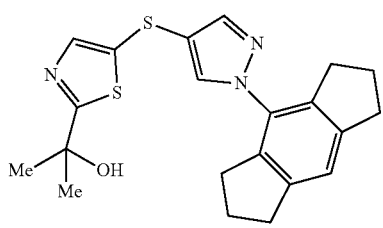 [SMILES: CC(C)(O)c1ncc(Sc2cnn(-c3c4c(cc5c3CCC5)CCC4)c2)s1] |
| 124 | 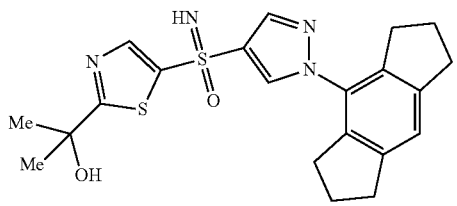 [SMILES: CC(C)(O)c1ncc(S(=N)(=O)c2cnn(-c3c4c(cc5c3CCC5)CCC4)c2)s1] |
| 125 | 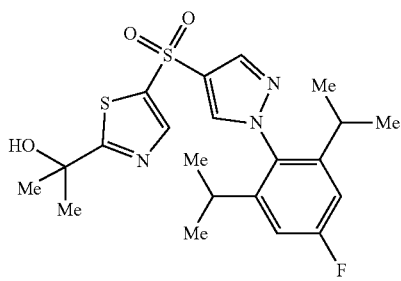 [SMILES: CC(C)c1cc(F)cc(C(C)C)c1-n1cc(S(=O)(=O)c2cnc(C(C)(C)O)s2)cn1] |
| 126 | 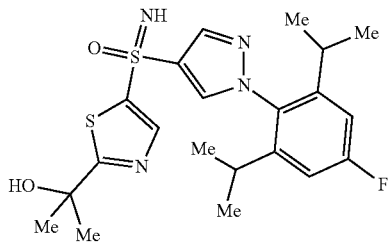 [SMILES: CC(C)c1cc(F)cc(C(C)C)c1-n1cc(S(=N)(=O)c2cnc(C(C)(C)O)s2)cn1] |
| 127 | 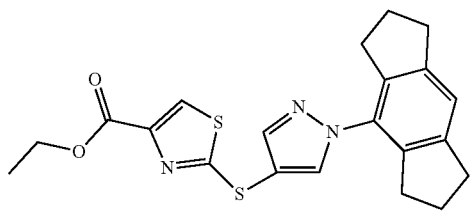 [SMILES: CCOC(=O)c1csc(Sc2cnn(-c3c4c(cc5c3CCC5)CCC4)c2)n1] |

TABLE 1-continued
| Compound # | Structure |
|---|---|
| 128 | 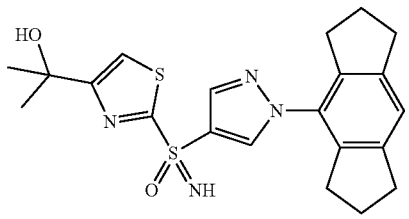 [SMILES: CC(C)(O)c1csc(S(=N)(=O)c2cnn(-c3c4c(cc5c3CCC5)CCC4)c2)n1] |
| 129 | 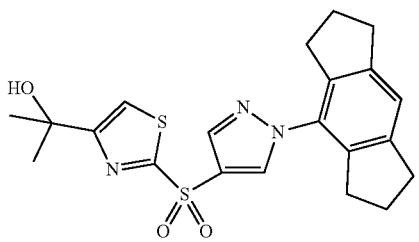 [SMILES: CC(C)(O)c1csc(S(=O)(=O)c2cnn(-c3c4c(cc5c3CCC5)CCC4)c2)n1] |
| 130 | 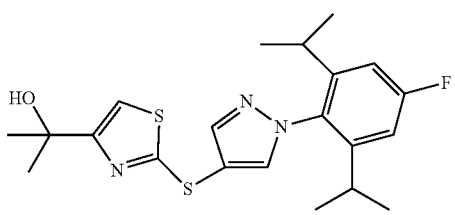 [SMILES: CC(C)c1cc(F)cc(C(C)C)c1-n1cc(Sc2nc(C(C)(C)O)cs2)cn1] |
| 131 | 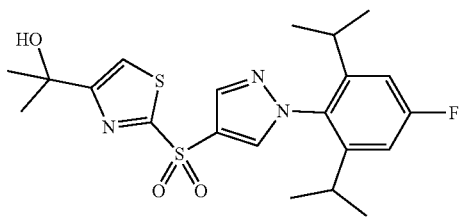 [SMILES: CC(C)c1cc(F)cc(C(C)C)c1-n1cc(S(=O)(=O)c2nc(C(C)(C)O)cs2)cn1] |
| 132 | 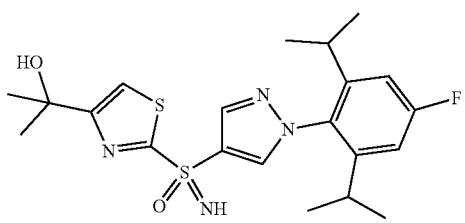 [SMILES: CC(C)c1cc(F)cc(C(C)C)c1-n1cc(S(=N)(=O)c2nc(C(C)(C)O)cs2)cn1] |
| 133 | 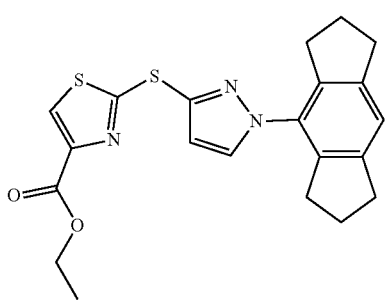 [SMILES: CCOC(=O)c1csc(Sc2ccn(-c3c4c(cc5c3CCC5)CCC4)n2)n1] |

TABLE 1-continued
| Compound # | Structure |
|---|---|
| 134 | 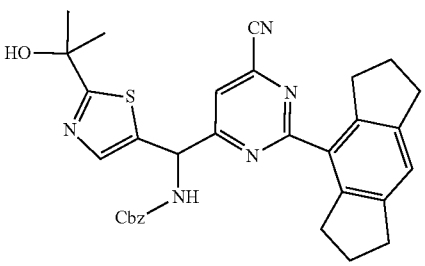 [SMILES: CC(C)(O)c1ncc(C(NC(=O)OCc2ccccc2)c2cc(C#N)nc(-c3c4c(cc5c3CCC5)CCC4)n2)s1] |
| 135 | 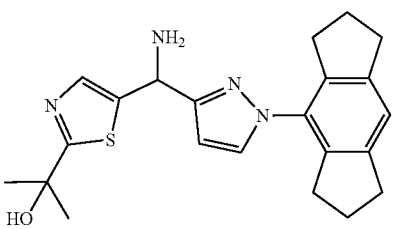 [SMILES: CC(C)(O)c1ncc(C(N)c2ccn(-c3c4c(cc5c3CCC5)CCC4)n2)s1] |
| 136 | 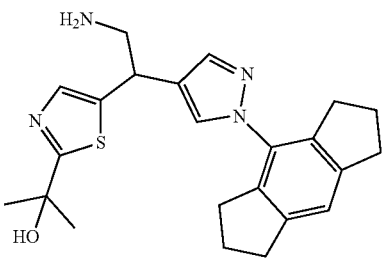 [SMILES: CC(C)(O)c1ncc(C(CN)c2cnn(-c3c4c(cc5c3CCC5)CCC4)c2)s1] |
| 137 | 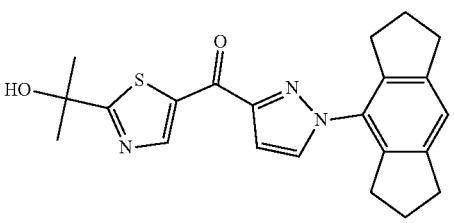 [SMILES: CC(C)(O)c1ncc(C(=O)c2ccn(-c3c4c(cc5c3CCC5)CCC4)n2)s1] |
| 138 | 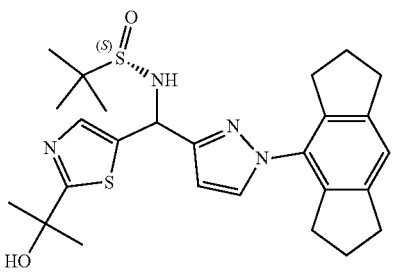 |
| 139 | 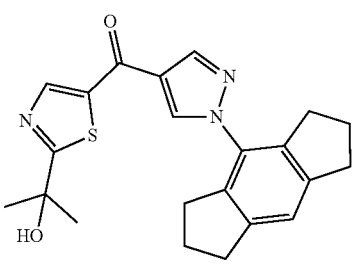 [SMILES: CC(C)(O)c1ncc(C(=O)c2cnn(-c3c4c(cc5c3CCC5)CCC4)c2)s1] |

TABLE 1-continued
| Compound # | Structure |
|---|---|
| 140 | 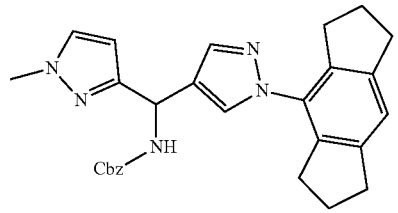 [SMILES: Cn1ccc(C(NC(=O)OCc2ccccc2)c2cnn(-c3c4c(cc5c3CCC5)CCC4)c2)n1] |
| 141 | 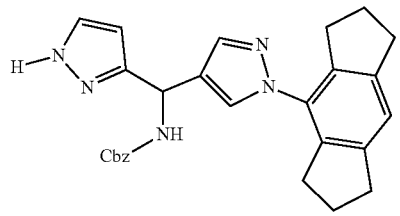 [SMILES: O=C(NC(c1cnn(-c2c3c(cc4c2CCC4)CCC3)c1)c1cc[nH]n1)OCc1ccccc1] |
| 142 | 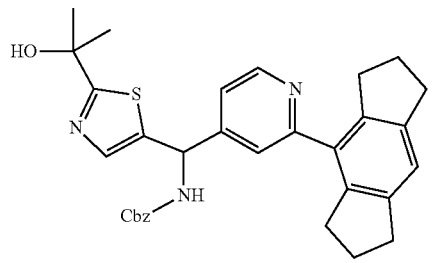 [SMILES: CC(C)(O)c1ncc(C(NC(=O)OCc2ccccc2)c2ccnc(-c3c4c(cc5c3CCC5)CCC4)c2)s1] |
| 143 | 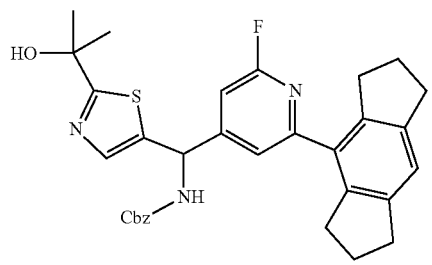 |
| 144 | 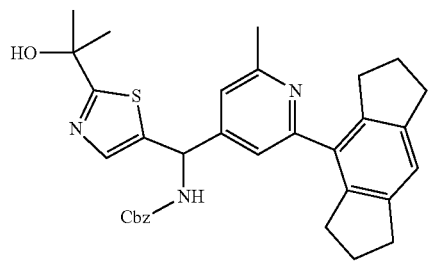 [SMILES: Cc1cc(C(NC(=O)OCc2ccccc2)c2cnc(C(C)(C)O)s2)cc(-c2c3c(cc4c2CCC4)CCC3)n1] |
| 145 | 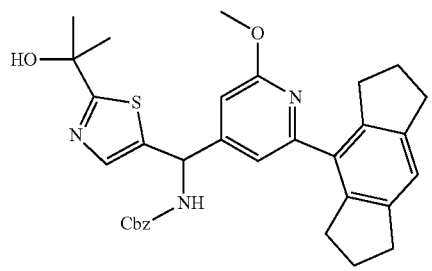 |

TABLE 1-continued
| Compound # | Structure |
|---|---|
| 146 | 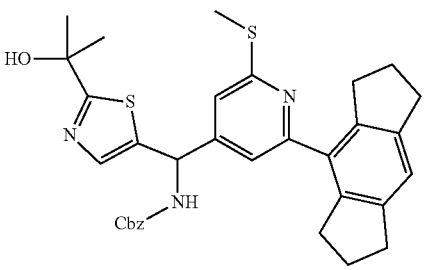 [SMILES: COc1cc(C(NC(=O)OCc2ccccc2)c2cnc(C(C)(C)O)s2)cc(-c2c3c(cc4c2CCC4)CCC3)n1] |
| 147 | 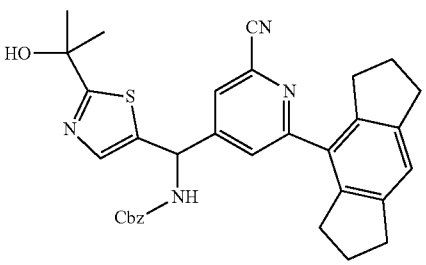 [SMILES: CC(C)(O)c1ncc(C(NC(=O)OCc2ccccc2)c2cc(C#N)nc(-c3c4c(cc5c3CCC5)CCC4)c2)s1] |
| 148 | 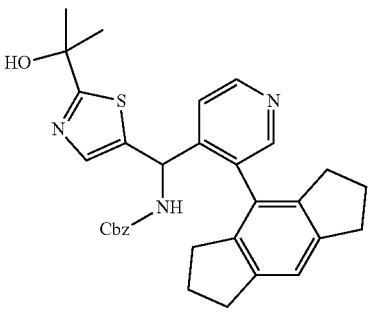 [SMILES: CC(C)(O)c1ncc(C(NC(=O)OCc2ccccc2)c2ccncc2-c2c3c(cc4c2CCC4)CCC3)s1] |
| 149 | 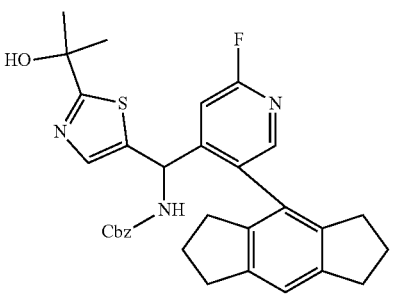 |
| 150 | 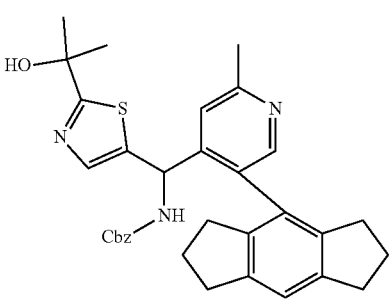 [SMILES: Cc1cc(C(NC(=O)OCc2ccccc2)c2cnc(C(C)(C)O)s2)c(-c2c3c(cc4c2CCC4)CCC3)cn1] |

TABLE 1-continued
| Compound # | Structure |
|---|---|
| 151 | 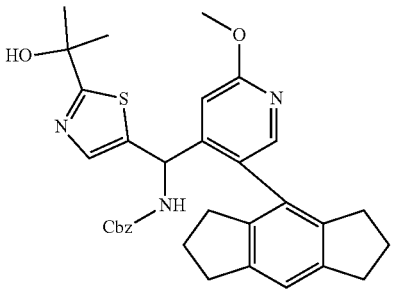 [SMILES: COc1cc(C(NC(=O)OCc2ccccc2)c2cnc(C(C)(C)O)s2)c(-c2c3c(cc4c2CCC4)CCC3)cn1] |
| 152 | 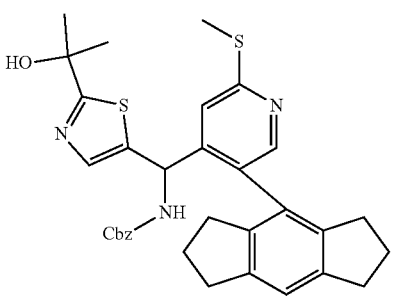 [SMILES: CSc1cc(C(NC(=O)OCc2ccccc2)c2cnc(C(C)(C)O)s2)c(-c2c3c(cc4c2CCC4)CCC3)cn1] |
| 153 | 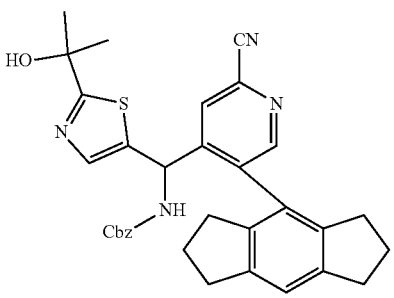 [SMILES: CC(C)(O)c1ncc(C(NC(=O)OCc2ccccc2)c2cc(C#N)ncc2-c2c3c(cc4c2CCC4)CCC3)s1] |
| 154 | 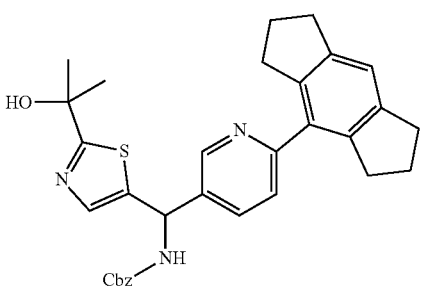 [SMILES: CC(C)(O)c1ncc(C(NC(=O)OCc2ccccc2)c2ccc(-c3c4c(cc5c3CCC5)CCC4)nc2)s1] |
| 155 | 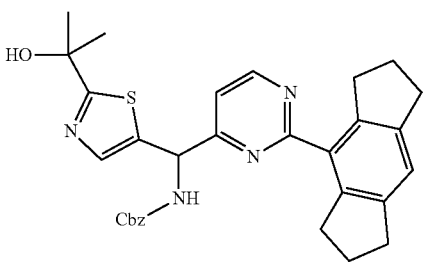 [SMILES: CC(C)(O)c1ncc(C(NC(=O)OCc2ccccc2)c2ccnc(-c3c4c(cc5c3CCC5)CCC4)n2)s1] |

TABLE 1-continued

| Compound # | Structure |
|---|---|
| 156 | 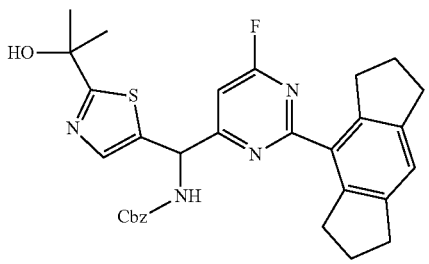 [SMILES: CC(C)(O)c1ncc(C(NC(=O)OCc2ccccc2)c2cc(F)nc(-c3c4c(cc5c3CCC5)CCC4)n2)s1] |
| 157 | 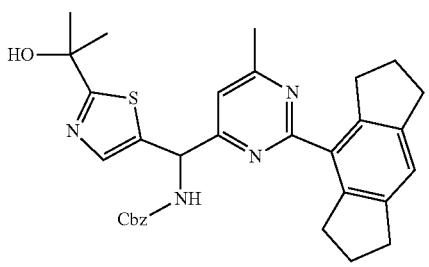 [SMILES: Cc1cc(C(NC(=O)OCc2ccccc2)c2cnc(C(C)(C)O)s2)nc(-c2c3c(cc4c2CCC4)CCC3)n1] |
| 158 | 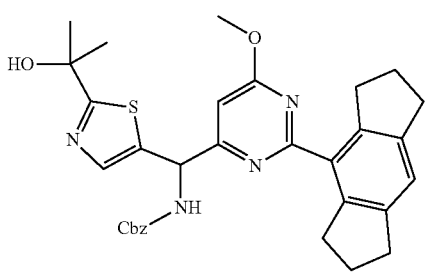 [SMILES: COc1cc(C(NC(=O)OCc2ccccc2)c2cnc(C(C)(C)O)s2)nc(-c2c3c(cc4c2CCC4)CCC3)n1] |
| 159 | 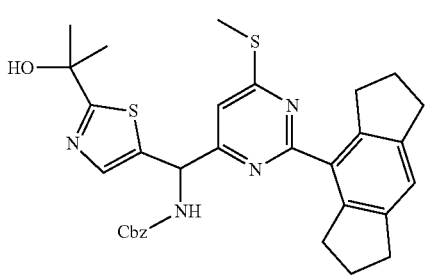 [SMILES: CSc1cc(C(NC(=O)OCc2ccccc2)c2cnc(C(C)(C)O)s2)nc(-c2c3c(cc4c2CCC4)CCC3)n1] | and pharmaceutically acceptable salts thereof.

In some embodiments, disclosed herein is a compound selected from the group consisting of:

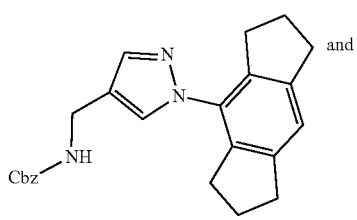 and (200)

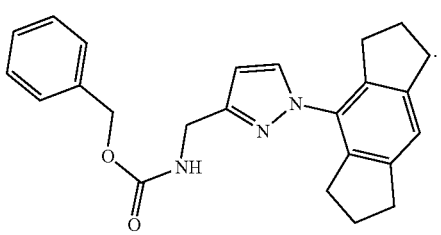

(201)

In one embodiment, provided herein is a pharmaceutical composition comprising any NLRP3 antagonist species defined here (for example, and example of 1 to 22, or a compound of Table 1), and an anti-TNFα agent disclosed herein. Preferably wherein the anti-TNFα agent is Infliximab, Etanercept, Certolizumab pegol, Golimumab or Adalimumab, more preferably wherein the anti-TNFα agent is Adalimumab.

In one embodiment, provided herein is a pharmaceutical combination of a compound of any NLRP3 antagonist species defined here (for example, example of 1 to 22, or a compound of Table 1), and an anti-TNFα agent Preferably wherein the anti-TNFα agent is Infliximab, Etanercept, Certolizumab pegol, Golimumab or Adalimumab, more preferably wherein the anti-TNFα agent is Adalimumab.

Pharmaceutical Compositions and Administration

General

In some embodiments, a chemical entity (e.g., a compound that modulates (e.g., antagonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium tri silicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

In some embodiments, an NLRP3 antagonist and/or an anti-TNFα agent disclosed herein is administered as a pharmaceutical composition that includes the NLRP3 antagonist and/or anti-TNFα agent and one or more pharmaceutically acceptable excipients, and optionally one or more additional therapeutic agents as described herein. Preferably the pharmaceutical composition that includes an NLRP3 antagonist and an anti-TNFα agent.

Preferably the above pharmaceutical composition embodiments comprise an NLRP3 antagonist disclosed herein. More preferably the above pharmaceutical composition embodiments comprise an NLRP3 antagonist and an anti-TNFα agent disclosed herein.

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intraci sternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acidmethyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selected from thickeners, viscosity enhancing agents, bulking agents, mucoadhesive agents, penetration enhancers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selected from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selected from thickeners, viscosity enhancing agents, bulking agents, mucoadhesive agents, buffers, preservatives, and fillers.

In certain embodiments, each of the one or more pharmaceutically acceptable excipients can be independently selected from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phospahate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, poly sorbate 80 (polyoxyethylenesorbitan oleate), starch, sodium starch glycolate, hydroxypropyl cellulose pregelatinized starch, clays, cellulose, alginine, gums or cross linked polymers, such as crosslinked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dxtrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:

One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;

One or more (e.g., one or two; e.g., two) buffers, such as phosphate buffer system (e.g., sodium dihydrogen phosphate dehydrate, disodium phosphate dodecahydrate);

One or more (e.g., one or two, e.g., two) glidants and/or lubricants, such as magnesium stearate and/or talc;

One or more (e.g., one or two; e.g., one) disintegrants, such as crospovidone; and One or more (e.g., one or two; e.g., one) diluents, such as lactose (e.g., lactose monohydrate).

In certain of these embodiments, the chemical entity is a compound of Formula AA, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phosphate dehydrate, disodium phosphate dodecahydrate, crospovidone, lactose monohydrate, magnesium stearate, and talc. In certain of these embodiments, the chemical entity is a compound of Formula AA, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (i) and (ii) is provided in its own separate kit or pack.

In certain of these embodiments, component (i) includes the chemical entity (e.g., a compound of Formula AA, or a pharmaceutically acceptable salt and/or hydrate and/or cocrystal thereof; e.g., a compound of Formula AA) and one or more (e.g., all) of the following excipients:

(a) One or more (e.g., one) binders (e.g., a polyvinyl polymer, such as polyvinylpyrrolidone (povidone);

(b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a compound of Formula AA, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table A.

TABLE A

| Ingredient | Weight Percent |
| --- | --- |
| A compound of Formula AA | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (1) includes the ingredients and amounts as shown in Table B.

TABLE B

| Ingredient | Weight Percent |
| --- | --- |
| A compound of Formula AA | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging.

In certain of the foregoing embodiments, component (ii) includes water and one or more (e.g., all) of the following excipients:

(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof; and (c') One or more (e.g., one or two; e.g., two) buffers, such as phosphate buffer system (e.g., sodium dihydrogen phosphate dihydrate, disodium phosphate dodecahydrate);

In certain of the foregoing embodiments, component (ii) includes water and one or more (e.g., all) of the following excipients:

(a") a first thickener, viscosity enhancing agent, binder, and/or mucoadhesive agent (e.g., a cellulose or cellulose ester or ether or derivative or salt thereof (e.g., methyl cellulose));

(a''') a second thickener, viscosity enhancing agent, binder, and/or mucoadhesive agent (e.g., a polyvinyl polymer, such as polyvinylpyrrolidone (povidone));

(b") a first preservative, such as a paraben, e.g., propyl 4-hydroxybenzoate (propylparaben), or a pharmaceutically acceptable salt or ester thereof;

(b''') a second preservative, such as a paraben, e.g., methyl 4-hydroxybenzoate (methylparaben), or a pharmaceutically acceptable salt or ester thereof, (c") a first buffer, such as phosphate buffer system (e.g., disodium phosphate dodecahydrate);

(c''') a second buffer, such as phosphate buffer system (e.g., sodium dihydrogen phosphate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a''').

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b''').

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c''').

In certain of these embodiments, each of (a")-(c''') is present.

In certain embodiments, component (ii) includes water (up to 100%) and the ingredients and amounts as shown in Table C.

TABLE C

| Ingredient | Weight Percent |
| --- | --- |
| methyl cellulose (Methocel A15C premium) | 0.05 weight percent to about 5 weight percent (e.g., from about 0.05 weight percent to about 3 weight percent, from |

TABLE C-continued

| Ingredient | Weight Percent |
| --- | --- |
| | about 0.1 weight percent to about 3 weight percent; e.g., about 1.4 weight percent |
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table D.

TABLE D

| Ingredient | Weight Percent |
| --- | --- |
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 10 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 150 mg of a compound of Formula AA in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 450 mg of a compound of Formula AA in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is a compound of Formula AA, or a pharmaceutically acceptable salt and/or hydrate and/or cocrystal thereof. For example, enema formulations can include about 2.5 mg/mL or about 7.5 mg/mL of a compound of Formula AA in liquid carrier.

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., an increase, e.g., NLRP3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as carbiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke. In some embodiments, the condition, disease or disorder is obesity. In some embodiments, the condition, disease or disorder is Type 2 Diabetes. In some embodiments, the condition, disease or disorder is NASH. In some embodiments, the condition, disease or disorder is Alzheimer's disease. In some embodiments, the condition, disease or disorder is gout. In some embodiments, the condition, disease or disorder is SLE. In some embodiments, the condition, disease or disorder is rheumatoid arthritis. In some embodiments, the condition, disease or disorder is IBD. In some embodiments, the condition, disease or disorder is multiple sclerosis. In some embodiments, the condition, disease or disorder is COPD. In some embodiments, the condition, disease or disorder is asthma. In some embodiments, the condition, disease or disorder is scleroderma. In some embodiments, the condition, disease or disorder is pulmonary fibrosis. In some embodiments, the condition, disease or disorder is age related macular degeneration (AMD). In some embodiments, the condition, disease or disorder is cystic fibrosis. In some embodiments, the condition, disease or disorder is Muckle Wells syndrome. In some embodiments, the condition, disease or disorder is familial cold autoinflammatory syndrome (FCAS). In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CIVIL); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS. In some embodiments, the indication is non-small lung cancer in patients carrying mutation or overexpression of NLRP3. In some embodiments, the indication is ALL in patients resistant to glucocorticoids treatment. In some embodiments, the indication is LCH. In some embodiments, the indication is multiple myeloma. In some embodiments, the indication is promyelocytic leukemia. In some embodiments, the indication is gastric cancer. In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR 014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20.

In some embodiments, the methods described herein further include the step of identifying a subject (e.g., a patient) in need of treatment for an indication related to NLRP3 activity, such as an indication related to point mutation of NLRP3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibitreduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (JNK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSF1A associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., Cell Death Differentiation 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., a cell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), JNK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, LBP, MEK1/2, MEK3/6, MEK4/7, MK2, MyD88, NF-κB, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)2, a minibody, or a BiTE.

In some embodiments, an antibody can be a crossmab, a diabody, a scDiabody, a scDiabody-CH3, a Diabody-CH3, a DutaMab, a DT-IgG, a diabody-Fc, a scDiabody-HAS, a charge pair antibody, a Fab-arm exchange antibody, a SEEDbody, a Triomab, a LUZ-Y, a Fcab, a Ia-body, an orthogonal Fab, a DVD-IgG, an IgG(H)-scFv, a scFv-(H) IgG, an IgG(L)-scFv, a scFv-(L)-IgG, an IgG (L,H)-Fc, an IgG(H)-V, a V(H)-IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-CH₃ KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., Autoimmunity Rev. 13(1):24-30, 2014; Bongartz et al., JAMA 295(19):2275-2285, 2006; Butler et al., Eur. Cytokine Network 6(4):225-230, 1994; Cohen et al., Canadian J. Gastroenterol. Hepatol. 15(6):376-384, 2001; Elliott et al., Lancet 1994; 344: 1125-1127, 1994; Feldmann et al., Ann. Rev. Immunol. 19(1):163-196, 2001; Rankin et al., Br. J Rheumatol. 2:334-342, 1995; Knight et al., Molecular Immunol. 30(16):1443-1453, 1993; Lorenz et al., J. Immunol. 156(4):1646-1653, 1996; Hinshaw et al., Circulatory Shock 30(3):279-292, 1990; Ordas et al., Clin. Pharmacol. Therapeutics 91(4):635-646, 2012; Feldman, Nature Reviews Immunol. 2(5):364-371, 2002; Taylor et al., Nature Reviews Rheumatol. 5(10):578-582, 2009; Garces et al., Annals Rheumatic Dis. 72(12):1947-1955, 2013; Palladino et al., Nature Rev. Drug Discovery 2(9):736-746, 2003; Sandborn et al., Inflammatory Bowel Diseases 5(2):119-133, 1999; Atzeni et al., Autoimmunity Reviews 12(7):703-708, 2013; Maini et al., Immunol. Rev. 144(1):195-223, 1995; Wanner et al., Shock 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1\times10^{-5}$M (e.g., less than $0.5\times10^{-5}$ M, less than $1\times10^{-6}$ M, less than $0.5\times10^{-6}$ M, less than $1\times10^{-7}$ M, less than $0.5\times10^{-7}$M, less than $1\times10^{-8}$M, less than $0.5\times10^{-8}$M, less than $1\times10^{-9}$M, less than $0.5\times10^{-9}$M, less than $1\times10^{-10}$ M, less than $0.5\times10^{-10}$ M, less than $1\times10^{-11}$M, less than $0.5\times10^{-11}$M, or less than $1\times10^{-12}$M), e.g., as measured in phosphate buffered saline using surface plasmon resonance (SPR).

In some embodiments, any of the antibodies or antigen-binding fragments described herein has a $K_D$ of about $1\times10^{-12}$M to about $1\times10^{-5}$M, about $0.5\times10^{-5}$M, about $1\times10^{-6}$ M, about $0.5\times10^{-6}$ M, about $1\times10^{-7}$M, about $0.5\times10^{-7}$M, about $1\times10^{-8}$M, about $0.5\times10^{-8}$M, about $1\times10^{-9}$M, about $0.5\times10^{-9}$M, about $1\times10^{-10}$ M, about $0.5\times10^{-10}$ M, about $1\times10^{-11}$M, or about $0.5\times10^{-11}$M (inclusive); about $0.5\times10^{-11}$M to about $1\times10^{-5}$M, about $0.5\times10^{-5}$M, about $1\times10^{-6}$ M, about $0.5\times10^{-6}$ M, about $1\times10^{-7}$M, about $0.5\times10^{-7}$M, about $1\times10^{-8}$M, about $0.5\times10^{-8}$M, about $1\times10^{-9}$M, about $0.5\times10^{-9}$M, about $1\times10^{-10}$ M, about $0.5\times10^{-10}$ M, or about $1\times10^{-11}$M (inclusive); about $1\times10^{-11}$M to about $1\times10^{-5}$M, about $0.5\times10^{-5}$M, about $1\times10^{-6}$ M, about $0.5\times10^{-6}$ M, about $1\times10^{-7}$ M, about $0.5\times10^{-7}$ M, about $1\times10^{-8}$M, about $0.5\times10^{-8}$M, about $1\times10^{-9}$M, about $0.5\times10^{-9}$M, about $1\times10^{-10}$ M, or about $0.5\times10^{-10}$ M (inclusive); about $0.5\times10^{-10}$ M to about $1\times10^{-5}$M, about $0.5\times10^{-5}$M, about $1\times10^{-6}$ M, about $0.5\times10^{-6}$ M, about $1\times10^{-7}$ M, about $0.5\times10^{-7}$ M, about $1\times10^{-8}$M, about $0.5\times10^{-8}$M, about $1\times10^{-9}$M, about $0.5\times10^{-9}$M, or about $1\times10^{-10}$ M (inclusive); about $1\times10^{-10}$ M to about $1\times10^{-5}$M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$M, about $0.5\times10^{-8}$M, about $1\times10^{-9}$M, or about $0.5\times10^{-9}$M (inclusive); about $0.5\times10^{-9}$M to about $1\times10^{-5}$M, about $0.5\times10^{-5}$M, about $1\times10^{-6}$ M, about $0.5\times10^{-6}$ M, about $1\times10^{-7}$ M, about $0.5\times10^{-7}$ M, about $1\times10^{-8}$M, about $0.5\times10^{-8}$M, or about $1\times10^{-9}$M (inclusive); about $1\times10^{-9}$M to about $1\times10^{-5}$M, about $0.5\times10^{-5}$M, about $1\times10^{-6}$ M, about $0.5\times10^{-6}$ M, about $1\times10^{-7}$ M, about $0.5\times10^{-7}$ M, about $1\times10^{-8}$M, or about $0.5\times10^{-8}$M (inclusive); about $0.5\times10^{-8}$ M to about $1\times10^{-5}$M, about $0.5\times10^{-5}$M, about $1\times10^{-6}$ M, about $0.5\times10^{-6}$ M, about $1\times10^{-7}$ M, about $0.5\times10^{-7}$ M, or about $1\times10^{-8}$M (inclusive); about $1\times10^{-8}$M to about $1\times10^{-5}$M, about $0.5\times$ $10^{-5}$M, about $1\times10^{-6}$ M, about $0.5\times10^{-6}$ M, about $1\times10^{-7}$ M, or about $0.5\times10^{-7}$ M (inclusive); about $0.5\times10^{-7}$M to about $1\times10^{-5}$M, about $0.5\times10^{-5}$M, about $1\times10^{-6}$ M, about $0.5\times10^{-6}$ M, or about $1\times10^{-7}$M (inclusive); about $1\times10^{-7}$M to about $1\times10^{-5}$M, about $0.5\times10^{-5}$M, about $1\times10^{-6}$ M, or about $0.5\times10^{-6}$ M (inclusive); about $0.5\times10^{-6}$ M to about $1\times10^{-5}$ M, about $0.5\times10^{-5}$M, or about $1\times10^{-6}$ M (inclusive); about $1\times10^{-6}$ M to about $1\times10^{-5}$M or about $0.5\times10^{-5}$M (inclusive); or about $0.5\times10^{-5}$M to about $1\times10^{-5}$M (inclusive), e.g., as measured in phosphate buffered saline using surface plasmon resonance (SPR).

In some embodiments, any of the antibodies or antigen-binding fragments described herein has a $K_{off}$ of about $1\times10^{-6}$ s$^{-1}$ to about $1\times10^{-3}$ s$^{-1}$, about $0.5\times10^{-3}$ s$^{-1}$, about $1\times10^{-4}$ s$^{-1}$, about $0.5\times10^{-4}$ s$^{-1}$, about $1\times10^{-5}$ s$^{-1}$, or about $0.5\times10^{-5}$ s$^{-1}$ (inclusive); about $0.5\times10^{-5}$ s$^{-1}$ to about $1\times10^{-3}$ s$^{-1}$, about $0.5\times10^{-3}$ s$^{-1}$, about $1\times10^{-4}$ s$^{-1}$, about $0.5\times10^{-4}$ s$^{-1}$, or about $1\times10^{-5}$ s$^{-1}$ (inclusive); about $1\times10^{-5}$ s$^{-1}$ to about $1\times10^{-3}$ s$^{-1}$, about $0.5\times10^{-3}$ s$^{-1}$, about $1\times10^{-4}$ s$^{-1}$, or about $0.5\times10^{-4}$ s$^{-1}$ (inclusive); about $0.5\times10^{-4}$ s$^{-1}$ to about $1\times10^{-3}$ s$^{-1}$, about $0.5\times10^{-3}$ s$^{-1}$, or about $1\times10^{-4}$ s$^{-1}$ (inclusive); about $1\times10^{-4}$ s$^{-1}$ to about $1\times10^{-3}$ s$^{-1}$, or about $0.5\times10^{-3}$ s$^{-1}$ (inclusive); or about $0.5\times10^{-5}$ s$^{-1}$ to about $1\times10^{-3}$ s$^{-1}$ (inclusive), e.g., as measured in phosphate buffered saline using surface plasmon resonance (SPR).

In some embodiments, any of the antibodies or antigen-binding fragments described herein has a $K_{on}$ of about $1\times10^2$ M$^{-1}$ s$^{-1}$ to about $1\times10^6$ M$^{-1}$ s$^{-1}$, about $0.5\times10^6$ M$^{-1}$ s$^{-1}$, about $1\times10^5$M$^{-1}$ s$^{-1}$, about $0.5\times10^5$ M$^{-1}$ s$^{-1}$, about $1\times10^4$ M$^{-1}$ s$^{-1}$, about $0.5\times10^4$ M$^{-1}$ s$^{-1}$, about $1\times10^3$ M$^{-1}$ s$^{-1}$, or about $0.5\times10^3$ M$^{-1}$ s$^{-1}$ (inclusive); about $0.5\times10^3$ M$^{-1}$ s$^{-1}$ to about $1\times10^6$M$^{-1}$ s$^{-1}$, about $0.5\times10^6$ M$^{-1}$ s$^{-1}$, about $1\times10^5$M$^{-1}$ s$^{-1}$, about $0.5\times10^5$ M$^{-1}$ s$^{-1}$, about $1\times10^4$ M$^{-1}$ s$^{-1}$, about $0.5\times10^4$ M$^{-1}$ s$^{-1}$, or about $1\times10^3$ M$^{-1}$ s$^{-1}$ (inclusive); about $1\times10^3$ M$^{-1}$ s$^{-1}$ to about $1\times10^6$M$^{-1}$ s$^{-1}$, about $0.5\times10^6$ M$^{-1}$ s$^{-1}$, about $1\times10^5$M$^{-1}$ s$^{-1}$, about $0.5\times10^5$ M$^{-1}$ s$^{-1}$, about $1\times10^4$ M$^{-1}$ s$^{-1}$, or about $0.5\times10^4$ M$^{-1}$ s$^{-1}$ (inclusive); about $0.5\times10^4$ M$^{-1}$ s$^{-1}$ to about $1\times10^6$ M$^{-1}$ s$^{-1}$, about $0.5\times10^6$ M$^{-1}$ s$^{-1}$, about $1\times10^5$M$^{-1}$ s$^{-1}$, about $0.5\times10^5$ M$^{-1}$ s$^{-1}$, or about $1\times10^4$ M$^{-1}$ s$^{-1}$ (inclusive); about $1\times10^4$ M$^{-1}$ s$^{-1}$ to about $1\times10^6$ M$^{-1}$ s$^{-1}$, about $0.5\times10^6$ M$^{-1}$ s$^{-1}$, about $1\times10^5$M$^{-1}$ s$^{-1}$, or about $0.5\times10^5$ M$^{-1}$ s$^{-1}$ (inclusive); about $0.5\times10^5$M$^{-1}$ s$^{-1}$ to about $1\times10^6$ M$^{-1}$ s$^{-1}$, about $0.5\times10^6$ M$^{-1}$ s$^{-1}$, or about $1\times10^5$ M$^{-1}$ s$^{-1}$ (inclusive); about $1\times10^5$M$^{-1}$ s$^{-1}$ to about $1\times10^6$ M$^{-1}$ s$^{-1}$ or about $0.5\times10^6$ M$^{-1}$ s$^{-1}$ (inclusive); or about $0.5\times10^6$ M$^{-1}$ s$^{-1}$ to about $1\times10^6$M$^{-1}$ s$^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J. Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269(1):R23-R29, 1995; Tsao et al., *Eur Respir* 14(3):490-495, 1999; Watt et al., *J Leukoc Biol.* 66(6):1005-1013, 1999; Mohler et al., *J. Immunol.* 151(3):1548-1561, 1993; Nophar et al., *EMBO J* 9(10):3269, 1990; Piguet et al., *Eur. Respiratory J* 7(3):515-518, 1994; and Gray et al., *Proc.*

*Natl. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., *J. Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is fully or partially complementary to all or part of a AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., fully or partially complementary to all or a part of any one of the sequences presented in Table E).

TABLE E

| Human gene | mRNA GenBank accession number(s) |
| --- | --- |
| Tumor necrosis factor (TNF, a.k.a. TNF-alpha) | NM_000594 |
| TNF receptor superfamily member 1A (TNFRSF1A) (a.k.a. TNFR1) | NM_001065 |
| | NM_001346091 |
| | NM_001346092 |
| TNF receptor superfamily member 1B (TNFRSF1B) (a.k.a. TNFR2) | NM_001066 |
| | XM_011542060 |
| | XM_011542063 |
| | XM_017002214 |
| | XM_017002215 |
| | XM_017002211 |
| TNFRSF1A associated via death domain (TRADD) | NM_003789 |
| | NM_001323552 |
| | XM_005256213 |
| | XM_017023815 |
| TNF receptor associated factor 2 (TRAF2) | NM_021138 |
| | XM_011518976 |
| | XM_011518977 |
| | XM_011518974 |
| JunD proto-oncogene, AP-1 transcription factor subunit (JUND) | NM_001286968 |
| | NM_005354 |
| Mitogen-activated protein kinase kinase kinase 5 (MAP3K5) (a.k.a. ASK1) | NM_005923 |
| | XM_017010875 |
| | XM_017010872 |
| | XM_017010873 |
| | XM_017010877 |
| | XM_017010874 |
| | XM_017010871 |
| | XM_017010870 |
| | XM_017010876 |
| | XM_011535839 |
| CD14 | NM_000591 |
| | NM_001040021 |
| | NM_001174104 |
| | NM_001174105 |
| Mitogen-activated protein kinase 3 (MAPK3) (a.k.a. ERK1) | NM_001040056 |
| | NM_001109891 |
| | NM_002746 |
| Mitogen-activated protein kinase 1 (MAPK1) (a.k.a. ERK2) | NM_002745 |
| | NM_138957 |
| Inhibitor of nuclear factor kappa B kinase subunit beta (IKBKB) | NM_001190720 |
| | NM_001242778 |
| | NM_001556 |
| | XM_005273491 |
| | XM_005273496 |
| | XM_005273493 |
| | XM_005273498 |

TABLE E-continued

| Human gene | mRNA GenBank accession number(s) |
| --- | --- |
| | XM_011544518 |
| | XM_005273492 |
| | XM_005273490 |
| | XM_005273494 |
| | 12XM_017013396 |
| | XM_011544521 |
| | XM_011544522 |
| | XM_005273495 |
| | XM_011544517 |
| | XM_011544520 |
| | XM_011544519 |
| NFKB inhibitor alpha (NFKBIA) | NM_020529 |
| Interleukin 1 receptor associated kinase 1 (IRAK1) | NM_001025242 |
| | NM_001025243 |
| | NM_001569 |
| | XM_005274668 |
| Mitogen-activated protein kinase 8 (MAPK8) (a.k.a. JNK) | NM_001278547 |
| | NM_001278548 |
| | NM_001323302 |
| | NM_001323320 |
| | NM_001323321 |
| | NM_001323322 |
| | NM_001323323 |
| | NM_001323324 |
| | NM_001323325 |
| | NM_001323326 |
| | NM_001323327 |
| | NM_001323328 |
| | NM_001323329 |
| | NM_001323330 |
| | NM_001323331 |
| | NM_139046 |
| | NM_139049 |
| | XM_024448079 |
| | XM_024448080 |
| Lipopolysaccharide binding protein (LBP) | NM_004139 |
| Mitogen-activated protein kinase kinase 1 (MAP2K1) (a.k.a. MEK1) | NM_002755 |
| | XM_017022411 |
| | XM_011521783 |
| | XM_017022412 |
| | XM_017022413 |
| Mitogen-activated protein kinase kinase 2 (MAP2K2) (a.k.a. MEK2) | NM_030662 |
| | XM_006722799 |
| | XM_017026990 |
| | XM_017026989 |
| | XM_017026991 |
| Mitogen-activated protein kinase kinase 3 (MAP2K3) (a.k.a. MEK3) | NM_001316332 |
| | NM_002756 |
| | NM_145109 |
| | XM_017024859 |
| | XM_005256723 |
| | XM_017024857 |
| | XM_011523959 |
| | XM_017024858 |
| | XM_011523958 |
| Mitogen-activated protein kinase kinase 6 (MAP2K6) (a.k.a. MEK6) | NM_001330450 |
| | NM_002758 |
| | XM_005257516 |
| | XM_011525027 |
| | XM_011525026 |
| | XM_006721975 |
| Mitogen-activated protein kinase kinase kinase 1 (MAP3K1) (a.k.a. MEKK1) | NM_005921 |
| | XM_017009485 |
| | XM_017009484 |
| Mitogen-activated protein kinase kinase kinase 3 (MAP3K3) (a.k.a. MEKK3) | NM_001330431 |
| | NM_001363768 |
| | NM_002401 |
| | NM_203351 |
| | XM_005257378 |
| Mitogen-activated protein kinase kinase kinase 4 (MAP3K4) (a.k.a. MEKK4) | NM_001291958 |
| | NM_001301072 |
| | NM_001363582 |
| | NM_005922 |
| | NM_006724 |
| | XM_017010869 |
| Mitogen-activated protein kinase kinase kinase 6 (MAP3K6) (a.k.a. MEKK6) | NM_001297609 |
| | NM_004672 |

TABLE E-continued

| Human gene | mRNA GenBank accession number(s) |
|---|---|
| | XM_017002771 |
| | XM_017002772 |
| Mitogen-activated protein kinase kinase kinase 7 (MAP3K7) (a.k.a. MEKK7) | NM_003188 |
| | NM_145331 |
| | NM_145332 |
| | NM_145333 |
| | XM_006715553 |
| | XM_017011226 |
| MAPK activated protein kinase 2 (MAPKAPK2) (a.k.a. MK2) | NM_004759 |
| | NM_032960 |
| | XM_005273353 |
| | XM_017002810 |
| MYD88, innate immune signal transduction adaptor (MYD88) | NM_001172566 |
| | NM_001172567 |
| | NM_001172568 |
| | NM_001172569 |
| | NM_001365876 |
| | NM_001365877 |
| | NM_002468 |
| Nuclear factor kappa B subunit 1 (NFKB1) | NM_001165412 |
| | NM_001319226 |
| | NM_003998 |
| | XM_024454069 |
| | XM_024454067 |
| | XM_011532006 |
| | XM_024454068 |
| Mitogen-activated protein kinase kinase kinase 14 (MAP3K14) (a.k.a. NIK) | NM_003954 |
| | XM_011525441 |
| Mitogen-activated protein kinase 14 (MAPK14) (a.k.a. p38) | NM_001315 |
| | NM_139012 |
| | NM_139013 |
| | NM_139014 |
| | XM_011514310 |
| | XM_017010300 |
| | XM_017010299 |
| | XM_017010301 |
| | XM_017010304 |
| | XM_017010303 |
| | XM_017010302 |
| | XM_006714998 |
| Eukaryotic translation initiation factor 2 alpha kinase 2 (EIF2AK2) (a.k.a. PKR) | NM_001135651 |
| | NM_001135652 |
| | NM_002759 |
| | XM_011532987 |
| | XM_017004503 |
| AKT serine/threonine kinase 1 (AKT1) (a.k.a. RAC) | NM_001014431 |
| | NM_001014432 |
| | NM_005163 |
| Zinc fingers and homeoboxes 2 (ZHX2) (a.k.a. RAF) | NM_001362797 |
| | NM_014943 |
| | XM_011516932 |
| | XM_005250836 |
| KRAS proto-oncogene, GTPase (KRAS) | NM_001369786 |
| | NM_001369787 |
| | NM_004985 |
| | NM_033360 |
| NRAS proto-oncogene, GTPase (NRAS) | NM_002524 |
| Receptor interacting serine/threonine kinase 1 (RIPK1) (a.k.a. RIP) | NM_001317061 |
| | NM_001354930 |
| | NM_001354931 |
| | NM_001354932 |
| | NM_001354933 |
| | NM_001354934 |
| | NM_003804 |
| | XM_017011405 |
| | XM_006715237 |
| | XM_017011403 |
| | XM_017011404 |
| TNF receptor associated factor 6 (TRAF6) | NM_004620 |
| | NM_145803 |
| | XM_017018220 |
| ZFP36 ring finger protein (ZFP36) (a.k.a. TTP) | NM_003407 |

An antisense nucleic acid molecule can be fully or partially complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein described herein. Antisense nucleic acids targeting a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid can also comprise a chimeric RNA-DNA analog (Inoue et al., *FEBS Lett.* 215:327-330, 1987) or a 2'-O-methylribonucleotide (Inoue et al., *Nucleic Acids Res.* 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of the sequences presented in Table E). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., *Science* 261:1411-1418, 1993.

Alternatively, a ribozyme having specificity for an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein (e.g., in Table E). For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, *Bioassays* 14(12):807-15, 1992; Helene, *Anticancer Drug Des.* 6(6):569-84, 1991; and Helene, *Ann. N.Y. Acad. Sci.* 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, JNK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, RO5126766 (CH5126766), PLX7904, and MLN2480).

In some examples, the anti-TNFα agent TNFα inhibitor is a small molecule that inhibits the activity of one of MK2 (PF 3644022 and PHA 767491), JNK (e.g., AEG 3482, BI 78D3, CEP 1347, c-JUN peptide, IQ 15, JIP-1 (153-163), SP600125, SU 3327, and TCS JNK6o), c-jun (e.g., AEG 3482, BI 78D3, CEP 1347, c-JUN peptide, IQ 15, JIP-1 (153-163), SP600125, SU 3327, and TCS JNK6o), MEK3/6

(e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl)amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

General

The following abbreviations have the indicated meanings:
aq.=aqueous
Ac=acetyl
ACN=acetonitrile
n-BuLi=n-butyl lithium
CbzCl=benzyl carbonochloridate
DCM=dichloromethane
DIEA=N-ethyl-N-isopropylpropan-2-amine
Dppf=1,1'-bis(diphenylphosphino)ferrocene
DMF=N,N-dimethylformamide
EtOH=ethanol
EDCI=1-ethyl-3-(3-dimethylaminopropyl)carbodiimide hydrochloride
HOBt=1-hydroxybenzotriazole
HATU=2-(7-azabenzotriazol-1-yl)-N,N,N',N'-tetramethyluronium hexafluorophosphate
HPLC=high performance liquid chromatography
Hex=hexane
LC-MS=liquid chromatograph mass spectrometer
LiHMDS=lithium hexamethyldisilazide
MSA=methanesulfonic acid
MeOH=methanol
ESI=electron spray ionization
NMR=nuclear magnetic resonance
Ph=phenyl
RT=room temperature
TLC thin layer chromatography
TFA=2,2,2-trifluoroacetic acid
TEA=triethylamine
THF=tetrahydrofuran
UV=ultraviolet The progress of reactions was often monitored by TLC or LC-MS. The identity of the products was often confirmed by LC-MS. The LC-MS was recorded using one of the following methods.

Method A: Shim-pack XR-ODS, C18, 3×50 min, 2.5 um column, 1.0 uL injection, 1.5 L/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, L5 mL/min flow rate, 90-900 amu scan range, 190-400 un LTV range, 10-95% (1.1 min), 95% (0.6 min) gradient with ACN and water (0.5% NH$_4$HCO$_3$), 2 minute total run time.

Method C: Shim-pack XR-ODS, C18, 3×50 mm, 2.5 urn column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 urn column, 1.0 uL injection, 1.5 mL/min flow rate, 90-900 amu scan range, 190-400 nm LTV range, 10-95% (2.1 min), 95% (0.6 min) gradient with ACN and water (0.5% NH$_4$HCO$_3$), 3 minute total run time.

Method F: Phenomenex, CHO-7644, Onyx Monolithic C18, 50×4.6 mm, 10.0 uL injection, 1.5 mL/min flow rate, 100-1500 amu scan range, 220 and 254 nm UV detection, 5% with ACN (0.1% TFA) to 100% water (0.1% TFA) over 9.5 min, with a stay at 100% (ACN, 0.1% TFA) for 1 min, then equilibration to 5% (ACN, 0.1% TFA) over 1.5 min.

The final targets were purified by Prep-HPLC. The Prep-HPLC was carried out using the following method.

Method E: Prep-HPLC: Column,)(Bridge Shield RP18 OBD (19×250 mm, 10 um); mobile phase, Water (10 mmol/L NH$_4$HCO$_3$) and ACN, UV detection 254/210 nm.

Method G: Prep-HPLC: Higgins Analytical Proto 200, C18 Column, 250×20 mm, 10 um; mobile phase, Water (0.1% TFA) and ACN (0.1% TFA), UV detection 254/210 nm.

NMR was recorded on BRUKER NMR 300.03 MHz, DUL-C-H, ULTRASHIELD™300, AVANCE II 300 B-ACS™120 or BRUKER NMR 400.13 MHz, BBFO, ULTRASHIELD™400, AVANCE III 400, B-ACS™120.

Scheme of final targets: Schemes below illustrate several conditions used for novel linker targets.

Scheme I

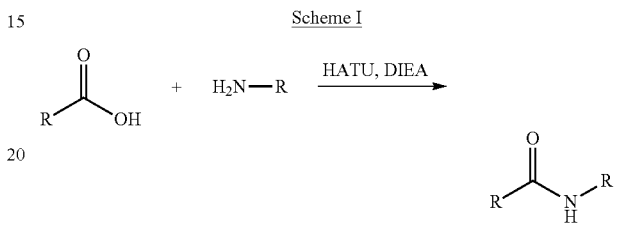

Scheme II

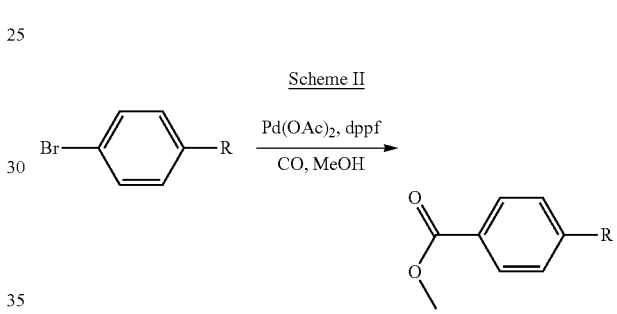

Scheme III

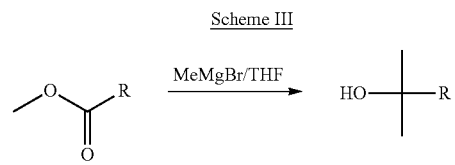

Scheme IV

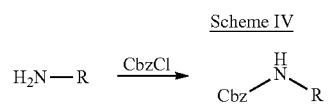

Racemic compounds of this invention can be resolved to give individual enantiomers using a variety of known methods. For example, chiral stationary phases can used and the elution conditions can include normal phase or super-critical fluid with or without acidic or basic additives. Enantiomerically pure acids or bases can be used to form diatereomeric salts with the racemic compounds whereby pure enantiomers can be obtained by fractional crystallization. The racemates can also be derivatized with enantiomerically pure auxiliary reagents to form diastereomeric mixtures that can be separated. The auxiliary is then removed to give pure enantiomers. Schemes for the Preparation of Final Targets:

c-S(O)$_q$—,—S(O)NH—

Examples 1-3 were prepared according to the scheme below:

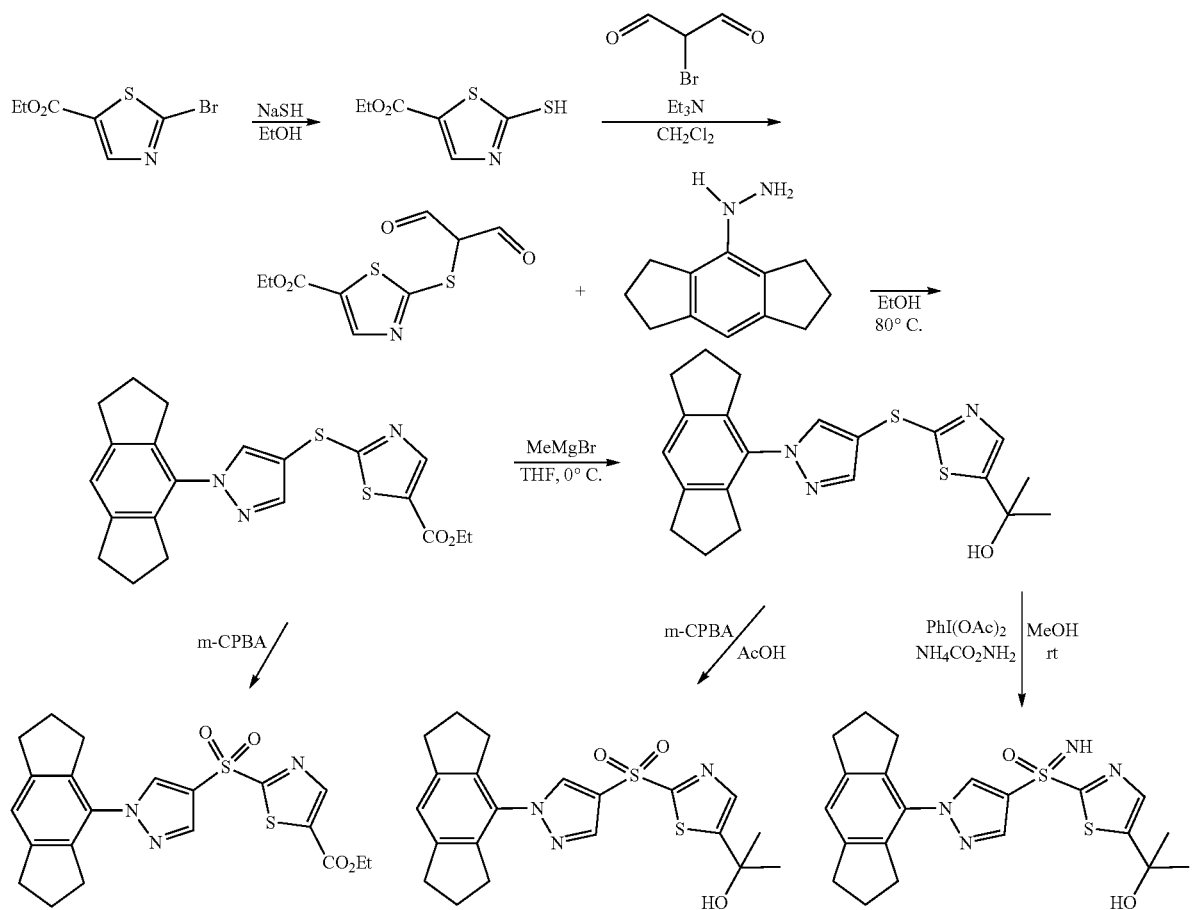

Example 1: Preparation of ethyl 2-((1-(1,2,3,5,6,7-hexahydro-s-indacen-4-yl)-1H-pyrazol-4-yl)sulfonyl)thiazole-5-carboxylate (Compound 120)

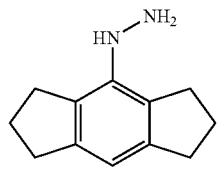

Step 1: Preparation of (1,2,3,5,6,7-hexahydro-s-indacen-4-yl)hydrazine

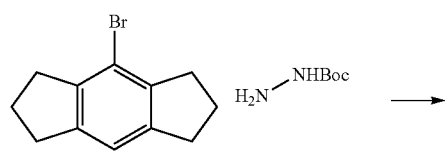

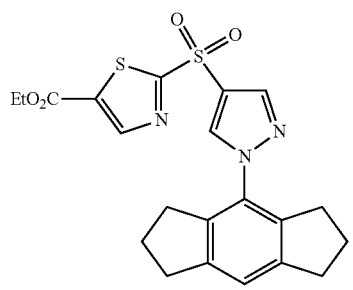 [SMILES: CCOC(=O)c1cnc(S(=O)(=O)c2cnn(-c3c4c(cc5c3CCC5)CCC4)c2)s1]

4-bromo-1,2,3,5,6,7-hexahydro-s-indacene (4.14 g, 17.5 mmol), tert-butyl carbazate (3.45 g, 26.2 mmol), cesium carbonate (11.4 g, 34.9 mmol), and toluene (40.0 mL) were added to a round bottom flask. The mixture was degassed with argon, and then palladium acetate (392 mg, 1.75 mmol), tri-tert-butylphosphonium tetrafluoroborate (506 mg, 1.75 mmol) were added. The vessel was fitted with a condenser, and then the reaction mixture was stirred and heated at 120° C. for 5 h. The mixture was cooled to room temperature and filtered. The solid was rinsed with ethyl acetate. The filtrate was concentrated in vacuo to furnish a crude residue. Quantitative deprotection was accomplished by treatment with HCl for 2.5 h at room temperature to afford 4.40 g of dried HCl salt after evaporation of the solvent and drying under vacuum.

Step 2: Preparation of ethyl 2-mercaptothiazole-5-carboxylate

A vial was charged with ethyl 2-bromothiazole-5-carboxylate (2.02 mL, 13.6 mmol), sodium hydrogen sulfide (1.57 g, 27.1 mmol), and ethanol (30.0 mL) and the resulting mixture was stirred for 2 h at 80° C. The solution was cooled to 0° C. in an ice/water bath. The pH was adjusted to ~3 with 1 M HCl, and the resulting solids collected by filtration to give the crude product as a light yellow solid. The filtrate was cooled in an ice bath and left overnight to precipitate additional product which was filtered and combined with the first crop. The crude product was used in the following reaction without further purification.

Step 3: Preparation of ethyl 2-((1,3-dioxopropan-2-yl)thio)thiazole-5-carboxylate

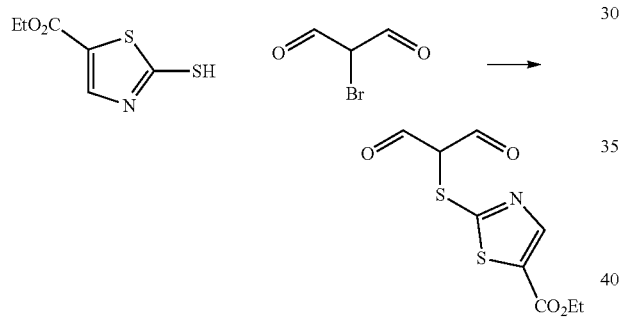

2-bromomalonaldehyde (797.6 mg, 5.28 mmol) was dissolved in methylene chloride (17.0 mL). Ethyl 2-mercaptothiazole-5-carboxylate (1.0 g, 5.28 mmol) was then added to the reaction mixture, followed by triethylamine (0.736 mL, 5.28 mmol). The reaction was stirred for 10 min at room temperature and then concentrated in vacuo. The crude material was used directly in the next step.

Step 4: ethyl 2-((1-(1,2,3,5,6,7-hexahydro-s-indacen-4-yl)-1H-pyrazol-4-yl)thio)thiazole-5-carboxylate

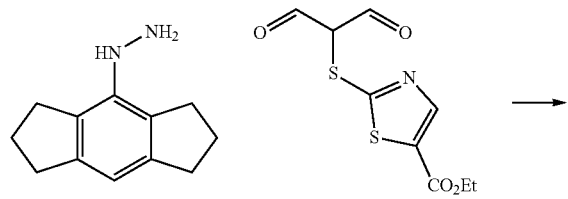

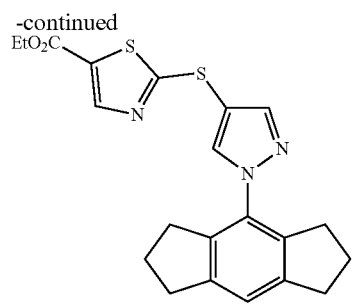

A vial was charged with ethyl 2-((1,3-dioxopropan-2-yl)thio)thiazole-5-carboxylate (1.37 g, 5.28 mmol), (1,2,3,5,6,7-hexahydro-s-indacen-4-yl)hydrazine (994.8 mg, 5.28 mmol), and methanol (27.0 mL). The mixture was stirred at 80° C. After 20 min, the mixture was concentrated in vacuo. The crude residue was purified using silica chromatography (0-10% ethyl acetate/hexane) to provide the desired product as an amber oil (448.4 mg, 20.6% yield) which eventually solidified to afford a light pumpkin orange solid.

Step 5: ethyl 2-((1-(1,2,3,5,6,7-hexahydro-s-indacen-4-yl)-1H-pyrazol-4-yl)sulfonyl)thiazole-5-carboxylate (Compound 120)

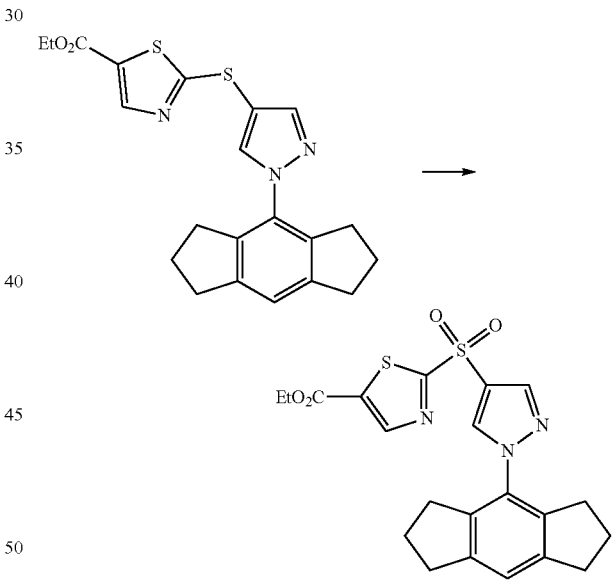

To a solution of ethyl 2-((1-(1,2,3,5,6,7-hexahydro-s-indacen-4-yl)-1H-pyrazol-4-yl)thio)thiazole-5-carboxylate (28.0 mg, 0.068 mmol) in acetic acid (0.68 mL) was added 3-chloroperoxybenzoic acid (58.7 mg, 0.34 mmol), and the mixture was stirred at room temperature for 12 h. Aqueous sodium thiosulfate solution was added to the reaction mixture, and the mixture was concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous sodium sulfate, and concentrated under reduced pressure. The crude residue was purified via preparative HPLC.

Example 2: Preparation of 2-(2-((1-(1,2,3,5,6,7-hexahydro-s-indacen-4-yl)-1H-pyrazol-4-yl)sulfonyl)thiazol-5-yl)propan-2-ol (Compound 104)

Step 1: Preparation of 2-(2-((1-(1,2,3,5,6,7-hexahydro-s-indacen-4-yl)-1H-pyrazol-4-yl)thio)thiazol-5-yl)propan-2-ol Step 2: Preparation of 2-(2-((1-(1,2,3,5,6,7-hexahydro-s-indacen-4-yl)-1H-pyrazol-4-yl)-sulfonyl)thiazol-5-yl)propan-2-ol

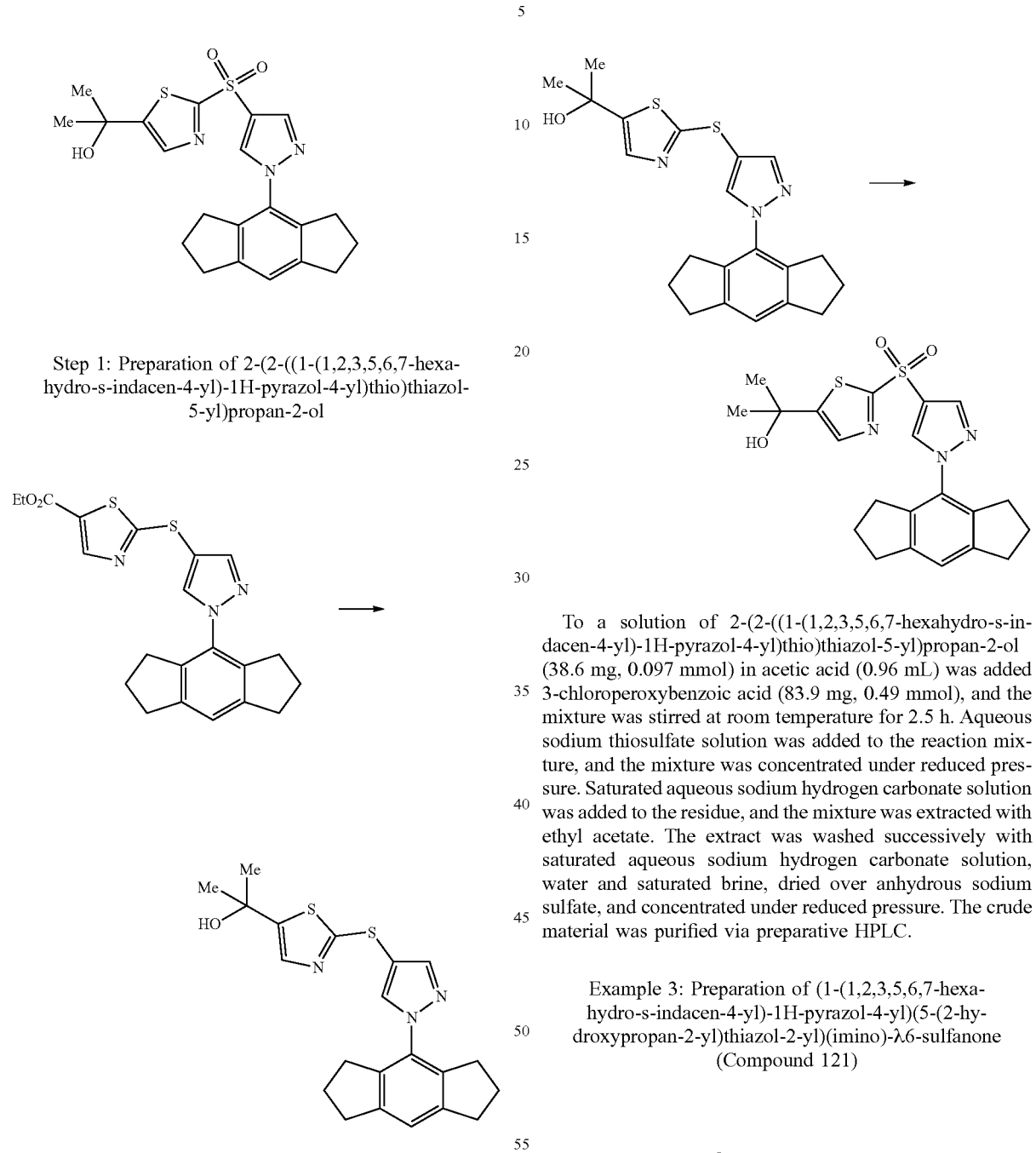

To a solution of ethyl 2-((1-(1,2,3,5,6,7-hexahydro-s-indacen-4-yl)-1H-pyrazol-4-yl)sulfonyl)-thiazole-5-carboxylate (50 mg, 0.122 mmol) in dry tetrahydrofuran (2.0 mL) at 0° C. under a nitrogen atmosphere was added dropwise methylmagnesium bromide (158 μL, 0.39 mmol) and the resulting mixture was stirred at 0° C. for 1 h. Saturated aqueous ammonium chloride was added and the mixture was extracted with EtOAc (50 mL×3). The combined organic layers were washed with brine, dried over MgSO$_4$, filtered, and concentrated in vacuo. The crude product was used directly in the next step.

To a solution of 2-(2-((1-(1,2,3,5,6,7-hexahydro-s-indacen-4-yl)-1H-pyrazol-4-yl)thio)thiazol-5-yl)propan-2-ol (38.6 mg, 0.097 mmol) in acetic acid (0.96 mL) was added 3-chloroperoxybenzoic acid (83.9 mg, 0.49 mmol), and the mixture was stirred at room temperature for 2.5 h. Aqueous sodium thiosulfate solution was added to the reaction mixture, and the mixture was concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous sodium sulfate, and concentrated under reduced pressure. The crude material was purified via preparative HPLC.

Example 3: Preparation of (1-(1,2,3,5,6,7-hexahydro-s-indacen-4-yl)-1H-pyrazol-4-yl)(5-(2-hydroxypropan-2-yl)thiazol-2-yl)(imino)-λ6-sulfanone (Compound 121)

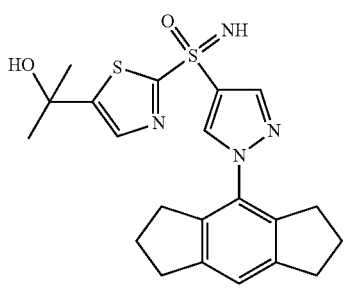

277
-continued

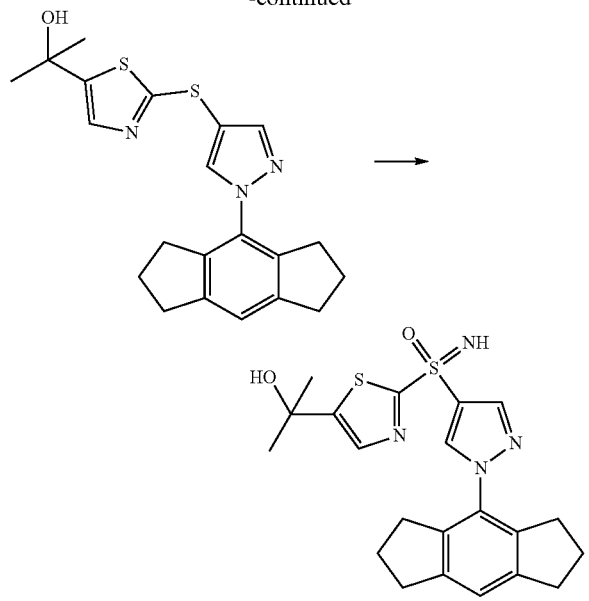

278

2-(2-((1-(1,2,3,5,6,7-hexahydro-s-indacen-4-yl)-1H-pyrazol-4-yl)thio)thiazol-5-yl)propan-2-ol (143 mg, 0.36 mmol) was dissolved in methanol (1.8 mL) and then treated with phenyliodine(III) diacetate (PIDA) (290.6 mg) and ammonium carbamate (56.4 mg) with stirring at room temperature for 90 min. The solvent was evaporated to dryness and the residue was partitioned between dichloromethane and water. The water layer was extracted with dichloromethane (2×) and the combined organic extracts were dried over sodium sulfate, filtered and concentrated under vacuum. The crude material was purified by preparative HPLC to afford pure (1-(1,2,3,5,6,7-hexahydro-s-indacen-4-yl)-1H-pyrazol-4-yl)(5-(2-hydroxypropan-2-yl)thiazol-2-yl)(imino)-λ6-sulfanone.

Examples 4-6 were prepared according to the scheme below:

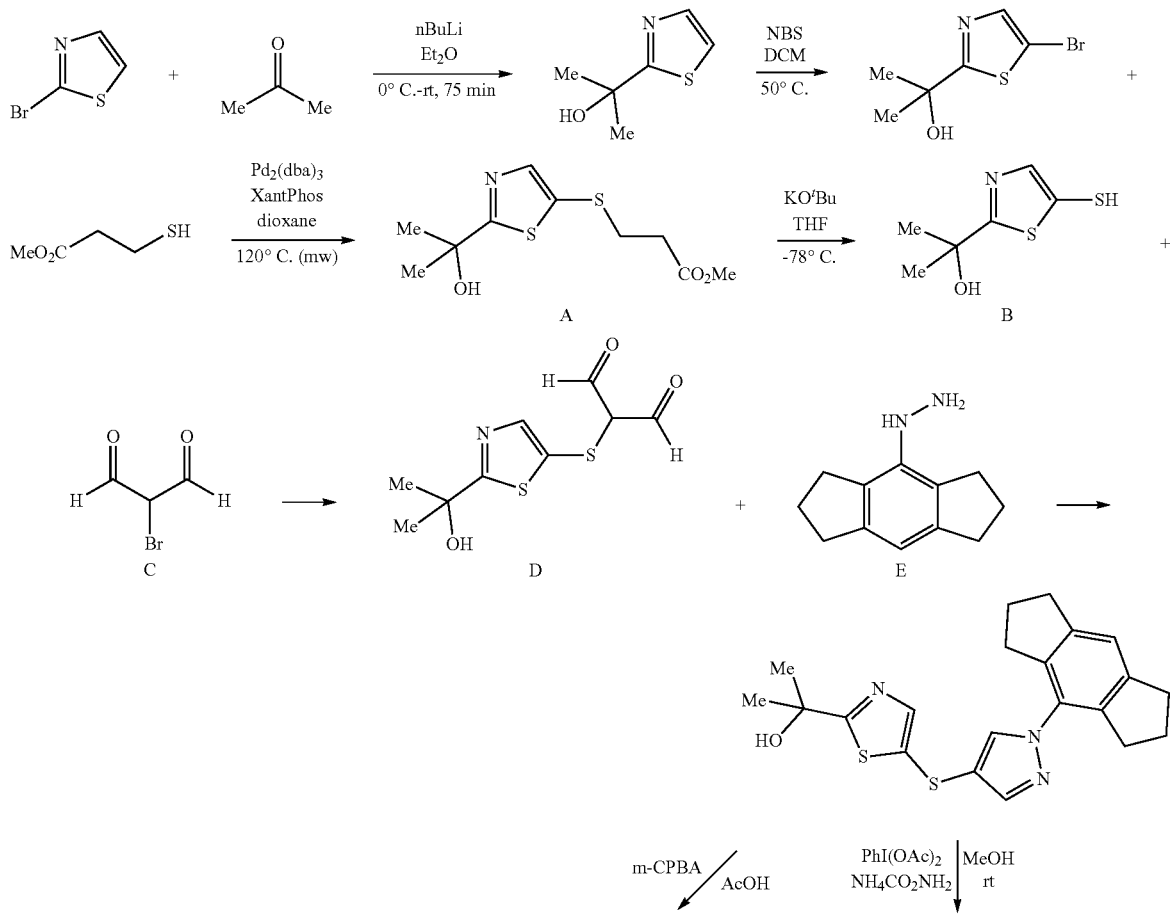

279

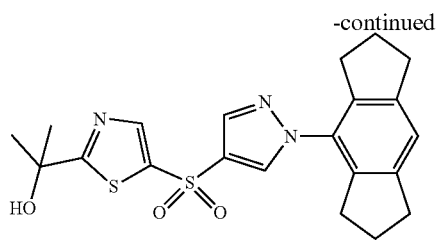

280

-continued

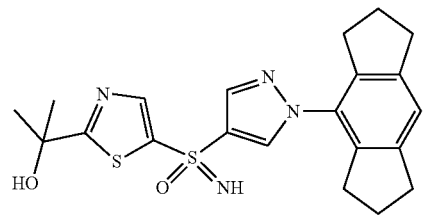

Example 4: Preparation of 2-(5-((1-(1,2,3,5,6,7-hexahydro-s-indacen-4-yl)-1H-pyrazol-4-yl)thio)thiazol-2-yl)propan-2-ol (Compound 122)

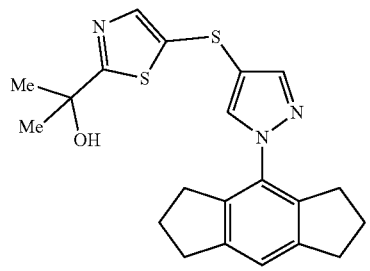 [SMILES: CC(C)(O)c1ncc(Sc2cnn(-c3c4c(cc5c3CCC5)CCC4)c2)s1]

Step 1: Preparation of 2-(thiazol-2-yl)propan-2-ol

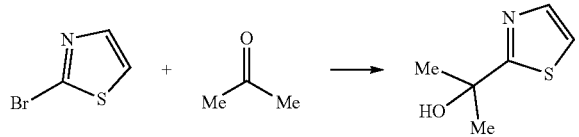

2-bromothiazole (5.5 mL, 61.0 mmol) was slowly added to a solution of n-butyllithium (2.5 M in hexane, 36.9 mL, 81.3 mmol) in diethyl ether (61.0 mL) at −78° C. After 30 min, acetone (6.42 mL, 87.4 mmol) was added dropwise at −78° C. The reaction mixture was then warmed to ambient temperature, quenched with saturated aqueous NH₄Cl, and then extracted with EtOAc. The organic layer was concentrated in vacuo to give a crude residue. The crude product was purified by chromatography on silica gel (20% EtOAc/hexane) to give the desired product. (5.60 g, 95% pure) as an orange oil which solidified to a pale orange-yellow solid.

Step 2: Preparation of 2-(5-bromothiazol-2-yl)propan-2-ol

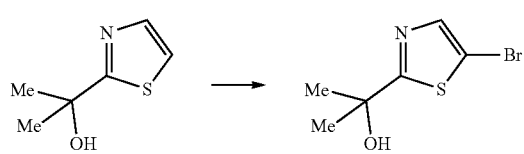 [SMILES: CC(C)(O)c1nccs1 ; CC(C)(O)c1ncc(Br)s1]

N-bromosuccinimide (11.2 g, 62.8 mmol) was added to a solution of 2-(thiazol-2-yl)propan-2-ol (3.0 g, 20.9 mmol) in methylene chloride (42.0 mL) at 0° C. The reaction was stirred at 50° C. for 2 h, monitoring by LC-MS. DMF (1 mL) was added and the reaction was stirred at 50° C. for a further 30 min to complete the reaction. The reaction mixture was diluted with saturated aqueous Na₂S₂O₃ (~6 mL) and extracted with DCM (3×2 mL). The combined organic layers were washed with H₂O (2 mL), sat. aq. NaCl (2 mL), then dried with Na₂SO₄, and concentrated in vacuo to provide crude material.

Step 3: Preparation of methyl 3-((2-(2-hydroxypropan-2-yl)thiazol-5-yl)thio)propanoate

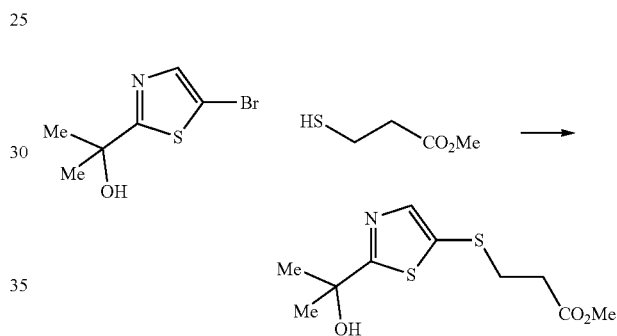

2-(5-bromothiazol-2-yl)propan-2-ol (2.0 g, 9.00 mmol), methyl 3-mercaptopropionate (1.10 mL, 9.91 mmol), Pd₂dba₃ (412.3 mg, 0.45 mmol), Xantphos (469.0 mg, 0.811 mmol), DIPEA (3.14 mL, 18.0 mmol), and 1,4-dioxane (18.0 mL) were added to a microwave vial. The mixture was purged with N₂, then stirred and heated in a microwave reactor at 120° C. for 90 min until LC/MS indicated complete reaction. The reaction mixture was filtered, rinsing with DCM. The filtrate was subsequently washed with H₂O and brine, then dried with Na₂SO₄, and the organic layer was concentrated in vacuo to afford the crude product. The procedure was repeated on four more batches of 1.2 g starting material (5.40 mmol) each for a total of 6.8 g. The combined batches were purified by prep HPLC to give the pure product as a clear yellow oil. Upon storage in freezer overnight, the oil solidified as a sticky white solid.

Step 4: Preparation of 2-((2-(2-hydroxypropan-2-yl)thiazol-5-yl)thio)malonaldehyde

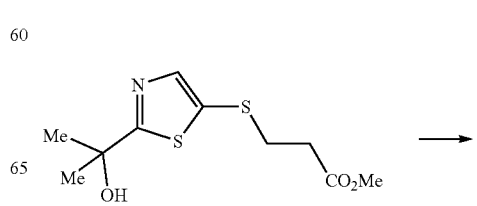

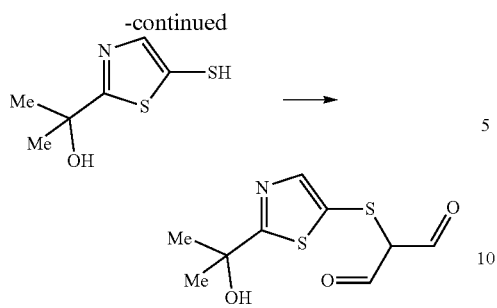

Methyl 3-((2-(2-hydroxypropan-2-yl)thiazol-5-yl)thio)propanoate (100.0 mg, 0.383 mmol) was dissolved in tetrahydrofuran (2.55 mL), and cooled to −78° C. at which temperature was added potassium tert-butoxide (0.37 mL, 1 M in THF, 0.37 mmol). The reaction stirred vigorously at −78° C. until completion. Upon completion, the reaction was directly quenched with 2-bromomalonaldehyde (57.8 mg, 0.383 mmol) at −78° C. and warmed to room temperature. The presence of the displacement product was confirmed by LC-MS. The organic layer was then concentrated in vacuo to provide the desired product which was carried on directly to the next step.

Step 5: Preparation of 2-(5-((1-(1,2,3,5,6,7-hexahydro-s-indacen-4-yl)-1H-pyrazol-4-yl)thio)thiazol-2-yl)propan-2-ol (Compound 122)

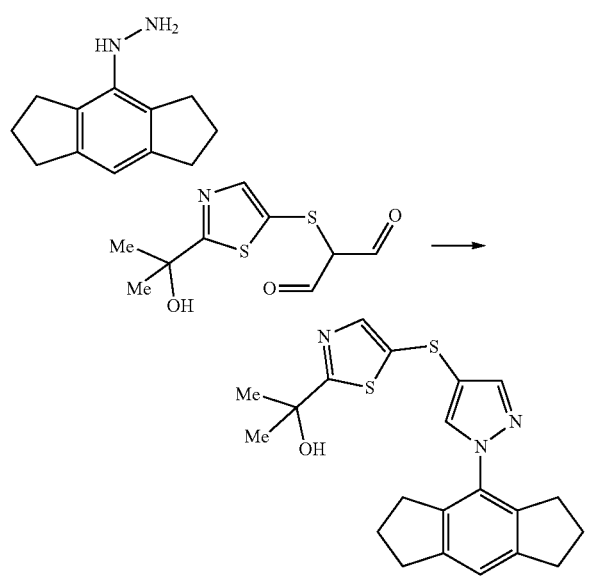

A round bottom flask was charged with a mixture of methyl 2-((2-(2-hydroxypropan-2-yl)-thiazol-5-yl)thio)malonaldehyde (470.5 mg, 1.92 mmol), (1,2,3,5,6,7-hexahydro-s-indacen-4-yl)hydrazine (541.7 mg, 2.88 mmol), and methanol (6.6 mL). The mixture was stirred at 80° C. for 20 min, and then concentrated in vacuo. The crude product was purified using silica chromatography (0-10% ethyl acetate/hexane) to provide the desired product (156 mg, 20.5% yield) as a pasty dark olive brown solid obtained (31 mg was characterized by HPLC as 12.4 mg of a white powder).

Example 5: Preparation of 2-(5-((1-(1,2,3,5,6,7-hexahydro-s-indacen-4-yl)-1H-pyrazol-4-yl)sulfonyl)thiazol-2-yl)propan-2-ol (Compound 115)

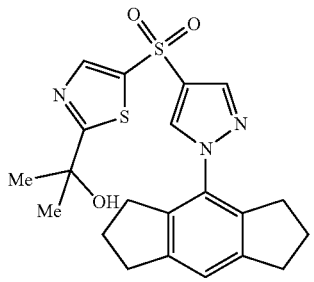

To a solution of ethyl 2-(5-(((1-(1,2,3,5,6,7-hexahydro-s-indacen-4-yl)-1H-pyrazol-4-yl)thio)-thiazol-2-yl)propan-2-ol (50.0 mg, 0.126 mmol) in acetic acid (1.25 mL) was added 3-chloroperoxybenzoic acid (144.7 mg, 0.63 mmol), and the mixture was stirred at room temperature for 2.5 h. Aqueous sodium thiosulfate solution was added to the reaction mixture which was then concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, dried over anhydrous sodium sulfate, and concentrated under reduced pressure. The crude material was purified via preparative HPLC.

Example 6: Preparation of (1-(1,2,3,5,6,7-hexa-hydro-s-indacen-4-yl)-1H-pyrazol-4-yl)(2-(2-hy-droxypropan-2-yl)thiazol-5-yl)(imino)-λ6-sulfanone (Compound 123)

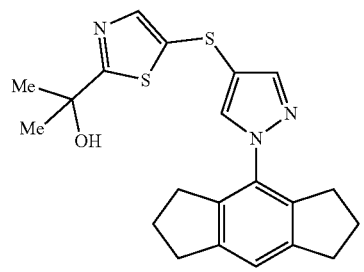

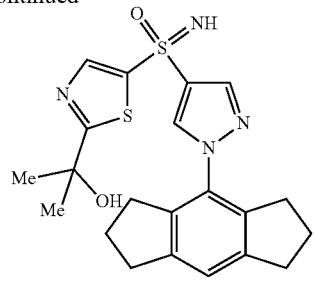

2-(5-(((1-(1,2,3,5,6,7-hexahydro-s-indacen-4-yl)-1H-pyrazol-4-yl)thio)thiazol-2-yl)propan-2-ol (70.0 mg, 0.176 mmol), phenyliododiacetate (141.8 mg, 0.44 mmol), and ammonium carbamate (27.5 mg, 0.352 mmol) were added to a reaction vial. Methanol (0.88 mL, 0.2 M) was added and the reaction subsequently stirred at 25° C. for 3 h. After completion, the solvent was evaporated and 20 mL of water was added. The mixture was extracted with DCM and the combined organic phases were dried over anhydrous $Na_2SO_4$. The crude material was purified via preparative HPLC.

Examples 7-8 were prepared according to the Scheme below:

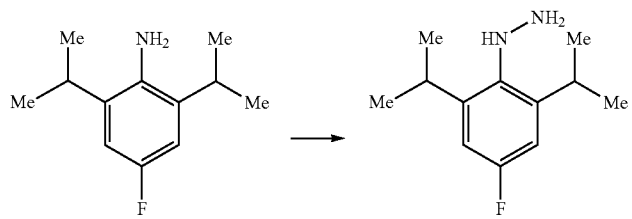

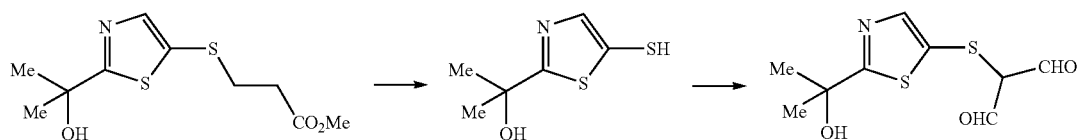

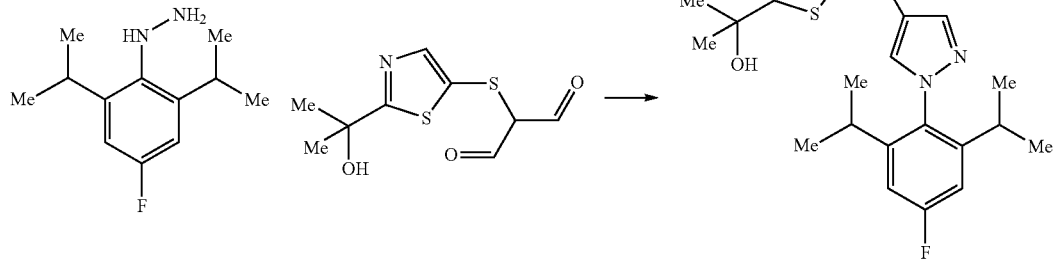

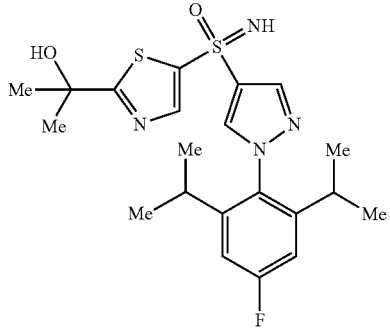

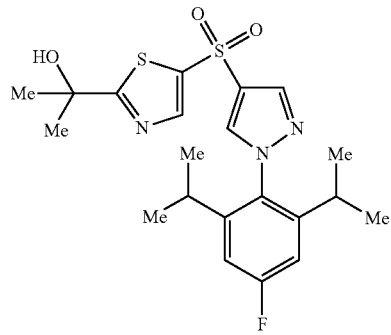

Example 7: Preparation of 2-(5-((1-(4-fluoro-2,6-diisopropylphenyl)-1H-pyrazol-4-yl)sulfonyl)thiazol-2-yl)propan-2-ol (Compound 124)

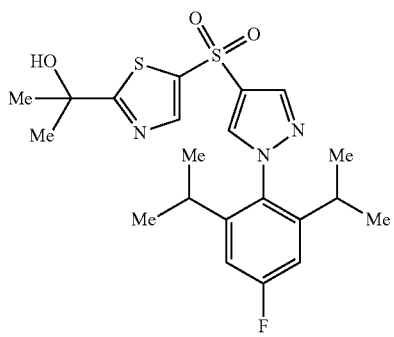 [SMILES: CC(C)c1cc(F)cc(C(C)C)c1-n1cc(S(=O)(=O)c2cnc(C(C)(C)O)s2)cn1]

Step 1: Preparation of (4-fluoro-2,6-diisopropylphenyl)hydrazine

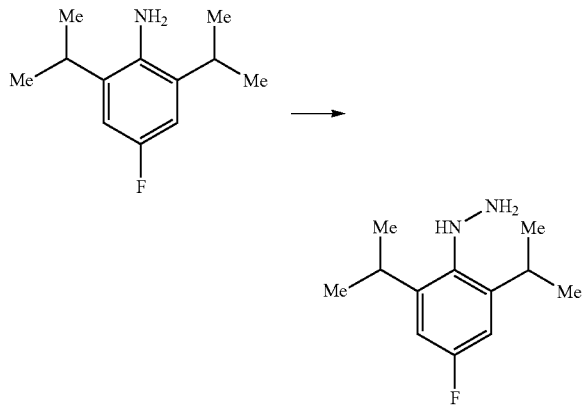

4-fluoro-2,6-diisopropylaniline (1.01 g, 5.17 mmol) was dissolved in ethanol (25.6 mL) and treated at −5-0° C. with t-butylnitrite (90%, 2.70 mL) and HBF$_4$ (3.28 mL) for 4 h. The cold solution of the diazonium salt thus formed was added dropwise to a solution of SnCl$_2$ in 12 M HCl (10 mL) with stirring at 0° C. The reaction mixture was stirred for 90 min at which time, analysis showed the disappearance of the diazonium salt. The mixture was concentrated under reduced pressure. The residue was partitioned between water (50 mL) and ethyl acetate (50 mL). The aqueous layer was further extracted with ethyl acetate (2×50 mL). The combined organic layers were washed with saturated sodium bicarbonate solution (100 mL), water, and brine, then dried over sodium sulfate, filtered and concentrated to afford (4-fluoro-2,6-diisopropylphenyl)hydrazine (0.926 g) which was used without further purification in the following step.

Step 2: Preparation of 2-((2-(2-hydroxypropan-2-yl)thiazol-5-yl)thio)malonaldehyde

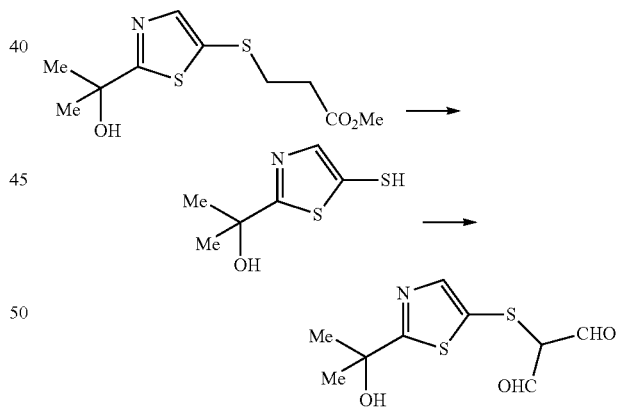

Methyl 3-((2-(2-acetoxypropan-2-yl)thiazol-5-yl)thio)propanoate (2.35 g, 9.00 mmol) was dissolved in tetrahydrofuran (60.0 mL), and the resulting solution was stirred at −78° C. Potassium tert-butoxide (22.5 mL, 1 M in THF, 22.5 mmol) was added to the reaction mixture, and the reaction stirred vigorously at −78° C. until completion. Upon completion, the reaction was directly quenched with 2-bromomalonaldehyde at −78° C. and warmed to room temperature. The presence of the alkylated product was confirmed by LC-MS. The organic layer was then concentrated in vacuo to provide the crude desired product. The crude material was purified by preparative HPLC to afford pure 2-((2-(2-hydroxypropan-2-yl)thiazol-5-yl)thio)malonaldehyde (489 mg, 22.1% yield) as a fluffy white powder.

Step 3: Preparation of 2-(5-((1-(4-fluoro-2,6-diisopropylphenyl)-1H-pyrazol-4-yl)thio)thiazol-2-yl)propan-2-ol

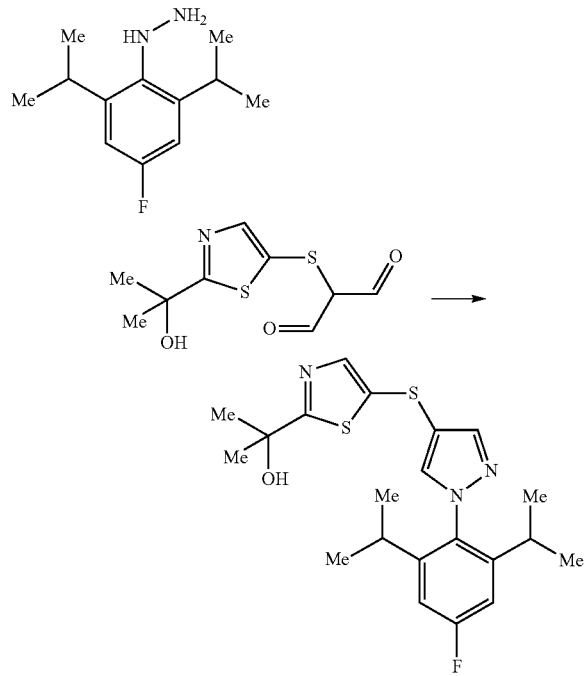

A round bottom flask was charged with methyl 2-((2-(2-hydroxypropan-2-yl)thiazol-5-yl)thio)-malonaldehyde (61.2 mg, 0.25 mmol), (4-fluoro-2,6-diisopropylphenyl)hydrazine (944.5 mg crude, 4.49 mmol), and methanol (1.25 mL). The reaction was stirred at 80° C. for 20 min, at which time the mixture was concentrated in vacuo. The crude material was purified by silica chromatography (0-15% ethyl acetate/hexanes) to afford pure 2-(5-((1-(4-fluoro-2,6-diisopropylphenyl)-1H-pyrazol-4-yl)thio)thiazol-2-yl)propan-2-ol (87.1 mg, 78.3% yield).

Step 4: Preparation of 2-(5-((1-(4-fluoro-2,6-diisopropylphenyl)-1H-pyrazol-4-yl)sulfonyl)-thiazol-2-yl)propan-2-ol (Compound 124)

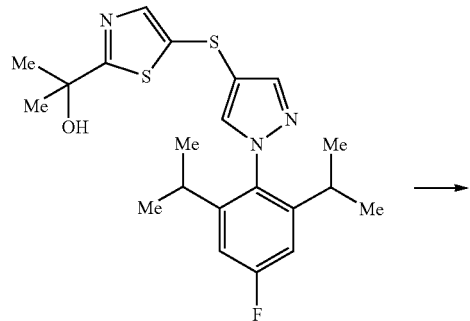

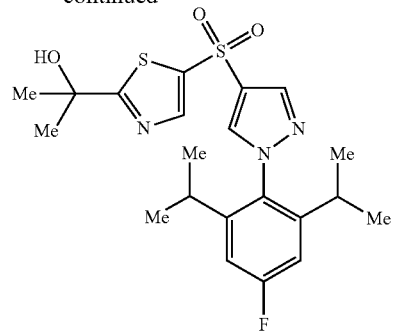

To a solution of ethyl 2-(5-((1-(4-fluoro-2,6-diisopropylphenyl)-1H-pyrazol-4-yl)thio)thiazol-2-yl)propan-2-ol (43.6 mg, 0.104 mmol) in acetic acid (1.00 mL) was added 3-chloroperoxybenzoic acid (119.42 mg, 0.52 mmol), and the mixture was stirred at room temperature for 2.5 h. Aqueous sodium thiosulfate solution was added to the reaction mixture, and the mixture was concentrated under reduced pressure. Saturated aqueous sodium hydrogen carbonate solution was added to the residue, and the mixture was extracted with ethyl acetate. The extract was washed successively with saturated aqueous sodium hydrogen carbonate solution, water and saturated brine, then dried over anhydrous sodium sulfate, and concentrated under reduced pressure. The crude material was purified via preparative HPLC to afford 2-(5-((1-(4-fluoro-2,6-diisopropylphenyl)-1H-pyrazol-4-yl)sulfonyl)thiazol-2-yl)propan-2-ol (2.6 mg, 5.5% yield).

Example 8: Preparation of (1-(4-fluoro-2,6-diisopropylphenyl)-1H-pyrazol-4-yl)(2-(2-hydroxypropan-2-yl)thiazol-5-yl)(imino)-16-sulfanone (Compound 125)

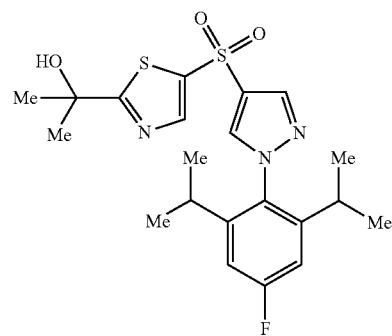

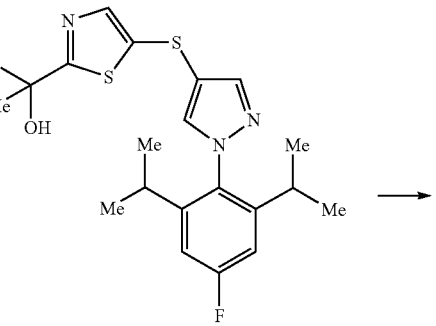

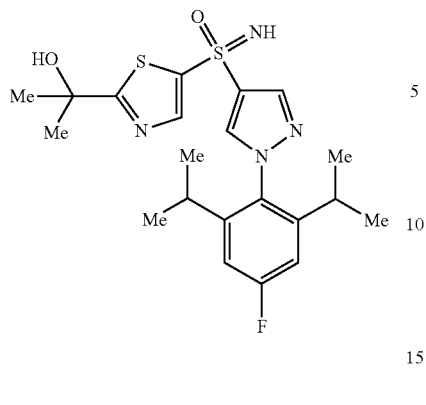

2-(5-((1-(4-fluoro-2,6-diisopropylphenyl)-1H-pyrazol-4-yl)thio)thiazol-2-yl)propan-2-ol (43.6 mg, 0.104 mmol), phenyliododiacetate (83.6 mg, 0.260 mmol), and ammonium carbamate (16.2 mg, 0.208 mmol) were added to a reaction vial. Methanol (0.52 mL, 0.2 M) was added and the reaction subsequently was stirred at 25° C. for 1 h. After completion of the reaction, the solvent was evaporated and 20 mL of water was added. The mixture was extracted with methylene chloride and the combined organic phases were dried over anhydrous sodium sulfate. The product solution then concentrated in vacuo to provide the crude desired product which was purified via preparative HPLC to afford pure (1-(4-fluoro-2,6-diisopropylphenyl)-1H-pyrazol-4-yl)(2-(2-hydroxypropan-2-yl)thiazol-5-yl)(imino)-λ6-sulfanone (38.5 mg, 82.3% yield).

Examples 9-12 were prepared according to the scheme below:

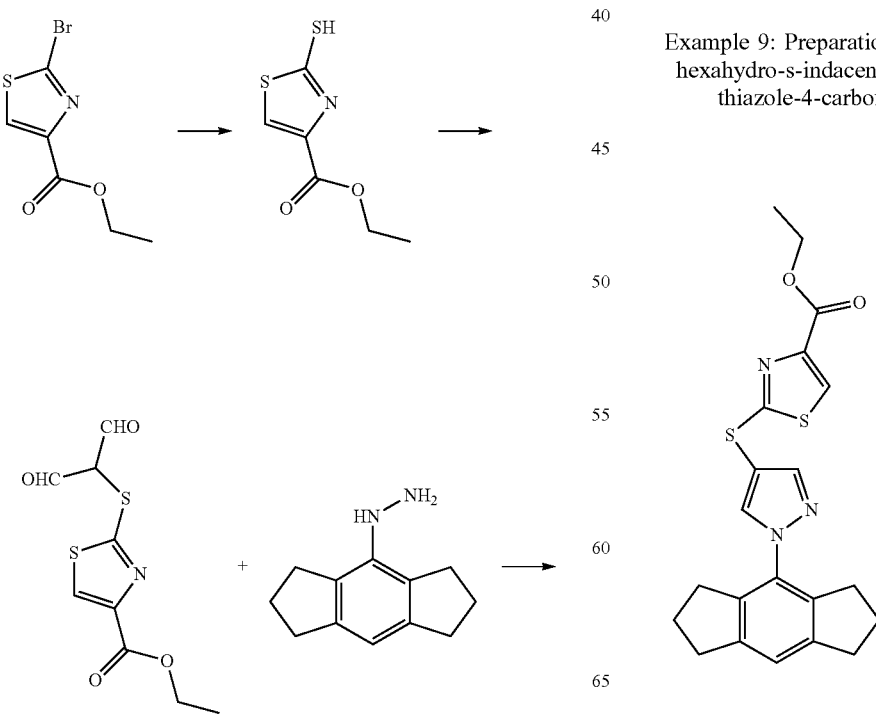

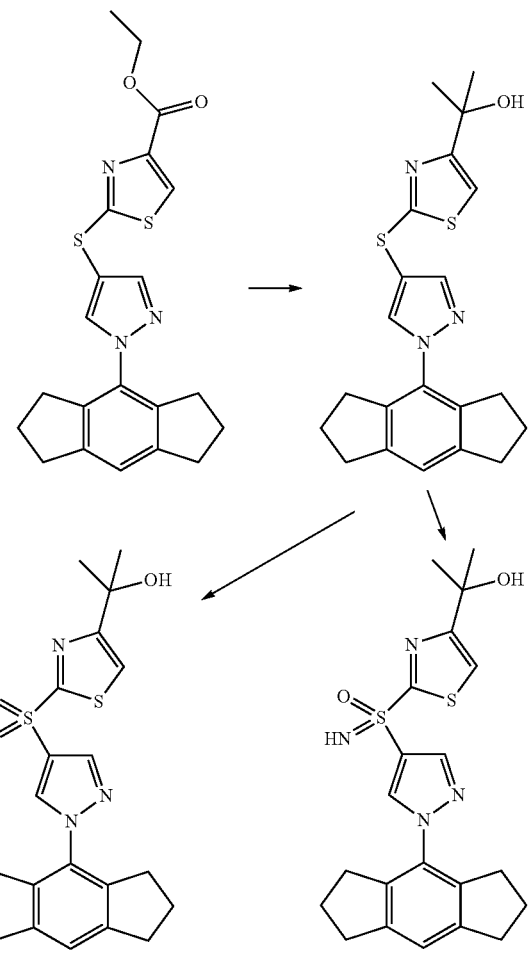

Example 9: Preparation of ethyl 2-((1-(1,2,3,5,6,7-hexahydro-s-indacen-4-yl)-1H-pyrazol-4-yl)thio)thiazole-4-carboxylate (Compound 126)

Step 1: Preparation of ethyl 2-mercaptothiazole-4-carboxylate

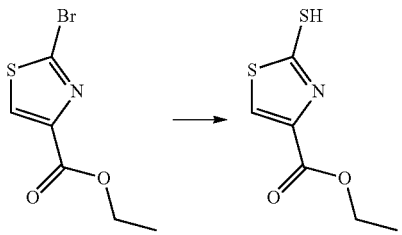

Using similar procedures as Example 1/Step 2 described above for the preparation of ethyl 2-mercaptothiazole-5-carboxylate, ethyl 2-bromothiazole-4-carboxylate (3.41 g) was reacted with sodium hydrosulfide hydrate (2.65 g) in ethanol (31 mL) to afford ethyl 2-mercaptothiazole-4-carboxylate (1.97 g).

Step 2: Preparation of ethyl 2-((1,3-dioxopropan-2-yl)thio)thiazole-4-carboxylate

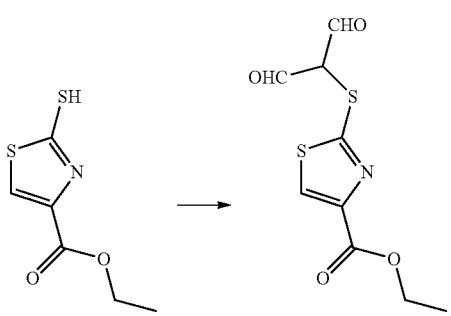 [SMILES: CCOC(=O)c1csc(S)n1 ; CCOC(=O)c1csc(SC(C=O)C=O)n1]

Using similar procedures as Example 1/Step 3 described above for the preparation of ethyl 2-((1,3-dioxopropan-2-yl)thio)thiazole-5-carboxylate, ethyl 2-mercaptothiazole-4-carboxylate (755.3 mg) was reacted with 2-bromomalonaldehyde (602 mg) in dichloromethane (13.3 mL) to afford ethyl 2-((1,3-dioxopropan-2-yl)thio)thiazole-4-carboxylate (1.03 g) which was used in the following step without further purification.

Step 3: Preparation of ethyl 2-((1-(1,2,3,5,6,7-hexahydro-s-indacen-4-yl)-1H-pyrazol-4-yl)-thio)thiazole-4-carboxylate (Compound 126)

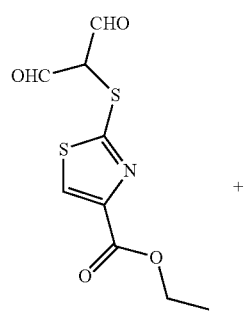

+

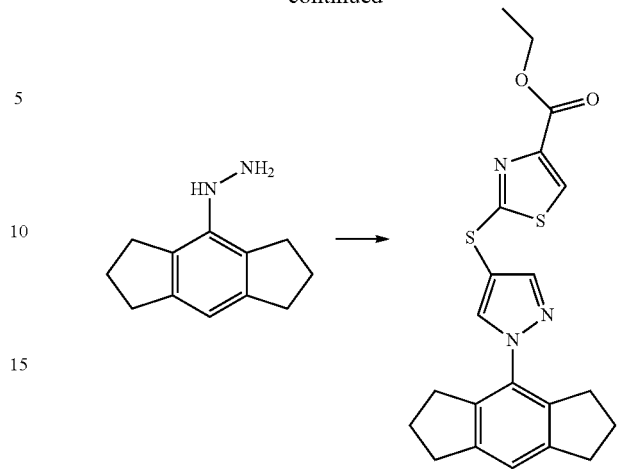

Using similar procedures as Example 7 7/Step 3 described above, (1,2,3,5,6,7-hexahydro-s-indacen-4-yl)hydrazine (625.6 mg, ~80% purity) was reacted with ethyl 2-((1,3-dioxopropan-2-yl)thio)thiazole-4-carboxylate (1.03 g) in methanol (13.3 mL) to afford ethyl 2-((1-(1,2,3,5,6,7-hexahydro-s-indacen-4-yl)-1H-pyrazol-4-yl)thio)thiazole-4-carboxylate (265.7 mg combined product from 2 reactions) after flash chromatography (ethyl acetate/hexane). A small aliquot of the product was repurified by preparative HPLC to afford material for biological testing (25.3 mg).

Example 10: Preparation of 2-(2-((1-(1,2,3,5,6,7-hexahydro-s-indacen-4-yl)-1H-pyrazol-4-yl)thio)thiazol-4-yl)propan-2-ol (Compound 119)

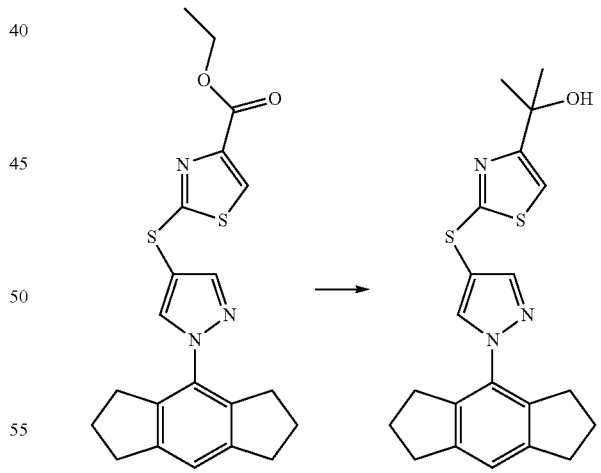

Using similar procedures as Example 2/Step 1 described above, ethyl 2-((1-(1,2,3,5,6,7-hexa-hydro-s-indacen-4-yl)-1H-pyrazol-4-yl)thio)thiazole-4-carboxylate (147 mg/87.9 mg) was reacted with methylmagnesium bromide (770 µL/510 µL, 2.5 M in ether) in THF (6 mL/3.6 mL) in two batches which were combined and purified by preparative HPLC to afford 2-(2-((1-(1,2,3,5,6,7-hexahydro-s-indacen-4-yl)-1H-pyrazol-4-yl)thio)thiazol-4-yl)propan-2-ol (150 mg) after flash chromatography (ethyl acetate/hexane). An aliquot of the purified product was further purified by preparative HPLC provide the sample for biological testing (7.9 mg).

Example 11: Preparation of 2-(2-((1-(1,2,3,5,6,7-hexahydro-s-indacen-4-yl)-1H-pyrazol-4-yl)sulfonyl)thiazol-4-yl)propan-2-ol (Compound 128)

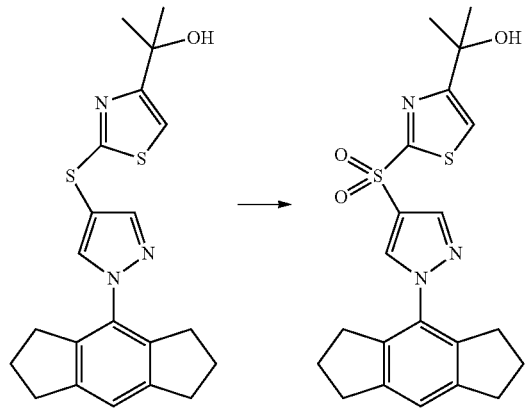 [SMILES: CC(C)(O)c1csc(Sc2cnn(-c3c4c(cc5c3CCC5)CCC4)c2)n1 ; CC(C)(O)c1csc(S(=O)(=O)c2cnn(-c3c4c(cc5c3CCC5)CCC4)c2)n1]

Using similar procedures as Example 7/Step 4, 2-(2-((1-(1,2,3,5,6,7-hexahydro-s-indacen-4-yl)-1H-pyrazol-4-yl)thio)thiazol-4-yl)propan-2-ol (45 mg) was oxidized with meta-chloroperoxybenzoic acid (137.9 mg, 75%) in acetic acid (1.1 mL) to afford 2-(2-((1-(1,2,3,5,6,7-hexahydro-s-indacen-4-yl)-1H-pyrazol-4-yl)sulfonyl)thiazol-4-yl)propan-2-ol (28.9 mg, 59% yield) after purification by preparative HPLC.

Example 12: Preparation of (1-(1,2,3,5,6,7-hexahydro-s-indacen-4-yl)-1H-pyrazol-4-yl)(4-(2-hydroxypropan-2-yl)thiazol-2-yl)(imino)-λ6-sulfanone (Compound 127)

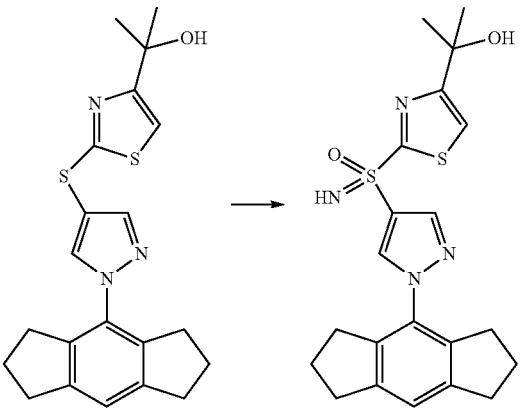 [SMILES: CC(C)(O)c1csc(Sc2cnn(-c3c4c(cc5c3CCC5)CCC4)c2)n1 ; CC(C)(O)c1csc(S(=N)(=O)c2cnn(-c3c4c(cc5c3CCC5)CCC4)c2)n1]

Using similar procedures as Example 8, 2-(2-((1-(1,2,3,5,6,7-hexahydro-s-indacen-4-yl)-1H-pyrazol-4-yl)thio)thiazol-4-yl)propan-2-ol (93 mg) was reacted with PIDA(192.5 mg) and ammonium carbamate (37.6 mg) in methanol (1.2 mL) to afford (1-(1,2,3,5,6,7-hexahydro-s-indacen-4-yl)-1H-pyrazol-4-yl)(4-(2-hydroxypropan-2-yl)thiazol-2-yl)(imino)-λ6-sulfanone (51.2 mg) after purification by preparative HPLC.

Examples 13-15 were prepared according to the scheme below:

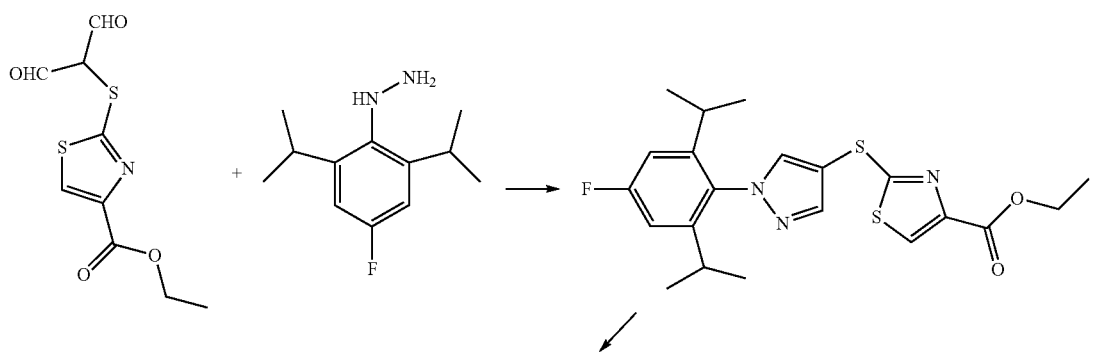

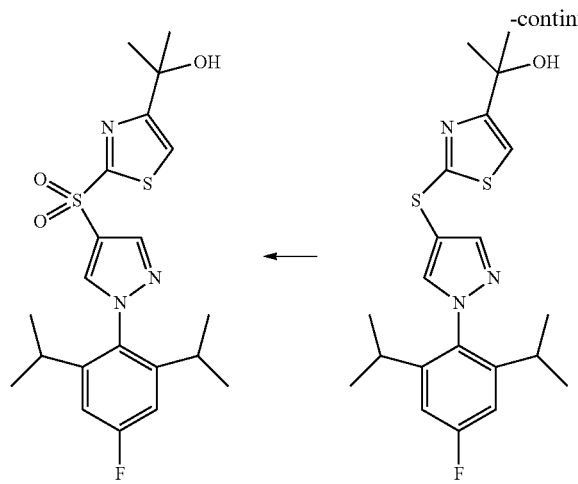

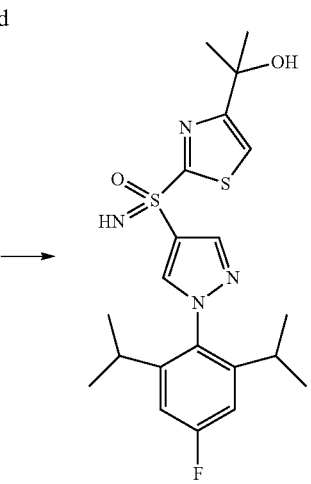

Example 13: Preparation of 2-(2-((1-(4-fluoro-2,6-diisopropylphenyl)-1H-pyrazol-4-yl)thio)thiazol-4-yl)propan-2-ol (Compound 129)

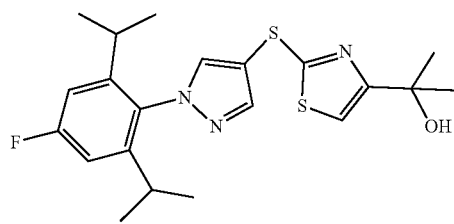 [SMILES: CC(C)c1cc(F)cc(C(C)C)c1-n1cc(Sc2nc(C(C)(C)O)cs2)cn1]

Step 1: Preparation of ethyl 2-((1-(4-fluoro-2,6-diisopropylphenyl)-1H-pyrazol-4-yl)thio)-thiazole-4-carboxylate

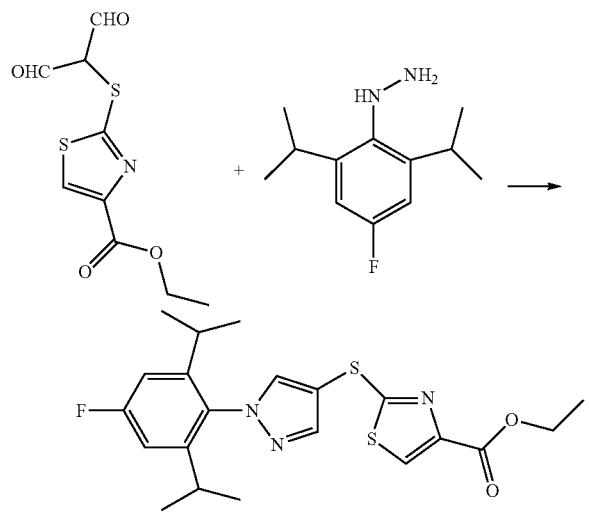

Using similar procedures as Example 1/Step 4 described above, 4-fluoro-2,6-diisopropylphenyl)hydrazine (925 mg) was reacted with ethyl 2-((1,3-dioxopropan-2-yl)thio)thiazole-4-carboxylate (described above) in ethanol (20 mL) to afford ethyl 2-((1-(4-fluoro-2,6-diisopropylphenyl)-1H-pyrazol-4-yl)thio)thiazole-4-carboxylate (782.8 mg) after purification by flash chromatography (ethyl acetate/hexane).

Step 2: Preparation of 2-(2-((1-(4-fluoro-2,6-diisopropylphenyl)-1H-pyrazol-4-yl)thio)thiazol-4-yl)propan-2-ol (Compound 129)

Using similar procedures as Example 2/Step 1 described above, ethyl 2-((1-(4-fluoro-2,6-diiso-propylphenyl)-1H-pyrazol-4-yl)thio)thiazole-4-carboxylate (782.8 mg) was reacted with methylmagnesium bromide (2.5 M in ether, 7.8 mL) in THF (30 mL) to afford crude 2-(2-((1-(4-fluoro-2,6-diisopropylphenyl)-1H-pyrazol-4-yl)thio)thiazol-4-yl)propan-2-ol (478.8 mg) which was used in the following procedure without further purification. A small sample was purified by HPLC (4.3 mg) for biological evaluation.

Example 14: Preparation of 2-(2-((1-(4-fluoro-2,6-diisopropylphenyl)-1H-pyrazol-4-yl)sulfonyl)thiazol-4-yl)propan-2-ol (Compound 130)

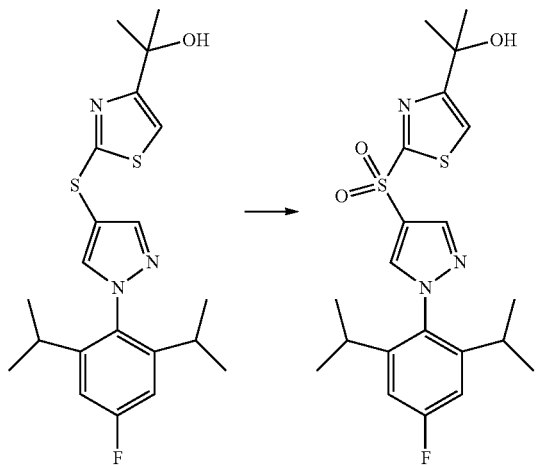 [SMILES: CC(C)c1cc(F)cc(C(C)C)c1-n1cc(Sc2nc(C(C)(C)O)cs2)cn1 ; CC(C)c1cc(F)cc(C(C)C)c1-n1cc(S(=O)(=O)c2nc(C(C)(C)O)cs2)cn1]

Using similar procedures as Example 7/Step 4 described above, 2-(2-((1-(4-fluoro-2,6-diiso-propylphenyl)-1H-pyrazol-4-yl)thio)thiazol-4-yl)propan-2-ol (224 mg) was oxidized with meta-chloroperoxybenzoic acid (619.3 mg, 75%) in acetic acid (5.34 mL) to afford 2-(2-((1-(4-fluoro-2,6-diisopropylphenyl)-1H-pyrazol-4-yl)sulfonyl)thiazol-4-yl)propan-2-ol (40 mg) after preparative HPLC purification.

Example 15: Preparation of (1-(4-fluoro-2,6-diisopropylphenyl)-1H-pyrazol-4-yl)(4-(2-hydroxypropan-2-yl)thiazol-2-yl)(imino)-λ6-sulfanone (Compound 131)

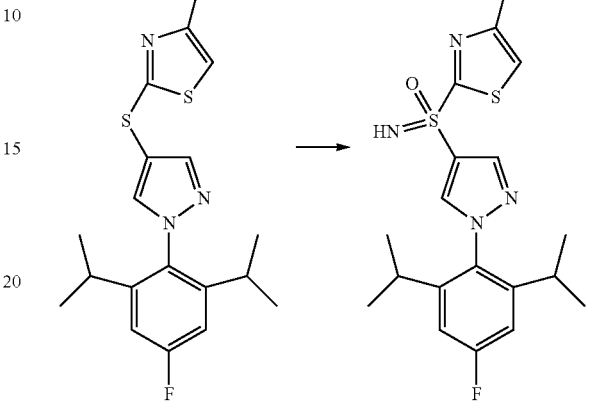

Using similar procedures as Example 8 described, 2-(2-((1-(4-fluoro-2,6-diisopropylphenyl)-1H-pyrazol-4-yl)thio)thiazol-4-yl)propan-2-ol (424 mg) was reacted with PIDA (816.6 mg) and ammonium carbamate (245.7 mg) in methanol (5.34 mL) to afford (1-(4-fluoro-2,6-diisopropyl-phenyl)-1H-pyrazol-4-yl)(4-(2-hydroxypropan-2-yl)thiazol-2-yl)(imino)-λ6-sulfanone (38.5 mg) after purification by preparative HPLC.

Example 16 was prepared according to the scheme below:

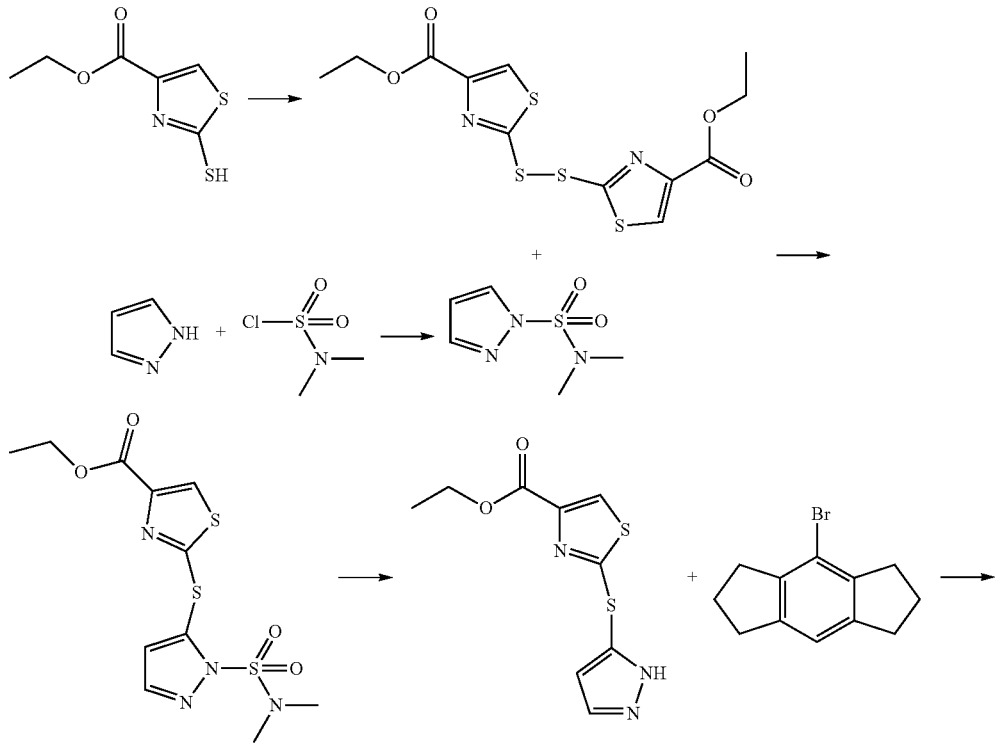

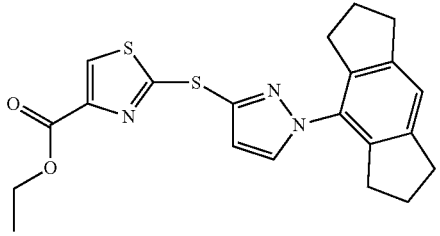

Example 16: Preparation of ethyl 2-(1-(1,2,3,5,6,7-hexahydros-indacen-4-yl)-1H-pyrazol-3-ylthio)thiazole-4-carboxylate (Compound 132)

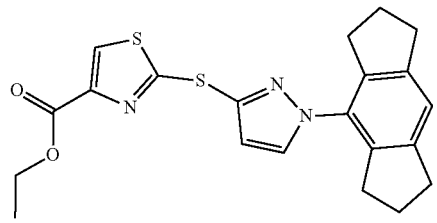 [SMILES: CCOC(=O)c1csc(Sc2ccn(-c3c4c(cc5c3CCC5)CCC4)n2)n1]

Step 1: Ethyl 2-{[4-(ethoxycarbonyl)-1,3-thiazol-2-yl]disulfanyl}-1,3-thiazole-4-carboxylate

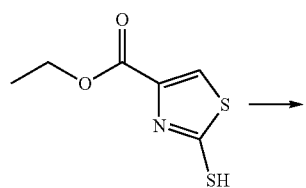

To a solution of ethyl 2-mercaptothiazole-4-carboxylate (1 g, 5.28 mmol) in EtOH (15 mL) was added t-BuNO$_2$ (3.14 mL, 26.4 mmol) at 0° C. in an ice/water bath. The resulting mixture was stirred at 0° C. for 1 h. Pale yellow precipitates formed. Reaction mixture was filtered. The residue was rinsed with ethanol and dried under high vacuum to afford desired product ethyl 2-{[4-(ethoxycarbonyl)-1,3-thiazol-2-yl]disulfanyl}-1,3-thiazole-4-carboxylate as yellow solid (900 mg, 91%).

Step 2: N,N-dimethyl-1H-pyrazole-1-sulfonamide

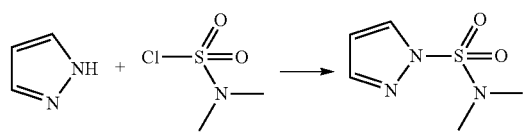

To a solution of pyrazole (500 mg, 7.34 mmol) in anhydrous THF was added NaH (382 mg, 9.54 mmol, 60% dispersion in mineral oil) at 0° C. in an ice/water bath. After 15 min ice/water bath was removed and the reaction mixture was further stirred for 30 min at room temperature. Reaction mixture was again submerged in an ice/water bath and a solution of N,N-dimethylsulfamoyl chloride (0.95 mL, 8.81 mmol) in anhydrous THF (7.5 mL) was added. Resulting mixture was stirred at 0° C. for 30 min and then poured into saturated aqueous ammonium chloride solution (30 mL). Mixture was extracted with EtOAc (35 mL×3) and the combined organic layer was washed with brine, dried over anhydrous sodium sulfate, filtered and concentrated in vacuo to provide crude product which was purified by silica gel flash chromatography to (EtOAc/hexanes 0-50%) to obtain N,N-dimethyl-1H-pyrazole-1-sulfonamide (770 mg, 60%) as pale yellow liquid.

Step 3: Ethyl 2-{[1-(dimethylsulfamoyl)-1H-pyrazol-5-yl]sulfanyl}-1,3thiazole-4-carboxylate

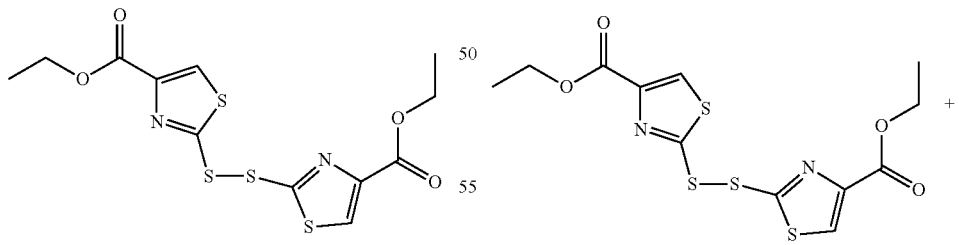

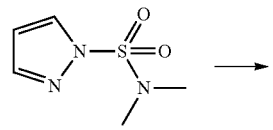

-continued

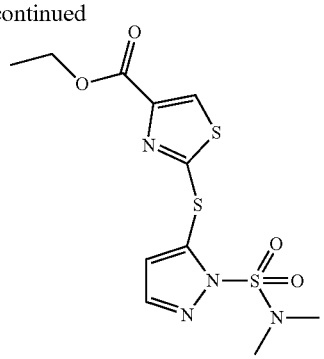

A solution of N,N-dimethyl-1H-pyrazole-1-sulfonamide (465 mg, 2.65 mmol) in anhydrous THF (15 mL) was cooled down to −78° C. in a dry ice/acetone bath. A solution of n-BuLi (1.06 mL, 2.5M in hexanes) was added drop wise (solution A). A solution of 2-{[4-(ethoxycarbonyl)-1,3-thiazol-2-yl]disulfanyl}-1,3-thiazole-4-carboxylate (1 g, 2.65 mmol) was prepared in THF (10 mL) by heating at 60° C. for 5 min (solution B). This solution B of disulfide was immediately added to solution A at once at −78° C. with efficient stirring, the dry ice/acetone bath was removed and after 20 min, reaction mixture was quenched by the addition of water (30 mL). 1M HCl (5 mL) was added and the resulting mixture was extracted with EtOAc (40 mL×3). Combined organic layer was washed with brine, dried over anhydrous sodium sulfate, filtered and concentrated to give crude product which was used in the next step without any purification.

Step 4: Ethyl 2-(1H-pyrazol-5-ylsulfanyl)-1,3-thiazole-4-carboxylate

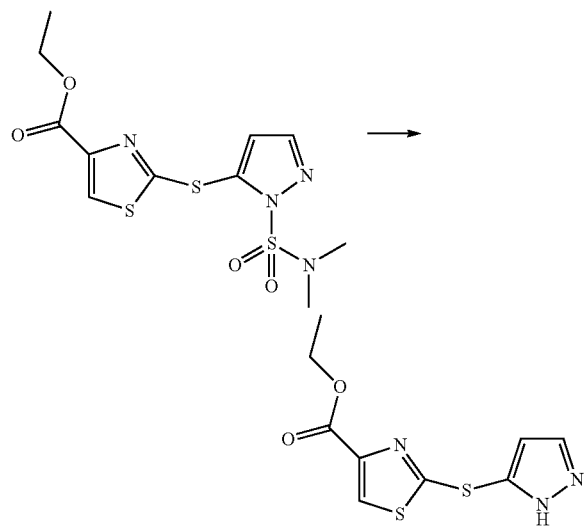

Crude material from step 3 was stirred in 30% TFA/DCM (10 mL) solution for 1 h at room temperature. After completion of the reaction, the solvent was evaporated in vacuo and the resulting residue was purified by silica gel chromatography (70% EtOAc/hexanes) to afford desired product ethyl 2-(1H-pyrazol-5-ylsulfanyl)-1,3-thiazole-4-carboxylate (150 mg, 22% over two steps).

Step 5: Preparation of ethyl 2-(1-(1,2,3,5,6,7-hexahydros-indacen-4-yl)-1H-pyrazol-3-ylthio)thiazole-4-carboxylate (Compound 132)

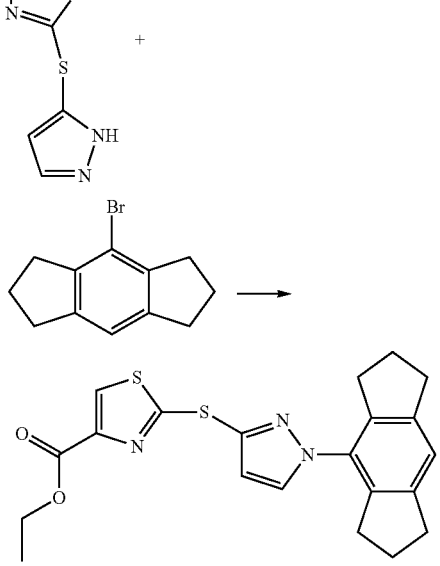

To a solution of ethyl 2-(1H-pyrazol-5-ylsulfanyl)-1,3-thiazole-4-carboxylate (120 mg, 0.47 mmol) in dioxane (3 mL) was added 4-bromoindacene (133 mg, 0.56 mmol), Pd$_2$(dba)$_3$ (43 mg, 0.047 mmol), Xantphos (54 mg, 0.094 mmol) and K$_2$CO$_3$ (194 mg, 1.41 mmol). The resulting mixture was screw capped under nitrogen and stirred at 100° C. for 48 h. Reaction mixture was then brought to room temperature, filtered through a pad of celite and concentrated in vacuo. The crude product was purified by HPLC to afford ethyl 2-(1-(1,2,3,5,6,7-hexahydros-indacen-4-yl)-1H-pyrazol-3-ylthio)thiazole-4-carboxylate (1.7 mg, 0.9%).

Targets wherein X=CR$^3$NHR$^4$

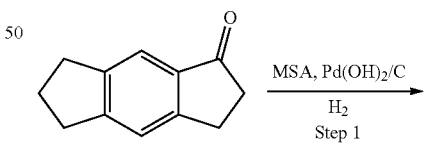

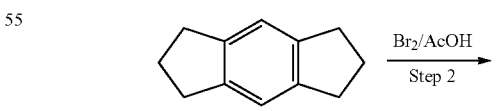

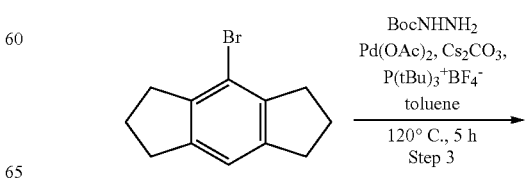

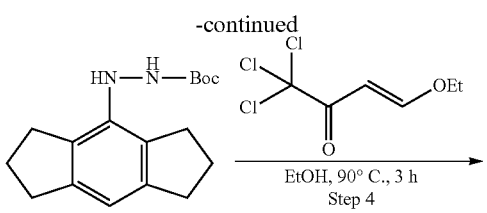

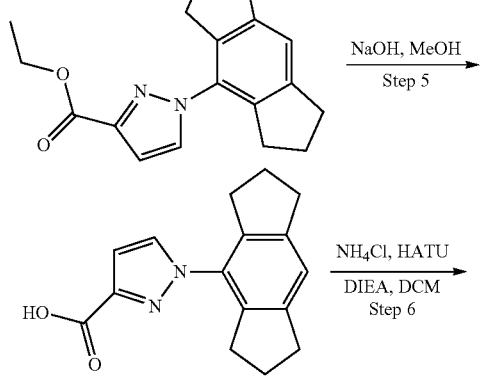

Intermediate 1

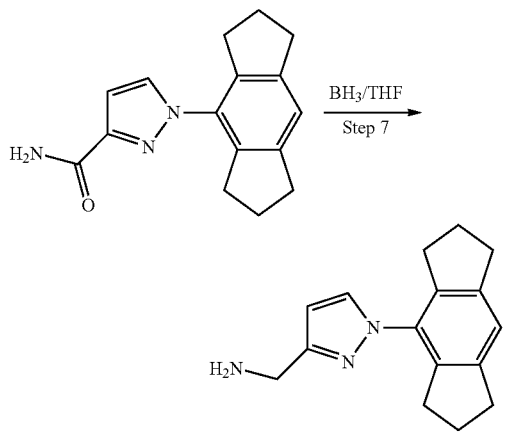

Intermediate 2

Intermediate 1

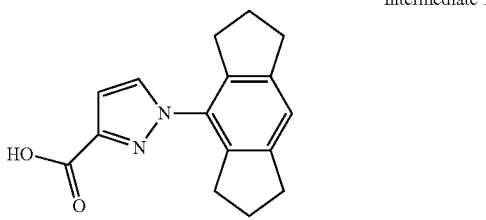

1-(1,2,3,5,6,7-Hexahydros-indacen-4-yl)-1H-pyrazole-3-carboxylic acid

Step 1: 1,2,3,5,6,7-Hexahydros-indacene

Into a 1000-mL round-bottom flask purged and maintained with an inert atmosphere of nitrogen, was placed a solution of 3,5,6,7-tetrahydro-s-indacen-1(2H)-one (37.2 g, 216 mmol) in MeOH (300 mL), to this was added MSA (42 g, 0.44 mol), Pd(OH)$_2$/C (20% wt., 8 g) under atmosphere of nitrogen. The solution was degassed and back filled with hydrogen. The resulting solution was stirred for 16 h at RT. The solids were filtered out. The resulting mixture was concentrated under vacuum. The residue was applied onto a silica gel column and eluted with ethyl acetate/petroleum ether (1:100). This resulted in 27.1 g (79%) of 1,2,3,5,6,7-hexahydro-s-indacene as a white solid. $^1$H NMR (300 MHz, DMSO-d$_6$) δ 7.04 (s, 2H), 2.78 (t, J=7.4 Hz, 8H), 2.10-1.90 (m, 4H).

Step 2: 4-Bromo-1,2,3,5,6,7-hexahydros-indacene

Into a 250-mL 3-necked round-bottom flask, was placed 1,2,3,5,6,7-hexahydro-s-indacene (5 g, 31.59 mmol) was dissolved in DCM (50 mL) and AcOH (30 mL). To this was added Br$_2$ (5.3 g, 33.17 mmol) dropwise below 5° C. The resulting solution was stirred for 48 h at 25° C. The resulting mixture was concentrated under vacuum. The residue was applied onto a silica gel column and eluted with petroleum ether. This resulted in 5.1 g (crude) of the title compound as an off-white liquid.

Step 3: Tert-butyl 2-(1,2,3,5,6,7-hexahydros-indacen-4-yl)hydrazinecarboxylate

Into a 250-mL round-bottom flask purged and maintained with an inert atmosphere of nitrogen, was placed 4-bromo-1,2,3,5,6,7-hexahydro-indacene (7.5 g, 31.63 mmol) in toluene (100 mL). To this was added tert-butyl hydrazinecarboxylate (6.3 g, 47.44 mmol), P(tBu)$_3^+$ BF$_4^-$ (0.9 g, 3.16 mmol), Pd(OAc)$_2$ (0.7 g, 3.16 mmol), Cs$_2$CO$_3$ (20.7 g, 63.25 mmol). The resulting solution was stirred for 16 h at 120° C. under atmosphere of nitrogen. The solids were filtered out.

The filtrate was concentrated. The residue was applied onto a silica gel column and eluted with ethyl acetate/petroleum ether (1/5). This resulted in 2.2 g (24.1%) of the title compound as a yellow solid. MS-ESI: 289.2 (M+1).

Step 4: Ethyl 1-(1,2,3,5,6,7-hexahydros-indacen-4-yl)-1H-pyrazole-3-carboxylate

Into a 500-mL round-bottom flask, was placed a solution of tert-butyl 2-(1,2,3,5,6,7-hexahydros-indacen-4-yl)hydrazinecarboxylate (11 g, 38.14 mmol) in EtOH (200 mL), to this was added (E)-1,1,1-trichloro-4-ethoxybut-3-en-2-one (10.8 g, 49.59 mmol). The resulting solution was stirred for 12 h at RT. The resulting solution was concentrated. The crude product was applied onto a silica gel column and eluted with ethyl acetate/petroleum ether (1/10). This resulted in 4 g (35.4%) of the title compound as a yellow solid. MS-ESI: 297.2 (M+1).

Step 5: 1-(1,2,3,5,6,7-Hexahydros-indacen-4-yl)-1H-pyrazole-3-carboxylic acid

Into a 500-mL round-bottom flask, was placed a solution of ethyl 1-(1,2,3,5,6,7-hexahydros-indacen-4-yl)-1H-pyrazole-3-carboxylate (4 g, 13.51 mmol) in MeOH (50 mL), to this was added NaOH(2N) (1.08 g, 27.03 mmol) dropwise at RT. The resulting solution was stirred for 2 h at RT. Solvent MeOH was removed and adjusted the pH value of the solution to 3 with HCl(1M), solid predicated and collected by filtration, dried by infra-red drying. This resulted in 3.2 g (88.4%) of the title compound as a white solid. MS-ESI: 269.1 (M+1).

Intermediate 2

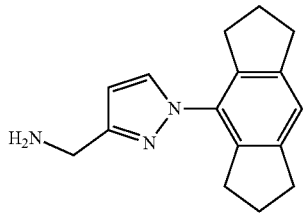 [SMILES: NCc1ccn(-c2c3c(cc4c2CCC4)CCC3)n1]

(1-(1,2,3,5,6,7-Hexahydros-indacen-4-yl)-1H-pyrazol-3-yl)methanamine

Step 6: 1-(1,2,3,5,6,7-Hexahydros-indacen-4-yl)-1H-pyrazole-3-carboxamide

Into a 250-mL round-bottom flask, was placed 1-(1,2,3,5,6,7-Hexahydros-indacen-4-yl)-1H-pyrazole-3-carboxylic acid (800 mg, 2.98 mmol), DCM (15 mL), HATU (1.7 g, 4.47 mmol), DIEA (1.2 g, 8.95 mmol), NH$_4$Cl (797 mg, 14.91 mmol). The resulting solution was stirred for 12 h at RT. The crude product was purified by Prep-HPLC with the following conditions: Column, XBridge Prep OBD C18 Column, 30×150 mm Sum; mobile phase, water (10 MMOL/L NH4HCO3) and ACN (10% Phase B up to 75% in 7 min); Detector, UV 254/210 nm. This resulted in 400 mg (50.2%) of the title compound as a white solid. MS-ESI: 268.1 (M+1). $^1$H NMR (400 MHz, MeOH-d$_4$) δ 7.87 (d, J=2.4 Hz, 1H), 7.20 (s, 1H), 6.93 (d, J=2.4 Hz, 1H), 2.96 (t, J=7.4 Hz, 4H), 2.83 (t, J=7.4 Hz, 4H), 2.10-1.90 (m, 4H).

Step 7: (1-(1,2,3,5,6,7-Hexahydros-indacen-4-yl)-1H-pyrazol-3-yl)methanamin

Into a 100-mL round-bottom flask, was placed a solution of 1-(1,2,3,5,6,7-hexahydros-indacen-4-yl)-1H-pyrazole-3-carboxamide (400 mg, 1.50 mmol) in THF (5 mL), BH$_3$·THF(1N) (10 mL, 10.0 mmol). The resulting solution was stirred for 10 min at 0° C. The resulting solution was stirred for 12 h at 65° C. The crude product was purified by Prep-HPLC with the following conditions: Column, XBridge Prep OBD C18 Column, 30×150 mm Sum; mobile phase, water (10 MMOL/L NH4HCO3) and ACN (20% Phase B up to 59% in 7 min); Detector, UV 254/210 nm. This resulted in 100 mg (25.8%) of the title compound as a white solid. MS-ESI: 254.2 (M+1). $^1$H NMR (400 MHz, DMSO-d$_6$) δ 7.86 (d, J=2.4 Hz, 1H), 7.12 (s, 1H), 6.39 (d, J=2.4 Hz, 1H), 3.72 (s, 2H), 2.87 (t, J=7.4 Hz, 4H), 2.77 (t, J=7.3 Hz, 4H), 2.10-1.95 (m, 4H), 1.82 (br s, 2H).

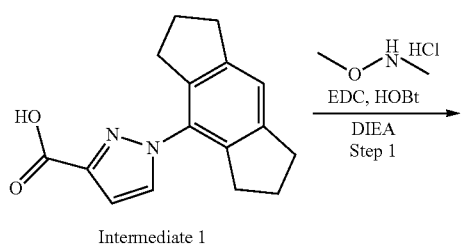

Intermediate 1

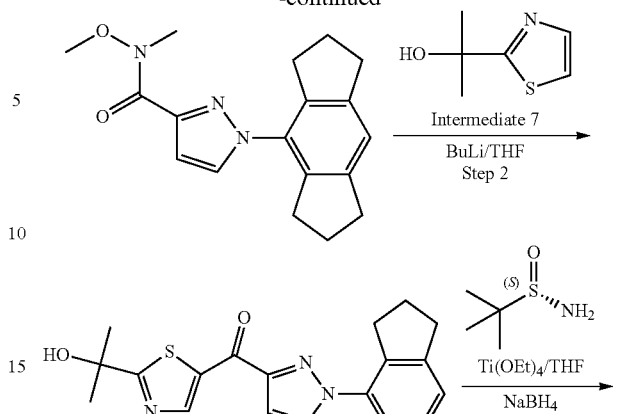

Compound 137

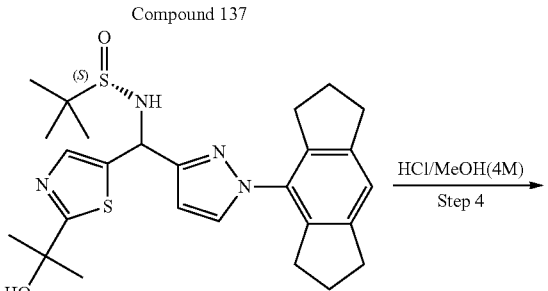

Compound 138

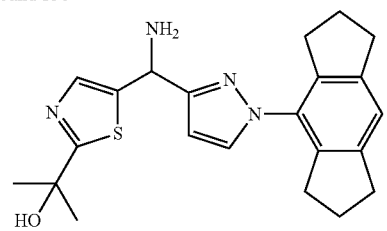

Intermediate 3 (Compound 135)

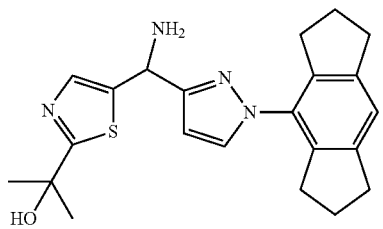

2-(5-(amino(1-(1,2,3,5,6,7-hexahydro-s-indacen-4-yl)-1H-pyrazol-3-yl)methyl)thiazol-2-yl)propan-2-ol

Step 1: 1-(1,2,3,5,6,7-Hexahydros-indacen-4-yl)-N-methoxy-N-methyl-1H-pyrazole-3-carboxamide Into a 100-mL round-bottom flask purged and maintained with an inert atmosphere of nitrogen, was placed a solution of 1-(1,2,3,5,6,7-hexahydros-indacen-4-yl)-1H-pyrazole-3-carboxylic acid (3.20 g, 11.93 mmol) in DMF (40 mL), N,O-dimethylhydroxylamine hydrochloride (1.74 g, 17.89 mmol), EDCI (3.43 g, 17.89 mmol), HOBt (2.42 g, 17.89 mmol), TEA (4.83 g, 47.71 mmol). The resulting solution was stirred for 2 h at RT. The reaction was then quenched by the addition of 30 mL of water/ice. The resulting solution was extracted with 3×40 mL of ethyl acetate. The resulting mixture was washed with 3×30 ml of brine. The mixture was dried over anhydrous sodium sulfate and concentrated. The residue was applied onto a silica gel column and eluted with ethyl acetate/petroleum ether (1:10). This resulted in 2.8 g (75.4%) of the title compound as a light-yellow solid. MS-ESI: 312.2 (M+1).

Step 2: (1-(1,2,3,5,6,7-Hexahydros-indacen-4-yl)-1H-pyrazol-3-yl)(2-(2-hydroxypropan-2-yl)thiazol-5-yl)methanone Into a 100-mL round-bottom flask purged and maintained with an inert atmosphere of nitrogen, was placed a solution of 2-(1,3-thiazol-2-yl)propan-2-ol (300 mg, 2.10 mmol) in THF (5 mL), n-BuLi (1.26 ml, 2.5 M in THF, 3.14 mmol) was added dropwise at −78° C. The resulting solution was stirred for 1 h at −78° C. Then 1-(1,2,3,5,6,7-hexahydros-indacen-4-yl)-N-methoxy-N-methyl-1H-pyrazole-3-carboxamide (652 mg, 2.10 mmol) in THF (2 mL) was added dropwise at −78° C. The resulting solution was stirred for 16 h at RT. The reaction was then quenched by the addition of 10 mL of NH₄Cl(aq.). The resulting solution was extracted with 2×10 mL of ethyl acetate. The combined organic layer was washed with 2×10 mL of brine. The mixture was dried over anhydrous sodium sulfate and concentrated under vacuum. The crude product was purified by HP-Flash with MeCN/water. This resulted in 250 mg (30.3%) of the title compound as a yellow solid. MS-ESI: 394.2 (M+1).

Step 3: (2S)—N-((1-(1-(1,2,3,5,6,7-hexahydros-indacen-4-yl)-1H-pyrazol-3-yl)(2-(2-hydroxypropan-2-yl)thiazol-5-yl)methyl)-2-methylpropane-2-sulfinamide Into a 100-mL round-bottom flask purged and maintained with an inert atmosphere of nitrogen, was placed (1-(1,2,3,5,6,7-hexahydros-indacen-4-yl)-1H-pyrazol-3-yl)(2-(2-hydroxypropan-2-yl)thiazol-5-yl)methanone (100 mg, 0.25 mmol) in THF (10 mL), to this was added (S)-2-methylpropane-2-sulfinamide (154 mg, 1.27 mmol), then Ti(OEt)₄ (289 mg, 1.27 mmol) was added dropwise below 5° C. The resulting solution was stirred for 16 h at 85° C. Then NaBH₄ (96 mg, 2.54 mmol) was added in portions below 5° C. and 5 mL MeOH was added. The resulting solution was stirred for 2 h at RT. The reaction was then quenched by the addition of 10 mL of water/ice. The resulting solution was extracted with 2×10 mL of ethyl acetate and the combined organic layer was dried over anhydrous sodium sulfate, then concentrated under vacuum. The crude product was purified by HP-Flash with MeCN/water. This resulted in 32 mg (25.3%) of the title compound as a yellow solid. MS-ESI: 399.2 (M+1).

Step 4: 2-(5-(Amino(1-(1,2,3,5,6,7-hexahydros-indacen-4-yl)-1H-pyrazol-3-yl)methyl)thiazol-2-yl)propan-2-ol Into a 50-mL round-bottom flask, was placed a solution of (2S)—N-((1-(1,2,3,5,6,7-hexahydros-indacen-4-yl)-1H-pyrazol-3-yl)(2-(2-hydroxypropan-2-yl)thiazol-5-yl)methyl)-2-methylpropane-2-sulfinamide (25 mg, 0.050 mmol) in DCM (2 mL), to this was added HCl (0.1 mL, 1M in dioxane) below 5° C. The resulting solution was stirred for 30 min at room temperature. The resulting mixture was concentrated. The crude product was purified by Prep-HPLC with the following conditions: Column, Xselect CSH OBD Column 30*150 mm 5 um, n; mobile phase, Water (0.05% TFA) and ACN (30% Phase B up to 60% in 7 min); Detector, UV 254/210 nm. This resulted in 18.1 mg (91.5%) of the title compound as a solid. MS-ESI: 395.2 (M+1).

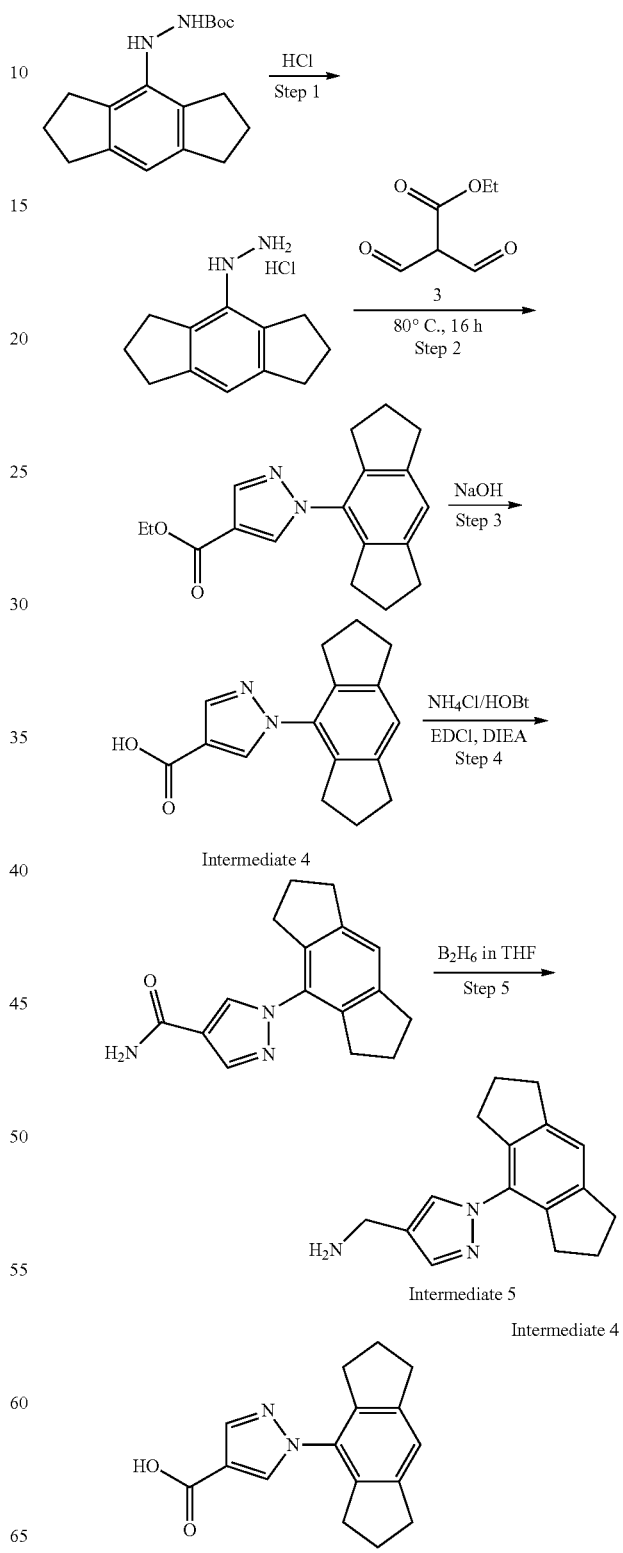

1-(1,2,3,5,6,7-Hexahydro-s-indacen-4-yl)-1H-pyrazole-4-carboxylic acid

Step 1: (1,2,3,5,6,7-Hexahydros-indacen-4-yl)hydrazine hydrochloride

Into a 100-mL round-bottom flask, was placed tert-butyl 2-(1,2,3,5,6,7-hexahydro-s-indacen-4-yl)hydrazine-1-carboxylate (5 g, 17.34 mmol), HCl/dioxane(4 N) (40 mL). The resulting solution was stirred for 16 h at 40° C. The resulting mixture was concentrated. This resulted in 4.5 g (crude) of the title compound as a brown solid. MS-ESI: 189.1 (M+1).

Step 2: Ethyl 1-(1,2,3,5,6,7-hexahydros-indacen-4-yl)-1H-pyrazole-4-carboxylate Into a 50-mL round-bottom flask, was placed (1,2,3,5,6,7-hexahydro-s-indacen-4-yl)hydrazine hydrogen chloride (1.5 g, 7.97 mmol) in ethanol (20 mL), to this was added ethyl 2-formyl-3-oxopropanoate (1.1 g, 7.97 mmol). The resulting solution was stirred for 16 h at 80° C. The resulting mixture was concentrated. The residue was applied onto a silica gel column and eluted with ethyl acetate/petroleum ether (1/5). This resulted in 1.4 g (59.3%) of the title compound as a white solid. MS-ESI: 297.2 (M+1).

Step 3: 1-(1,2,3,5,6,7-Hexahydros-indacen-4-yl)-1H-pyrazole-4-carboxylic acid Into a 100-mL round-bottom flask, was placed ethyl 1-(1,2,3,5,6,7-hexahydros-indacen-4-yl)-1H-pyrazole-4-carboxylate (1.7 g, 5.74 mmol) in MeOH (10 mL), NaOH (2.3 g, 57.36 mmol) in water (20 mL) was added. The resulting solution was stirred for 16 h at 40° C. The pH value of the solution was adjusted to 2 with HCl (6 N). The solids were collected by filtration. This resulted in 1.3 g (84.5%) of the title compound as a white solid. MS-ESI: 269.1 (M+1).

Intermediate 5

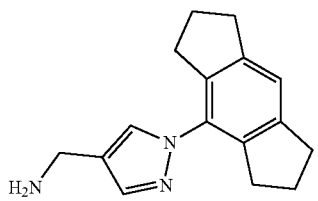 [SMILES: NCc1cnn(-c2c3c(cc4c2CCC4)CCC3)c1]

(1-(1,2,3,5,6,7-Hexahydro-s-indacen-4-yl)-1H-pyrazol-4-yl)methanamine

Step 4: 1-(1,2,3,5,6,7-Hexahydros-indacen-4-yl)-1H-pyrazole-4-carboxamide

Into a 100-mL round-bottom flask, was placed 1-(1,2,3,5,6,7-hexahydro-s-indacen-4-yl)-1H-pyrazole-4-carboxylic acid (400 mg, 1.49 mmol), NH₄Cl (159.5 mg, 2.98 mmol), DMF (50 mL), HOBT (302.2 mg, 2.24 mmol), EDCI (428.7 mg, 2.24 mmol), TEA (754.3 mg, 7.45 mmol). The resulting solution was stirred for 4 h at 80° C. in an oil bath. The reaction was then quenched by the addition of 200 mL of water. The resulting solution was extracted with 2×100 mL of ethyl acetate and the combined organic layer was dried over anhydrous sodium sulfate and concentrated. The residue was applied onto a silica gel column and eluted with ethyl acetate/petroleum ether (20/80). This resulted in 350 mg (87.8%) of the title compound as a light-yellow oil. MS-ESI: 268.1 (M+1).

Step 5: (1-(1,2,3,5,6,7-Hexahydros-indacen-4-yl)-1H-pyrazol-4-yl)methanamine Into a 50-mL round-bottom flask, was placed 1-(1,2,3,5,6,7-hexahydro-s-indacen-4-yl)-1H-pyrazole-4-carboxamide (300 mg, 1.12 mmol) in THF (15 mL), to this was added BH₃-THF(1N) (5 mL, 5 mmol). The resulting solution was stirred for 16 h at 50° C. in an oil bath. The reaction was then quenched by the addition of 5 mL of MeOH. The resulting mixture was concentrated.

The residue was applied onto a silica gel column and eluted with ethyl acetate/petroleum ether (25/75). This resulted in 200 mg (70.4%) of the title compound as light-yellow oil. MS-ESI: 254.2 (M+1).

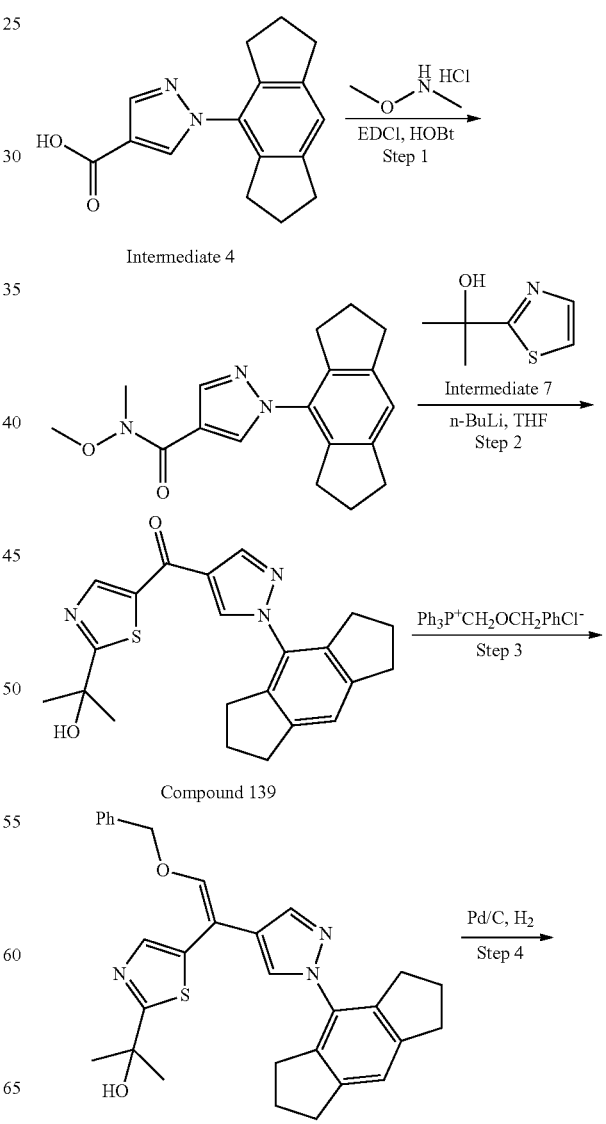

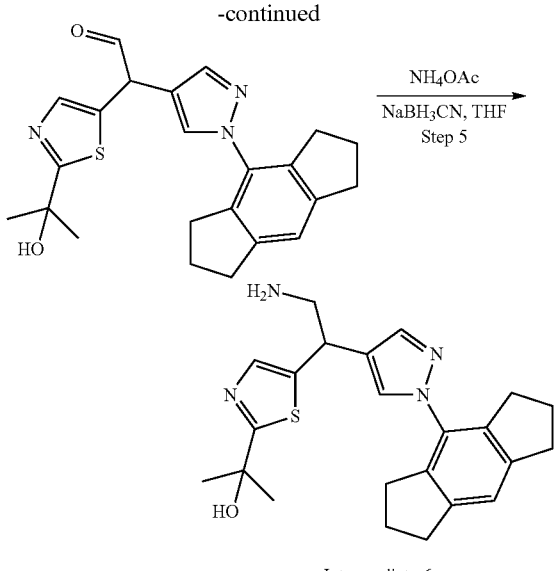

Intermediate 6

Intermediate 6 (Compound 136)

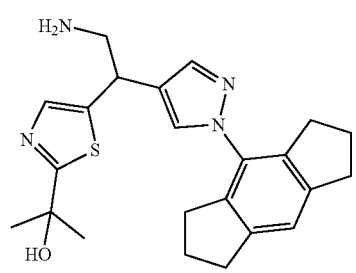 [SMILES: CC(C)(O)c1ncc(C(CN)c2cnn(-c3c4c(cc5c3CCC5)CCC4)c2)s1]

2-(5-(2-Amino-1-(1-(1,2,3,5,6,7-hexahydro-s-indacen-4-yl)-1H-pyrazol-4-yl)ethyl)thiazol-2-yl)propan-2-ol Step 1: 1-(1,2,3,5,6,7-Hexahydros-indacen-4-yl)-N-methoxy-N-methyl-1H-pyrazole-4-carboxamide Into a 100-mL round-bottom flask, was placed 1-(1,2,3,5,6,7-hexahydro-s-indacen-4-yl)-1H-pyrazole-4-carboxylic acid (1.3 g, 4.85 mmol) in DMF (25 mL), N,O-dimethylhydroxylamine hydrogen chloride (0.4 g, 7.27 mmol), HOBt (1.0 g, 7.27 mmol), EDC (1.1 g, 7.27 mmol, 1.5 equiv), TEA (2.5 g, 24.23 mmol, 5 equiv) was added. The resulting solution was stirred for 16 h at 50° C. The reaction was then quenched by the addition of 50 mL of water. The resulting solution was extracted with 3×35 mL of ethyl acetate and the combined organic layer was dried over anhydrous sodium sulfate, concentrated under vacuum. The residue was applied onto a silica gel column eluted with ethyl acetate/petroleum ether (1/1). This resulted in 580 mg (38.4%) of the title compound as a white solid. MS-ESI: 312.2 (M+1).

Step 2: (1-(1,2,3,5,6,7-Hexahydros-indacen-4-yl)-1H-pyrazol-4-yl)(2-(2-hydroxypropan-2-yl)thiazol-5-yl)methanone Into a 100-mL 3-necked round-bottom flask, was placed 2-(thiazol-2-yl)propan-2-ol (460 mg, 3.2 mmol), THF (30 mL), to this was added n-BuLi/THF (2.5N) (2 mL, 5 mmol) dropwise at −78° C., the resulting solution was stirred for 1 h at −78° C. This was followed by the addition of 1-(1,2,3,5,6,7-hexahydro-s-indacen-4-yl)-N-methoxy-N-methyl-1H-pyrazole-4-carboxamide (500 mg, 1.6 mmol). The resulting solution was stirred for 16 h at 25° C. The reaction was then quenched by the addition of 20 mL of water. The resulting solution was extracted with 3×25 mL of ethyl acetate and the combined organic layer was dried over anhydrous sodium sulfate and concentrated. The crude product was purified by Prep-HPLC with the following conditions: Column: Xselect CSH OBD Column 30*150 mm 5 um n; Mobile Phase A: Water (0.05% TFA), Mobile Phase B: ACN; Flow rate: 60 mL/min; Gradient: 40% B to 60% B in 9 min; 254/210 nm; Rt: 8.65 min. This resulted in 90 mg (14.2%) of the title compound as a white solid. MS-ESI: 394.2 (M+1).

Step 3: (Z)-2-(5-(2-(Benzyloxy)-1-(1-(1,2,3,5,6,7-hexahydros-indacen-4-yl)-1H-pyrazol-4-yl)vinyl)thiazol-2-yl)propan-2-ol Into a 50-mL 3-necked round-bottom flask, was placed ((benzyloxy)methyl)triphenylphosphonium chloride (512 mg, 1.23 mmol) in THF (25 mL), then LiHMDS(1N) (2.34 mL, 2.34 mmol) was added dropwise below −5° C., this was followed by the addition of (1-(1,2,3,5,6,7-hexahydro-s-indacen-4-yl)-1H-pyrazol-4-yl)(2-(2-hydroxypropan-2-yl)thiazol-5-yl)methanone (400 mg, 1.02 mmol) in THF (5 mL) dropwise below −5° C. The resulting solution was stirred for 24 h at 0-5° C. The reaction was then quenched by the addition of 30 mL of water. The resulting solution was extracted with 3×30 mL of ethyl acetate and the combined organic layer was dried over anhydrous sodium sulfate. The residue was applied onto a silica gel column eluted with (MeOH/DCM=1/10). This resulted in 270 mg (53.2%) of the title compound as an off-white solid. MS-ESI: 498.2 (M+1).

Step 4: 2-(1-(1,2,3,5,6,7-Hexahydros-indacen-4-yl)-1H-pyrazol-4-yl)-2-(2-(2-hydroxypropan-2-yl)thiazol-5-yl)acetaldehyde Into a 50-mL round-bottom flask, was placed (Z)-2-(5-(2-(benzyloxy)-1-(1-(1,2,3,5,6,7-hexahydro-s-indacen-4-yl)-1H-pyrazol-4-yl)vinyl)thiazol-2-yl)propan-2-ol (500 mg, 1.01 mmol) in MeOH (50 mL), Pd/C (wet. 10% wt.) (50 mg) was added. The flask was evacuated and filled three times with hydrogen. The resulting solution was stirred for 16 h at RT. The solids were filtered out. The resulting mixture was concentrated. The residue was purified by prep-TLC (EA/PE=1/1). This resulted in 100 mg (24.2%) of the title compound as a yellow solid. MS-ESI: 408.2 (M+1).

Step 5: 2-(5-(2-Amino-1-(1-(1,2,3,5,6,7-hexahydros-indacen-4-yl)-1H-pyrazol-4-yl)ethyl)thiazol-2-yl)propan-2-ol Into a 25-mL round-bottom flask, was placed 2-(1-(1,2,3,5,6,7-hexahydro-s-indacen-4-yl)-1H-pyrazol-4-yl)-2-(2-(2-hydroxypropan-2-yl)thiazol-5-yl)acetaldehyde (100 mg, 0.25 mmol) MeOH (10 mL), NH₄OAc (100 mg, 1.25 mmol) was added, then NaCNBH₃ (46 mg, 0.75 mmol) was added in portions below 5° C. The resulting solution was stirred for 2 h at RT. The reaction was then quenched by the addition of 10 mL of water. The resulting solution was extracted with 3×10 mL of ethyl acetate and the organic layers combined and dried over anhydrous sodium sulfate and concentrated. The crude product was purified by Prep-HPLC with the following conditions: Column: Xselect CSH OBD Column 30*150 mm 5 um; Mobile Phase A: Water (0.05% TFA), Mobile Phase B: ACN; Flow rate: 60 mL/min; Gradient: 17% B to 40% B in 8 min; 254/210 nm; Rt: 7.65 min. This resulted in 20 mg (20.0%) of the title compound as a white solid. MS-ESI: 409.2 (M+1).

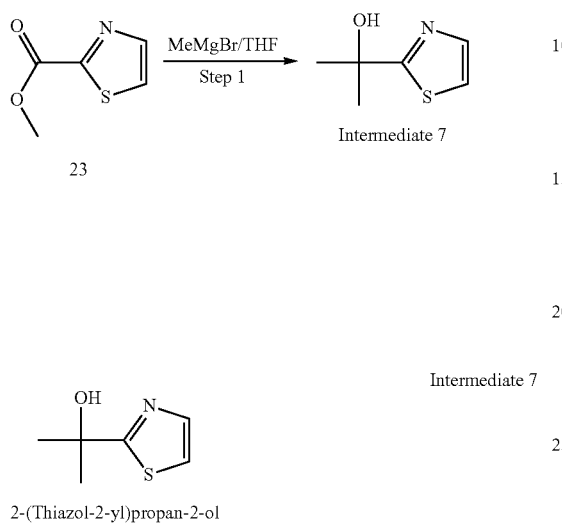

Intermediate 7

2-(Thiazol-2-yl)propan-2-ol

Step 1: 2-(Thiazol-2-yl)propan-2-ol

Into a 2000-mL 3-necked round-bottom flask purged and maintained with an inert atmosphere of nitrogen, was placed MeMgBr/THF (262 mL, 2.27 mol). This was followed by the addition of methyl thiazole-2-carboxylate (50 g, 0.39 mmol) in THF (500 mL) dropwise with stirring below 5° C. The resulting solution was stirred for 3 h at RT. The reaction was then quenched by the addition of 30 mL of NH₄Cl(sat.). The resulting solution was extracted with 3×1 L of ethyl acetate. The combined organic layer was dried over anhydrous $Na_2SO_4$ and concentrated under vacuum. The crude product was purified by normal phase with ethyl acetate/ petroleum (1/1) This resulted in 38 g (67.5%) of the title compound as yellow oil. MS-ESI: 144.0 (M+1).

Example 17 (Compound 102)

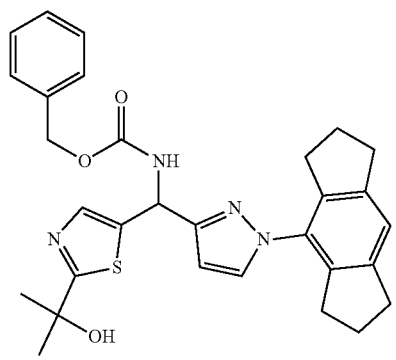 [SMILES: CC(C)(O)c1ncc(C(NC(=O)OCc2ccccc2)c2ccn(-c3c4c(cc5c3CCC5)CCC4)n2)s1]

Benzyl (1-(1,2,3,5,6,7-hexahydros-indacen-4-yl)-1H-pyrazol-3-yl)(2-(2-hydroxypropan-2-yl)thiazol-5-yl)methylcarbamate (Scheme IV)

Examples 18 (Compound 117) and 19 (Compound 116)

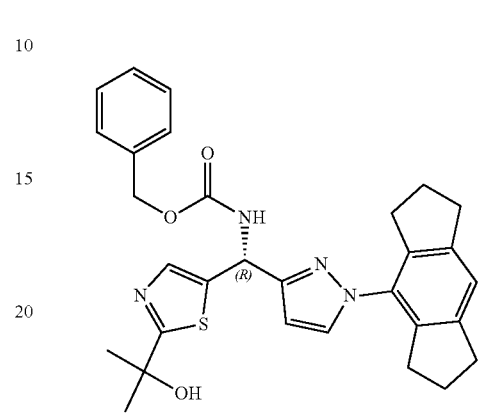

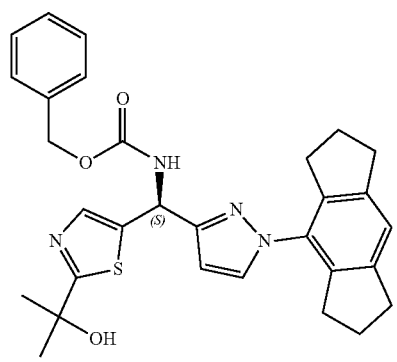

Examples 18 and 19 (stereochemistry tentatively assigned)

(R)- and (S)-(1-(1,2,3,5,6,7-hexahydros-indacen-4-yl)-1H-pyrazol-3-yl)(2-(2-hydroxypropan-2-yl)thiazol-5-yl)methylcarbamate

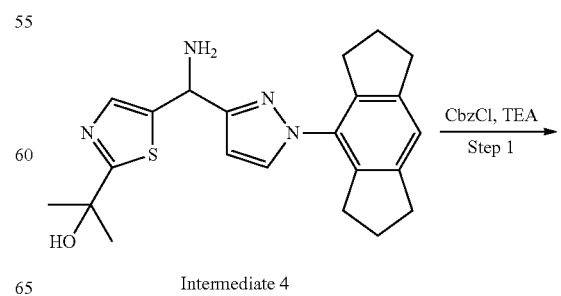

Intermediate 4

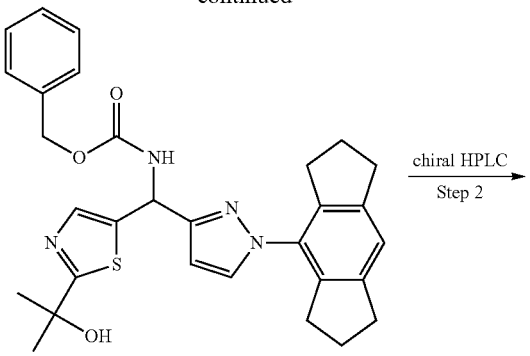

Example 17

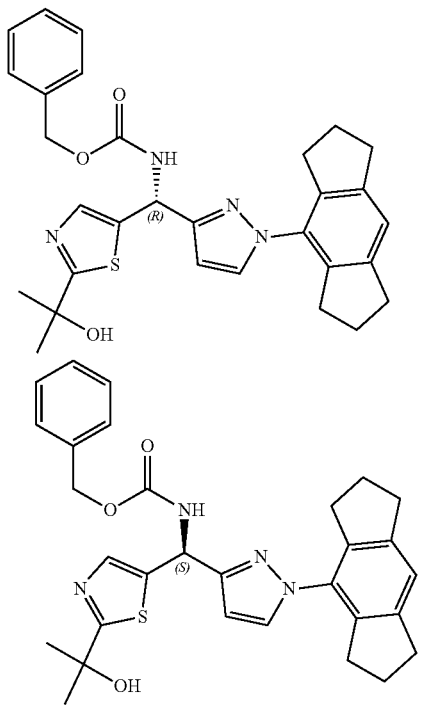

Examples 18 and 19 (stereochemistry tentatively assigned)

Step 1: Benzyl ((1-(1,2,3,5,6,7-hexahydro-s-indacen-4-yl)-1H-pyrazol-3-yl)(2-(2-hydroxypropan-2-yl)thiazol-5-yl)methyl)carbamate Into a 25-mL round-bottom flask, was placed a solution of 2-(5-(amino(1-(1,2,3,5,6,7-hexahydro-s-indacen-4-yl)-1H-pyrazol-3-yl)methyl)thiazol-2-yl)propan-2-ol (120 mg, 0.30 mmol) in DCM (20 mL), to this was added TEA (92 mg, 0.90 mmol) and CbzCl (71 mg, 0.50 mmol) below 5° C. The resulting solution was stirred for 30 min at RT. The resulting mixture was concentrated directly. The crude product was purified by Prep-HPLC with the following conditions: Column, Xselect CSH OBD Column 30*150 mm Sum; mobile phase, Water (0.05% TFA) and ACN (30% Phase B up to 50% in 9 min); Detector, UV 254/210 nm. This resulted in 50 mg (31.2%) of Example 17 (Compound 102) as a white solid. MS-ESI: 529.2 (M+1). $^1$H NMR (400 MHz, DMSO-$d_6$): 7.79 (d, J=2.0 Hz, 1H), 7.48 (br s, 1H), 7.45-7.25 (m, 5H), 7.17 (s, 1H), 6.52 (d, J=2.4 Hz, 1H), 6.31 (s, 1H), 5.17 (s, 2H), 2.94 (t, J=7.2 Hz, 4H), 2.79 (t, J=7.2 Hz, 4H), 2.20-2.00 (m, 4H), 1.59 (s, 6H)

Step 2: Chiral Resolution 50 mg of Example 4 was separated by Chiral-Prep-HPLC with the following conditions: Column CHIRALPAK IE, 2*25 cm, 5 um; Mobile Phase A: Hex (8 mmol/L NH$_3$·MeOH), Mobile Phase B: EtOH; Flow rate: 20 mL/min; Gradient: 20% B to 20% B in 32 min; 220/254 nm; RT1: 15.99; RT2: 18.62 min. This resulted in 10 mg of Example 18 (Compound 117) and 12 mg of Example 19 (Compound 116) both as a white solid.

Example 18 (Compound 117) 99.6% ee, MS-ESI: 529.2 (M+1). $^1$H NMR (400 MHz, DMSO-$d_6$): 7.79 (d, J=2.0 Hz, 1H), 7.48 (s, 1H), 7.45-7.25 (m, 5H), 7.17 (s, 1H), 6.52 (d, J=2.4 Hz, 1H), 6.31 (s, 1H), 5.16 (s, 2H), 2.94 (t, J=7.2 Hz, 4H), 2.79 (t, J=7.2 Hz, 4H), 2.20-2.00 (m, 4H), 1.59 (s, 6H)

Example 19 (Compound 116) 90.0% ee, MS-ESI: 529.2 (M+1). $^1$H NMR (400 MHz, DMSO-$d_6$): 7.79 (d, J=2.0 Hz, 1H), 7.48 (s, 1H), 7.45-7.25 (m, 5H), 7.17 (s, 1H), 6.52 (d, J=2.4 Hz, 1H), 6.31 (s, 1H), 5.17 (s, 2H), 2.94 (t, J=7.2 Hz, 4H), 2.79 (t, J=7.2 Hz, 4H), 2.20-2.00 (m, 4H), 1.59 (s, 6H)

TABLE 2

Examples in the following table were prepared using similar conditions as described in Example 17 and Scheme IV from appropriate starting materials.

| Example # | Compound Number | Structure | IUPAC Name | Exact Mass [M + H]$^+$ |
|---|---|---|---|---|
| 20 | Compound 200 | 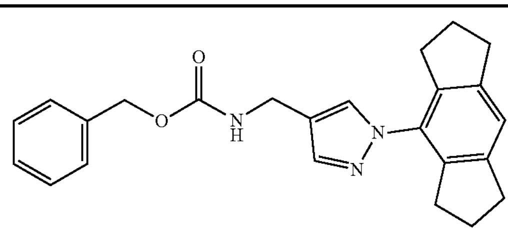 | Benzyl ((1-(1,2,3,5,6,7-hexahydro-s-indacen-4-yl)-1H-pyrazol-4-yl)methyl)carbamate | 388.2 |

TABLE 2-continued

Examples in the following table were prepared using similar conditions as described in
Example 17 and Scheme IV from appropriate starting materials.

| Example # | Compound Number | Structure | IUPAC Name | Exact Mass [M + H]⁺ |
|---|---|---|---|---|
| 21 | Compound 134 | 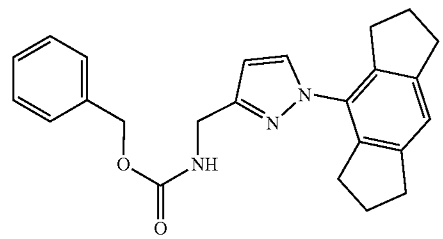 [SMILES: O=C(NCc1ccn(-c2c3c(cc4c2CCC4)CCC3)n1)OCc1ccccc1] | Benzyl ((1-(1,2,3,5,6,7-hexahydro-s-indacen-4-yl)-1H-pyrazol-3-yl)methyl) carbamate | 388.2 |
| 22 | Compound 101 | 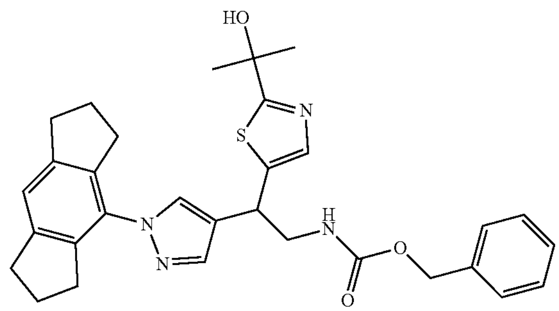 [SMILES: CC(C)(O)c1ncc(C(CNC(=O)OCc2ccccc2)c2cnn(-c3c4c(cc5c3CCC5)CCC4)c2)s1] | Benzyl (2-(1-(1,2,3,5,6,7-hexahydro-s-indacen-4-yl)-1H-pyrazol-4-yl)-2-(2-(2-hydroxypropan-2-yl)thiazol-5-yl)ethyl) carbamate | 543.2 |

The following protocol is suitable for testing the activity of the compounds disclosed herein.

Procedure 1: IL-1β Production in PMA-Differentiated THP-1 Cells Stimulated with Gramicidin.

THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g. 100, 33, 11, 3.7, 1.2, 0.41, 0.14, 0.046, 0.015, 0.0051, 0.0017 μM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 μg/ml). The cells were plated in the 384-well assay plate containing the spotted compounds at a density of 50,000 cells/well (final assay volume 50 μl). Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 2: IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were first dissolved in assay medium to obtain a 5× top concentration of 500 μM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 μM). Final DMSO concentration was at 0.37%. Cells were incubated with compounds for 1 hour and then stimulated with gramicidin (5 μM) (Enzo) for 2 hours. Plates were then centrifuged at 340 g for 5 min. Cell free supernatant (40 µL) was collected using a 96-channel PlateMaster (Gilson) and the production of IL-1β was evaluated by HTRF (cisbio). A vehicle only control and a dose titration of CRID3 (100-0.0017 µM) were run concurrently with each experiment. Data was normalized to vehicle-treated samples (equivalent to 0% inhibition) and CRID3 at 100 (equivalent to 100% inhibition). Compounds exhibited a concentration-dependent inhibition of IL-1β production in PMA-differentiated THP-1 cells.

Procedure 3

1. Experimental Procedure 1.1 Cell Culture
   1) Culture THP-1 cells in the complete RPMI-1640 medium with 10% FBS at 37° C., 5% $CO_2$.
   2) Passage the cells every 3 days by inoculating $3 \times 10^5$ cells per ml.

Figure 5:
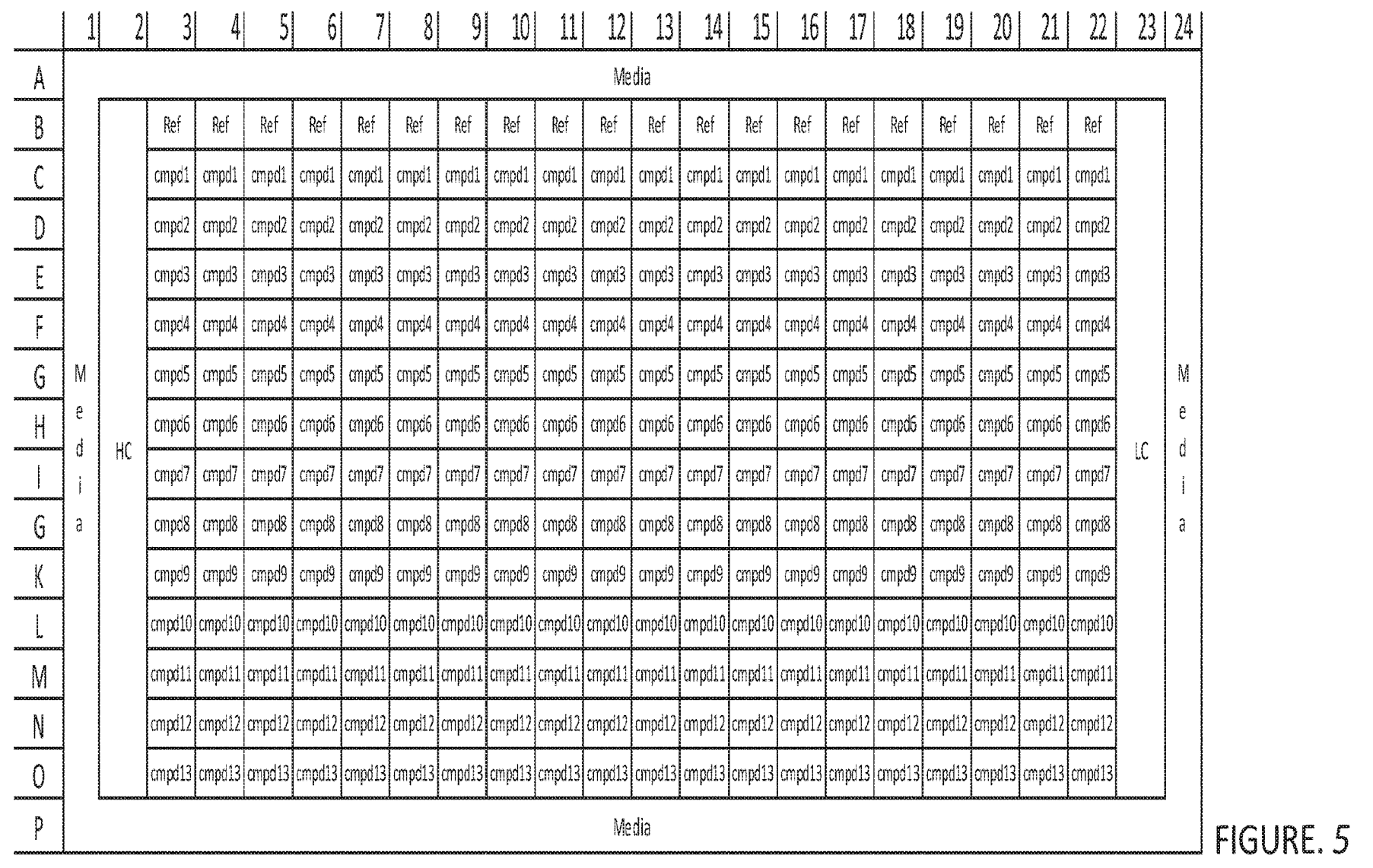

1.2 Compound Preparation
   Prepare the 3-fold serial dilution of the compounds with DMSO in a 384-well LDV Microplate using TECAN EVO system to generate the compound source plate with 10 concentrations. Top concentration is 30 mM. FIG. 5 depicts the layout of the microplate.

1.3 Cell Preparation
   1) Centrifuge THP-1 cells at 350 g for 5 min.
   2) Re-suspend cells with complete RMPI-1640 medium, and count cells.
   3) Seed cells in T225 flask, about $2.5 \times 10^7$ per flask, treat cells with 20 ng/ml PMA (final DMSO concentration<1%).
   4) Incubate overnight.

1.4 THP-1 Stimulation
   1) Wash adherent THP-1 cells with PBS, and detach cells with 4 ml trypsin for T225 flask.
   2) Centrifuge cells at 350 g for 5 min, re-suspend cells with RPMI-1640 containing 2% FBS and count cells with trypan blue.
   3) Transfer 50 nl/well the serial dilution of test compound to 384-well plate by Echo; For the high control and first point of CRID3 (MCC950), transfer 165 nl, then backfill to make the DMSO concentration is consistent in all wells, the plate layout is as below.
   4) Seed 50 k cells in 40 ul RPMI-1640 with 2% FBS per well in 384-well plate.
   5) Incubate for 1 h at 37° C., 5% $CO_2$.
   6) Prepare 5× gramicidin, add 10 µl per well, the final concentration is 5 µM, incubate for 2 hrs at 37° C., 5% $CO_2$.
   7) Centrifuge at 350 g for 1 min.
   8) Pipet 16 µl supernatant by apricot, and transfer into white 384 proxiplate. FIG. 5 depicts the layout of the plates: HC: 100 µM CRID3 (MCC950)+5 µM gramicidin LC: 5 µM Gramicidin.

1.5 IL-1β Detection
   1) Homogenize the 5× diluent #5 with a vortex and add 1 volume of stock solution in 4 volumes of distilled water.
   2) Thaw 20× stock solution of anti-IL1β-Cryptate-antibody and anti-IL1β XL-antibody. Dilute these two antibodies to 1× with detection buffer #3.
   3) Pre-mix the two ready-to-use antibody solutions just prior to use.
   4) Dispense 4 ul of pre-mixed Anti-IL1β antibodies working solution into all wells.
   5) Seal the plate and incubate overnight at 4° C.
   6) Read the cell plate using EnVison and plot Readout vs. the test compound concentration to calculate the $IC_{50}$.

2. Data Analysis:
   1. $IC_{50}$ of compounds can be calculated using the following formulas % inhibition=100−100×[$HC_{ave}$−Readout/($HC_{ave}$−$LC_{ave}$)]   Formula for $IC_{50}$ 2. Fit the normalized data in a dose-response manner using XLfit, and calculate the compound concentration.

Table 3 shows the biological activity of compounds in hTHP-1 assay containing 2% fetal bovine serum: <0.008 µM="++++++"; ≥0.008 and <0.04 µM="+++++"; ≥0.04 and <0.2 µM="++++"; ≥0.2 and <1 µM="+++"; ≥1 and <5 µM="++"; ≥5 and <30 µM="+".

TABLE 3

Average $IC_{50}$ of compounds in hTHP-1 assay

| Compound # | THP-1 $IC_{50}$ |
|---|---|
| 101 | ++ |
| 102 | + |
| 103 | + |
| 104 | + |
| 105 | + |
| 114 | + |
| 115 | + |
| 116 | + |
| 118 | + |
| 119 | + |
| 120 | + |
| 200 | + |

Study Example 1

The CARD8 gene is located within the inflammatory bowel disease (IBD) 6 linkage region on chromosome 19. CARD8 interacts with NLRP3, and Apoptosis-associated Speck-like protein to form a caspase-1 activating complex termed the NLRP3 inflammasome. The NLRP3 inflammasome mediates the production and secretion of interleukin-1β, by processing pro-IL-1β into mature secreted IL-1β. In addition to its role in the inflammasome, CARD8 is also a potent inhibitor of nuclear factor NF-κB. NF-κB activation is essential for the production of pro-IL-14. Since overproduction of IL-1β and dyregulation of NF-κB are hallmarks of Crohn's disease, CARD8 is herein considered to be a risk gene for inflammatory bowel disease. A significant association of CARD8 with Crohn's disease was detected in two British studies with a risk effect for the minor allele of the non-synonymous single-nucleotide polymorphism (SNP) of a C allele at rs2043211. This SNP introduces a premature stop codon, resulting in the expression of a severely truncated protein. This variant CARD8 protein is unable to suppress NF-κB activity, leading to constitutive production of pro-IL-1β, which is a substrate for the NLRP3 inflammasome. It is believed that a gain-of-function mutation in an NLRP3 gene (e.g., any of the gain-of-function mutations described herein, e.g., any of the gain-of-function mutations in an NLRP3 gene described herein) combined with a loss-of-function mutation in a CARD8 gene (e.g., a C allele at rs2043211) results in the development of diseases related to increased NLRP3 inflammasome expression and/or activity. Patients having, e.g., a gain-of-function mutation in an NLRP3 gene and/or a loss-of-function mutation in a CARD8 gene are predicted to show improved therapeutic response to treatment with an NLRP3 antagonist.

A study is designed to determine: whether NLRP3 antagonists inhibit inflammasome function and inflammatory activity in cells and biopsy specimens from patients with Crohn's disease or ulcerative colitis; and whether the specific genetic variants identify patients with Crohn's disease or ulcerative colitis who are most likely to respond to treatment with an NLRP3 antagonist.

The secondary objectives of this study are to: determine if an NLRP3 antagonist reduces inflammasome activity in Crohn's disease and ulcerative biopsy samples (comparing Crohn's disease and ulcerative colitis results with control patient results); determine if an NLRP3 antagonist reduced inflammatory cytokine RNA and protein expression in Crohn's disease and ulcerative colitis samples; determine if baseline (no ex vivo treatment) RNA levels of NLRP3, ASC, and IL-1β are greater in biopsy samples from patients with anti-TNFα agent resistance status; and stratify the results according to presence of specific genetic mutations in genes encoding ATG16L1, NLRP3, and CARD8 (e.g., any of the mutations in the ATG16L1 gene, NLRP3 gene, and CARD8 gene described herein).

Methods

Evaluation of baseline expression of NLRP3 RNA and quantify inhibition of inflammasome activity by an NLRP3 antagonist in biopsies of disease tissue from patients with Crohn's disease and ulcerative colitis.

Determine if NLRP3 antagonist treatment reduces the inflammatory response in biopsies of disease from patients with Crohn's disease based on decreased expression of inflammatory gene RNA measured with Nanostring.

Sequence patient DNA to detect specific genetic mutations in the ATG16L1 gene, NLRP3 gene, and CARD8 gene (e.g., any of the exemplary mutations in these genes described herein) and then stratify the results of functional assays according to the presence of these genetic mutations.

Experimental Design

Human subjects and tissue:

Endoscopic or surgical biopsies from areas of disease in patients with Crohn's disease and ulcerative colitis who are either anti-TNFα treatment naïve or resistant to anti-TNFα treatment; additionally biopsies from control patients (surveillance colonoscopy or inflammation-free areas from patients with colorectal cancer) are studied.

Ex vivo Treatment Model:

Organ or LPMC culture as determined appropriate

Endpoints to be measured:

Before ex vivo treatment—NLRP3 RNA level

After ex vivo treatment-inflammasome activity (either processed IL-1β, processed caspase-1, or secreted IL-1β); RNA for inflammatory cytokines (Nanostring); viable T cell number and/or T cell apoptosis.

Data Analysis Plan:

Determine if NLRP3 antagonist treatment decreases processed IL-1β, processed caspase-1 or secreted IL-1β, and inflammatory cytokine RNA levels.

Stratify response data according to treatment status at biopsy and the presence of genetic mutations in the NLRP3 gene, CARD8 gene, and ATG16L1 gene (e.g., any of the exemplary genetic mutations of these genes described herein).

Study Example 2. Treatment of Anti-TNFα Resistant Patients with NLRP3 Antagonists PLoS One 2009 Nov. 24; 4(11):e7984, describes that mucosal biopsies were obtained at endoscopy in actively inflamed mucosa from patients with Ulcerative Colitis, refractory to corticosteroids and/or immunosuppression, before and 4-6 weeks after their first infliximab (an anti-TNFα agent) infusion and in normal mucosa from control patients. The patients in this study were classified for response to infliximab based on endoscopic and histologic findings at 4-6 weeks after first infliximab treatment as responder or non-responder. Transcriptomic RNA expression levels of these biopsies were accessed by the inventors of the invention disclosed herein from GSE 16879, the publically available Gene Expression Omnibus (https://www.ncbi.nlm.nih.gov/geo/geo2r/?acc=GSE16879).

Figure 2:
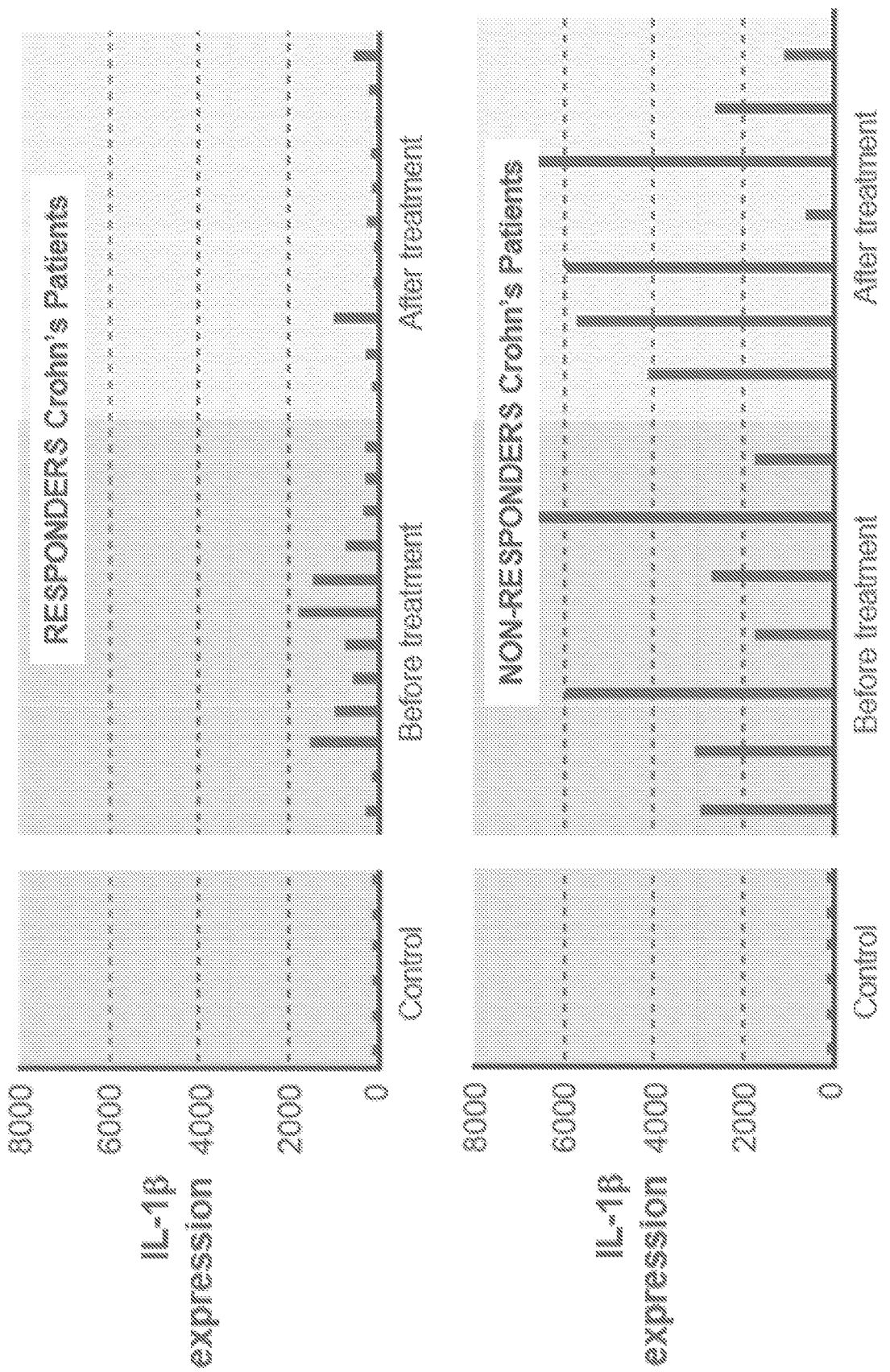
FIG. 2: Expression levels of RNA encoding IL-1β in Crohn's Disease patients who are responsive and non-responsive to infliximab.
Figure 3:
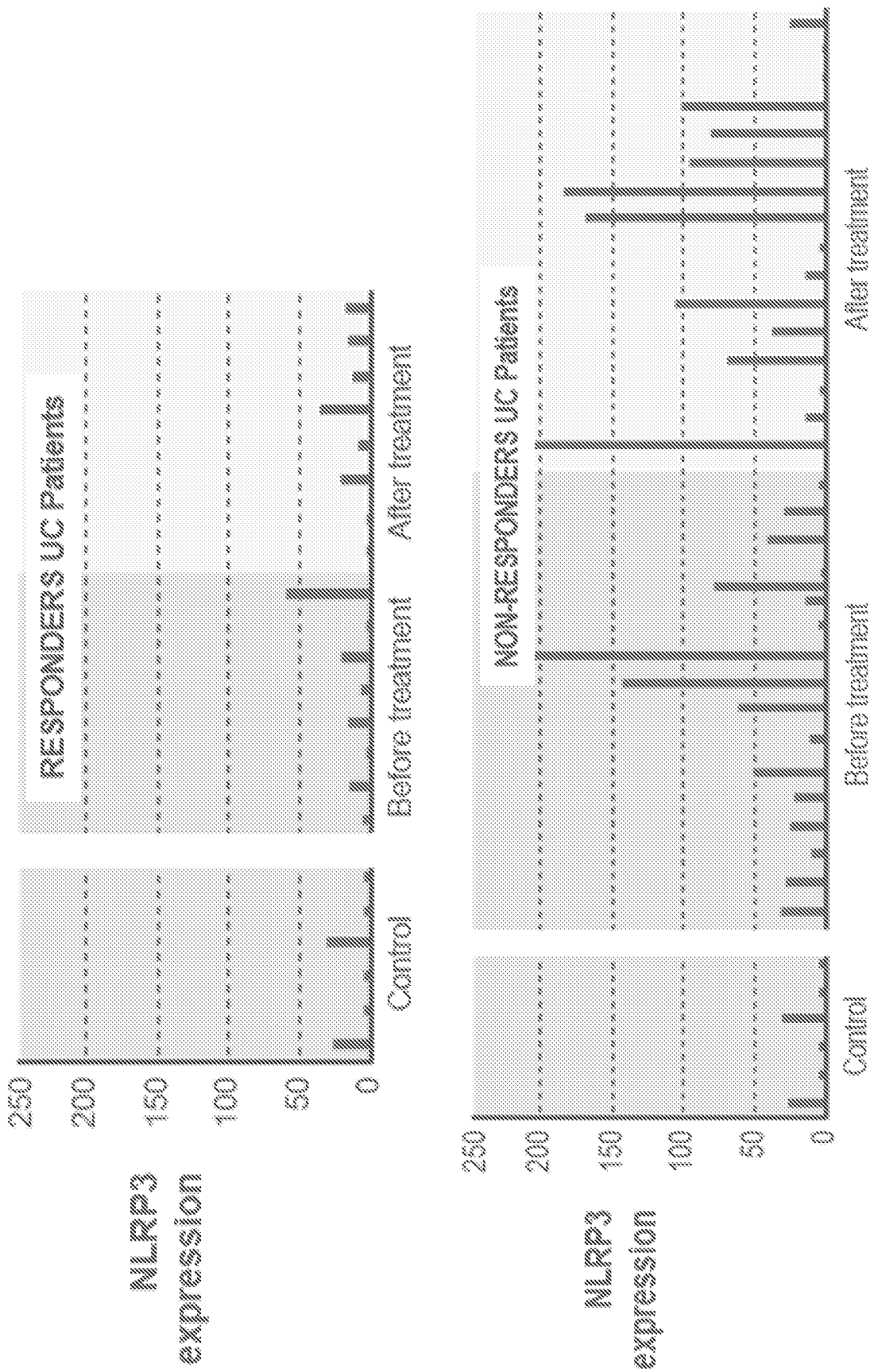
FIG. 3: Expression levels of RNA encoding NLRP3 in Ulcerative Colitis (UC) patients who are responsive and non-responsive to infliximab.
Figure 4:
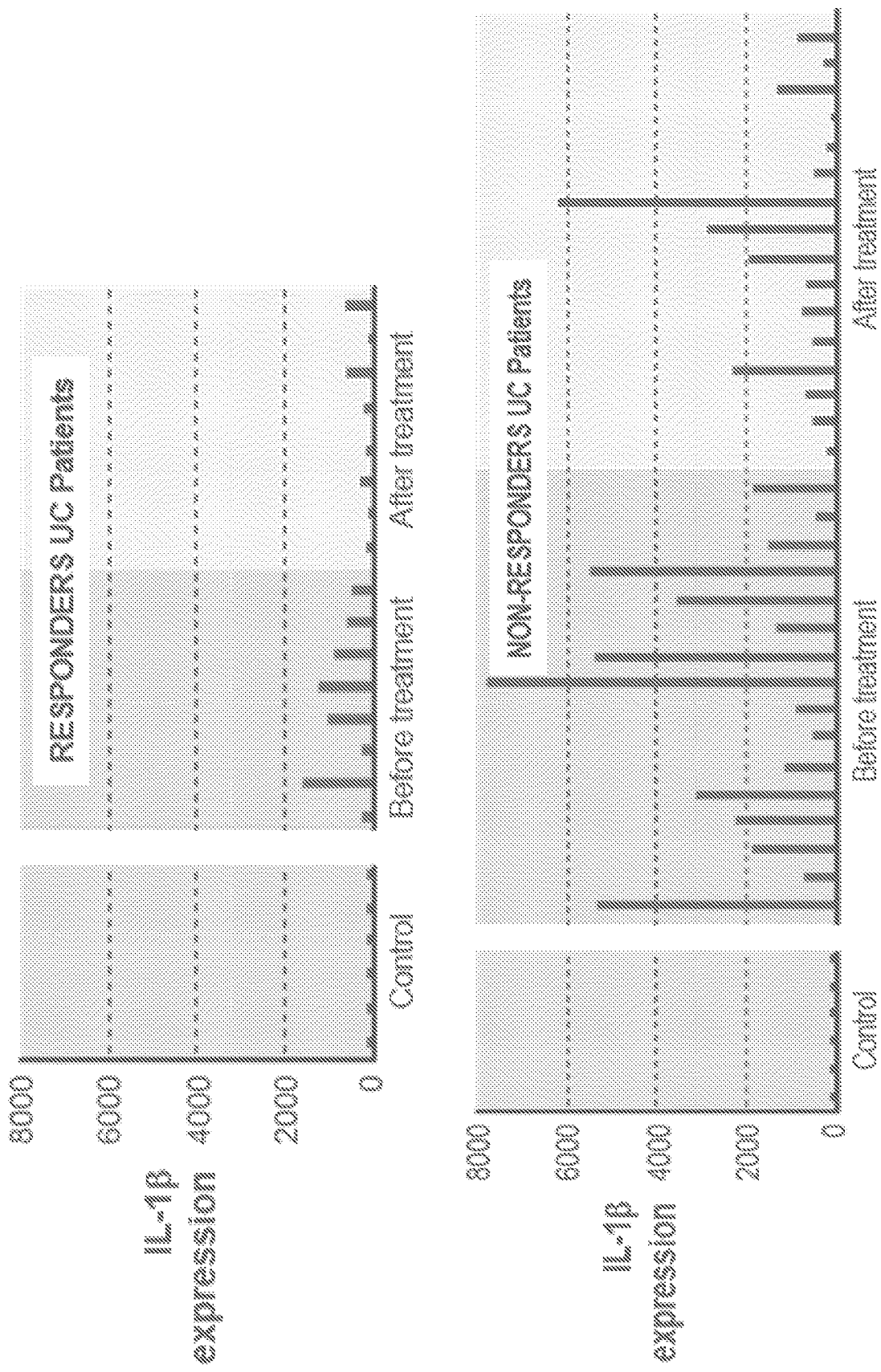
FIG. 4: Expression levels of RNA encoding IL-1β in Ulcerative Colitis (UC) patients who are responsive and non-responsive to infliximab.

Expression levels of RNA encoding NLRP3 and IL-1β were determined using GEO2R (a tool available on the same website), based on probe sets 207075_at and 205067_at, respectively. It was surprisingly found that in Crohn's disease patients that are non-responsive to the infliximab (an anti-TNFα agent) have higher expression of NLRP3 and IL-1β RNA than responsive patients (FIGS. 1 and 2). Similar surprising results of higher expression of NLRP3 and IL-1β RNA in UC patients that are non-responsive to infliximab (an anti-TNFα agent) compared to infliximab (an anti-TNFα agent) responsive patients (FIGS. 3 and 4) were found.

Said higher levels of NLRP3 and IL-1β RNA expression levels in anti-TNFα agent non-responders, is hypothesised herein to lead to NLRP3 activation which in turns leads of release of IL-1β that induces IL-23 production, leading to said resistance to anti-TNFα agents. Therefore, treatment of Crohn's and UC anti-TNFα non-responders with an NLRP3 antagonist would prevent this cascade, and thus prevent development of non-responsiveness to anti-TNFα agents. Indeed, resistance to anti-TNFα agents is common in other inflammatory or autoimmune diseases. Therefore, use of an NLRP3 antagonist for the treatment of inflammatory or autoimmune diseases will block the mechanism leading to non-responsiveness to anti-TNFα☐ agents. Consequently, use of NLRP3 antagonists will increase the sensitivity of patients with inflammatory or autoimmune diseases to anti-TNFα agents, resulting in a reduced dose of anti-TNFα agents for the treatment of these diseases. Therefore, a combination of an NLRP3 antagonist and an anti-TNFα agent can be used in the treatment of diseases wherein TNFα is overexpressed, such as inflammatory or autoimmune diseases, to avoid such non-responsive development of patients to anti-TNFα agents. Preferably, this combination treatment can be used in the treatment of IBD, for example Crohn's disease and UC.

Further, use of NLRP3 antagonists offers an alternative to anti-TNFα agents for the treatment of diseases wherein TNFα is overexpressed. Therefore, NLRP3 antagonists offers an alternative to anti-TNFα agents inflammatory or autoimmune diseases, such as IBD (e.g. Crohn's disease and UC).

Systemtic anti-TNFα agents are also known to increase the risk of infection. Gut restricted NLRP3 antagonists, however, offers a gut targeted treatment (i.e. non-systemic treatment), preventing such infections. Therefore, treatment of TNFα gut diseases, such as IBD (i.e. Crohn's disease and UC), with gut restricted NLRP3 antagonists has the additional advantage of reducing the risk of infection compared to anti-TNFα agents.

Proposed Experiment:

Determine the expression of NLRP3 and caspase-1 in LPMCs and epithelial cells in patients with non-active disease, in patients with active disease, in patients with active disease resistant to corticosteroids, patients with active disease resistant to TNF-blocking agents. The expression of NLRP3 and caspase-1 in LPMCs and epithelial cells will be analyzed by RNAScope technology. The expression of active NLRP3 signature genes will be analyzed by Nanostring technology. A pilot analysis to determine feasibility will be performed with 5 samples from control, 5 samples from active CD lesions, and 5 samples from active UC lesions.

Study Example 3

It is presented that NLRP3 antagonists reverse resistance to anti-TNF induced T cell depletion/apoptosis in biopsy samples from IBD patients whose disease is clinically considered resistant or unresponsive to anti-TNF therapy.

A study is designed to determine: whether NLRP3 antagonists inhibit inflammasome function and inflammatory activity in cells and biopsy specimens from patients with Crohn's disease or ulcerative colitis; and whether an NLRP3 antagonist will synergize with anti-TNFα therapy in patients with Crohn's disease or ulcerative colitis.

The secondary objectives of this study are to: determine if an NLRP3 antagonist reduces inflammasome activity in Crohn's disease and ulcerative biopsy samples (comparing Crohn's disease and ulcerative colitis results with control patient results); determine if an NLRP3 antagonist reduced inflammatory cytokine RNA and protein expression in Crohn's disease and ulcerative colitis samples; determine if an NLRP3 antagonist in the absence of co-treatment with anti-TNFα antibody induces T cell depletion in Crohn's disease and ulcerative colitis biopsy samples; and determine if baseline (no ex vivo treatment) RNA levels of NLRP3, ASC, and IL-1β are greater in biopsy samples from patients with anti-TNFα agent resistance status.

Methods
  Evaluation of baseline expression of NLRP3 RNA and quantify inhibition of inflammasome activity by an NLRP3 antagonist in biopsies of disease tissue from patients with Crohn's disease and ulcerative colitis.
  Determine if there is synergy between an NLRP3 antagonist and anti-TNF antibody with respect to effects on T cell depletion/apoptosis in biopsies of disease from patients with Crohn's disease and ulcerative colitis.
  Determine if NLRP3 antagonist treatment reduces the inflammatory response in biopsies of disease from patients with Crohn's disease based on decreased expression of inflammatory gene RNA measured with Nanostring.

Experimental Design
  Human subjects and tissue:
    Endoscopic or surgical biopsies from areas of disease in patients with Crohn's disease and ulcerative colitis who are either anti-TNFα treatment naïve or resistant to anti-TNFα treatment; additionally biopsies from control patients (surveillance colonoscopy or inflammation-free areas from patients with colorectal cancer) are studied.
  Ex vivo Treatment Model:
    Organ or LPMC culture as determined appropriate
  Ex vivo Treatments:
    NLRP3 antagonist (2 concentrations), negative control (vehicle), positive control (caspase-1 inhibitor) each in the presence or absence of anti-TNF antibody at a concentration appropriate to distinguish differences in the T cell apoptotic between biopsies from anti-TNF resistant and anti-TNF-sensitive Crohn's disease patients. Each treatment condition is evaluated in a minimum in duplicate samples.

Endpoints to be measured:
  Before ex vivo treatment—NLRP3 RNA level
  After ex vivo treatment-inflammasome activity (either processed IL-1β, processed caspase-1, or secreted IL-1β); RNA for inflammatory cytokines (Nanostring); viable T cell number and/or T cell apoptosis.

Data Analysis Plan:
  Determine if NLRP3 antagonist co-treatment increases T cell apoptosis/deletion in response to anti-TNF.
  Determine if the level of NLRP3 RNA expression is greater in TNF-resistant Crohn's disease and ulcerative colitis samples compared to anti-TNF treatment-nave samples.
  Determine if NLRP3 antagonist treatment decreases processed IL-1β, processed caspase-1 or secreted IL-1β, and inflammatory cytokine RNA levels.

Biological Assay—Nigericin-Stimulated IL-1β Secretion Assay in THP-1 Cells

Monocytic THP-1 cells (ATCC: TIB-202) were maintained according to providers' instructions in RPMI media (RPMI/Hepes+10% fetal bovine serum+Sodium Pyruvate+ 0.05 mM Beta-mercaptoethanol (1000× stock)+Pen-Strep). Cells were differentiated in bulk with 0.5 µM phorbol 12-myristate 13-acetate (PMA; Sigma #P8139) for 3 hours, media was exchanged, and cells were plated at 50,000 cells per well in a 384-well flat-bottom cell culture plates (Greiner, #781986), and allowed to differentiate overnight. Compound in a 1:3.16 serial dilution series in DMSO was added 1:100 to the cells and incubated for 1 hour. The NLRP3 inflammasome was activated with the addition of 15 µM (final concentration) Nigericin (Enzo Life Sciences, #BML-CA421-0005), and cells were incubated for 3 hours. 10 µL supernatant was removed, and IL-1β levels were monitored using an HTRF assay (CisBio, #62IL1PEC) according to manufacturers' instructions. Viability and pyroptosis was monitored with the addition of PrestoBlue cell viability reagent (Life Technologies, #A13261) directly to the cell culture plate.

A number of embodiments of the invention have been described. Nevertheless, it will be understood that various modifications may be made without departing from the spirit and scope of the invention. Accordingly, other embodiments are within the scope of the following claims.

What is claimed is:
1. A compound selected from:

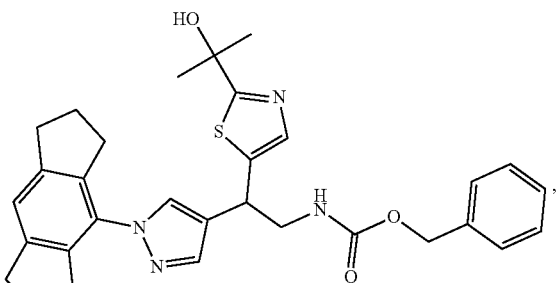

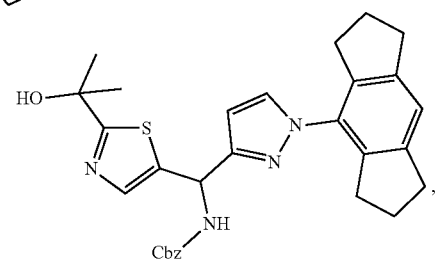

325
-continued
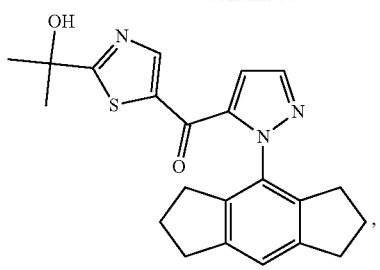
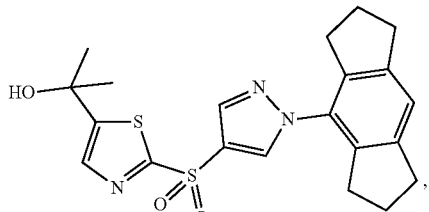
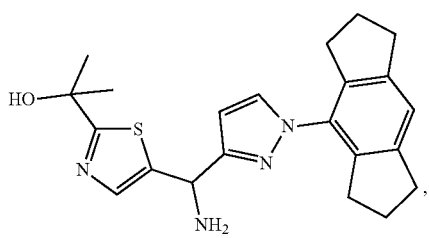
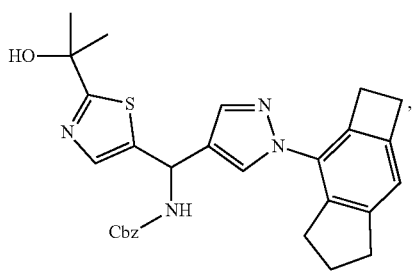
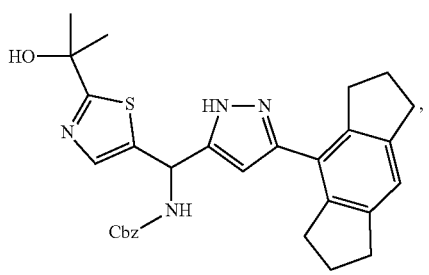
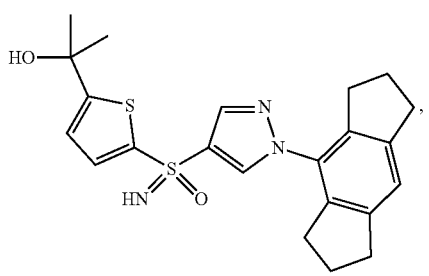
326
-continued
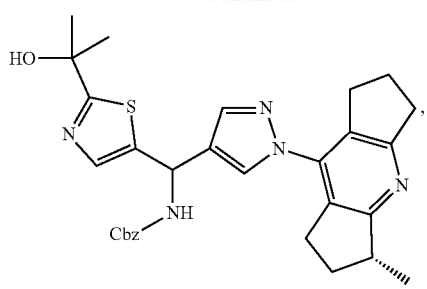
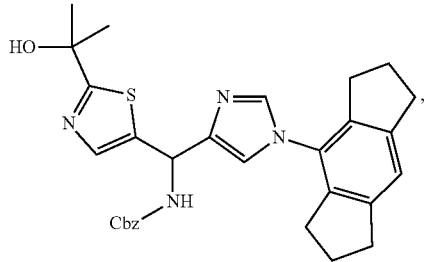
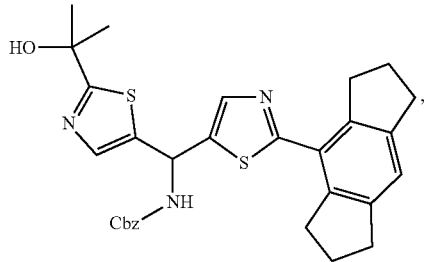
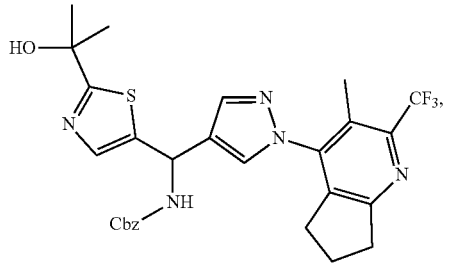
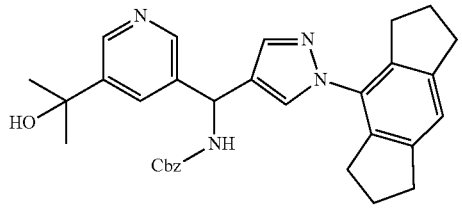
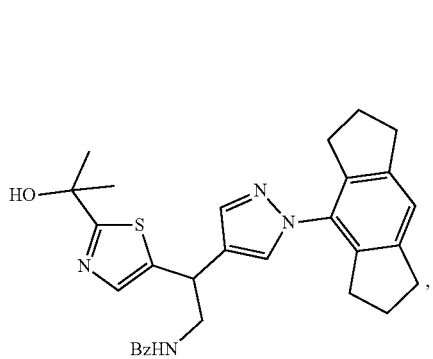

327
-continued
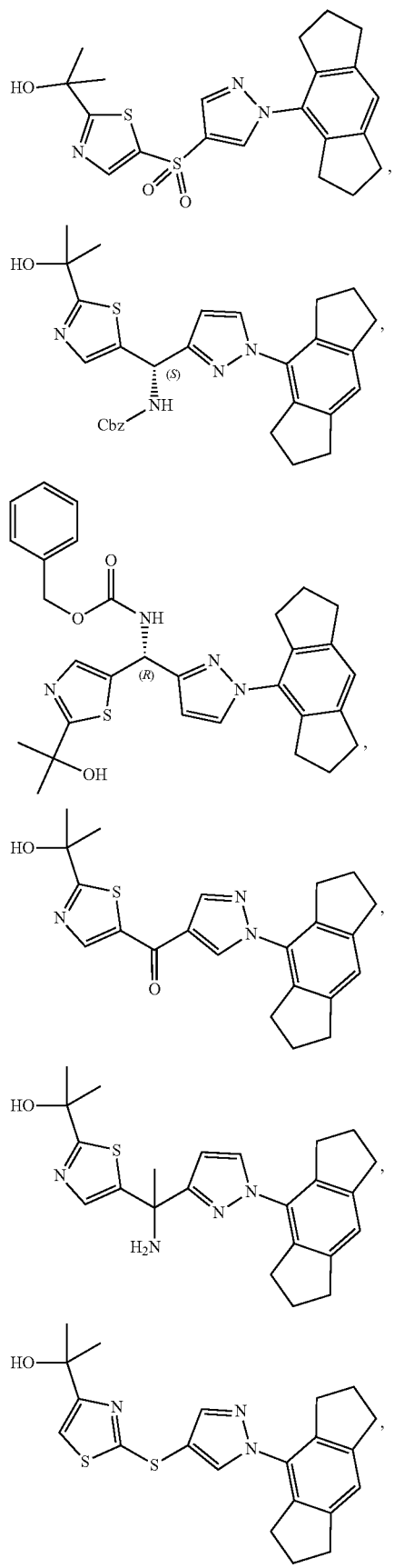
328
-continued
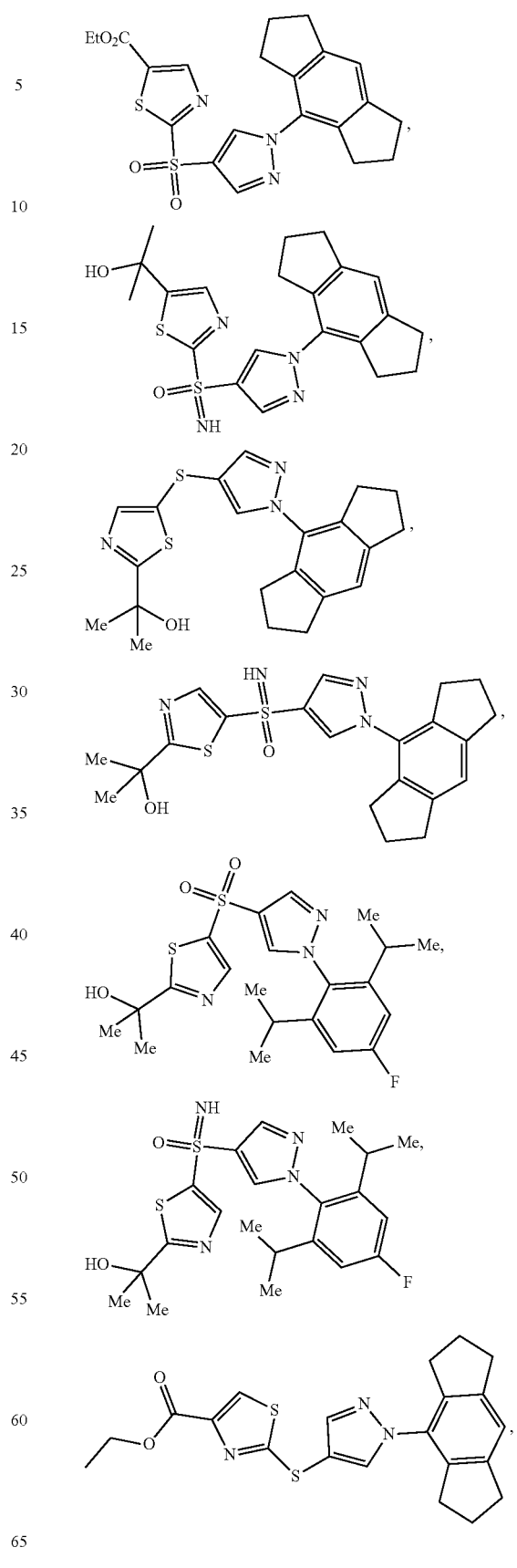

329
-continued
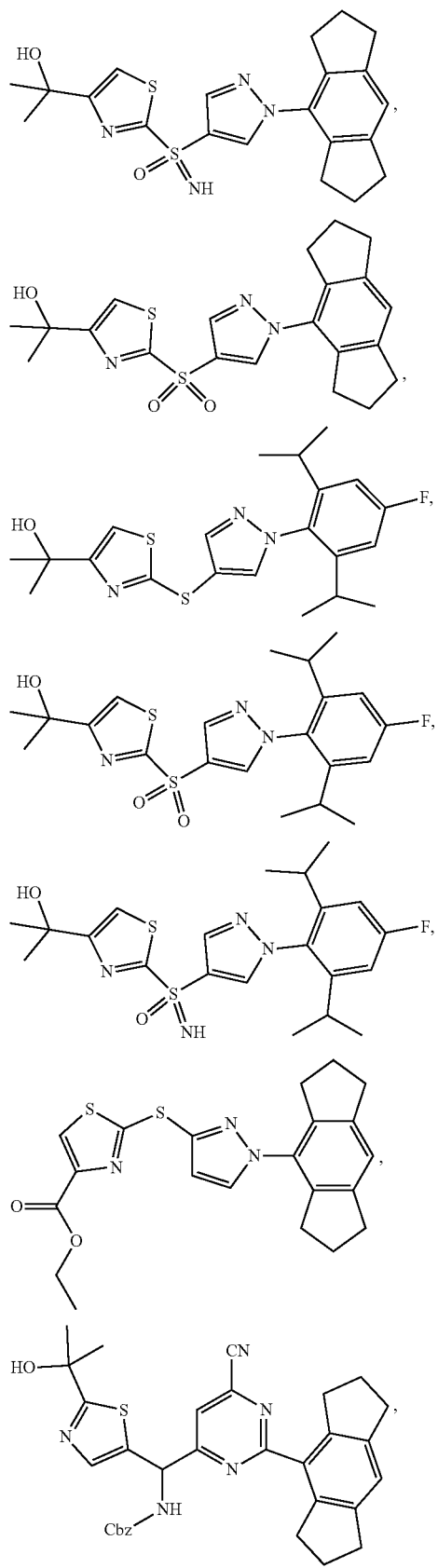
330
-continued
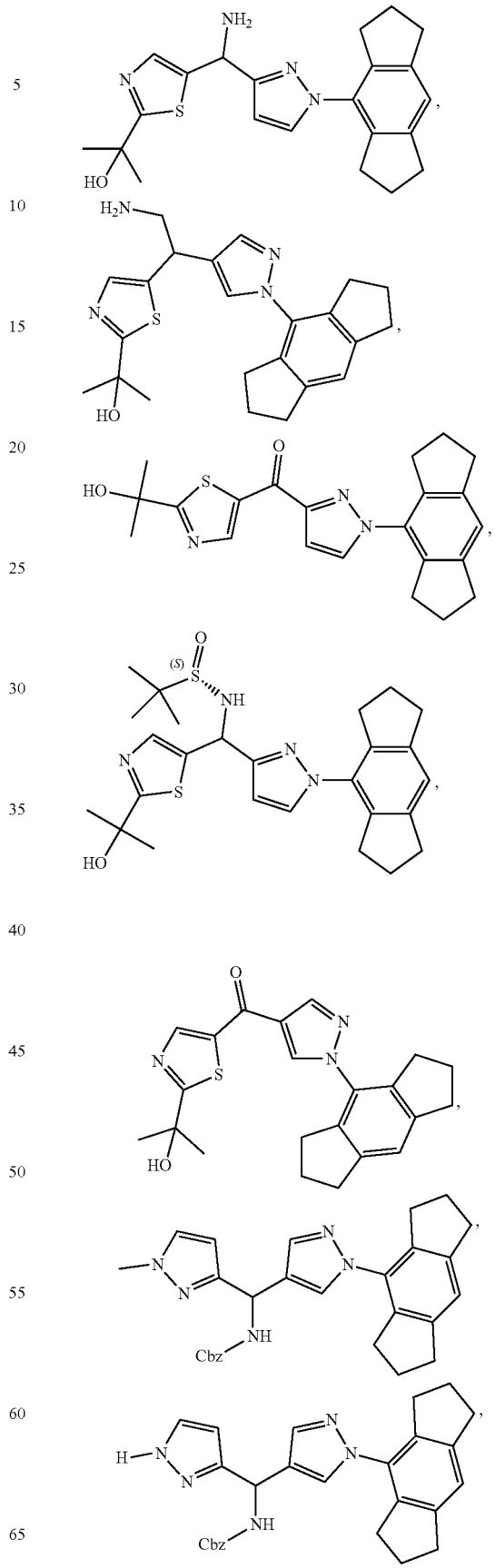

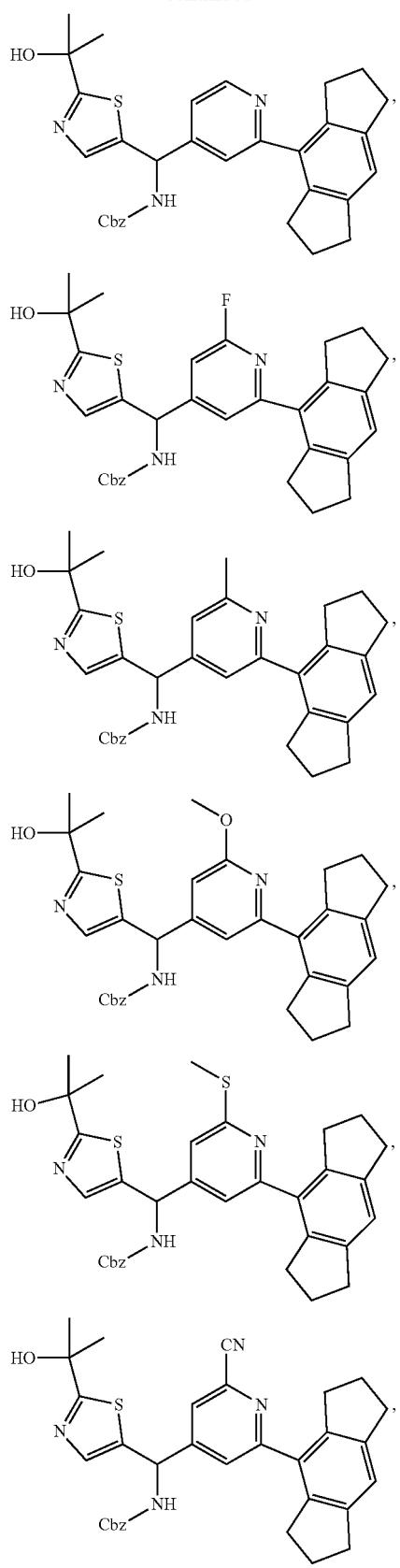
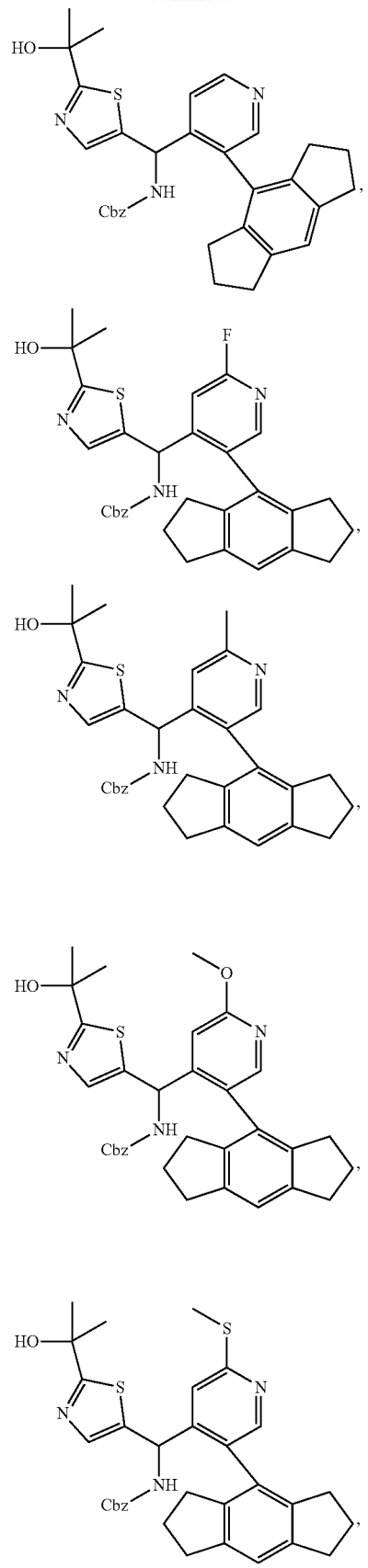

333
-continued
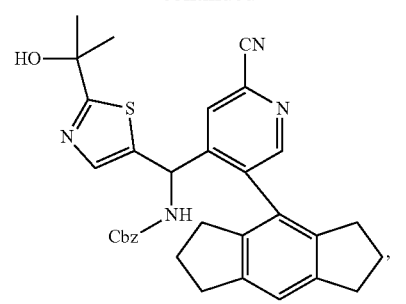
334
-continued
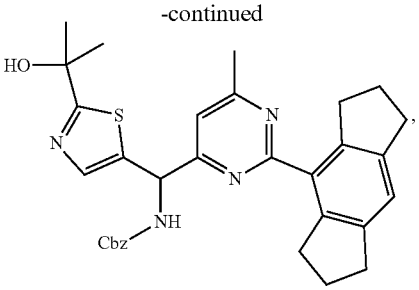
, and
* * * * *